US011718589B2

(12) United States Patent
Markowitz et al.

(10) Patent No.: US 11,718,589 B2
(45) Date of Patent: Aug. 8, 2023

(54) COMPOSITIONS AND METHODS OF MODULATING SHORT-CHAIN DEHYDROGENASE

(71) Applicants: CASE WESTERN RESERVE UNIVERSITY, Cleveland, OH (US); Board of Regents of the University of Texas System, Austin, TX (US)

(72) Inventors: Sanford Markowitz, Cleveland, OH (US); Yiyuan Yuan, Cleveland, OH (US); Yongyou Zhang, Cleveland, OH (US); Joseph Ready, Carrollton, TX (US); Bin Hu, Shanghai (CN)

(73) Assignees: Case Western Reserve University, Cleveland, OH (US); Board of Regents of the University of Texas System, Austin, TX (US)

(*) Notice: Subject to any disclaimer, the term of this patent is extended or adjusted under 35 U.S.C. 154(b) by 0 days.

(21) Appl. No.: 16/484,045

(22) PCT Filed: Feb. 6, 2018

(86) PCT No.: PCT/US2018/017044
§ 371 (c)(1),
(2) Date: Aug. 6, 2019

(87) PCT Pub. No.: WO2018/145080
PCT Pub. Date: Aug. 9, 2018

(65) Prior Publication Data
US 2020/0095206 A1 Mar. 26, 2020

Related U.S. Application Data

(60) Provisional application No. 62/455,399, filed on Feb. 6, 2017, provisional application No. 62/510,589, filed on May 24, 2017.

(51) Int. Cl.
| | |
|---|---|
| *C07D 235/18* | (2006.01) |
| *C07D 239/74* | (2006.01) |
| *C07D 241/42* | (2006.01) |
| *C12N 9/04* | (2006.01) |
| *A61K 45/06* | (2006.01) |
| *A61K 31/4164* | (2006.01) |

(52) U.S. Cl.
CPC ......... *C07D 235/18* (2013.01); *C07D 239/74* (2013.01); *C07D 241/42* (2013.01); *C12N 9/0006* (2013.01); *A61K 31/4164* (2013.01); *A61K 45/06* (2013.01)

(58) Field of Classification Search
CPC . C07D 235/18; C07D 239/74; A61K 31/4164
See application file for complete search history.

(56) References Cited

U.S. PATENT DOCUMENTS

| | | |
|---|---|---|
| 3,382,247 A | 5/1968 | Anthony et al. |
| 4,725,676 A | 2/1988 | Agback et al. |
| 4,889,846 A | 12/1989 | Crossley |
| 4,910,226 A | 3/1990 | Holt et al. |
| 4,966,974 A | 10/1990 | Klausener et al. |
| 4,973,474 A | 11/1990 | Hocquaux et al. |
| 5,006,532 A | 4/1991 | Baker et al. |
| 5,015,629 A | 5/1991 | diZerega |
| 5,041,157 A | 8/1991 | Seiler et al. |
| 5,217,521 A | 6/1993 | Durr |
| 5,405,842 A | 4/1995 | Silverman |
| 5,411,981 A | 5/1995 | Gaillard-Kelly et al. |
| 5,438,058 A | 8/1995 | Dufetel et al. |
| 5,445,164 A | 8/1995 | Worthen et al. |
| 5,460,964 A | 10/1995 | McGlave et al. |
| 5,466,694 A | 11/1995 | Terranova et al. |
| 5,468,888 A | 11/1995 | Bouboutou et al. |
| 5,480,913 A | 1/1996 | Liao et al. |
| 5,516,779 A | 5/1996 | Von Langen et al. |
| 5,529,769 A | 6/1996 | Cho et al. |
| 5,565,467 A | 10/1996 | Batchelor et al. |
| 5,631,282 A | 5/1997 | Goetz |
| 5,635,387 A | 6/1997 | Fei et al. |
| 5,650,145 A | 7/1997 | Saint-Leger |
| 5,677,136 A | 10/1997 | Simmons et al. |
| 5,681,559 A | 10/1997 | DiGiusto et al. |
| 5,716,827 A | 2/1998 | Tsukamoto et al. |
| 5,750,397 A | 5/1998 | Tsukamoto et al. |
| 5,756,092 A | 5/1998 | Michelet et al. |
| 5,759,793 A | 6/1998 | Schwartz et al. |
| 5,760,043 A | 6/1998 | Dufetel et al. |
| 5,772,990 A | 6/1998 | Hocquaux et al. |
| 5,807,895 A | 9/1998 | Stratton et al. |

(Continued)

FOREIGN PATENT DOCUMENTS

| | | |
|---|---|---|
| AR | 060498 A1 | 6/2008 |
| AU | 2013/249434 B2 | 10/2017 |

(Continued)

OTHER PUBLICATIONS

Chinese Office Action for Application No. 201680034932.5 dated May 8, 2020.
European Office Action for Application No. 17 194 305.3-1110 dated Apr. 9, 2020.
Cho et al.: "Thiazolidinediones as a novel class of NAD+dependent 15-hydroxyprostaglandin dehydrogenase inhibitors", Archives of Biochemistry and Biophysics, Academic Press, US, vol. 405, Jan. 1, 2002 (Jan. 1, 2002), pp. 247-251, XP002292688, ISSN: 0003-9861, DOI: 10.1016/S0003-9861 (02)00352-1.
Applicant: Case Western Reserve University; "Inhibitors of Short-Chain Dehydrogenase Activity for Treating Coronary Disorders"; European Patent Application No. 18781322; Extended European Search Report dated Dec. 9, 2020; 12 pgs.

(Continued)

*Primary Examiner* — Kevin E Weddington
(74) *Attorney, Agent, or Firm* — Barnes & Thornburg LLP

(57) ABSTRACT

Compounds and methods of modulating 15-PGDH activity, modulating tissue prostaglandin levels, treating disease, diseases disorders, or conditions in which it is desired to modulate 15-PGDH activity and/or prostaglandin levels include 15-PGDH inhibitors described herein.

7 Claims, No Drawings

(56) References Cited

U.S. PATENT DOCUMENTS

| | | |
|---|---|---|
| 6,027,896 A | 2/2000 | Roses et al. |
| 6,121,254 A | 9/2000 | Saint-Leger |
| 6,214,533 B1 | 4/2001 | Ho et al. |
| 6,281,227 B1 | 8/2001 | Choi-Sledeski et al. |
| 6,414,027 B1 | 7/2002 | Neal |
| 6,465,421 B1 | 10/2002 | Duranton et al. |
| 6,468,972 B1 | 10/2002 | Pruche et al. |
| 7,004,913 B1 | 2/2006 | Rutenberg et al. |
| 7,022,675 B2 | 4/2006 | Rodgers et al. |
| 7,091,216 B2 | 8/2006 | Toupence et al. |
| 7,131,958 B2 | 11/2006 | Deverre |
| 7,147,626 B2 | 12/2006 | Goodman et al. |
| 7,189,724 B2 | 3/2007 | An et al. |
| 7,294,641 B2 | 11/2007 | Boulle et al. |
| 7,320,967 B2 | 1/2008 | Michelet et al. |
| 7,396,525 B2 | 7/2008 | Rozot et al. |
| 7,629,112 B1 | 12/2009 | Zengerle et al. |
| 7,705,041 B2 | 4/2010 | Michelet et al. |
| 8,068,897 B1 | 11/2011 | Gazdzinski |
| 8,202,882 B2 | 6/2012 | Hoelzemann et al. |
| 8,637,558 B2 | 1/2014 | Cho et al. |
| 8,642,660 B2 | 2/2014 | Goldfarb |
| 9,649,350 B2 | 5/2017 | Choi et al. |
| 9,789,116 B2 | 10/2017 | Markowitz et al. |
| 9,790,233 B2 | 10/2017 | Markowitz et al. |
| 9,801,863 B2 | 10/2017 | Markowitz et al. |
| 10,301,320 B2 | 5/2019 | Markowitz et al. |
| 10,420,752 B2 | 9/2019 | Markowitz et al. |
| 10,869,871 B2 | 12/2020 | Markowitz et al. |
| 10,945,998 B2 | 3/2021 | Markowitz et al. |
| 11,426,420 B2 | 8/2022 | Markowitz et al. |
| 2002/0044953 A1 | 4/2002 | Michelet et al. |
| 2002/0045659 A1 | 4/2002 | Michelet et al. |
| 2003/0083381 A1 | 5/2003 | Kumagai et al. |
| 2003/0096823 A1 | 5/2003 | Asp et al. |
| 2004/0052760 A1 | 3/2004 | Michelet et al. |
| 2004/0087593 A1 | 5/2004 | Clark et al. |
| 2004/0241726 A1 | 12/2004 | Liew |
| 2004/0241727 A1 | 12/2004 | Liew |
| 2004/0241729 A1 | 12/2004 | Liew |
| 2005/0026923 A1 | 2/2005 | An et al. |
| 2005/0187221 A1 | 8/2005 | Matsuda et al. |
| 2006/0019976 A1 | 1/2006 | Karp et al. |
| 2006/0034786 A1 | 2/2006 | Michelet et al. |
| 2006/0051540 A1 | 3/2006 | Kagawa |
| 2006/0089349 A1 | 4/2006 | Gundertofte et al. |
| 2006/0233797 A1 | 10/2006 | Gujrathi |
| 2006/0287284 A1 | 12/2006 | Schutze et al. |
| 2007/0049603 A1 | 3/2007 | Miknis et al. |
| 2007/0059265 A1 | 3/2007 | Boulle |
| 2007/0071699 A1 | 3/2007 | Boulle |
| 2007/0078175 A1 | 4/2007 | Boulle et al. |
| 2007/0155884 A1 | 7/2007 | Pellegatti et al. |
| 2007/0219234 A1 | 9/2007 | Oizumi et al. |
| 2008/0039459 A1 | 2/2008 | Folkes et al. |
| 2008/0206320 A1 | 8/2008 | Michelet et al. |
| 2008/0249117 A1 | 10/2008 | Michelet et al. |
| 2009/0105210 A1 | 4/2009 | Ashton et al. |
| 2009/0118337 A1 | 5/2009 | Davis |
| 2009/0163545 A1 | 6/2009 | Goldfarb |
| 2010/0022521 A1 | 1/2010 | Nogradi et al. |
| 2010/0076041 A1 | 3/2010 | Kilburn et al. |
| 2010/0099672 A1 | 4/2010 | Karp et al. |
| 2010/0120732 A1 | 5/2010 | Tabunoki |
| 2010/0190853 A1 | 7/2010 | Rethore et al. |
| 2010/0234369 A1 | 9/2010 | Hoelzemann et al. |
| 2011/0009374 A1 | 1/2011 | Keller |
| 2011/0014250 A1 | 1/2011 | Michelet et al. |
| 2011/0034564 A1 | 2/2011 | Parkkinen |
| 2011/0142816 A1 | 6/2011 | Landry et al. |
| 2011/0195031 A1 | 8/2011 | Du |
| 2011/0269954 A1 | 11/2011 | Cho et al. |
| 2012/0302586 A1 | 11/2012 | Rathod et al. |
| 2013/0078632 A1 | 3/2013 | Krishnadath |
| 2013/0190297 A1 | 7/2013 | DeJonghe et al. |
| 2015/0072998 A1 | 3/2015 | Markowitz et al. |
| 2015/0118744 A1 | 4/2015 | Tanaka et al. |
| 2015/0202241 A1 | 7/2015 | Choi et al. |
| 2016/0136185 A1 | 5/2016 | Shin et al. |
| 2016/0311825 A1 | 10/2016 | Farmer et al. |
| 2016/0376430 A1 | 12/2016 | Kusumoto et al. |
| 2017/0165241 A1 | 6/2017 | Markowitz et al. |
| 2017/0173028 A1 | 6/2017 | Markowitz et al. |
| 2017/0174704 A1 | 6/2017 | Gigstad et al. |
| 2017/0216265 A1 | 8/2017 | Markowitz |
| 2017/0266141 A1 | 9/2017 | Nagy |
| 2018/0064694 A1 | 3/2018 | Markowitz et al. |
| 2018/0118756 A1 | 5/2018 | Markowitz et al. |
| 2018/0125829 A1 | 5/2018 | Markowitz et al. |
| 2019/0126044 A1 | 5/2019 | Lozano |
| 2019/0275014 A1 | 9/2019 | Markowitz et al. |
| 2019/0365769 A1 | 12/2019 | Markowitz et al. |
| 2020/0030348 A1 | 1/2020 | Markowitz et al. |
| 2020/0061073 A1 | 2/2020 | Markowitz et al. |
| 2020/0095206 A1 | 3/2020 | Markowitz et al. |
| 2020/0140453 A1 | 5/2020 | Markowitz et al. |
| 2020/0147063 A1 | 5/2020 | Markowitz et al. |
| 2021/0032265 A1 | 2/2021 | Markowitz et al. |
| 2021/0094968 A1 | 4/2021 | Markowitz et al. |
| 2021/0100778 A1 | 4/2021 | Markowitz et al. |
| 2021/0100779 A1 | 4/2021 | Markowitz et al. |
| 2021/0106587 A1 | 4/2021 | Markowitz et al. |
| 2021/0108177 A1 | 4/2021 | Di Santo et al. |
| 2021/0165249 A1 | 6/2021 | Wang et al. |
| 2021/0283113 A1 | 9/2021 | Markowitz et al. |
| 2021/0317132 A1 | 10/2021 | Markowitz et al. |
| 2021/0386070 A1 | 12/2021 | Arlt et al. |

FOREIGN PATENT DOCUMENTS

| | | |
|---|---|---|
| AU | 2016/248080 A1 | 11/2017 |
| AU | 2014/342811 B2 | 1/2019 |
| AU | 2018/200368 B2 | 7/2019 |
| AU | 2018/215678 A1 | 8/2019 |
| AU | 2018/249956 A1 | 11/2019 |
| AU | 2019/250163 A1 | 11/2019 |
| AU | 2016/229918 B2 | 10/2020 |
| AU | 2019/247838 A1 | 10/2020 |
| AU | 2019/202208 B2 | 12/2020 |
| AU | 2021/201332 A1 | 3/2021 |
| AU | 2019/384821 A1 | 6/2021 |
| AU | 2021/204985 A1 | 8/2021 |
| AU | 2017/300377 B2 | 4/2022 |
| AU | 2022/201982 A1 | 4/2022 |
| AU | 2022/205248 A1 | 8/2022 |
| AU | 2018/272108 B2 | 9/2022 |
| AU | 2021/200610 B2 | 9/2022 |
| AU | 2021/224268 A1 | 9/2022 |
| AU | 2021/201332 B2 | 11/2022 |
| AU | 2021/275122 A1 | 12/2022 |
| CA | 2007351 A1 | 7/1990 |
| CA | 2870666 A1 | 10/2013 |
| CA | 2927730 A1 | 4/2016 |
| CA | 2979203 A1 | 9/2016 |
| CA | 2974266 A1 | 7/2017 |
| CA | 2984594 A1 | 10/2017 |
| CA | 3031091 A1 | 1/2018 |
| CA | 3052466 A1 | 8/2018 |
| CA | 3059255 A1 | 10/2018 |
| CA | 3068445 A1 | 11/2018 |
| CA | 2984588 C | 10/2019 |
| CA | 3095308 A1 | 10/2019 |
| CA | 3120858 A1 | 5/2020 |
| CA | 3168728 A1 | 8/2021 |
| CA | 3183262 A1 | 11/2021 |
| CL | 2020002741 A1 | 1/2021 |
| CL | 2021001288 A1 | 1/2022 |
| CL | 2021003378 A1 | 8/2022 |
| CN | 1589793 A | 3/2005 |
| CN | 102888208 B | 2/2015 |
| CN | 107921025 A | 4/2018 |
| CN | 108012528 A | 5/2018 |
| CN | 110573154 A | 12/2019 |
| CN | 110582277 A | 12/2019 |

(56) References Cited

FOREIGN PATENT DOCUMENTS

| | | |
|---|---|---|
| CN | 110891568 A | 3/2020 |
| CN | 111132982 A | 5/2020 |
| CN | 11273944 A | 4/2021 |
| CN | 113507931 A | 10/2021 |
| EP | 0142811 A2 | 3/1985 |
| EP | 0271273 A2 | 6/1988 |
| EP | 0378508 A2 | 7/1990 |
| EP | 0434624 A1 | 6/1991 |
| EP | 0648488 B1 | 11/2000 |
| EP | 1080728 A1 | 3/2001 |
| EP | 1175890 A1 | 1/2002 |
| EP | 1175891 A1 | 1/2002 |
| EP | 0854700 B1 | 5/2002 |
| EP | 0680745 B1 | 11/2002 |
| EP | 2564841 B1 | 5/2015 |
| EP | 2838533 B1 | 10/2017 |
| EP | 3267995 A1 | 1/2018 |
| EP | 3280398 A1 | 2/2018 |
| EP | 3283074 A1 | 2/2018 |
| EP | 3295940 A1 | 3/2018 |
| EP | 3484473 A1 | 5/2019 |
| EP | 3057973 B1 | 9/2019 |
| EP | 3548035 A1 | 10/2019 |
| EP | 3576737 A1 | 12/2019 |
| EP | 3606520 A1 | 2/2020 |
| EP | 3630773 A1 | 4/2020 |
| EP | 3781154 A1 | 2/2021 |
| EP | 3883577 A1 | 9/2021 |
| EP | 4106748 | 12/2022 |
| FR | 2838641 A1 | 10/2003 |
| FR | 2860431 A1 | 4/2005 |
| JP | S60-172984 A | 9/1985 |
| JP | H02-288810 A | 11/1990 |
| JP | H04-234888 A | 8/1992 |
| JP | H09-295921 A | 11/1997 |
| JP | H10-287532 A | 10/1998 |
| JP | 2003-286171 A | 10/2003 |
| JP | 2004/528319 A | 9/2004 |
| JP | 2006-522750 A | 3/2005 |
| JP | 2005/515182 A | 5/2005 |
| JP | 2005/325099 A | 11/2005 |
| JP | 2004/528319 A5 | 1/2006 |
| JP | 2006/522750 A5 | 5/2007 |
| JP | 2007/527850 A | 10/2007 |
| JP | 2008/507518 A | 3/2008 |
| JP | 2008/527011 A | 7/2008 |
| JP | 2008/536855 A | 9/2008 |
| JP | 2008/536855 A5 | 5/2009 |
| JP | 2009/520016 A | 5/2009 |
| JP | 2009/535335 A | 10/2009 |
| JP | 2009/535335 A5 | 1/2010 |
| JP | 2010/053332 A | 3/2010 |
| JP | 2010/520864 A | 6/2010 |
| JP | 2007/527850 A5 | 7/2010 |
| JP | 2011/500610 A | 1/2011 |
| JP | 2013/506004 A | 2/2013 |
| JP | 2013/506004 A5 | 10/2013 |
| JP | 2015514770 A | 5/2015 |
| JP | 2016-531864 A | 10/2016 |
| JP | 2016/537328 A | 12/2016 |
| JP | 2017/514809 A | 6/2017 |
| JP | 6203820 B2 | 9/2017 |
| JP | 2018/511581 A | 4/2018 |
| JP | 2018/511616 A | 4/2018 |
| JP | 2018/511616 A5 | 5/2019 |
| JP | 6517197 B2 | 5/2019 |
| JP | 2019/135253 A | 8/2019 |
| JP | 2020/502070 A | 1/2020 |
| JP | 2020/503851 A | 2/2020 |
| JP | 2020/514323 A | 5/2020 |
| JP | 2020/516617 A | 6/2020 |
| JP | 2020/516617 A5 | 7/2020 |
| JP | 6789542 B2 | 11/2020 |
| JP | 2020/502070 A5 | 1/2021 |
| JP | 2021/020942 A | 2/2021 |
| JP | 2020/514323 A5 | 3/2021 |
| JP | 2021/038247 A | 3/2021 |
| JP | 2021/519797 A | 8/2021 |
| JP | 2022/507888 A | 1/2022 |
| JP | 2021/519797 A5 | 4/2022 |
| JP | 2022/141390 A | 9/2022 |
| JP | 7139308 B2 | 9/2022 |
| JP | 2022/163172 A | 10/2022 |
| JP | 2022/174196 A | 11/2022 |
| JP | 2022/191415 A | 12/2022 |
| KR | 2008/0112764 A | 12/2008 |
| KR | 2010/0137090 A | 12/2010 |
| KR | 2013/0103945 A | 9/2013 |
| RU | 2006/127472 A | 2/2008 |
| WO | WO 1990/006100 A1 | 6/1990 |
| WO | WO 1993/013664 A2 | 7/1993 |
| WO | WO 1995/011003 A1 | 4/1995 |
| WO | 1998/0027092 A1 | 6/1998 |
| WO | WO 1998/033497 A1 | 8/1998 |
| WO | WO 2001/017480 A2 | 3/2001 |
| WO | WO 2001/072268 A1 | 10/2001 |
| WO | WO 2001/074307 A2 | 10/2001 |
| WO | WO 2001/074313 A2 | 10/2001 |
| WO | WO 2001/074314 A2 | 10/2001 |
| WO | WO 2001/074315 A2 | 10/2001 |
| WO | 2004/012671 A2 | 2/2004 |
| WO | 2004012671 A2 | 2/2004 |
| WO | WO 2004/089415 A2 | 10/2004 |
| WO | WO 2004/089416 A2 | 10/2004 |
| WO | WO 2004/089471 A2 | 10/2004 |
| WO | WO 2004/099204 A1 | 11/2004 |
| WO | 2005/021552 A1 | 3/2005 |
| WO | WO 2005/028676 A2 | 3/2005 |
| WO | WO 2005/030773 A1 | 4/2005 |
| WO | WO 2005/046434 A2 | 5/2005 |
| WO | WO 2005/062735 A2 | 7/2005 |
| WO | WO 2005/090333 A1 | 9/2005 |
| WO | 2006/019832 A1 | 2/2006 |
| WO | WO 2006/048264 A2 | 5/2006 |
| WO | WO 2006/048266 A2 | 5/2006 |
| WO | WO 2006/074226 A2 | 7/2006 |
| WO | WO 2006/078676 A2 | 7/2006 |
| WO | WO 2006/096649 A2 | 9/2006 |
| WO | WO 2006/098961 A2 | 9/2006 |
| WO | WO 2006/138275 A2 | 12/2006 |
| WO | WO 2007/013665 A2 | 2/2007 |
| WO | WO 2007/019180 A2 | 2/2007 |
| WO | WO 2007/027855 A2 | 3/2007 |
| WO | WO 2007/038519 A1 | 4/2007 |
| WO | WO 2007/072095 A1 | 6/2007 |
| WO | WO 2007/100775 A2 | 9/2007 |
| WO | WO 2007/101224 A2 | 9/2007 |
| WO | WO 2007/127183 A1 | 11/2007 |
| WO | WO 2008/063671 A2 | 5/2008 |
| WO | WO 2008/156614 A2 | 12/2008 |
| WO | WO 2009/029669 A1 | 3/2009 |
| WO | WO 2009/073460 A2 | 6/2009 |
| WO | WO 2009/082691 A1 | 7/2009 |
| WO | WO 2009/111648 A1 | 9/2009 |
| WO | WO 2009/120877 A2 | 10/2009 |
| WO | WO 2010/023181 A1 | 3/2010 |
| WO | WO 2010/045017 A1 | 4/2010 |
| WO | WO 2010/052569 A2 | 5/2010 |
| WO | WO 2010/077101 A2 | 7/2010 |
| WO | WO 2010/080996 A1 | 7/2010 |
| WO | WO 2010/091808 A1 | 8/2010 |
| WO | WO 2010/111711 A2 | 9/2010 |
| WO | WO 2011/041304 A2 | 4/2011 |
| WO | WO 2011/042860 A2 | 4/2011 |
| WO | WO 2011/094847 A1 | 8/2011 |
| WO | WO 2011/147753 A1 | 12/2011 |
| WO | WO 2012/146933 A1 | 11/2012 |
| WO | WO 2013/034927 A1 | 3/2013 |
| WO | WO 2013/082243 A1 | 6/2013 |
| WO | WO 2013/083991 A1 | 6/2013 |
| WO | 2013/0112699 A2 | 8/2013 |
| WO | WO 2013/158649 A1 | 10/2013 |
| WO | 2013/180336 A1 | 12/2013 |
| WO | WO 2014/081617 A1 | 5/2014 |

(56) References Cited

FOREIGN PATENT DOCUMENTS

| | | |
|---|---|---|
| WO | WO 2014/081878 A2 | 5/2014 |
| WO | WO 2014/160183 A1 | 10/2014 |
| WO | WO 2014/160947 A1 | 10/2014 |
| WO | WO 2015/005239 A1 | 1/2015 |
| WO | 2015/065716 A1 | 5/2015 |
| WO | WO 2015/077382 A2 | 5/2015 |
| WO | WO 2015/161142 A1 | 10/2015 |
| WO | WO 2016/106340 A2 | 6/2016 |
| WO | WO 2016/124939 A1 | 8/2016 |
| WO | 2016/144958 A1 | 9/2016 |
| WO | 2016/168472 A1 | 10/2016 |
| WO | 2017/152044 A1 | 9/2017 |
| WO | 2018017582 A1 | 1/2018 |
| WO | WO 2018/102552 A1 | 6/2018 |
| WO | WO 2018/145080 A1 | 8/2018 |
| WO | WO 2018/187810 A1 | 10/2018 |
| WO | 2018218251 A1 | 11/2018 |
| WO | WO 2018/227134 A1 | 12/2018 |
| WO | WO 2019/010482 A1 | 1/2019 |
| WO | 2016144958 A1 | 9/2019 |
| WO | WO 2019/195565 A1 | 10/2019 |
| WO | WO 2020/051207 A2 | 3/2020 |
| WO | 2020/106998 A1 | 5/2020 |
| WO | WO 2020/160151 | 8/2020 |
| WO | WO 2020/252146 A1 | 12/2020 |
| WO | WO 2021/151014 A1 | 7/2021 |
| WO | WO 2021/168430 A1 | 8/2021 |
| WO | WO 2021/236779 A1 | 11/2021 |
| WO | WO 2021/252936 A1 | 12/2021 |
| WO | WO 2021/236779 A9 | 1/2022 |
| WO | WO 2022/032230 A1 | 2/2022 |

OTHER PUBLICATIONS

Applicant: Case Western Reserve University; "Inhibitors of Short-Chain Dehydrogenase Activity for Treating Coronary Disorders"; PCT International Application No. PCT/US2018/026739; PCT International Filing Date: Apr. 9, 2018; Date of Completion of Search: Jun. 15, 2018; 9 pgs.

Applicant: Case Western Reserve University; "Compositions and Methods of Modulating 15-PGDH Activity"; Canadian Patent Application No. 2870666; Office Action dated Nov. 18, 2020; 4 pgs.

Applicant: Case Western Reserve University; "Inhibitors of Short-Chain Dehydrogenase Activity for Treating Fibrosis"; Chinese Patent Application No. 201680026631.8; Chinese Office Action dated Dec. 11, 2020; 12 pgs.

Applicant: Case Western Reserve University; Canadian Application No. 2927730; "Compositions and Methods of Modulating Short-Chain Dehydrogenase Activity"; Canadian Office Action dated Dec. 3, 2020; 5 pgs.

Applicant: Case Western Reserve University; European Office Action; dated Dec. 17, 2020; 5 pgs.

Kalugin, V.E., Shestopalov, A.M. & Litvinov, V.P. Functionalized sulfur-containing compounds. 13. Synthesis of substituted 3-amino-2-(organylsulfinyl)-and-(organylsulfonyl)thieno[2,3-b]pyridines. Russ Chem Bull 55, 529-534 (2006). https://doi.org/10.1007/s11172-006-0287-y.

Mordente et al. "Human Heart Cytosolic Reductases and Anthracycline Cardiotoxicity," IUBMB Life, Jan. 3, 2008 (Jan. 3, 2008), vol. 52, pp. 83-88.

Olson et al. "Protection from Doxorubicin-Induced Cardiac Toxicity in Mice with a Null Allele of Carbonyl Reductase 1," Cancer Research, Oct. 15, 2003 (Oct. 15, 2003), vol. 63, pp. 6602-6606.

Piska et al. "Metabolic carbonyl reduction of anthracyclines role in cardiotoxicity and cancer resistance: Reducing enzymes as putative targets for novel cardioprotective and chemosensitizing agents," Invest New Drugs, Mar. 10, 2017 (Mar. 10, 2017), vol. 35, No. 3, pp. 375-385.

Applicant: Case Western Reserve University; Title: Inhibitors of Short-Chain Dehydrogenase Activity for Treating Fibrosis; Australian Patent Application No. 2016229918; Examination report No. 2 for your standard patent application; dated Jul. 30, 2020, 8 pgs.

Sanford Markowitz, "Inhibitors of Short-Chain Dehydrogenase Activity for Modulating Hematopoietic Stem Cells and Hematopoiesis"; U.S. Appl. No. 16/581,024, filed Sep. 24, 2019; 7 pgs.

Sanford Markowitz, "Compositions and Methods of Modulating 15-PGOH Activity"; U.S. Appl. No. 16/421,867, filed May 24, 2019; Jul. 2, 2020; 65 pgs.

Applicant: Case Western Reserve University; Australian Patent Application No. 2018215678; Australian Office Action dated Mar. 23, 2021; 8 pgs.

Applicant: Case Western Reserve University; Australian Patent Application No. 2017300377; Australian Office Action dated Apr. 9, 2021; 7 pgs.

Cudaback E, Jorstad NL, Yang Y, Montine TJ, Keene CD. Therapeutic implications of the prostaglandin pathway in Alzheimer's disease. Biochem Pharmacol. 2014;88(4):565-572. doi:10.1016/j.bcp.2013.12.014; 9 pgs.

H. Cho, et al.; "Inhibition of NAD+-dependent 15-hydroxyprostaglandin dehydrogenase (15-PGDH) by cyclooxygenase inhibitors and chemopreventive agents"; Elsevier; vol. 67, Issue 6, Dec. 3, 2002, pp. 461-465.

Japanese Patent Application No. 2019-503202; JP OA dated Jul. 6, 2021; 12 pgs.

Japanese Patent Application No. 2019-554986; JP OA dated Jun. 22, 2021; 10 pgs.

Coteron, J.M., et al., "Structure-Guided Lead Optimization of Triazolopyrimidine-Ring Substituents Identifies Potent *Plasmodium falciparum* Dihydroorotate Dehydrogenase Inhibitors with Clinical Candidate Potential", *Journal of Medicinal Chemistry*, Aug. 11, 2011, pp. 5540-5561, vol. 54, No. 15, American Chemical Society, Washington, DC, US.

Rocchiccioli, F., et al., "Quantitative Gas Chromatography-Chemical Ionization Mass Spectrometry of 2-Ketoglutarate from Urine as its O-trimethylsilyl-quinoxalinol Derivative", *Journal of Chromatography*, Dec. 11, 1981, pp. 325-332, vol. 226, No. 2, Elsevier, Amsterdam, NL.

Wang, Q., et al., "Discovery of Novel Allosteric Effectors Based on the Predicted Allosteric Sites for *Escherichia coli* D-3-Phosphoglycerate Dehydrogenase", *PLOS ONE*, Apr. 14, 2014, e94829—8 pages, vol. 9, issue 4, Public Library of Science, San Francisco, CA, US.

CAS Registry No. 348151-19-9 [online database], STN Entry Date Jul. 25, 2001 (searched Apr. 26, 2021), Retrieved from: STN, 1 page.

Office Action and search report issued in Chinese Patent Application No. 201880023858.6, dated Sep. 5, 2022, CNIPA, Beijing, CN, 9 pages.

Partial Supplementary European Search Report issued in European Application No. 18747826.8, dated Nov. 5, 2020, European Patent Office, Munich, DE, 16 pages.

Extended European Search Report issued in European Application No. 18747826.8, dated Mar. 19, 2021, European Patent Office, Munich, DE, 20 pages.

Decision of Rejection issued in Japanese Patent Application No. 2019-542115, dated May 18, 2021, Japan Patent Office, Tokyo, JP, 15 pages including English-language translation.

Decision of Rejection issued in Japanese Patent Application No. 2019-542115, dated Apr. 12, 2022, Japan Patent Office, Tokyo, JP, 5 pages including English-language translation.

International Search Report, Written Opinion, and International Preliminary Report on Patentability issued in PCT International Application No. PCT/US2013/036790, ISA/KR Korean Intellectual Property Office, Daejeon Metropolitan City, Republic of Korea. 13 pages.

International Search Report, Written Opinion, and International Preliminary Report on Patentability issued in PCT/US2014/060761, ISA/US United States Patent and Trademark Office, Alexandria, VA. 14 pages.

International Search Report and Written Opinion and International Preliminary Report on Patentability issued in PCT International Application No. PCT/US2016/021374, ISA/US United States Patent and Trademark Office, Alexandria, VA. 15 pages.

(56) References Cited

OTHER PUBLICATIONS

International Search Report, Written Opinion, and International Preliminary Report on Patentability issued in PCT/US2016/027549, ISA/US United States Patent and Trademark Office, Alexandria, VA. 16 pages.
International Search Report, Written Opinion, and International Preliminary Report on Patentability issued in PCT/US2017/042620, ISA/US United States Patent and Trademark Office, Alexandria, VA. 24 pages.
International Search Report, Written Opinion, and International Preliminary Report on Patentability issued in PCT/US2017/063959, ISA/US United States Patent and Trademark Office, Alexandria, VA. 31 pages.
International Search Report, Written Opinion, and International Preliminary Report on Patentability issued in PCT/US2018/017044, ISA/US United States Patent and Trademark Office, Alexandria, VA. 15 pages.
International Search Report and Written Opinion and International Preliminary Report on Patentability issued in PCT International Application No. PCT/US2018/026739, ISA/US United States Patent and Trademark Office, Alexandria, VA. 17 pages.
International Search Report, Written Opinion, and International Preliminary Report on Patentability issued in PCT/US2018/034944, ISA/US United States Patent and Trademark Office, Alexandria, VA. 15 pages.
International Search Report, Written Opinion, and International Preliminary Report on Patentability issued in PCT/US2019/025812, ISA/US United States Patent and Trademark Office, Alexandria, VA. 16 pages.
International Search Report and Written Opinion and International Preliminary Report on Patentability issued in PCT/US2019/062686, ISA/RU Federal Institute of Industrial Property, Moscow, RU. 15 pages.
International Search Report, Written Opinion, and International Preliminary Report on Patentability issued in PCT/US2021/019084, ISA/US United States Patent and Trademark Office, Alexandria, VA. 13 pages.
International Search Report, Written Opinion, and International Preliminary Report on Patentability issued in PCT/US2021/033170, ISA/EP European Patent Office, NL. 28 pages.
International Search Report and Written Opinion issued in PCT/US2021/045231, ISA/US United States Patent and Trademark Office, Alexandria, VA. 9 pages.
International Search Report and Written Opinion issued in PCT/US2022/12423, ISA/US United States Patent and Trademark Office, Alexandria, VA. 12 pages.
Abulwerdi, F.A., et al., "Development of Small Molecules with a Non-Canonical Binding Mode to HIV-1 Trans Activation Response (TAR) RNA," *Journal of Medicinal Chemistry*, Dec. 22, 2016, pp. 11148-11160, 59(24), American Chemical Society, Washington, DC, US.
Ahmad, Muzamil, et al., "The $PGE_2EP2$ receptor and its selective actibvation are beneficial against ischemic stroke," *Experimental & Translational Stroke Medicine*, 2010, 8 pages, vol. 2, No. 12, BioMed Central, UK.
"AKos Screening Samples ca. 3.5 million compounds Version December 2007," Web page <www/akosgmbh.de/AKosSamples/Index.html>, 3 pages, Dec. 19, 2007, retrieved from the Internet Archive Wayback Machine via Page Vault <http://web.archive.org/web/20071219115313/http://www.akosgmbh.de/AKosSamples/index.html> on Sep. 29, 2022.
Almeida, Camila Bononi, et al., "High Expression of the cGMP-specific Phosphodiesterase, PDE9A, in Sickle Cell Disease (SCD) and the Effects of its Inhibition in Erythroid Cells and SCD Neutrophils," *British Journal of Haematology*, Sep. 2008, pp. 836-844, 142(5), Blackwell Publishing Ltd, Oxford, UK.
Almeida, Camila Bononi, et al., "Hydroxyurea and a cGMP-amplifying Agent Have Immediate Benefits on Acute Vaso-Occlusive Events in Sickle Cell Disease Mice," *Blood*, Oct. 4, 2012, 23 pages, 120(14), American Society of Hematology, Washington, DC, US.
Al-Najjar, Belal O., et al., "Pharmacophore Modeling and 3D-QSAR Studies of 15-Hydroxyprostaglandin Dehydrogenase (15-PGDH) Inhibitors," *Indian Journal of Chemistry*, Nov. 2017, pp. 1200-1207, vol. 56B, Scientific Publishers of India, IN.
Alvarez, F.J., and Slade, R.T., "Kinetics and Mechanism of Degradation of Zileuton, a Potent 5-Lipoxygenase Inhibitor," *Pharmaceutical Research*, 1992, pp. 1465-1473, vol. 9, No. 11, Plenum Publishing Corporation-Springer Science and Business Media, DE.
Antczak, M.I., et al., "Inhibitors of 15-Prostaglandin Dehydrogenase to Potentiate Tissue Repair", *Journal of Medicinal Chemistry*, 2017, pp. 3979-4001, vol. 60, No. 9, American Chemical Society, Washington, DC, US.
Archelas, A., et al., "Absolute Configuration of α-Methylstyrene Oxide: The Correct Absolute Configuration/Optical Rotation Correlation", *The Journal of Organic Chemistry*, Aug. 1, 1999, pp. 6112-6114, vol. 64, No. 16, American Chemical Society, Washington, DC, US.
Asati, V., et al., "Molecular Modeling Studies of Some Thiazolidine-2,4-Dione Derivatives as 15-PGDH Inhibitors," *Medicinal Chemistry Research*, Aug. 29, 2015, pp. 94-108, vol. 25, Springer Science + Business Media, DE.
AstaTech, "AstaTech Inc. Catalog Product Search Result," Compound: 6-Bromo-3-Methylpyrimidin-4(3H)-One, 2 pages, Oct. 18, 2022, retrieved via Page Vault https://astatechnic.com/CPSResult.php?CRNO=183100 on Oct. 18, 2022.
Bagshaw, S. M., et al., "A comparison of the RIFLE and AKIN criteria for acute kidney injury in critically ill patients," *Nephrology Dialysis Transplantation*, May 2008, pp 1569-1574, vol. 23, Issue 5, Oxford University Press, Oxford, UK, retrieved from https://academic.oup.com/ndt/article/23/5/1569/1809429, on Oct. 18, 2022.
Baker, Michael E. "Licorice and Enzymes Other Than 11β-Hydroxysteroid Dehydrogenase: An Evolutionary Perspective," *Steroids*, Feb. 1994, pp. 136-141, vol. 59, Issue 2, Butterworth-Heinemann, Elsevier, Ltd, Oxford, UK.
Bakhle, Y.S., "Action of Prostaglandin Dehydrogenase Inhibitors on Prostaglandin Uptake in Rat Isolated Lung," *British Journal of Pharmacology*, Apr. 1979, pp. 635-639, 65(4), British Pharmacological Society, Macmillan Journals Ltd, UK.
Baliga, B.S, et al., "Combined Effects of Arginine and Hydroxyurea on BFU-E Derived Colony Growth and HbF Synthesis in Erythroid Progenitors Isolated from Sickle Cell Blood," *Cellular and Molecular Biology*, 2010, pp. OL1290-OL1298, vol.56, No. 3, Cellular and Molecular Biology Association, Paris, FR.
Bärnthaler, Thomas, et al., "Inhibiting Eicosanoid Degradation Exerts Antifibrotic Effects in a Pulmonary Fibrosis Mouse Model and Human Tissue," *Journal of Allergy and Clinical Immunology*, Mar. 2020, pp. 818-833, vol. 145, No. 3, Elsevier Inc, Amsterdam, NL.
Battistini, Bruno, et al., "COX-1 and COX-2: Toward the Development of More Selective NSAIDS," *Advances in prostaglandin research were presented at the $9^{th}$ International Conference on Prostaglandins and Related Compounds* in Florence, Italy, Jun. 6-10, 1994, and the $12^{th}$ *International Congress of Pharmacology* in Montreal, Canada, Jul. 24-29, 1994, *Drug News & Perspectives Meeting Report*, Oct. 1994, pp. 501-512, 7(8).
Becker, C., et al., "In Vivo Imaging of Colitis and Colon Cancer Development in Mice Using High-Resolution Chromoendoscopy," *Gut*, 2005, pp. 950-954, vol. 54, BMJ, UK.
Berg, Daniel J., et al. "Rapid Development of Colitis in NSAID-Treated IL-10-Deficient Mice", *Gastroenterology*, 2002, pp. 1527-1542, vol. 123, No. 5, American Gastroenterological Association, W.B. Saunders, Philadelphia, PA.
Berk, L.B., et al., "16,16-Dimethyl Prostaglandin E2 and/or Syngeneic Bone Marrow Transplantation Increase Mouse Survival After Supra-Lethal Total Body Irradiation," *International Journal of Radiation Oncology Biology Physics*, Jun. 1990, pp. 1387-1392, vol. 18, No. 6, Pergamon Press plc, Oxford, UK.
Berry, C.N., et al., "Inhibition of Prostaglandin 15-Hydroxydehydrogenase by Sulphasalazine and a Novel Series of

(56) References Cited

OTHER PUBLICATIONS

Potent Analogues," *Biochemical Pharmacology*, Oct. 1, 1983, pp. 2863-2871, vol. 32, No. 19, Pergamon Press Ltd., GB.
Bertram, Lars, et al., "Systematic meta-analyses of Alzheimer disease genetic association studies: the AlzGene database," *Nature Genetics*, Jan. 2007, pp. 17-23, vol. 39, No. 1, Nature Publishing Group, UK.
Bertram, Lars, et al., "Is α-T catenin (VR22) an Alzheimer's disease risk gene?", *Journal of Medical Genetics, Electronic Letters*, Jan. 2007, pp 1-4, vol. 44, No 1, BMJ Group, UK.
Blackwell, G.J., and Flower, R.J., "A Rapid Method for the Estimation of Prostaglandin 15-Hydroxydehydrogenase Activity and its Application to Pharmacology," *British Journal of Pharmacology*, 1976, pp. 589-597, vol. 57, Issue 4, British Pharmacological Society, UK.
Blake, Martin I., et al., "Studies with Deuterated Drugs", *Journal of Pharmaceutical Sciences*, Mar. 1975, pp. 367-391, vol. 64, No. 3, Elsevier, Amsterdam, NL.
Borm, Michelle E.A., and Bouma, Gerd, "Animal Models of Inflammatory Bowel Disease," *Drug Discovery Today: Disease Models*, Dec. 2004, pp. 437-443, vol. 1, Issue 4, Elsevier, Amsterdam, NL.
Bray, James E., et al., "The Human Short-Chain Dehydrogenase/Reductase (SPR) Superfamily: A Bioinformatics Summary," *Chemico-Biological Interactions*, Mar. 16, 2009, pp. 99-109, vol. 178, Issues 1-3, Elsevier, Amsterdam, NL.
Breyer, Richard M., et al., "Prostanoid Receptors: Subtypes and Signaling," *Annual Review of Pharmacology and Toxicology*, 2001, 32 pages including pp. 661-690, vol. 41, Annual Reviews, San Mateo, CA, US.
Brown, J.R., et al., "COX-2: A Molecular Target for Colorectal Cancer Prevention," *Journal of Clinical Oncology*, Apr. 20, 2005, pp. 2840-2855, vol. 23, No. 12, American Society of Clinical Oncology, Lippincott Williams and Wilkins, Philadelphia, PA, US.
Cahn, R.S., and Ingold, C.K., "Specification of Configuration about Quadricovalent Asymmetric Atoms," *Journal of the Chemical Society*, 1951, pp. 612-622, Chemical Society, UK.
Cahn, R.S., et al., "The Specification of Asymmetric Configuration in Organic Chemistry," *Experientia*, 1956, pp. 81-94, vol. 12, No. 3, Springer Science + Business Media, Berlin, DE.
Cahn, R.S., "An Introduction to the Sequence Rule: A System for the Specification of Absolute Configuration," *Journal of Chemical Education*, Mar. 1964, pp. 116-125, vol. 41, No. 3, American Chemical Society, Washington, DC.
Cahn, R.S., et al., "Specification of Molecular Chirality," *Angew. Chem. Inter. Edit.*, 1966, pp. 385-415, vol. 5, No. 4, Wiley-VCH, Weinheim, DE.
Cahn, R.S., et al., Errata "Specification of Molecular Chirality," *Angew. Chem. Inter. Edit.*, 1966, p. 511, vol. 5, No. 5, Wiley-VCH, Weinheim, DE.
Cancer Genome Atlas Network, "Comprehensive molecular characterization of human colon and rectal cancer," *Nature*, Jul. 19, 2012, pp. 330-337, vol. 487, Macmillan Publishers Limited, UK.
Cancer Genome Atlas Network, "Comprehensive molecular portraits of human breast tumours," *Nature*, Oct. 4, 2012, pp. 61-70, vol. 490, Macmillan Publishers Limited, UK.
Cancer Genome Atlas Network, "Integrated genomic analyses of ovarian carcinoma," *Nature*, Jun. 30, 2011, pp. 609-615, vol. 474, and Erratum, *Nature*, Oct. 11, 2012, p. 292, vol. 490, Macmillan Publishers Limited, UK.
Castellone, M.D., et al., "Prostaglandin $E_2$ Promotes Colon Cancer Cell Growth Through a $G_S$-Axin-β-Catenin Signaling Axis," *Science*, Dec. 2, 2005, pp. 1504-1510, vol. 310, Issue 5753, American Association for the Advancement of Science, Washington, DC, US.
Chang, Kyung Hee., et al., "Vasculopathy-Associated Hyperangiotensinemia Mobilizes Haematopoietic Stem Cells/Progenitors Through Endothelial $AT_2R$ and Cytoskeletal Dysregulation," *Nature Communications*, Jan. 9, 2015, 11 pages, 6, Article 5914, Macmillan Publishers Limited, Nature Research, London, UK.

"ChemBridge | Screening Libraries: Key Facts," Web page <www.chembridge.com/screening_libraries/>, 2 pages, Jan. 22, 2013, retrieved from the Internet Archive Wayback Machine via Page Vault <http://www.archive.org/web/20130122020518/https://www.chembridge.com/screening_libraries/> on Sep. 29, 2022.
Chemtob, Sylvain, et al., "Deficiency in Prostaglandin $E_2$ ($PGE_2$) Receptors, Mainly $EP_2$ Subtype, on Brain Synaptosomes in Early Development: Implications on Cerebral Metabolism," *Seminars in Perinatology*, Feb. 1994, pp. 23-29, vol. 18, No. 1, W.B. Saunders Company, Philadelphia, PA, US.
Chen, H., et al., "Prostaglandin E2 Mediates Sensory Nerve Regulation of Bone Homeostasis," *Nature Communications*, Jan. 14, 2019, pp. 1-13, vol. 10, Issue 1, Article No. 181, Nature Research, London, UK.
Chi, Xiuling, et al., "15-Hydroxyprostaglandin Dehydrogenase (15-PGDH) is Up-Regulated by Flurbiprofen and Other Non-Steroidal Anti-Inflammatory Drugs in Human Colon Cancer HT29 Cells," *Archives of Biochemistry and Biophysics*, Jul. 15, 2009, pp. 139-145, vol. 487, No. 2, Elsevier, Amsterdam, NL.
Childs, April C., et al., "Doxorubicin Treatment in Vivo Causes Cytochrome c Release and Cardiomyocyte Apoptosis, as Well as Increased Mitochondrial Efficiency, Superoxide Dismutase Activity, and Bcl-2:Bax Ratio," *Cancer Research*, Aug. 15, 2002, pp. 4592-4598, vol. 62, American Association for Cancer Research, Philadelphia, PA, US.
Cho, Hoon, et al., "Role of glutamine 148 of human 15-hydroxyprostaglandin dehydrogenase in catalytic oxidation of prostaglandin E2", *Bioorganic & Medicinal Chemistry*, 2006, pp. 6486-6491, vol. 14, Elsevier Ltd, Amsterdam, NL.
Choi, Dubok, et al., "Control of the Intracellular Levels of Prostaglandin $E_2$ Through Inhibition of the 15-Hydroxyprostaglandin Dehydrogenase for Wound Healing," *Bioorganic and Medicinal Chemistry*, 2013, 8 pages, Elsevier, Amsterdam, NL.
Clifford, P.C., et al., "Treatment of Vasospastic Disease with Prostaglandin $E_1$," *British Medical Journal*, Oct. 18, 1980, pp. 1031-1034, vol. 281, British Medical Association, UK.
Colombe, L., "Prostaglandin Metabolism in Human Hair Follicle," *Experimental Dermatology*, 2007, pp. 762-769, vol. 16, No. 9, Blackwell Munksgaard, Copenhagen, DK.
Combrinck, M., et al. "Levels of CSF Prostaglandin $E_2$, Cognitive Decline, and Survival in Alzheimer's disease," *Journal of Neurology, Neurosurgery, and Psychiatry*, Jun. 8, 2005, pp. 85-88, vol. 77, pp. 85-88, BMJ Group, London, UK.
Cooper, H. S. et al., "Clinicopathologic Study of Dextran Sulfate Sodium Experimentai Murine Colitis," *Laboratory Investigation*, (1993), pp. 238-2493, vol. 69, No. 2, The United States and Canadian Academy of Pathology, Inc, USA.
Croft, D., et al., "The Reactome pathway knowledgebase," *Nucleic acids research*, 2014, pp. D472-D477, vol. 42, Oxford University Press, UK.
Cutler, Corey, et al., "Prostaglandin-Modulated Umbilical Cord Blood Hematopoietic Stem Cell Transplantation," *Blood*, 2013, 30 pages, American Society of Hematology, Washington, DC, US.
Dai, Liying, et al., "Inverse Expression of Prostaglandin $E_2$-Related Enzymes Highlights Differences Between Diverticulitis and Inflammatory Bowel Disease," *Digestive Diseases and Sciences*, 2015, pp. 1236-1246, vol. 60, Springer Science + Business Media, Berlin, DE.
Dalvi, Siddhartha, et al., "Exogenous Arachidonic Acid Mediates Permeability of Human Brain Microvessel Endothelial Cells through Prostaglandin $E_2$ Activation of $EP_3$ and $EP_4$ Receptors," *Journal of Neurochemistry*, Apr. 27, 2015, pp. 867-879, vol. 135, International Society for Neurochemistry, Wiley-Blackwell, Hoboken, NJ, US.
Deng, Yang, et al., "Lipopolysaccharide Stimulates Bovine Endometrium Explants through Toll-Like Receptor 4 Signaling and $PGE_2$ Synthesis," *Prostaglandins, Leukotrienes, and Essential Fatty Acids*, May 2021, Abstract only—2pages, vol. 168, Elsevier Ltd., Amsterdam, NL.
Desai, A., et al., "A Second-Generation 15-PGDH Inhibitor Promotes Bone Marrow Transplant Recovery Independently of Age, Transplant Dose, and Granulocyte Colony-Stimulating Factor Support," *Haematologica*, 2018, pp. 1054-1064, 103(6), Ferrata Storti Foundation, IT.

(56) References Cited

OTHER PUBLICATIONS

Dong, Yuanqiang, et al., "Effects of SW033291 on the Myogenesis of Muscle-Derived Stem Cells and Muscle Regeneration," *Stem Cell Research and Therapy*, 2020, 17 pages, vol. 11, Issue 76, BioMedCentral, London, UK.

Douville, Christopher, et al., "Assessing Aneuploidy with Repetitive Element Sequencing," *Proceedings of the National Academy of Sciences*, Mar. 3, 2020, pp. 4858-4863, vol. 117, No. 9, United States National Academy of Sciences, Washington, DC, US.

Dowd, Noreen P., et al., "Inhibition of Cyclooxygenase-2 Aggravates Doxorubicin-Mediated Cardiac Injury in Vivo," *The Journal of Clinical Investigation*, Aug. 15, 2001, pp. 585-590, vol. 108, No. 4, American Society for Clinical Investigation, US.

Doxorubicin Hydrochloride Package Insert and Package Label Display Panel, Revised: Jan. 2021, 16 pages, Teva Pharmaceuticals USA, Inc., Labeler: Actavis Pharma, Inc.

Duveau, Damien Y., et al., "Discovery of two small molecule inhibitors, ML387 and ML388, of human $NAD^+$-dependent 15-hydroxyprostaglandin dehydrogenase," *Probe Reports from the NIH Molecular Libraries Program*, 2013, 26 pages, National Center for Biotechnology Information, US.

Duveau, Damien Y., et al., "Structure-activity relationship studies and biological characterization of human $NAD^+$-dependent 15 hydroxyprostaglandin dehydrogenase inhibitors", *Bioorganic and Medicinal Chemistry Letters*, Jan. 15, 2014, pp. 630-635, vol. 24, Elsevier, Amsterdam, NL.

Echeverria, Valentina, et al., "Stimulation of $PGE_2$ Receptors $EP_2$ and $EP_4$ Protects Cultured Neurons Against Oxidative Stress and Cell Death Following β-Amyloid Exposure," *European Journal of Neuroscience*, 2005, pp. 2199-2206, vol. 22, Federation of European Neuroscience Societies, Wiley-Blackwell, Hoboken, NJ.

"Enamine—Screening Compounds," Web page <http://www.enamine.net/index.php?option=com_content&task=view&id=22&menuid=51&PHPSESSID=64a4f248f69d671a413f487bb62c4d90>, 2 pages, Jun. 30, 2007, retrieved from the Internet Archive Wayback Machine via Page Vault <http://web.archive.org/web/20070630171813/http://www.enamine.net/index.php?option=com_content&task=view&id=22&menueid=51&PHPSESSID=64a4f248f69d671a413f487bb62c4d90> on Sep. 29, 2022.

Ensor, C.M, et al., "Site-Directed Mutagenesis of the Conserved Tyrosine 151 of Human Placental $NAD^+$-dependent 15-Hydroxyprostaglandin Dehydrogenase Yields a Catalytically Inactive Enzyme", *Biochemical and Biophysical Research Communications*, Apr. 30, 1991, pp. 840-845, vol. 176, No. 2, Academic Press, Inc., Elsevier, Amsterdam, NL.

Ensor, Charles Mark, et al., "Bacterial expression and site-directed mutagenesis of two critical residues (tyrosine-151 and lysine-155) of human placental $NAD^+$-dependent 15-hydroxyprostaglandin dehydrogenase", *Biochimica et Biophysica Acta*, 1994, pp. 151-156, vol. 1208, Elsevier Science B.B., Amsterdam, NL.

Eridani, S., and Mosca, A., "Fetal hemoglobin reactivation and cell engineering in the treatment of sickle dell anemia," *Journal of Blood Medicine*, Feb. 28, 2011, pp. 23-30, vol. 2, Dove Medical Press, UK.

Esrick, Erica B., et al., "Inactivation of HDAC1 or HDAC2 induces gamma globulin expression without altering cell cycle or proliferation," *American Journal of Hematology*, Jul. 2015, pp. 624-628, vol. 90, No. 7, Wiley Pharmaceuticals, Inc., Hoboken, NJ, US.

European Directorate for the Quality of Medicines & Healthcare, Structure/Nomenclature Guide, "A Guide to the Graphic Representation and Nomenclature of Chemical Formulae in the European Pharmacopoeia," *European Pharmacopoeia*, 2011, 40 pages, 2nd Edition, Council of Europe, Strasbourg, FR.

Fauchier, L., et al., "Use of Anticoagulants and Antiplatelet Agents in Stable Outpatients with Coronary Artery Disease and Atrial Fibrillation. International CLARIFY Registry," *PLOS One*, Apr. 27, 2015, 23 pages, 10(4), Public Library of Science, San Francisco, CA, US.

Filippini, A., et al., "Covid-19 Acute Respiratory Distress Syndrome: Can Iloprost Have a Role for This Treatment?"*Respiratory Medicine Case Reports*, 2021, 101358, 4 pages, vol. 32, Elsevier, NL.

Fitzpatrick, F.A., et al., "The Stability of 13,14-Dihydro-15 Keto-$PGE_2$," *Prostaglandins*, Jun. 1980, pp. 917-931, vol. 19, No. 6., Elsevier Inc., NL.

Frias, M.A., et al., "The $PGE_2$-Stat3 Interaction in Doxorubicin-Induced Myocardial Apoptosis," *Cardiovascular Research*, 2008, pp. 69-77, vol. 80, Published on behalf of the European Society of Cardiology, Oxford University Press, Oxford, UK.

Frisch, Benjamin, et al., "In Vivo Prostaglandin $E_2$ Treatment Alters the Bone Marrow Microenvironment and Preferentially Expands Short-Term Hematopoietic Stem Cells," *Blood*, Nov. 5, 2009, 12 pages including pp. 4054-4063, vol. 114, No. 19, American Society of Hematology, Washington, DC, US.

Galiè, Nazzareno, et al., "Guidelines for the diagnosis and treatment of pulmonary hypertension," *European Heart Journal*, 2009, pp. 2493-2537, vol. 30, European Society of Cardiology, Oxford University Press, Oxford, UK.

Gentile, P., et al., "In Vivo Modulation of Murine Myelopoiesis Following Intravenous Administration of Prostaglandin E2", *Blood*, 1983, 8 pages including pp. 1100-1107, vol. 62, No. 5, American Society of Hematology, Washington, DC, US.

Ghiso, Jorge, et al., "Cerebral amyloidosis, amyloid angiopathy, and their relationship to stroke and dementia," *Journal of Alzheimer's Disease*, 2001, pp. 65-73, vol 3, No. 1, IOS Press, Amsterdam, NL.

Girgis, Adel S., et al., "Synthesis of new 3-pyridinecarboxylates of potential vasodilation properties," *European Journal of Medicinal Chemistry*, 2008, vol. 43, pp 1818-1827, Elsevier, NL.

Giugliano, Robert P., et al., "Edoxaban versus Warfarin in Patients with Atrial Fibrillation," *The New England Journal of Medicine*, Nov. 28, 2013, pp. 2093-2104, vol. 369, No. 22, Massachusetts Medical Society, Waltham, MA, US.

Goessling, Wolfram, et al., "Genetic Interaction of PGE2 and Wnt Signaling Regulates Developmental Specification of Stem Cells and Regeneration," *Cell*, Mar. 20, 2009, pp. 1136-1147, vol. 136, Issue 6, Cell Press, Elsevier Inc., Cambridge, MA, US.

Goessling, Wolfram, et al., "Prostaglandin E2 Enhances Human Cord Blood Stem Cell Xenotransplants and Shows Long-Term Safety in Preclinical Nonhuman Primate Transplant Models," *Cell Stem Cell*, Apr. 8, 2011, pp. 445-458, vol. 8, Cell Press, Elsevier Inc., Cambridge, MA, US.

Gu, Xiaosong, et al., "Prostaglandin E2 Reduces Cardiac Contractility via EP3 Receptor," *Circulation: Heart Failure*, Aug. 2016, 8 pages, e003291, vol. 9, Issue 8, American Heart Association, Lippincott Williams & Wilkins, Philadelphia, PA, US.

Guo, Jian-You, et al., "Chronic unpredictable mild stress induces parallel reductions of 15-PGDH in the hypothalamus and lungs in rats," *Behavioural Brain Research*, 2015, pp. 278-284, vol. 286, Elsevier B.V., NL.

Hagedorn, E. J., et al., "Getting More for Your Marrow: Boosting Hematopoietic Stem Cell Numbers with PGE2", *Experimental Cell Research*, 2014, 7 pages, Elsevier Inc., Amsterdam, NL.

Hall, P. R. et al., "Small Molecule Inhibitors of Hantavirus Infection", *Bioorganic & Medicinal Chemistry Letters*, Dec. 1, 2010, pp. 7085-7091, vol. 20, No. 23, Elsevier, Amsterdam, NL.

Hamed, S., et al., "Erythropoietin Improves Myocardial Performance in Doxorubicin-Induced Cardiomyopathy," *European Heart Journal*, 2006, pp. 1876-1883, vol. 27, Oxford University Press, Oxford, UK.

Hamid, N., et al., "A Neural System Dynamics Modeling Platform and Its Applications In Randomized Controlled Trial Data Analysis," *Informatics in Medicine Unlocked*, 2021, 13 pages, 100612, vol. 24, Elsevier Ltd., Amsterdam, NL.

Hamza, Adel, et al., "Understanding human 15-hydroxyprostaglandin dehydrogenase binding with $NAO^+$ and $PGE_2$ by homology modeling, docking and molecular dynamics simulation," *Bioorganic & Medicinal Chemistry*, pp. 4544-4551, vol 13, Elsevier Ltd., Amsterdam, NL.

Hanai, H., et al., "Curcumin Maintenance Therapy for Ulcerative Colitis: Randomized, Multicenter, Double-Blind, Placebo-

(56) References Cited

OTHER PUBLICATIONS

Controlled Trial," *Clinical Gastroenterology and Hepatology*, Dec. 2006, pp. 11502-1506, vol. 4, Issue 5, Elsevier, Amsterdam, NL.

Hao, C.M., "Physiological Regulation of Prostaglandins in the Kidney," *Annual Review of Physiology*, 2008, 25 pages including pp. 357-377, vol. 70, Annual Reviews, San Mateo, CA, US.

Hao, G., et al., "Protective Effects of Berberine Against Doxorubicin-Induced Cardiotoxcity in Rats by Inhibiting Metabolism of Doxorubicin," *Xenobiotica*, 2015, pp. 1024-1029, vol. 45, Issue 11, Informa, London, UK.

Harrowven, D. C. "'Cascade' Radical Reactions in Synthesis: Condensed Thiophenes from Ketenethioacetals," *Tetrahedron Letters*, 1993, pp. 5653-5656, vol. 34, No. 35, Elsevier, Amsterdam, NL.

Hassan, M., et al., "Modulatory Effects of Meloxicam on Cardiotoxicity and Antitumor Activity of Doxorubicin in Mice," *Cancer Chemotherapy and Pharmacology*, Jul. 23, 2014, pp. 559-569, vol. 74, Springer Science + Business Media, Berlin, DE.

Heyman, Samuel N., et al., "Animal models of renal dysfunction: acute kidney injury," *Expert Opinon on Drug Discovery*, 2009, pp. 629-641, 4(6), Taylor & Francis, UK.

Heyman, Samuel N. , et al., "Acute Kidney Injury: Lessons from Experimental Models," *Experimental Models for Renal Diseases: Pathogenesis and Diagnosis*, 2011, pp. 286-296, vol. 169, Karger, Basel, CH.

Hoffman, Corey M., et al., "Minireview: Complexity of Hematopoietic Stem Cell Regulation in the Bone Marrow Microenvironment", *Molecular Endocrinology*, 2014, pp. 1-11, vol. 28, The Endocrine Society, Washington, DC, US.

Hoggatt, J., et al., "Prostaglandin E2 Enhances Hematopoietic Stem Cell Homing, Survival, and Proliferation," *Blood*, May 28, 2009, cover page, pp. 5444-5455, vol. 113, No. 22, American Society for Hematology, Washington, DC, US.

Hoggatt, J., et al., "Differential Stem- and Progenitor-Cell Trafficking by Prostaglandin E2", *Nature*, 00 Month 2013, 7 pages, vol. 000, Nature Portfolio, London, UK.

Hoggatt, J., et al., "Prostaglandin $E_2$ Enhances Long-Term Repopulation but Does not Permanently Alter Inherent Stem Cell Competitiveness", *Blood*, Oct. 24, 2013, pp. 2997-3000, vol. 122, No. 17, American Society of Hematology, Washington, DC, US.

Hoggatt, Jonathan, et al., "Recovery from Hematopoietic Injury by Modulating Prostaglandin $E_2$ Signaling Post-Irradiation", *Blood Cells, Molecules and Diseases*, 2013, pp. 147-153, vol. 50, Elsevier Inc., Amsterdam, NL.

Hong, Yu Ah, et al., Paricalcitol Pretreatment Attenuates Renal Ischemia-Reperfusion Injury via Prostaglandin $E_2$ Receptor E4 Pathway, *Oxidative Medicine and Cellular Longevity*, 2017, 17 pages, vol. 2017, Hindawi Publishing Corporation, London, UK.

Hoult, J.R.S., and Moore, P.K., "Sulphasalazine is a Potent Inhibitor of Prostaglandin 15-Hydroxydehydrogenase: Possible Basis for Therapeutic Action in Ulcerative Colitis," *British Journal of Pharmacology*, 1978, pp. 6-8, vol. 64, Macmillan Journals Ltd, UK.

Hoyt, A. L., et al., "On the nature of the chain-extending species in organolithium initiated stereospecific reagent-controlled homologation reactions using α-chloroalkyl aryl sulfoxides," *Tetrahedron Letters*, 2015, vol. I 56, pp. 2980-2982, Elsevier Ltd., NL.

Huang, X., et al., "Safety and Efficacy of Bivalirudin Monotherapy in Patients with Non-ST-Segment Elevation Acute Coronary Syndromes with Positive Biomarkers Undergoing Percutaneous Coronary Intervention: A Report From The Acute Catheterization and Urgent Intervention Triage Strategy Trial," *Coronary Artery Disease*, Jan. 1, 2020, pp. 59-65, vol. 31, Issue 1, Wolters Kluwer Health, Inc., Lippincott Williams & Wilkins, Philadelphia, PA, US.

Huang, W.J., and Tang, X.X., "Virus Infection Induced Pulmonary Fibrosis," *Journal of Translational Medicine*, 2021, 15 pages, vol. 19, Issue 496, BioMedCentral, UK.

Hughes, P.A., et al., "Experimental Colitis Models," *TRP Channels in Drug Discovery: vol. II*, Chapter 23, Jan. 1, 2012, pp 379-390, Humana Press, Springer, Munich, DE.

Hunt, T. K., et al., "Coagulation and Macrophage Stimulation of Angiogenesis and Wound Healing," *The Surgical Wound*, ed. F. Dineen & G. Hildrick-Smith, 1981, 21 pages including pp. 1-18, Lea & Febiger, Philadelphia, PA.

"Inflammatory Bowel Disease," Web page <http://www.healthline.com/health/inflammatory-bowel-disease>, 6 pages, Jan. 7, 2015, retrieved from the Internet Archive Wayback Machine via Page Vault <http://web.archive.org/web/20070630171813/http://www.enamine.net/index.php?option=com_content&task=view&id=22&menuid=51&PHPSESSID=64a4f248f69d671a413f487bb62c4d90> on Oct. 25, 2022.

Iqubal, A., et al., "Clinical Updates on Drug-Induced Cardiotoxicity," *International Journal of Pharmaceutical Sciences and Research*, 2018, pp. 16-26, vol. 9, Issue 1, Society of Pharmaceutical Sciences and Research, Panchkula, Haryana, IN.

Jadapalli, J.K., et al., "Doxorubicin Triggers Splenic Contraction and Irreversible Dysregulation of COX and LOX That Alters the Inflammation-Resolution Program in the Myocardium," *American Journal of Physiology—Heart and Circulatory Physiology*, 2018, pp. H1091-H1100, vol. 315, American Physiological Society, Rockville, MD, US.

Jadhav, A., et al., "Potent and Selective Inhibitors of $NAD^+$-Dependent 15-Hydroxyprostaglandin Dehydrogenase (HPGD)", *Molecular Libraries, Pathways to Discovery*, Jul. 8, 2011, 36 pages, NIH.

Jain, D., et al., "Cardiac Complications of Cancer Therapy: Pathophysiology, Identification, Prevention, Treatment, and Future Directions," *Current Cardiology Reports*, 2017, 12 pages, vol. 19, Issue 36, Springer Science + Business Media, Berlin, DE.

Johnston, Dudley E., "Wound Healing in Skin," *Plastic and Reconstructive Surgery, Veterinary Clinics of North American: Small Animal Practice*, Jan. 1990, pp. 1-25, vol. 20, No. 1, W.B. Saunders Ltd., US.

Jolly, L., et al. "Influenza Promotes Collagen Deposition via αvβG Integrin-Mediated Transforming Growth Factor β activation," *The Journal of Biological Chemistry*, Dec. 19, 2014, pp. 35246-35263, vol. 289, No. 51, pp. 35246-35263, American Society for Biochemistry and Molecular Biology, Rockville, MD, US.

Julkunen, I., et al., "Inflammatory Response to Influenza A Virus Infection," *Vaccine*, 2001, pp. S32-S37, vol. 19, Elsevier Science Ltd., Amsterdam, NL.

Jung, P., et al., "Isolation and in vitro Expansion of Human Colonic Stem Cells," *Nature Medicine*, Oct. 2011, pp. 1225-1227, vol. 17, No. 10, Nature Publishing Group, London, UK.

Kabashima, K., et al., "The Prostaglandin Receptor EP4 Suppresses Colitis, Mucosal Damage and CD4 Cell Activation in the Gut", *The Journal of Clinical Investigation*, Apr. 2002, pp. 883-893, vol. 109, No. 7, American Society for Clinical Investigation, US.

Kalugin, V.E., et al., "Utilization of Potassium Carbonate for the Synthesis of 2-(organylsulfonyl)thieno[2,3-b]pyridine Derivatives," *Russian Chemical Bulletin, International Edition*, Feb. 2019, pp. 357-364, vol. 68, No. 2, Springer Science + Business Media, Berlin, DE.

Kang, G.-J., et al., "High-Mobility Group Box 1 Suppresses Resolvin D1-Induced Phagocytosis via Induction of Resolvin D1-Inactivating Enzyme, 15-Hydroxyprostaglandin Dehydrogenase," *Biochimica et Biophysica Acta*, 2015, pp. 1981-1988, vol. 1852, No. 9, Elsevier B.V., Amsterdam, NL.

Karna, Sandeep, et al., "Novel Potent 15-Hydroxyprostaglandin Dehydrogenase Inhibitors," *Journal of Advanced Engineering and Technology*, 2010, pp. 301-304, vol. 3, No. 3.

Karna, Sandeep, "In-vitro Wound Healing Effect of 15-Hydroxyprostaglandin Dehydrogenase Inhibitor from Plant," *Pharmacognosy Magazine*, Apr. 7, 2017, pp. S122- S126, vol. 13, Issue 49, Supplement 1, Wolters Kluwer—Medkenow Publications, Mumbai, IN.

Katz, J.A., "The Practical Use of Corticosteroids in the Treatment of Inflammatory Bowel Disease," *Practical Gastroenterology*, Jan. 2005, pp. 14, 16, 18, 21, 22, 25, Shugar Publishing, Westhampton Beach, NY, US.

(56) References Cited

OTHER PUBLICATIONS

Kawaguchi, H., et al., "The Role of Prostaglandins in the Regulation of Bone Metabolism," *Clinical Orthopaedics and Related Research*, 1995, pp. 36-46, No. 313, J.B. Lippincott and Company, Philadelphia, PA.

Keller, M.D., J., et al., "Short-term Effect of Local Application of $PGE_2$ on Callus in Rabbit Osteotomy," *Eur J Exp Musculoskel Res*, 1992, vol. 1, pp. 86-92.

Kim, M. et al., "Decreased Catalytic Activity of the Insulin-degrading Enzyme in Chromosome 10-Linked Alzheimer Disease Families," *The Journal of Biological Chemistry*, Mar. 16, 2007, pp. 7825-7832, vol. 282, No. 11, The American Society for Biochemistry and Molecular Biology, Inc, USA.

Kim, H.J., et al., "Inhibition of 15-PGDH Prevents Ischemic Renal Injury by the $PGE_2/EP_4$ Signaling Pathway Mediating Vasodilation, Increased Renal Blood Flow, and Increased Adenosine/$A_{2A}$ Receptors," *American Journal of Physiology—Renal Physiology*, 2020, F1054-F1066, vol. 319, American Physiological Society, Rockville, MD.

Kimball, Frances A., et al., "Plasma Concentrations of 9-Deoxo-16,16-Dimethyl-9-methylene-$PGE_2$ in Rhesus Monkeys after Administration by Various Routes," *Prostaglandins*, Sep. 1980, pp. 559-569, vol. 20, No. 3, Elsevier, Amsterdam, NL.

Kishore, A.H., et al., "Prostaglandin Dehydrogenase is a Target for Successful Induction of Cervical Ripening," *Proceedings of the National Academy of Sciences*, Jul. 17, 2017, pp. E6427-E6436, vol. 114, No. 29, United States National Academy of Sciences, Washington, DC, US.

Kishore, B.K, et al., "Ticagrelor Reduces Urinary Concentration and Arginine Vasopressin (AVP) Levels: Potential Use in AVP Excess States," *Kidney Week*, Oct. 23, 2018, Poster SA-PO1018, San Diego, CA, in the Journal of the American Society of Nephrology, 2018, p. 1002, vol. 29, American Society of Nephrology, Washington, DC, US.

Konturek, P.C., et al., "Prostaglandins as Mediators of Cox-2 Derived Carcinogenesis in Gastrointestinal Tract," Journal of Physiology and Pharmacology, Sep. 1, 2005, 12 pages, vol. 56, Suppl. 5.

Konturek, S.J., et al., "Prostaglandins and Ulcer Healing," Journal of Physiology and Pharmacology, 2005, 22 pages, vol. 56, No. 5.

Kurland, J.I., et al., "Role for Monocyte-Macrophage-Derived Colony-Stimulating Factor and Prostaglandin E in the Positive and Negative Feedback Control of Myeloid Stem Cell Proliferation," *Blood*, 1978, 21 pages including pp. 388-407, vol. 52, American Society of Hematology, Washington, DC, US.

Lakatos et al., "The Role of PPARs in Lung Fibrosis," *PPAR Research*, Jul. 2, 2007, pp. 1-10, Hindawi Publishing Corporation, London, UK.

Lam, P.-Y., et al., "Cyp1 Inhibition Prevents Doxorubicin-Induced Cardiomyopathy in a Zebrafish Heart Failure Model," *ChemBioChem*, Jul. 1, 2020, pp. 1905-1910, vol. 21, Issue 13, Wiley-VCH, Weinheim, DE.

Lewis, J.D., et al., "An Open-Label Trial of the PPARγ Ligand Rosiglitazone for Active Ulcerative Colitis," *The American Journal of Gastroenterology*, 2001, pp. 3323-3328, vol. 96, No. 12, Elsevier Science Inc., NL.

Li, J., et al., "Neutrophil AKT2 Regulates Heterotypic Cell-Cell Interactions During Vascular Inflammation," *Journal of Clinical Investigation*, Apr. 2014, 15 pages including pp. 1483-1496, vol. 124, Issue 4, American Society for Clinical Investigation, US.

Li, T., et al., "$PGE_2$ Increases Inflammatory Damage in *Escherichia coli*-infected Bovine Endometrial Tissue in vitro Vva the EP4-PKA Signaling Pathway," *Biology of Reproduction*, 2019, pp. 175-186, vol. 100, Issue 1, Oxford University Press, Oxford, UK.

Li, T., et al., "Prostaglandin $E_2$ Promotes Nitric Oxide Synthase 2, Platelet-Activating Factor Receptor, and Matrix Metalloproteinase-2 Expression in *Escherichia coli*-challenged ex vivo Endometrial Explants via the Prostaglandin $E_2$ Receptor 4/Protein Kinase A Signaling Pathway," *Theriogenology*, Aug. 2019, pp. 65-73, vol. 134, Elsevier, Amsterdam, NL.

Li, N., et al., "Ferritinophagy-Mediated Ferroptosis is Involved in Sepsis-Induced Cardiac Injury," *Free Radical Biology and Medicine*, 2020, pp. 303-318, vol. 160, Elsevier, Amsterdam, NL. Submitted in 2 parts.

Lian, W.-S., et al., "The Prostaglandin Agonist Beraprost Aggravates Doxorubicin-Mediated Apoptosis by Increasing iNOS Expression in Cardiomyocytes," *Current Vascular Pharmacology*, Jan. 1, 2015, pp. 54-63, vol. 13, No. 1, Bentham Science Publishers, UK.

Liu, Y.-C. et al., "Triazolopyrimidines as a New Herbicidal Lead for Combating Weed Resistance Associated with Acetohydroxyacid Synthase Mutation", *Journal of Agricultural and Food Chemistry*, 2016, pp. 4845-4857, vol. 64, No. 24, American Chemical Society, Washington, DC, US.

Liu, C., et al., "Development and Stimulation of a Sensitive and Rapid UHPLC-MS/MS Method for the Simultaneous Quantification of the Common Active and Inactive Metabolites of Vicagrel and Clopidogrel in Human Plasma," *Journal of Pharmaceutical and Biomedical Analysis*, Feb. 5, 2018, pp. 394-402, vol. 149, Elsevier, Amsterdam, NL.

Liu, C., et al., "Pharmacokinetics and Pharmacokinetic/Pharmacodynamic Relationship of Vicagrel, a Novel Thineopyridine $P2Y_{12}$ Inhibitor, Compared with Clopidogrel in Healthy Chinese Subjects Following Single Oral Dosing," *European Journal of Pharmaceutical Sciences*, Jan. 15, 2019, pp. 151-160, vol. 127, Elsevier, Amsterdam, NL.

Lopes, J.A., et al., "The RIFLE and AKIN Classifications for Acute Kidney Injury: A Critical and Comprehensive Review," *Clinical Kidney Journal*, 2013, pp. 8-14, vol. 6, Oxford University Press, Oxford, UK.

Lorente, A., et al., "Synthesis of Heterocyclic Compounds. XXXIX [1]. Synthesis of 5-Cyano-2-Phenyl-4-Thioxo-3,4-Dihydropyrimidines," *Journal of Heterocyclic Chemistry*, 1985, pp. 49-51, vol. 22, Wiley-Blackwell, Hoboken, NJ, US.

Lovgren, A. K., et al., "COX-2-Derived Prostacyclin Protects Against Bleomycin-Induced Pulmonary Fibrosis," *American Journal of Physiology—Lung Cellular and Molecular Physiology*, pp. L144-L156, Feb. 10, 2006, vol. 291, The American Physiological Society, Rockville, MD, US.

Lu, L., et al., "Animal Models of Gastrointestinal Inflammation and Cancer," *Life Sciences*, 2014, pp. 1-6, vol. 108, Issue 1, Elsevier, Amsterdam, NL.

Luca, G., "The Future of Targeted Therapy: Combining Novel Agents," *Oncology*, 2002, pp. 47-56, vol. 63 (Supplement 1), Karger Publishers, Basel, CH.

Luu, A.Z., "Role of Endothelium in Doxorubicin-Induced Cardiomyopathy," *JACC: Basic to Translational Science*, Dec. 2018, pp. 861-870, vol. 3, No. 6, Elsevier on behalf of American College of Cardiology, Amsterdam, NL.

Ma, F., et al., "Discovery and Structure-Activity Relationships Study of Thieno[2,3-b]pyridine Analogues as Hepatic Gluconeogenesis Inhibitors," *European Journal of Medicinal Chemistry*, May 25, 2018, Abstract, vol. 152, Elsevier, Amsterdam, NL.

Makala, L., et al., "FK228 Analogues Induce Fetal Hemoglobin in Human Erythroid Progenitors," *Anemia*, 2012, Article ID 428137, 13 pages, vol. 2012, Hindawi Publishing Corporation, London, UK.

Mallipeddi, P.L., et al., "Structural Insights into Novel 15-Prostaglandin Dehydrogenase Inhibitors," *Molecules*, 2021, 17 pages, 5903, Multidisciplinary Digital Publishing Institute, Basel, CH.

Markowitz, S., et al., "Aspirin and Colon Cancer—Targeting Prevention", *The New England Journal of Medicine*, May 24, 2007, pp. 2195-2198, vol. 356, No. 21, Massachusetts Medical Society, MA, US.

Markowitz, S., et al., "Molecular Origins of Cancer—Molecular Basis of Colorectal Cancer," *The New England Journal of Medicine*, Dec. 17, 2009, pp. 2449-2460, vol. 361, No. 25, Massachusetts Medical Society, MA, US.

Mayo Clinic, "Diseases and Conditions—Chronic Kidney Disease," Web page <www.mayoclinic.org/diseases-conditions/kidney-disease/basics/causes/con20026778>, Jan. 7, 2015, retrieved from the Internet Archive Wayback Machine via Page Vault <http://web.archive.org/web/20150107203836/www.mayoclinic.org/diseases-conditions/kidney-disease/basics/causes/con-20026778> on Oct. 26, 2022.

(56) References Cited

OTHER PUBLICATIONS

Mayo Clinic, "Diseases and Conditions—Chronic kidney disease", Jan. 30, 2015, http://www.mayoclinic.org/diseases-conditions/kidney-diseases/basics/causes/con-20026778, accessed Dec. 11, 2015.

Mayo Clinic, "Chronic kidney disease—Care at Mayo Clinic," Oct. 25, 2022, retrieved from Page Vault https://www.mayoclinic.org/diseases-conditions/chronic-kidney-disease/care-at-mayo-clinic/mac-20354531 on Oct. 25, 2022.

Mayo Clinic, "Chronic kidney disease—Diagnosis and treatment," Oct. 25, 2022, retrieved from Page Vault https://www.mayoclinic.org/diseases-conditions/chronic-kidney-disease/diagnosis-treatment/drc-20354527 on Oct. 25, 2022.

Mayo Clinic, "Chronic kidney disease—Doctors and departments," Oct. 25, 2022, retrieved from Page Vault https://www.mayoclinic.org/diseases-conditions/chronic-kidney-disease/doctors-departments/ddc-20354530 on Oct. 25, 2022.

Mayo Clinic, "Chronic kidney disease—Symptoms and causes," Oct. 25, 2022, retrieved from Page Vault https://www.mayoclinic.org/diseases-conditions/chronic-kidney-diseases/symptoms-causes/syc-20354521 on Oct. 25, 2022.

McCaffrey, T.A., et al., "Genomic Profiling Reveals the Potential Role of TCLIA and MDRI Deficiency in Chemotherapy-Induced Cardiotoxicity," *International Journal of Biological Sciences*, 2013, pp. 350-360, vol. 9, Issue 4, Ivyspring International Publisher Pty Ltd, AU.

McCullough, Louise, et al., "Neuroprotecive Function of the $PGE_2$ EP2 Receptor in Cerebral Ischemia," *The Journal of Neuroscience*, Jan. 7, 2004, pp. 257-268, vol. 24, No. 1, Society for Neuroscience, Washington, DC, US.

Michelet, J.F., et al., "Expression of $NAD^+$ Dependent 15-Hydroxyprostaglandin Dehydrogenase and Protection of Prostaglandins in Human Hair Follicle," *Experimental Dermatology*, 2008, pp. 821-828, vol. 17, No. 10, Wiley, Hoboken, NJ, US.

Mitchell, C., and Willenbring, H., "A Reproducible and Well-Tolerated Method for ⅔ Partial Hepatectomy in Mice," *Nature Protocols*, 2008, pp. 1167-1170, vol. 3, No. 7, Nature Publishing Group, London, UK.

Montrose, D.C., et al., "The Role of $PGE_2$ in Intestinal Inflammation and Tumorigenesis," *Prostaglandins and Other Lipid Mediators*, 2015, 23 pages, Elsevier, Amsterdam, NL.

Morishita, Yoshiyuki, et al., "Establishment of Acute Kidney Injury Mouse Model by 0.75% Adenine Ingestion," *Renal Failure*, 2011, pp. 1013-1018, vol. 33, No. 10, Informa Healthcare USA, Inc., US.

Moustafa, Y.M., et al., "15-PGDH Inhibitors: The Antiulcer Effects of Carbenoxolone, Pioglitazone and Verapamil in Indomethacin Induced Peptic Ulcer Rats," *European Review for Medical and Pharmacological Sciences*, 2013, pp. 2000-2009, vol. 17, Verduci Editore, Rome, IT.

Myung, Seung-Jae, et al., "15-Hydroxyprostaglandin dehydrogenase is an in vivo suppressor of colon tumorigenesis," *Proceedings of the National Academy of Sciences*, Aug. 8, 2006, pp. 12098-12102, vol. 103, No. 32, United States National Academy of Sciences, Washington, DC, US.

Na, H.-K., et al., "15-Hydroxyprostaglandin Dehydrogenase as a Novel Molecular Target for Cancer Chemoprevention and Therapy," *Biochemical Pharmacology*, 2011, pp. 1352-1360, vol. 82, Elsevier, Amsterdam, NL.

Nakanishi, M., and Rosenberg, D.W., "Multifaceted Roles of $PGE_2$ in Inflammation and Cancer," *Seminars in Immunopathology*, 2013, pp. 123-137, vol. 35, Springer, Berlin, DE.

Nasrallah, Rania, et al., "$PGE_2$, Kidney Disease, and Cardiovascular Risk: Beyond Hypertension and Diabetes," *Journal of the American Society of Nephrology*, 2016, pp 666-676, vol. 27, American Society of Nephrology, US.

Neilan, T.G., et al., "Disruption of COX-2 Modulates Gene Expression and the Cardiac Injury Response to Doxorubicin," *American Journal of Physiology—Heart and Circulatory Physiology*, Apr. 14, 2006, pp. H532-H536, vol. 291, American Physiological Society, Rockville, MD, US.

Niesen., F.H., et al., "High-Affinity Inhibitors of Human $NAD^+$-Dependent 15-Hydroxyprostaglandin Dehydrogenase: Mechanisms of Inhibition and Structure-Activity Relationships", *PLoS ONE*, Nov. 2010, e13719, 12 pages, vol. 5, issue 11, Public Library of Science, San Francisco, CA, US.

Noe, A., et al., "High Incidence of Severe Cyclosporine Neurotoxicity in Children Affected by Haemoglobinopaties Undergoing Myeloablative Haematopoietic Stem Cell Transplantation: Early Diagnosis and Prompt Intervention Ameliorates Neurological Outcome," *Italian Journal of Pediatrics*, Feb. 6, 2010, Article No. 14, pp. 1-6, vol. 36, BioMedCentral, London, UK.

Nogradi, K., et al., "Thieno[2,3-b]pyridines as Negative Allosteric Modulators of Metabotropic GluR5 Receptors: Hit-To-Lead Optimization," *Bioorganic and Medicinal Chemistry Letters*, 2014, pp. 3845-3849, vol. 24, Elsevier, Amsterdam, NL.

North, T.E., et al., "Prostaglandin E2 Regulates Vertebrate Haematopoietic Stem Cell Homeostasis," *Nature*, Jun. 21, 2007, pp. 1007-1011, vol. 447, Nature Research, London, UK.

North, Trista E., "PGE2-Regulated wnt Signaling and N-Acetylcysteine Are Synergistically Hepatoprotective in Zebrafish Acetaminophen Injury", *Proceedings of the National Academy of Sciences*, Oct. 5, 2010, pp. 17315-17320, vol. 107, No. 40, United States National Academy of Sciences, Washington, DC, US.

Obeid, J., et al., "TYR-179 and LYS-183 are Essential for Enzymatic Activity of 11 β-Hydroxysteroid Dehydroxysteroid Dehydrogenase," *Biochemical and Biophysical Research Communications*, Oct. 15, 1992, Abstract, vol. 188, Issue 1, Academic Press, Elsevier, Amsterdam, NL.

Oh, S.Y., et al., "Comparison of Experimental Mouse Models of Inflammatory Bowel Disease," *International Journal of Molecular Medicine*, 2014, pp. 333-340, vol. 33, Issue 2, Spandidos Publications, UK.

Otani, T., et al., "Levels of $NAD^+$-dependent 15-Hydroxyprostaglandin Dehydrogenase are Reduced in Inflammatory Bowel Disease: Evidence for Involvement of TNF-α", *American Journal of Physiology—Gastrointestinal and Liver Physiology*, 2006, G361-G368, vol. 290, American Physiological Society, Rockville, MD, US.

Packer, Milton, et al., "Consensus recommendations for the management of chronic heart failure. On behalf of the membership of the advisory council to improve outcomes nationwide in heart failure," *The American Journal of Cardiology*, Jan. 21, 1999, pp. 1a-38a, vol. 83 (2a), Elsevier Inc., NL.

Park, S.H., et al., "Effect of Thiazolidinedione Phenylacetate Derivatives on Wound-Healing Activity," *Archives of Pharmacal Research*, 2019, pp. 790-814, vol. 42, Springer Science + Business Media, Berlin, DE.

Parveen, H., et al., "Synthesis and Characterization of a New Series of Hydroxy Pyrazolines," *Synthetic Communications*, 2008, pp. 3973-3983, vol. 38, Taylor and Francis, London, UK.

Patani, L., et al., "Bioisosterism: A Rational Approach in Drug Design," *Chemical Reviews*, 1996, pp. 3147-3176, vol. 96, No. 8, American Chemical Society, Washington, DC, US.

Pelus, L.M., et al., "Pleiotropic Effects of Prostaglandin $E_2$ in Hematopoiesis; Prostaglandin $E_2$ and Other Eicosanoids Regulate Hematopoietic Stem and Progenitor Cell Function," *Prostaglandins and Other Lipid Mediators*, 2011, pp. 3-9, vol. 96, Elsevier, Amsterdam, NL.

Pelus, L.M., et al., "Pulse Exposure of Haematopoietic Grafts to Prostaglandin $E_2$ in vitro Facilitates Engraftment and Recovery," *Cell Proliferation*, 2011, pp. 22-29, vol. 44, Suppl. 1, Wiley, Hoboken, NJ, US.

Perse, M., and Cerar, A., "Dextran Sodium Sulphate Colitis Mouse Model: Traps and Tricks," *Journal of Biomedicine and Biotechnology*, 2012, Article ID 718617, 13 pages, vol. 2012, Hindawi Publishing Corporation, London, UK.

Piao, Y. L., et al., "Wound Healing Effects of New 15-Hydroxyprostaglandin Dehydrogenase Inhibitors," *Prostaglandins, Leukotrienes and Essential Fatty Acids*, 2014, pp. 325-332, vol. 91, Elsevier, Amsterdam, NL.

Piao, Y.L., et al., "Cell-based Biological Evaluations of 5-(3-bromo-4-phenethoxybenzylidene)thiazolidine-2,4-dione as Promising Wound Healing Agent," *Bioorganic and Medicinal Chemistry*, May 1, 2015, pp. 2098-2103, vol. 23, Issue 9, Elsevier, Amsterdam, NL.

(56) References Cited

OTHER PUBLICATIONS

Porter, G.A., "Contrast-Associated Nephropathy," *The American Journal of Cardiology*, Sep. 5, 1989, pp. 22E-26E, vol. 64, Issue 9, Elsevier, Amsterdam, NL.

Porter, R.L., et al., "Prostaglandin E2 Increases Hematopoietic Stem Cell Survival and Accelerates Hematopoietic Recovery After Radiation Injury," *Stem Cells*, 2013, pp. 372-383, vol. 31, AlphaMed Press, Hoboken, NJ, US.

Randhawa, P.K., et al., "A Review on Chemical-Induced Inflammatory Bowel Disease Models in Rodents," *Korean Journal of Physiology and Pharmacology*, Aug. 2014, pp. 279-288, vol. 18, Issue 4, The Korean Journal of Physiology and Pharmacology, KR.

Renneville, A., et al., "EHMT1 and EHMT2 Inhibition Induces Fetal Hemoglobin Expression," *Blood*, Oct. 15, 2015, pp. 1930-1939, vol. 126, No. 16, American Society of Hematology, Washington, DC, US.

Rieder, F., et al., "Animal Models of Intestinal Fibrosis: New Tools for the Understandig of Pathogenesis and Therapy of Human Disease," *American Journal of Physiology—Gastrointestinal and Liver Physiology*, Aug. 9, 2012, G786-G801, 303(4, Pt. 1), American Physiological Society, Rockville, MD, US.

Roberts, C.R., "Is Asthma a Fibrotic Disease," *Chest*, Mar. 1995, vol. 107, pp. 111S-117S, American College of Chest Physicians, Glenview, IL, US.

Robison, T.W., and Giri, S.N., "Effects of Chronic Administration of Doxorubicin on Plasma Levels of Prostaglandins, Thromboxane $B_2$, and Fatty Acids in Rats," *Cancer Chemotherapy and Pharmacology*, May 1987, pp. 213-220, vol. 19, Springer Science + Business Media, Berlin, DE.

Rogaeva, Ekaterina, et al., "The neuronal sortilin-related receptor SORL1 is genetically associated with Alzheimer disease," *Nature Genetics*, Feb. 2007, pp. 168-177, vol. 39, No. 2, Nature Publishing Group, UK.

Ronzoni, L., et al., "Modulation of Gamma Globulin Genes Expression by Histone Deacetylase Inhibitors: An in vitro Study," Mar. 7, 2014, pp. 714-721, vol. 165, *British Journal of Hematology*, John Wiley & Sons, UK.

Rossi, F., et al., "Cardiotoxicity of Doxorubicin: Effects of Drugs Inhibiting the Release of Vasoactive Substances," *Pharmacology & Toxicology*, Aug. 1994, Abstract, vol. 75, Issue 2, Pharmacology & Toxicology, DK.

Sasaki, S., et al., "Prostaglandin $E_2$ Inhibits Lesion Formation in Dextran Sodium Sulphate-Induced Colitis in Rats and Reduces the Levels of Mucosal Inflammatory Cytokines", *Scandinavian Journal of Immunology*, 2000, pp. 23-28, vol. 51, Wiley, UK.

Schaefer, C.F., et al., "PID: The Pathway Interaction Database," *Nucleic Acids Research*, 2009, pp. D674-D679, vol. 37, Oxford University Press, Oxford, UK.

Seo, S.Y., et al., "Effect of 15-Hydroxyprostaglandin Dehydrogenase Inhibitor on Wound Healing," *Prostaglandins, Leukotrienes, and Essential Fatty Acids*, 2015, pp. 35-41, vol. 97, Elsevier, Amsterdam, NL.

Seto, M., et al., "Orally Active CCR5 Antagonists as Anti-HIV-1 Agents. Part 3: Synthesis and Biological Activities of 1-Benzazepine Derivatives Containing a Sulfoxide Moiety," *Bioorganic and Medicinal Chemistry*, 2005, pp. 363-386, vol. 13, Elsevier, Amsterdam, NL.

Shannon, P., et al., "Cytoscape: A Software Environment for Integrated Models of Biomolecular Interaction Networks," *Genome Research*, 2003, 8 pages including pp. 2498-2504, vol. 13, Cold Spring Harbor Laboratory Press, Cold Spring Harbor, NY, US.

Sharkey, L.C., et al., "Differential Cardiotoxicity in Response to Chronic Doxorubicin Treatment in Male Spontaneous Hypertension-Heart Failure (SHHF), Spontaneously Hypertensive (SHR), and Wistar Kyoto (WKY) Rats," *Toxicology and Applied Pharmacology*, 2013, pp. 47-57, vol. 273, Issue 1, Elsevier, Amsterdam, NL.

Smith, J.N.P., et al., "Inhibition of 15-PGDH Protects Mice from Immune-Mediated Bone Marrow Failure," *Biology of Blood and Marrow Transplantation*, 2020, pp. 1552-1556, vol. 26, Elsevier, Amsterdam, NL.

Smith, J.N.P., "Therapeutic Targeting of 15-PGDH in Murine Pulmonary Fibrosis," *Scientific Reports*, 2020, 11657, 10 pages, vol. 10, Nature Research, London, UK.

Smusz, S., et al., "Fingerprint-based Consensus Virtual Screening Towards Structurally New 5-$HT_6R$ Ligands," *Bioorganic and Medicinal Chemistry Letters*, 2015, pp. 1827-1830, vol. 25, Issue 9, Elsevier, Amsterdam, NL.

Solomon, L., et al., "The Dextran Sulphate Sodium (DSS) Model of Colitis: An Overview," *Comparative Clinical Pathology*, Mar. 4, 2010, pp. 235-239, vol. 19, Springer, Munich, DE.

Somasundaram, S., et al., "The DNMT1-Associated lincRNA DACOR1 Reprograms Genome-Wide DNA Methylation in Colon Cancer," *Clinical Epigenetics*, 2018, 15 pages, 10:127, BioMedCentral, London, UK.

Sood, A., et al., "A Prospective, Open-Label Trial Assessing Dexamethasone Pulse Therapy in Moderate to Sever Ulcerative Colitis," *Journal of Clinical Gastroenterology*, Oct. 2002, pp. 328-331, vol. 35, Issue 4, Lippincott Williams & Wilkins, Philadelphia, PA, US.

"Specs," Web page <www.specs.net/>, 2 pages, Dec. 25, 2003, retrieved from the Internet Archive Wayback Machine without Page Vault <http://www.archive.org/web/20031225052253/http://www.specs.net/> on Oct. 26, 2022.

"Specs," Web page <www.specs.net/>, 2 pages, Dec. 25, 2003, retrieved from the Internet Archive Wayback Machine via Page Vault <http://web.archive.org/web/20031225052253/http://www.specs.net/> on Sep. 29, 2022.

Speth, J. M., et al., "Pharmacologic Increase in HIF1α Enhances Hematopoietic Stem and Progenitor Homing and Engraftment," *Blood*, Jan. 9, 2014, six pages including pp. 203-207, vol. 123, No. 2, American Society of Hematology, Washington, DC, US.

St George-Hyslop, P.H., et al., "The Genetic Defect Causing Familial Alzheimer's Disease Maps on Chromosome 21," *Science*, Feb. 20, 1987, pp. 885-890, vol. 235, Issue 4791, American Association for the Advancement of Science, Washington, DC, US.

Tai, H.-H., et al., "Prostaglandin Catabolizing Enzymes", *Prostaglandins and Other Lipid Mediators*, 2002, pp. 483-493, Elsevier Science Inc, Amsterdam, NL.

Tanaka, N., et al., "Crystal Structures of the Binary and Ternary Complexes of 7α-Hydroxysteroid Dehydrogenase from *Escherichia coli,*" *Biochemistry*, Jun. 18, 1996, pp. 7715-7730, vol. 35, Issue 24, American Chemical Society, Washington, DC, US.

Tanaka, Y., et al., "Systems Analysis of ATF3 in Stress Response and Cancer Reveals Opposing Effects on Pro-Apoptotic Genes in p53 Pathway," *PLoS One*, Oct. 2011, e26848, 12 pages, vol. 6, Issue 10, Public Library of Science, San Francisco, CA, US.

Tatsuwaki, H., et al., "Reduction of 15-Hydroxyprostaglandin Dehydrogenase Expression Is an Independent Predictor of Poor Survival Associated with Enhanced Cell Proliferation in Gastric Adenocarcinoma," *Cancer Science*, Feb. 2010, pp. 550-558, vol. 101, No. 2, Wiley-Blackwell, Hoboken, NJ, US.

Tessner, T.G., et al., "Prostaglandins Prevent Decreased Epithelial Cell Proliferation Associated With Dextran Sodium Sulfate Injury in Mice", *Gastroenterology*, Oct. 1998, pp. 874-882, vol. 115, No. 4, Elsevier, Amsterdam, NL.

Tong, M., et al., "15-Hydroxyprostaglandin Dehydrogenase Can Be Induced by Dexamethasone and Other Glucocorticoids at the Therapeutic Level in A549 Human Lung Adenocarcinoma Cells," *Archives of Biochemistry and Biophysics*, Mar. 1, 2005, pp. 50-55, vol. 435, issue 1, Elsevier, Amsterdam, NL.

Valatas, V., et al., "Experimental Colitis Models: Insights into the Pathogenesis of Inflammatory Bowel Disease and Translational Issues," *European Journal of Pharmacology*, 2015, pp. 253-264, vol. 759, Elsevier, Amsterdam, NL.

Varadan, V., et al., "The Integration of Biological Pathway Knowledge in Cancer Genomics," *IEEE Signal Processing Magazine*, Jan. 2012, 20 pages, vol. 29, Issue 1, IEEE Signal Processing Society, Piscataway, NJ, US.

Vaske, C.J., et al, "Inference of patient-specific pathway activities from multi-dimensional cancer genomics data using PARADIGM," *Bioinformatics*, 2010, pp i237-i245, vol. 26, Oxford University Press, Oxford, UK.

(56) References Cited

OTHER PUBLICATIONS

Vukicevic, S., et al., "Role of EP2 and EP4 Receptor-Selective Agonists of Prostaglandin $E_2$ in Acute and Chronic Kidney Failure," *Kidney International*, 2006, pp. 1099-1106, vol. 70, Elsevier on behalf of the International Society of Nephrology, Amsterdam, NL.

Wallace, J.L., "Prostaglandins, NSAIDs, and Gastric Mucosal Protection: Why Doesn't the Stomach Digest Itself?" *Physiol Reviews*, 2008, pp. 1547-1565, vol. 88, No. 4, The American Physiological Society, Rockville, MD, US.

Wang, Y.F., et al., "Meta-Analysis of Drug-Eluting Versus Bare Mtal Stents in Patients with Indications for Oral Anticoagulation Undergoing Coronary Stenting," *Acta Cardiologica*, 2014, pp. 237-244, vol. 69, Issue 3, Belgian Society of Cardiology, BE, Springer.

Wang, J., et al., "Design, Synthesis, and Pharmacological Evaluation of Novel Piperlongumine Derivatives as Potential Antiplatelet Aggregation Candidate," *Chemical Biology and Drug Design*, 2016, pp. 883-840, vol. 87, Issue 6, John Wiley & Sonse A/S, Hoboken, NJ.

Wang, J., et al., "Chemopreventive Efficacy of the Cyclooxygenase-2 (Cox-2) Inhibitor, Celecoxib, is Predicted by Adenoma Expression of Cox-2 and 15-PGDH," *Cancer Epidemiology, Biomarkers, and Prevention*, Jul. 2018, 20 pages, vol. 27, Issue 7, American Association for Cancer Research, Philadelphia, PA, US.

Wei, Q., and Dong, Z., "Mouse Model of Ischemic Acute Kidney Injury: Technical Notes and Tricks," *American Journal of Physiology—Renal Physiology*, Sep. 19, 2012, F1487-F1494, vol. 303, American Physiological Society, Rockville, MD, US.

Westbrook, A.M., et al., "Mouse Models of Intestinal Inflammation and Cancer," *Archives of Toxicology*, 2016, 22 pages, vol. 90, Issue 9, Springer-Verlag, DE.

Wirtz, S., and Neurath, M.F., "Mouse Models of Inflammatory Bowel Disease," *Advanced Drug Delivery Reviews*, 2007, pp. 1073-1083, vol. 59, Issue 11, Elsevier B.V., Amsterdam, NL.

Wu, Y., et al., "Synthesis and SAR of Thiazolidinedione Derivatives as 15-PGDH Inhibitors," *Bioorganic and Medicinal Chemistry*, Feb. 15, 2010, Abstract, vol. 18, Issue 4, Elsevier Ltd., Amsterdam, NL.

Wu, Y., et al. "Synthesis and Biological Evaluation of Novel Thiazolidinedione Analogues as 15-Hydroxyprostaglandin Dehydrogenase Inhibitors," *Journal of Medicinal Chemistry*, 2011, pp. 5260-5264, vol. 54, American Chemical Society, Washington, DC, US.

Yan, M., et al., "15-Hydroxyprostaglandin dehydrogenase, a COX-2 oncogene antagonist, is a TGF-β-induced suppressor of human gastrointestinal cancers", *Proceedings of the National Academy of Sciences*, Dec. 14, 2004, pp. 17468-17473, vol. 101, No. 50, United States National Academy of Sciences, Washington, DC, US.

Yan, C., et al., "Cyclooxygenases, Microsomal Prostaglandin E Synthase-1, and Cardiovascular Function," *The Journal of Clinical Investigation*, 2006, pp. 1391-1399, vol. 116, Issue 5, American Society for Clinical Investigation, US.

Yan, Min, et al, "15-Hydroxyprostaglandin dehydrogenase inactivation as a mechanism of resistance to celecoxib chemoprevention of colon tumors", *Proceedings of the National Academy of Sciences*, Jun. 9, 2009, pp. 9409-9413, vol. 106, No. 23, United States National Academy of Sciences, Washington, DC, US.

Yang, H., et al., "Altered Hippocampal Long-Term Synaptic Plasticity in Mice Deficient in the PGE2 EP2 Receptor," *Journal of Neurochemistry*, 2009, pp. 295-304, vol. 108, Wiley-Blackwell, Hoboken, NJ, US.

Yao, R., et al., "Comparison of Clinical Efficacy of Different Statins on Cardiovascular Events Following Percutaneous Coronary Intervention," *International Journal of Clinical and Experimental Medicine*, 2017, 11286, vol. 10, Issue 7, e-Century Publishing Corporation, Madison, WI, US, Article Retracted.

Yeh, F.-L., et al., "Keloid-Derived Fibroblasts Have a Diminished Capacity to Produce Prostaglandin $E_2$," *Burns*, 2006, pp. 299-304, vol. 32, Elsevier Ltd., Amsterdam, NL.

Zhang, Y., "Inhibition of the Prostaglandin Degrading Enzyme 15-PGDH Potentiates Tissue Regeneration," *Science*, Jun. 12, 2015, p. 1223, pp. aaa2340-1 to aaa2340-8, vol. 348, Issue 6240, American Association for the Advancement of Science, Washington, DC, US.

Zhang, Y., et al., "Prasugrel Suppresses Development of Lithium-Induced Nephrogenic Diabetes Insipidus in Mice," *Purinergic Signalling*, 2017, pp. 239-248, vol. 13, Springer Science + Business Media, Berlin, DE.

Zhang, Y., et al., "Impacts of CYP2C19 Genetic Polymorphisms on Bioavailability and Effect on Platelet Adhesion of Vicagrel, a Novel Thienopyridine $P2Y_{12}$ Inhibitor," *British Journal of Clinical Pharmacology*, 2020, pp. 1860-1874, vol. 86, The British Pharmacological Society, Wiley-Blackwell, Hoboken, NJ, US.

Zhao, L., et al., "Design, Synthesis and SAR of Thienopyridines as Potent CHK1 Inhibitors," *Bioorganic and Medicinal Chemistry Letters*, Dec. 15, 2010, pp. 7216-7221, vol. 20, Issue 24, Elsevier Ltd., Amsterdam, NL.

Zhou, Y., and Gong, Y., "Asymmetric Copper(II)-Catalysed Nitroaldol (Henry) Reactions Utilizing a Chiral $C_1$-Symmetric Dinitrogen Ligand," *European Journal of Organic Chemistry*, 2011, pp. 6092-6099, vol. 2011, Issue 30, Wiley-VCH Verlag GmbH & Co. KGaA, Weinheim, DE.

CAS Registry No. 296798-64-6 [online database], STN Entry Date Oct. 18, 2000 [retrieved on Oct. 21, 2022], Retrieved from SciFinder <https://scifinder-n.cas.org/>, substance detail downloaded to PDF.

CAS Registry No. 299406-22-7 [online database], STN Entry Date Oct. 26, 2000 [retrieved on Oct. 24, 2022], Retrieved from SciFinder <https://scifinder-n.cas.org/>, substance detail downloaded to pdf.

CAS Registry No. 299920-58-4 [online database], STN Entry Date Oct. 27, 2000 [retrieved on Sep. 21, 2022], Retrieved from SciFinder <https://scifinder-n.cas.org/>, substance detail downloaded to pdf.

CAS Registry No. 299920-59-5 [online database], STN Entry Date Oct. 27, 2000 [retrieved on Sep. 21, 2022], Retrieved from SciFinder <https://scifinder-n.cas.org/>, substance detail downloaded to pdf.

CAS Registry No. 299920-61-9 [online database], STN Entry Date Oct. 27, 2000 [retrieved on Sep. 16, 2022], Retrieved from SciFinder <https://scifinder-n.cas.org/>, substance detail downloaded to pdf.

CAS Registry No. 299920-78-8 [online database], STN Entry Date Oct. 27, 2000 [retrieved on Sep. 21, 2022], Retrieved from SciFinder <https://scifinder-n.cas.org/>, substance detail downloaded to pdf.

CAS Registry No. 306766-39-2 [online database], STN Entry Date Dec. 5, 2000 [retrieved on Oct. 24, 2022], Retrieved from SciFinder <https://scifinder-n.cas.org/>, substance detail downloaded to pdf.

CAS Registry No. 313245-69-1 [online database], STN Entry Date Jan. 9, 2001 [retrieved on Oct. 24, 2022], Retrieved from SciFinder <https://scifinder-n.cas.org/>, substance detail downloaded to pdf.

CAS Registry No. 313245-70-4 [online database], STN Entry Date Jan. 9, 2001 [retrieved on Sep. 16, 2022], Retrieved from SciFinder <https://scifinder-n.cas.org/>, substance detail downloaded to pdf.

CAS Registry No. 331447-76-8 [online database], STN Entry Date Apr. 16, 2001 [retrieved on Sep. 16, 2022], Retrieved from SciFinder <https://scifinder-n.cas.org/>, substance detail downloaded to pdf.

CAS Registry No. 331655-85-7 [online database], STN Entry Date Apr. 17, 2001 [retrieved on Sep. 16, 2022], Retrieved from SciFinder <https://scifinder-n.cas.org/>, substance detail downloaded to pdf.

CAS Registry No. 331655-86-8 [online database], STN Entry Date Apr. 17, 2001 [retrieved on Sep. 16, 2022], Retrieved from SciFinder <https://scifinder-n.cas.org/>, substance detail downloaded to pdf.

CAS Registry No. 332945-05-8 [online database], STN Entry Date Apr. 26, 2001 [retrieved on Oct. 24, 2022], Retrieved from SciFinder <https://scifinder-n.cas.org/>, substance detail downloaded to pdf.

CAS Registry No. 350511-89-6 [online database], STN Entry Date Aug. 6, 2001 [retrieved on Oct. 24, 2022], Retrieved from SciFinder <https://scifinder-n.cas.org/>, substance detail downloaded to pdf.

CAS Registry No. 369400-43-1 [online database], STN Entry Date Nov. 13, 2001 [retrieved on Sep. 16, 2022], Retrieved from SciFinder <https://scifinder-n.cas.org/>, substance detail downloaded to pdf.

CAS Registry No. 369402-41-5 [online database], STN Entry Date Nov. 13, 2001 [retrieved on Sep. 16, 2022], Retrieved from SciFinder <https://scifinder-n.cas.org/>, substance detail downloaded to pdf.

CAS Registry No. 370572-70-6 [online database], STN Entry Date Nov. 16, 2001 [retrieved on Sep. 21, 2022], Retrieved from SciFinder <https://scifinder-n.cas.org/>, substance detail downloaded to pdf.

(56) References Cited

OTHER PUBLICATIONS

CAS Registry No. 370870-44-3 [online database], STN Entry Date Nov. 19, 2001 [retrieved on Sep. 21, 2022], Retrieved from SciFinder <https://scifinder-n.cas.org/>, substance detail downloaded to pdf.
CAS Registry No. 371116-23-3 [online database], STN Entry Date Nov. 20, 2001 [retrieved on Sep. 16, 2022], Retrieved from SciFinder <https://scifinder-n.cas.org/>, substance detail downloaded to pdf.
CAS Registry No. 371117-75-8 [online database], STN Entry Date Nov. 20, 2001 [retrieved on Sep. 21, 2022], Retrieved from SciFinder <https://scifinder-n.cas.org/>, substance detail downloaded to pdf.
CAS Registry No. 371118-22-8 [online database], STN Entry Date Nov. 20, 2001 [retrieved on Sep. 21, 2022], Retrieved from SciFinder <https://scifinder-n.cas.org/>, substance detail downloaded to pdf.
CAS Registry No. 371144-00-2 [online database], STN Entry Date Nov. 20, 2001 [retrieved on Sep. 16, 2022], Retrieved from SciFinder <https://scifinder-n.cas.org/>, substance detail downloaded to pdf.
CAS Registry No. 371208-33-2 [online database], STN Entry Date Nov. 21, 2001 [retrieved on Sep. 16, 2022], Retrieved from SciFinder <https://scifinder-n.cas.org/>, substance detail downloaded to pdf.
CAS Registry No. 371213-13-7 [online database], STN Entry Date Nov. 21, 2001 [retrieved on Sep. 21, 2022], Retrieved from SciFinder <https://scifinder-n.cas.org/>, substance detail downloaded to pdf.
CAS Registry No. 371222-38-7 [online database], STN Entry Date Nov. 21, 2001 [retrieved on Sep. 21, 2022], Retrieved from SciFinder <https://scifinder-n.cas.org/>, substance detail downloaded to pdf.
CAS Registry No. 371232-15-4 [online database], STN Entry Date Nov. 21, 2001 [retrieved on Sep. 21, 2022], Retrieved from SciFinder <https://scifinder-n.cas.org/>, substance detail downloaded to pdf.
CAS Registry No. 371926-65-7 [online database], STN Entry Date Nov. 27, 2001 [retrieved on Sep. 16, 2022], Retrieved from SciFinder <https://scifinder-n.cas.org/>, substance detail downloaded to pdf.
CAS Registry No. 384861-16-9 [online database], STN Entry Date Jan. 20, 2002 [retrieved on Sep. 21, 2022], Retrieved from SciFinder <https://scifinder-n.cas.org/>, substance detail downloaded to pdf.
CAS Registry No. 420824-06-2 [online database], STN Entry Date May 23, 2002 [retrieved on Sep. 16, 2022], Retrieved from SciFinder <https://scifinder-n.cas.org/>, substance detail downloaded to pdf.
CAS Registry No. 420825-11-2 [online database], STN Entry Date May 23, 2002 [retrieved on Sep. 21, 2022], Retrieved from SciFinder <https://scifinder-n.cas.org/>, substance detail downloaded to pdf.
CAS Registry No. 420825-38-3 [online database], STN Entry Date May 23, 2002 [retrieved on Sep. 21, 2022], Retrieved from SciFinder <https://scifinder-n.cas.org/>, substance detail downloaded to pdf.
CAS Registry No. 442152-75-2 [online database], STN Entry Date Aug. 2, 2002 [retrieved on Sep. 21, 2022], Retrieved from SciFinder <https://scifinder-n.cas.org/>, substance detail downloaded to pdf.
CAS Registry No. 442152-82-1 [online database], STN Entry Date Aug. 2, 2002 [retrieved on Sep. 16, 2022], Retrieved from SciFinder <https://scifinder-n.cas.org/>, substance detail downloaded to pdf.
CAS Registry No. 442152-88-7 [online database], STN Entry Date Aug. 2, 2002 [retrieved on Sep. 16, 2022], Retrieved from SciFinder <https://scifinder-n.cas.org/>, substance detail downloaded to pdf.
CAS Registry No. 442152-94-5 [online database], STN Entry Date Aug. 2, 2002 [retrieved on Sep. 16, 2022], Retrieved from SciFinder <https://scifinder-n.cas.org/>, substance detail downloaded to pdf.
CAS Registry No. 442153-01-7 [online database], STN Entry Date Aug. 2, 2002 [retrieved on Sep. 16, 2022], Retrieved from SciFinder <https://scifinder-n.cas.org/>, substance detail downloaded to pdf.
CAS Registry No. 442153-03-9 [online database], STN Entry Date Aug. 2, 2002 [retrieved on Sep. 21, 2022], Retrieved from SciFinder <https://scifinder-n.cas.org/>, substance detail downloaded to pdf.
CAS Registry No. 448191-85-3 [online database], STN Entry Date Sep. 9, 2002 [retrieved on Sep. 21, 2022], Retrieved from SciFinder <https://scifinder-n.cas.org/>, substance detail downloaded to pdf.
CAS Registry No. 448191-89-7 [online database], STN Entry Date Sep. 9, 2002 [retrieved on Sep. 21, 2022], Retrieved from SciFinder <https://scifinder-n.cas.org/>, substance detail downloaded to pdf.
CAS Registry No. 452922-28-0 [online database], STN Entry Date Sep. 19, 2002 [retrieved on Sep. 16, 2022], Retrieved from SciFinder <https://scifinder-n.cas.org/>, substance detail downloaded to pdf.
CAS Registry No. 457958-02-0 [online database], STN Entry Date Oct. 2, 2002 [retrieved on Sep. 16, 2022], Retrieved from SciFinder <https://scifinder-n.cas.org/>, substance detail downloaded to pdf.
CAS Registry No. 457958-03-1 [online database], STN Entry Date Oct. 2, 2002 [retrieved on Sep. 16, 2022], Retrieved from SciFinder <https://scifinder-n.cas.org/>, substance detail downloaded to pdf.
CAS Registry No. 457958-04-2 [online database], STN Entry Date Oct. 2, 2002 [retrieved on Sep. 16, 2022], Retrieved from SciFinder <https://scifinder-n.cas.org/>, substance detail downloaded to pdf.
CAS Registry No. 457958-05-3 [online database], STN Entry Date Oct. 2, 2002 [retrieved on Sep. 16, 2022], Retrieved from SciFinder <https://scifinder-n.cas.org/>, substance detail downloaded to pdf.
CAS Registry No. 457958-06-4 [online database], STN Entry Date Oct. 2, 2002 [retrieved on Sep. 21, 2022], Retrieved from SciFinder <https://scifinder-n.cas.org/>, substance detail downloaded to pdf.
CAS Registry No. 457958-16-6 [online database], STN Entry Date Oct. 2, 2002 [retrieved on Sep. 16, 2022], Retrieved from SciFinder <https://scifinder-n.cas.org/>, substance detail downloaded to pdf.
CAS Registry No. 457958-17-7 [online database], STN Entry Date Oct. 2, 2002 [retrieved on Sep. 16, 2022], Retrieved from SciFinder <https://scifinder-n.cas.org/>, substance detail downloaded to pdf.
CAS Registry No. 457958-18-8 [online database], STN Entry Date Oct. 2, 2002 [retrieved on Sep. 21, 2022], Retrieved from SciFinder <https://scifinder-n.cas.org/>, substance detail downloaded to pdf.
CAS Registry No. 457958-30-4 [online database], STN Entry Date Oct. 2, 2002 [retrieved on Sep. 16, 2022], Retrieved from SciFinder <https://scifinder-n.cas.org/>, substance detail downloaded to pdf.
CAS Registry No. 457958-31-5 [online database], STN Entry Date Oct. 2, 2002 [retrieved on Sep. 21, 2022], Retrieved from SciFinder <https://scifinder-n.cas.org/>, substance detail downloaded to pdf.
CAS Registry No. 457958-32-6 [online database], STN Entry Date Oct. 2, 2002 [retrieved on Sep. 16, 2022], Retrieved from SciFinder <https://scifinder-n.cas.org/>, substance detail downloaded to pdf.
CAS Registry No. 457958-38-2 [online database], STN Entry Date Oct. 2, 2002 [retrieved on Sep. 16, 2022], Retrieved from SciFinder <https://scifinder-n.cas.org/>, substance detail downloaded to pdf.
CAS Registry No. 457958-39-3 [online database], STN Entry Date Oct. 2, 2002 [retrieved on Sep. 16, 2022], Retrieved from SciFinder <https://scifinder-n.cas.org/>, substance detail downloaded to pdf.
CAS Registry No. 457958-40-6 [online database], STN Entry Date Oct. 2, 2002 [retrieved on Sep. 21, 2022], Retrieved from SciFinder <https://scifinder-n.cas.org/>, substance detail downloaded to pdf.
CAS Registry No. 457958-41-7 [online database], STN Entry Date Oct. 2, 2002 [retrieved on Sep. 16, 2022], Retrieved from SciFinder <https://scifinder-n.cas.org/>, substance detail downloaded to pdf.
CAS Registry No. 457958-49-5 [online database], STN Entry Date Oct. 2, 2002 [retrieved on Sep. 16, 2022], Retrieved from SciFinder <https://scifinder-n.cas.org/>, substance detail downloaded to pdf.
CAS Registry No. 457958-50-8 [online database], STN Entry Date Oct. 2, 2002 [retrieved on Sep. 21, 2022], Retrieved from SciFinder <https://scifinder-n.cas.org/>, substance detail downloaded to pdf.
CAS Registry No. 459147-27-4 [online database], STN Entry Date Oct. 4, 2002 [retrieved on Sep. 16, 2022], Retrieved from SciFinder <https://scifinder-n.cas.org/>, substance detail downloaded to pdf.
CAS Registry No. 459147-39-8 [online database], STN Entry Date Oct. 4, 2002 [retrieved on Sep. 16, 2022], Retrieved from SciFinder <https://scifinder-n.cas.org/>, substance detail downloaded to pdf.
CAS Registry No. 459147-74-1 [online database], STN Entry Date Oct. 4, 2002 [retrieved on Sep. 21, 2022], Retrieved from SciFinder <https://scifinder-n.cas.org/>, substance detail downloaded to pdf.
CAS Registry No. 459150-70-0 [online database], STN Entry Date Oct. 4, 2002 [retrieved on Sep. 21, 2022], Retrieved from SciFinder <https://scifinder-n.cas.org/>, substance detail downloaded to pdf.
CAS Registry No. 459150-74-4 [online database], STN Entry Date Oct. 4, 2002 [retrieved on Sep. 16, 2022], Retrieved from SciFinder <https://scifinder-n.cas.org/>, substance detail downloaded to pdf.
CAS Registry No. 459150-94-8 [online database], STN Entry Date Oct. 4, 2002 [retrieved on Sep. 16, 2022], Retrieved from SciFinder <https://scifinder-n.cas.org/>, substance detail downloaded to pdf.
CAS Registry No. 459151-05-4 [online database], STN Entry Date Oct. 4, 2002 [retrieved on Sep. 21, 2022], Retrieved from SciFinder <https://scifinder-n.cas.org/>, substance detail downloaded to pdf.

(56) References Cited

OTHER PUBLICATIONS

CAS Registry No. 459152-84-2 [online database], STN Entry Date Oct. 4, 2002 [retrieved on Sep. 16, 2022], Retrieved from SciFinder <https://scifinder-n.cas.org/>, substance detail downloaded to pdf.
CAS Registry No. 459153-20-9 [online database], STN Entry Date Oct. 4, 2002 [retrieved on Sep. 16, 2022], Retrieved from SciFinder <https://scifinder-n.cas.org/>, substance detail downloaded to pdf.
CAS Registry No. 459153-24-3 [online database], STN Entry Date Oct. 4, 2002 [retrieved on Sep. 21, 2022], Retrieved from SciFinder <https://scifinder-n.cas.org/>, substance detail downloaded to pdf.
CAS Registry No. 459153-30-1 [online database], STN Entry Date Oct. 4, 2002 [retrieved on Sep. 16, 2022], Retrieved from SciFinder <https://scifinder-n.cas.org/>, substance detail downloaded to pdf.
CAS Registry No. 459153-75-4 [online database], STN Entry Date Oct. 4, 2002 [retrieved on Sep. 21, 2022], Retrieved from SciFinder <https://scifinder-n.cas.org/>, substance detail downloaded to pdf.
CAS Registry No. 459154-25-7 [online database], STN Entry Date Oct. 4, 2002 [retrieved on Sep. 16, 2022], Retrieved from SciFinder <https://scifinder-n.cas.org/>, substance detail downloaded to pdf.
CAS Registry No. 459154-76-8 [online database], STN Entry Date Oct. 4, 2002 [retrieved on Sep. 16, 2022], Retrieved from SciFinder <https://scifinder-n.cas.org/>, substance detail downloaded to pdf.
CAS Registry No. 459154-80-4 [online database], STN Entry Date Oct. 4, 2002 [retrieved on Sep. 16, 2022], Retrieved from SciFinder <https://scifinder-n.cas.org/>, substance detail downloaded to pdf.
CAS Registry No. 459155-72-7 [online database], STN Entry Date Oct. 4, 2002 [retrieved on Sep. 16, 2022], Retrieved from SciFinder <https://scifinder-n.cas.org/>, substance detail downloaded to pdf.
CAS Registry No. 459155-77-2 [online database], STN Entry Date Oct. 4, 2002 [retrieved on Sep. 16, 2022], Retrieved from SciFinder <https://scifinder-n.cas.org/>, substance detail downloaded to pdf.
CAS Registry No. 459155-84-1 [online database], STN Entry Date Oct. 4, 2002 [retrieved on Sep. 21, 2022], Retrieved from SciFinder <https://scifinder-n.cas.org/>, substance detail downloaded to pdf.
CAS Registry No. 693820-48-3 [online database], STN Entry Date Jun. 16, 2004 [retrieved on Sep. 16, 2022], Retrieved from SciFinder <https://scifinder-n.cas.org/>, substance detail downloaded to pdf.
CAS Registry No. 924846-44-6 [online database], STN Entry Date Mar. 5, 2007 [retrieved on Sep. 16, 2022], Retrieved from SciFinder <https://scifinder-n.cas.org/>, substance detail downloaded to pdf.
CAS Registry No. 957625-42-2 [online database], STN Entry Date Dec. 11, 2007 [retrieved on Sep. 21, 2022], Retrieved from SciFinder <https://scifinder-n.cas.org/>, substance detail downloaded to pdf.
CAS Registry No. 957939-31-0 [online database], STN Entry Date Dec. 13, 2007 [retrieved on Sep. 16, 2022], Retrieved from SciFinder <https://scifinder-n.cas.org/>, substance detail downloaded to pdf.
CAS Registry No. 957948-58-2 [online database], STN Entry Date Dec. 13, 2007 [retrieved on Sep. 16, 2022], Retrieved from SciFinder <https://scifinder-n.cas.org/>, substance detail downloaded to pdf.
CAS Registry No. 957957-90-3 [online database], STN Entry Date Dec. 13, 2007 [retrieved on Sep. 21, 2022], Retrieved from SciFinder <https://scifinder-n.cas.org/>, substance detail downloaded to pdf.
CAS Registry No. 1015864-36-4 [online database], STN Entry Date Apr. 20, 2008 [retrieved on Sep. 16, 2022], Retrieved from SciFinder <https://scifinder-n.cas.org/>, substance detail downloaded to pdf.
CAS Registry No. 1015864-38-6 [online database], STN Entry Date Apr. 20, 2008 [retrieved on Sep. 21, 2022], Retrieved from SciFinder <https://scifinder-n.cas.org/>, substance detail downloaded to pdf.
CAS Registry No. 1020685-61-3 [online database], STN Entry Date May 14, 2008 [retrieved on Sep. 16, 2022], Retrieved from SciFinder <https://scifinder-n.cas.org/>, substance detail downloaded to pdf.
CAS Registry No. 1020685-65-7 [online database], STN Entry Date May 14, 2008 [retrieved on Sep. 16, 2022], Retrieved from SciFinder <https://scifinder-n.cas.org/>, substance detail downloaded to pdf.
CAS Registry No. 1020686-01-4 [online database], STN Entry Date May 14, 2008 [retrieved on Sep. 16, 2022], Retrieved from SciFinder <https://scifinder-n.cas.org/>, substance detail downloaded to pdf.
CAS Registry No. 1020686-06-9 [online database], STN Entry Date May 14, 2008 [retrieved on Sep. 21, 2022], Retrieved from SciFinder <https://scifinder-n.cas.org/>, substance detail downloaded to pdf.
CAS Registry No. 1020686-10-5 [online database], STN Entry Date May 14, 2008 [retrieved on Sep. 21, 2022], Retrieved from SciFinder <https://scifinder-n.cas.org/>, substance detail downloaded to pdf.
CAS Registry No. 1020686-49-0 [online database], STN Entry Date May 14, 2008 [retrieved on Sep. 16, 2022], Retrieved from SciFinder <https://scifinder-n.cas.org/>, substance detail downloaded to pdf.
CAS Registry No. 1020686-53-6 [online database], STN Entry Date May 14, 2008 [retrieved on Sep. 21, 2022], Retrieved from SciFinder <https://scifinder-n.cas.org/>, substance detail downloaded to pdf.
CAS Registry No. 1020686-57-0 [online database], STN Entry Date May 14, 2008 [retrieved on Sep. 16, 2022], Retrieved from SciFinder <https://scifinder-n.cas.org/>, substance detail downloaded to pdf.
CAS Registry No. 1020686-77-4 [online database], STN Entry Date May 14, 2008 [retrieved on Sep. 16, 2022], Retrieved from SciFinder <https://scifinder-n.cas.org/>, substance detail downloaded to pdf.
CAS Registry No. 1020686-81-0 [online database], STN Entry Date May 14, 2008 [retrieved on Sep. 21, 2022], Retrieved from SciFinder <https://scifinder-n.cas.org/>, substance detail downloaded to pdf.
CAS Registry No. 1020687-17-5 [online database], STN Entry Date May 14, 2008 [retrieved on Sep. 16, 2022], Retrieved from SciFinder <https://scifinder-n.cas.org/>, substance detail downloaded to pdf.
CAS Registry No. 1112019-47-2 [online database], STN Entry Date Feb. 26, 2009 [retrieved on Sep. 16, 2022], Retrieved from SciFinder <https://scifinder-n.cas.org/>, substance detail downloaded to pdf.
CAS Registry No. 1115479-64-5 [online database], STN Entry Date Mar. 4, 2009 [retrieved on Sep. 16, 2022], Retrieved from SciFinder <https://scifinder-n.cas.org/>, substance detail downloaded to pdf.
CAS Registry No. 1221411-67-1 [online database], STN Entry Date May 5, 2010 [retrieved on Sep. 16, 2022], Retrieved from SciFinder <https://scifinder-n.cas.org/>, substance detail downloaded to pdf.
CAS Registry No. 1221411-70-6 [online database], STN Entry Date May 5, 2010 [retrieved on Sep. 16, 2022], Retrieved from SciFinder <https://scifinder-n.cas.org/>, substance detail downloaded to pdf.
CAS Registry No. 1347499-81-3 [online database], STN Entry Date Dec. 2, 2011 [retrieved on Sep. 21, 2022], Retrieved from SciFinder <https://scifinder-n.cas.org/>, substance detail downloaded to pdf.
CAS Registry No. 1348234-90-1 [online database], STN Entry Date Dec. 4, 2011 [retrieved on Sep. 21, 2022], Retrieved from SciFinder <https://scifinder-n.cas.org/>, substance detail downloaded to pdf.
CAS Registry No. 1348857-03-3 [online database], STN Entry Date Dec. 5, 2011 [retrieved on Sep. 21, 2022], Retrieved from SciFinder <https://scifinder-n.cas.org/>, substance detail downloaded to pdf.
CAS Registry No. 1349215-63-9 [online database], STN Entry Date Dec. 5, 2011 [retrieved on Sep. 21, 2022], Retrieved from SciFinder <https://scifinder-n.cas.org/>, substance detail downloaded to pdf.
CAS Registry No. 1421694-45-2 [online database], STN Entry Date Feb. 22, 2013 [retrieved on Sep. 16, 2022], Retrieved from SciFinder <https://scifinder-n.cas.org/>, substance detail downloaded to pdf.
CAS Registry No. 1471306-25-8 [online database], STN Entry Date Nov. 11, 2013 [retrieved on Sep. 16, 2022], Retrieved from SciFinder <https://scifinder-n.cas.org/>, substance detail downloaded to pdf.
CAS Registry No. 1471306-27-0 [online database], STN Entry Date Nov. 11, 2013 [retrieved on Sep. 16, 2022], Retrieved from SciFinder <https://scifinder-n.cas.org/>, substance detail downloaded to pdf.
CAS Registry No. 1471306-29-2 [online database], STN Entry Date Nov. 11, 2013 [retrieved on Sep. 16, 2022], Retrieved from SciFinder <https://scifinder-n.cas.org/>, substance detail downloaded to pdf.
CAS Registry No. 1471306-31-6 [online database], STN Entry Date Nov. 11, 2013 [retrieved on Sep. 16, 2022], Retrieved from SciFinder <https://scifinder-n.cas.org/>, substance detail downloaded to pdf.
CAS Registry No. 1471306-33-8 [online database], STN Entry Date Nov. 11, 2013 [retrieved on Sep. 16, 2022], Retrieved from SciFinder <https://scifinder-n.cas.org/>, substance detail downloaded to pdf.
CAS Registry No. 1471306-35-0 [online database], STN Entry Date Nov. 11, 2013 [retrieved on Sep. 16, 2022], Retrieved from SciFinder <https://scifinder-n.cas.org/>, substance detail downloaded to pdf.
CAS Registry No. 1471306-37-2 [online database], STN Entry Date Nov. 11, 2013 [retrieved on Sep. 16, 2022], Retrieved from SciFinder <https://scifinder-n.cas.org/>, substance detail downloaded to pdf.
CAS Registry No. 1471306-39-4 [online database], STN Entry Date Nov. 11, 2013 [retrieved on Sep. 16, 2022], Retrieved from SciFinder <https://scifinder-n.cas.org/>, substance detail downloaded to pdf.

(56) References Cited

OTHER PUBLICATIONS

CAS Registry No. 1611464-74-4 [online database], STN Entry Date Jun. 20, 2014 [retrieved on Oct. 25, 2022], Retrieved from SciFinder <https://scifinder-n.cas.org/>, substance detail downloaded to pdf.
CAS Registry No. 1714959-81-5 [online database], STN Entry Date May 28, 2015 [retrieved on Sep. 16, 2022], Retrieved from SciFinder <https://scifinder-n.cas.org/>, substance detail downloaded to pdf.
CAS Registry No. 1714959-82-6 [online database], STN Entry Date May 28, 2015 [retrieved on Sep. 16, 2022], Retrieved from SciFinder <https://scifinder-n.cas.org/>, substance detail downloaded to pdf.
CAS Registry No. 1714959-83-7 [online database], STN Entry Date May 28, 2015 [retrieved on Sep. 16, 2022], Retrieved from SciFinder <https://scifinder-n.cas.org/>, substance detail downloaded to pdf.
CAS Registry No. 1714959-86-0 [online database], STN Entry Date May 28, 2015 [retrieved on Sep. 16, 2022], Retrieved from SciFinder <https://scifinder-n.cas.org/>, substance detail downloaded to pdf.
CAS Registry No. 1714959-92-8 [online database], STN Entry Date May 28, 2015 [retrieved on Sep. 16, 2022], Retrieved from SciFinder <https://scifinder-n.cas.org/>, substance detail downloaded to pdf.
CAS Registry No. 1714959-93-9 [online database], STN Entry Date May 28, 2015 [retrieved on Sep. 16, 2022], Retrieved from SciFinder <https://scifinder-n.cas.org/>, substance detail downloaded to pdf.
CAS Registry No. 1714959-95-1 [online database], STN Entry Date May 28, 2015 [retrieved on Sep. 16, 2022], Retrieved from SciFinder <https://scifinder-n.cas.org/>, substance detail downloaded to pdf.
CAS Registry No. 1714959-96-2 [online database], STN Entry Date May 28, 2015 [retrieved on Sep. 16, 2022], Retrieved from SciFinder <https://scifinder-n.cas.org/>, substance detail downloaded to pdf.
CAS Registry No. 1714961-85-9 [online database], STN Entry Date May 28, 2015 [retrieved on Sep. 16, 2022], Retrieved from SciFinder <https://scifinder-n.cas.org/>, substance detail downloaded to pdf.
CAS SciFinder Search Result on Jan. 27, 2022, at 5:14 pm (2 results)—1—Preparation of thienopyridines and related compounds, their compositions and methods of modulating short-chain dehydrogenase activity (WO 2018/218251);—2—Compositions and methods of modulating short-chain dehydrogenase activity (WO 2016/168472).
CAS SciFinder Search Result on Jan. 27, 2022, at 11:52 am (1 result)—1—Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 3:02 pm (2 results)—1—Preparation of thienopyridines and similar bicyclic heterocyclic compounds as modulators of 15-hydroxyprostaglandin dehydrogenase type I for therapy (WO 2015/065716);—2—Preparation of thienopyridines and related compounds, their compositions and methods of modulating short-chain dehydrogenase activity (WO 2018/218251).
CAS SciFinder Search Result on Jan. 27, 2022, at 3:25 pm (1 result)—1—Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 3:30 pm (2 results)—1—Preparation of thienopyridines and similar bicyclic heterocyclic compounds as modulators of 15-hydroxyprostaglandin dehydrogenase type I for therapy (WO 2015/065716);—2—Preparation of thienopyridines and related compounds, their compositions and methods of modulating short-chain dehydrogenase activity (WO 2018/218251).
CAS SciFinder Search Result on Jan. 27, 2022, at 4:08 pm (2 results)—1—Preparation of thienopyridines and similar bicyclic heterocyclic compounds as modulators of 15-hydroxyprostaglandin dehydrogenase type I for therapy (WO 2015/065716);—2—Preparation of thienopyridines and related compounds, their compositions and methods of modulating short-chain dehydrogenase activity (WO 2018/218251).
CAS SciFinder Search Result on Jan. 27, 2022, at 4:11 pm (2 results)—1—Preparation of thienopyridines and similar bicyclic heterocyclic compounds as modulators of 15-hydroxyprostaglandin dehydrogenase type I for therapy (WO 2015/065716);—2—Preparation of thienopyridines and related compounds, their compositions and methods of modulating short-chain dehydrogenase activity (WO 2018/218251).
CAS SciFinder Search Result on Jan. 27, 2022, at 4:14 pm (2 results)—1—Preparation of thienopyridines and similar bicyclic heterocyclic compounds as modulators of 15-hydroxyprostaglandin dehydrogenase type I for therapy (WO 2015/065716);—2—Preparation of thienopyridines and related compounds, their compositions and methods of modulating short-chain dehydrogenase activity (WO 2018/218251).
CAS SciFinder Search Result on Jan. 27, 2022, at 4:16 pm (2 results)—1—Preparation of thienopyridines and similar bicyclic heterocyclic compounds as modulators of 15-hydroxyprostaglandin dehydrogenase type I for therapy (2015/065716);—2—Preparation of thienopyridines and related compounds, their compositions and methods of modulating short-chain dehydrogenase activity (WO 2018/218251).
CAS SciFinder Search Result on Jan. 27, 2022, at 4:50 pm (2 results)—1—Preparation of thienopyridines and similar bicyclic heterocyclic compounds as modulators of 15-hydroxyprostaglandin dehydrogenase type I for therapy (WO 2015/065716);—2—Preparation of thienopyridines and related compounds, their compositions and methods of modulating short-chain dehydrogenase activity (WO 2018/218251).
CAS SciFinder Search Result on Jan. 27, 2022, at 5:09 pm (2 results)—1—Preparation of thienopyridines and similar bicyclic heterocyclic compounds as modulators of 15-hydroxyprostaglandin dehydrogenase type I for therapy (WO 2015/065716);—2—Preparation of thienopyridines and related compounds, their compositions and methods of modulating short-chain dehydrogenase activity (WO 2018/218251).
CAS SciFinder Search Result on Jan. 27, 2022, at 5:52 pm (2 results)—1—Preparation of thienopyridines and related compounds, their compositions and methods of modulating short-chain dehydrogenase activity (WO 2018/218251);—2—Compositions and methods of modulating short-chain dehydrogenase activity (WO 2016/168472).
CAS SciFinder Search Result on Jan. 27, 2022, at 5:58 pm (2 results)—1—Preparation of thienopyridines and related compounds, their compositions and methods of modulating short-chain dehydrogenase activity (WO 2018/218251);—2—Compositions and methods of modulating short-chain dehydrogenase activity (WO 2016/168472).
CAS SciFinder Search Result on Jan. 27, 2022, at 6:03 pm (6 results)—1—Preparation of thienopyridines and similar bicyclic heterocyclic compounds as modulators of 15-hydroxyprostaglandin dehydrogenase type I for therapy (WO 2015/065716);—2—Inhibitors of 15-Prostaglandin Dehydrogenase to Potentiate Tissue Repair (Antczak et al.);—3—Compositions and methods of modulating short-chain dehydrogenase activity (WO 2016/168472);—4—Preparation of thienopyridines and related compounds, their compositions and methods of modulating short-chain dehydrogenase activity (WO 2018/218251);—5—Preparation of alkylsulfinyl-, alkylsulfonyl- and alkylthio- thieno[2,3-b]pyridinamines as inhibitors of short-chain dehydrogenase activity for promoting neurogenesis and inhibiting nerve cell death (WO 2018/017582);—6—Preparation of thienopyridine compounds having sulfur-containing substituent as inhibitors of short-chain dehydrogenase activity for treating fibrosis (WO 2016/144958).
CAS SciFinder Search Result on Jan. 27, 2022, at 7:17 pm (6 results)—1—Compositions and methods of modulating short-chain dehydrogenase activity (WO 2016/168472);—2—Preparation of thienopyridines and similar bicyclic heterocyclic compounds as modulators of 15-hydroxyprotaglandin dehydrogenase type I for therapy (WO 2015/065716);—3—Inhibitors of 15-Prostaglandin Dehydrogenase to Potentiate Tissue Repair (Antczak et al.);—4—Preparation of thienopyridines and related compounds, their compositions and methods of modulating short-chain dehydrogenase activity (WO 2018/218251);—5—Preparation of alkylsulfinyl-, alkylsulfonyl- and alkylthio-thieno[2,3-b]pyridinamines as inhibitors of short-chain dehydrogenase activity for promoting neurogenesis and inhibiting nerve cell death (WO 2018/017582);—6—Preparation of thienopyridine compounds having sulfur-containing

(56) References Cited

OTHER PUBLICATIONS substituent as inhibitors of short-chain dehydrogenase activity for treating fibrosis (WO 2016/144958).
CAS SciFinder Search Result on Jan. 27, 2022, at 7:21 pm (2 results)—1—Preparation of thienopyridines and similar bicyclic heterocyclic compounds as modulators of 15-hydroxyprostaglandin dehydrogenase type I for therapy (WO 2015/065716);—2—Preparation of thienopyridines and related compounds, their compositions and methods of modulating short-chain dehydrogenase activity (WO 2018/218251).
CAS SciFinder Search Result on Jan. 27, 2022, at 7:30 pm (1 result)—1—Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 7:31 pm (1 result)—1—Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 7:32 pm (1 result)—1—Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 7:39 pm (6 results)—1—Preparation of thienopyridines and similar bicyclic heterocyclic compounds as modulators of 15-hydroxyprostaglandin dehydrogenase type I for therapy (WO 2015/065716);—2—Inhibitors of 15-Prostaglandin Dehydrogenase to Potentiate Tissue Repair (Antczak et al.);—3—Compositions and methods of modulating short-chain dehydrogenase activity (WO 2016/168472);—4—Preparation of thienopyridines and related compounds, their compositions and methods of modulating short-chain dehydrogenase activity (WO 2018/218251);—5—Preparation of alkylsulfinyl-, alkylsulfonyl- and alkylthio- thieno[2,3-b]pyridinamines as inhibitors of short-chain dehydrogenase activity for promoting neurogenesis and inhibiting nerve cell death (WO 2018/017582);—6—Preparation of thienopyridine compounds having sulfur-containing substituent as inhibitors of short-chain dehydrogenase activity for treating fibrosis (WO 2016/144958).
CAS SciFinder Search Result on Jan. 27, 2022, at 7:47 pm (2 results)—1—Preparation of thienopyridines and similar bicyclic heterocyclic compounds as modulators of 15-hydroxyprostaglandin dehydrogenase type I for therapy (WO 2015/065716);—2—Preparation of thienopyridines and related compounds, their compositions and methods of modulating short-chain dehydrogenase activity (WO 2018/218251).
CAS SciFinder Search Result on Jan. 27, 2022, at 7:50 pm (2 results)—1—Preparation of thienopyridines and similar bicyclic heterocyclic compounds as modulators of 15-hydroxyprostaglandin dehydrogenase type I for therapy;—2—Preparation of thienopyridines and related compounds, their compositions and methods of modulating short-chain dehydrogenase activity.
CAS SciFinder Search Result on Jan. 27, 2022, at 7:52 pm (2 results)—1—Preparation of thienopyridines and related compounds, their compositions and methods of modulating short-chain dehydrogenase activity (WO 2015/065716);—2—Preparation of thienopyridines and similar bicyclic heterocyclic compounds as modulators of 15-hydroxyprostaglandin dehydrogenase type I for therapy (WO 2018/218251).
CAS SciFinder Search Result on Jan. 27, 2022, at 7:55 pm (2 results)—1—Preparation of thienopyridines and related compounds, their compositions and methods of modulating short-chain dehydrogenase activity (WO 2018/218251);—2—Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 3:28 pm (0 results).
NCBI Database Accession No. CID 654955 [online database], create date Jun. 4, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 1826991 [online database], create date Jul. 12, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 3337838 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337839 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337991 [online database], create date Sep. 7, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 3337992 [online database], create date Sep. 7, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 3337993 [online database], create date Sep. 7, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 3337994 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337995 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337996 [online database], create date Sep. 7, 2005, modify date Sep. 10, 2022, [retrieved on Sep. 16, 2022], Retrieved from PubChem <https://pubchem.ncbi.nlm.nih.gov>, compound summary printed to pdf.
NCBI Database Accession No. CID 3337997 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337998 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 46864148 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 52943190 [online database], create date Jun. 16, 2011, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 72188203 [online database], create date Dec. 9, 2013, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 72188204 [online database], create date Dec. 9, 2013, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 92272562 [online database], create date Dec. 10, 2015, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 92272564 [online database], create date Dec. 10, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118050369 [online database], create date Feb. 23, 2016, modify date Sep. 10, 2022, [retrieved on

(56) References Cited

OTHER PUBLICATIONS

Sep. 15, 2022], Retrieved from PubChem <https://pubchem.ncbi.nlm.nih.gov>, compound summary printed to pdf.
NCBI Database Accession No. CID 118050655 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118050656 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118050707 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118050770 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118050833 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118050838 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118050952 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118051074 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118051078 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118059027 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118059055 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118059089 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118059090 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118059098 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 122624302 [online database], create date Dec. 8, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 123677271 [online database], create date Jan. 25, 2017, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 129266585 [online database], create date Aug. 4, 2017, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 129266602 [online database], create date Aug. 4, 2017, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 130296193 [online database], create date Oct. 7, 2017, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 130296194 [online database], create date Oct. 7, 2017, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 132012504 [online database], create date Jan. 29, 2018, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 134314069 [online database], create date Jun. 23, 2018, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 134474501 [online database], create date Jun. 23, 2018, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 134576829 [online database], create date Jun. 23, 2018, modify date Sep. 10, 2022, [retrieved on Sep. 16, 2022], Retrieved from PubChem <https://pubchem.ncbi.nlm.nih.gov>, compound summary printed to pdf.
NCBI Database Accession No. CID 135387726 [online database], create date Dec. 15, 2018, modify date Sep. 10, 2022, [retrieved on Sep. 16, 2022], Retrieved from PubChem <https://pubchem.ncbi.nlm.nih.gov>, compound summary printed to pdf.
NCBI Database Accession No. CID 135387830 [online database], create date Dec. 15, 2018, modify date Sep. 10, 2022, [retrieved on Sep. 16, 2022], Retrieved from PubChem <https://pubchem.ncbi.nlm.nih.gov>, compound summary printed to pdf.
NCBI Database Accession No. CID 139476465 [online database], create date Nov. 2, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 142484843 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 142485754 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 142485836 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 142485845 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 142485847 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 142485863 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 142485864 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 142485868 [online database], create date Dec. 6, 2019, modify date Sep. 17, 2022, [retrieved on

(56) References Cited

OTHER PUBLICATIONS

Sep. 19, 2022], Retrieved from PubChem <https://pubchem.ncbi.nlm.nih.gov>, compound summary printed to pdf.
NCBI Database Accession No. CID 142485879 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 142485896 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 142485929 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 142485938 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 142485953 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 142485954 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 144839639 [online database], create date Dec. 7, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 145656773 [online database], create date Dec. 12, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 145656809 [online database], create date Dec. 12, 2019, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 146410683 [online database], create date Jun. 27, 2020, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 146580152 [online database], create date Jun. 27, 2020, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 146580711 [online database], create date Jun. 27, 2020, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 146602898 [online database], create date Jun. 27, 2020, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 146602900 [online database], create date Jun. 27, 2020, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 146731064 [online database], create date Aug. 12, 2020, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 146835156 [online database], create date Aug. 12, 2020, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 147432252 [online database], create date Aug. 12, 2020, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 147594754 [online database], create date Aug. 12, 2020, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 148490795 [online database], create date Aug. 12, 2020, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 149178699 [online database], create date Aug. 12, 2020, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 152798992 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596863 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596870 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596898 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596904 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596919 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596924 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596928 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596948 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596953 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596968 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596975 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597016 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597047 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597069 [online database], create date Aug. 13, 2020, modify date Sep. 17, 2022, [retrieved on

(56) References Cited

OTHER PUBLICATIONS

Sep. 22, 2022], Retrieved from PubChem <https://pubchem.ncbi.nlm.nih.gov>, compound summary printed to pdf.
NCBI Database Accession No. CID 153597090 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597104 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597123 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597128 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597141 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597150 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597177 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597180 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597205 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597208 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597214 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597233 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 155786794 [online database], create date Feb. 22, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 156156400 [online database], create date Aug. 21, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 156837702 [online database], create date Nov. 10, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 156837721 [online database], create date Nov. 10, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 156837722 [online database], create date Nov. 10, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 156837731 [online database], create date Nov. 10, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 156837741 [online database], create date Nov. 10, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 156837742 [online database], create date Nov. 10, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157158417 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157167058 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157167059 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157167060 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157213480 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157216800 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157257517 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157294602 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157302941 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157386272 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157400808 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157440570 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157440572 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157456496 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157498212 [online database], create date Dec. 3, 2021, modify date Sep. 17, 2022, [retrieved on

(56) References Cited

OTHER PUBLICATIONS

Sep. 22, 2022], Retrieved from PubChem <https://pubchem.ncbi.nlm.nih.gov>, compound summary printed to pdf.
NCBI Database Accession No. CID 157526683 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157600443 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157604959 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157688874 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157717185 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157767490 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157848053 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157864542 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157864543 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157872044 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157901254 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157944805 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157949758 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 157955983 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158049978 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158088730 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158134580 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158145130 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158221946 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158221947 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158258231 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158329834 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158370045 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158404656 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158415066 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158432471 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158531185 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158540614 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158568511 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158628602 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158653266 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158660366 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158784514 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158829687 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158910891 [online database], create date Dec. 3, 2021, modify date Sep. 17, 2022, [retrieved on

(56) References Cited

OTHER PUBLICATIONS

Sep. 22, 2022], Retrieved from PubChem <https://pubchem.ncbi.nlm.nih.gov>, compound summary printed to pdf.
NCBI Database Accession No. CID 159056851 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159130668 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159144809 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159154352 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159191585 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159215478 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159233281 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159233282 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159474011 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159590113 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159820000 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159891397 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 160071422 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 160071423 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 160155004 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 160156242 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 161100344 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 162062070 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 162728470 [online database], create date Apr. 5, 2022, modify date Sep. 17, 2022, [retrieved on Sep. 22, 2022], Retrieved from PubChem <https://pubchem.ncbi.nlm.nih.gov>, compound summary printed to pdf.

COMPOSITIONS AND METHODS OF MODULATING SHORT-CHAIN DEHYDROGENASE

RELATED APPLICATION

This application is a U.S. national stage application under 35 U.S.C. § 371 of International Application No. PCT/US2018/017044, filed Feb. 6, 2018, which in turn claims priority from U.S. Provisional Application Nos. 62/455,399, filed Feb. 6, 2017, and 62/510,589, filed May 24, 2017, the subject matter of which are incorporated herein by reference in their entirety.

GOVERNMENT FUNDING

This invention was made with government support under Grant No. CA150964 awarded by The National Institutes of Health. The government has certain rights in the invention.

BACKGROUND

Short-chain dehydrogenases (SCDs) are a family of dehydrogenases that share only 15% to 30% sequence identity, with similarity predominantly in the coenzyme binding domain and the substrate binding domain. In addition to their role in detoxification of ethanol, SCDs are involved in synthesis and degradation of fatty acids, steroids, and some prostaglandins, and are therefore implicated in a variety of disorders such as lipid storage disease, myopathy, SCD deficiency, and certain genetic disorders.

The SCD, 15-hydroxy-prostaglandin dehydrogenase (15-PGDH), (hydroxyprostaglandin dehydrogenase 15-(nicotinamide adeninedinucleotide); 15-PGDH; Enzyme Commission number 1.1.1.141; encoded by the HPGD gene), represents the key enzyme in the inactivation of a number of active prostaglandins, leukotrienes and hydroxyeicosatetraenoic acids (HETEs) (e.g., by catalyzing oxidation of $PGE_2$ to 15-keto-prostaglandin E2, 15k-PGE). The human enzyme is encoded by the HPGD gene and consists of a homodimer with subunits of a size of 29 kDa. The enzyme belongs to the evolutionarily conserved superfamily of short-chain dehydrogenase/reductase enzymes (SDRs), and according to the recently approved nomenclature for human enzymes, it is named SDR36C1. Thus far, two forms of 15-PGDH enzyme activity have been identified, NAD+-dependent type I 15-PGDH that is encoded by the HPGD gene, and the type II NADP-dependent 15-PGDH, also known as carbonyl reductase 1 (CBR1, SDR21C1). However, the preference of CBR1 for NADP and the high Km values of CBR1 for most prostaglandin suggest that the majority of the in vivo activity can be attributed to type I 15-PGDH encoded by the HPGD gene, that hereafter, and throughout all following text, simply denoted as 15-PGDH.

Recent studies suggest that inhibitors of 15-PGDH could be therapeutically valuable. A recent study implicates increased 15-PGDH expression in the protection of thrombin-mediated cell death. It is well known that 15-PGDH is responsible for the inactivation of prostaglandin E2 ($PGE_2$), which is a downstream product of COX-2 metabolism. $PGE_2$ has been shown to be beneficial in a variety of biological processes, such as hair density, dermal wound healing, and bone formation. Recent work has shown that inhibitors of 15-PGDH promote tissue regeneration and wound healing in multiple tissues.

SUMMARY

Embodiments described herein relate to compounds and methods of modulating short chain dehydrogenase (SCD) (e.g., 15-PGDH) activities, modulating tissue prostaglandin levels, and/or treating diseases, disorders, or conditions in which it is desired to modulate SCD (e.g., 15-PGDH) activity and/or prostaglandin levels.

In some embodiments, the modulator of SCD can be an SCD inhibitor that can be administered to tissue or blood of a subject at an amount effective to inhibit the activity of a SCD enzyme. The SCD inhibitor can be a 15-PGDH inhibitor that can be administered to tissue or blood of a subject at an amount effective to increase prostaglandin levels in the tissue or blood. The 15-PGDH inhibitor can include a compound having at least one of the following formulas:

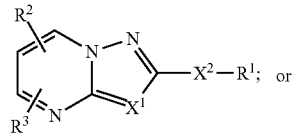

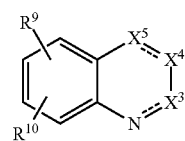

wherein $X^1$ is N or $CR^4$;

$X^2$ is S, S=O, S(=O)$_2$, or C=O;

$X^3$ is $CR^8$ (the compound forming a polycyclic heteroaryl with 10 ring atoms) or absent (the compound forming a polycyclic heteroaryl with 9 ring atoms);

$X^4$ is N, NH, or $CR^7$;

$X^5$ is N, C=O, or $CR^{16}$; and $X^5$ is N if $X^4$ is $CR^7$ or $X^3$ is absent; $X^4$ is NH if $X^5$ is C=O; and $X^5$ is $CR^{16}$ if $X^4$ is N and $X^3$ is $CR^8$;

$R^1$, $R^2$, $R^3$, $R^4$, $R^9$, $R^{10}$, and $R^{16}$ are the same or different and are independently selected from the group consisting of hydrogen, oxygen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-7 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$N (R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof;

$R^7$ and $R^8$ are same or different and are each independently selected from the group consisting of H, a substituted or unsubstituted aryl, a substituted or unsubstituted heteroaryl, a substituted or unsubstituted cycloalkyl, and a substituted or unsubstituted heterocyclyl, and at least one of $R^7$ or $R^8$ is not H; and pharmaceutically acceptable salts thereof.

In some embodiments, at least one of $R^2$ or $R^3$ is not H, and at least one of $R^9$ or $R^{10}$ is not H.

In some embodiments, the 15-PGDH inhibitor can inhibit the enzymatic activity of recombinant 15-PGDH at an $IC_{50}$ of less than 1 µM, or preferably at an $IC_{50}$ of less than 250 nM, or more preferably at an $IC_{50}$ of less than 50 nM, or more preferably at an $IC_{50}$ of less than 10 nM, or more preferably at an $IC_{50}$ of less than 5 nM at a recombinant 15-PGDH concentration of about 5 nM to about 10 nM.

The 15-PGDH inhibitor can be provided in a topical composition that can be applied to skin of a subject to promote and/or stimulate pigmentation of the skin and/or hair growth and/or inhibiting hair loss, and/or treat skin damage or inflammation.

The 15-PGDH inhibitor can also be administered to a subject to promote wound healing, tissue repair, and/or tissue regeneration and/or engraftment or regeneration of a tissue graft.

In one embodiment, the 15-PGDH inhibitor can be administered to a subject to treat at least one of oral ulcers, gum disease, colitis, ulcerative colitis, gastrointestinal ulcers, inflammatory bowel disease, vascular insufficiency, Raynaud's disease, Buerger's disease, diabetic neuropathy, pulmonary artery hypertension, cardiovascular disease, and renal disease.

In another embodiment, the 15-PGDH inhibitor can be administered to a subject in combination with a prostanoid agonist for the purpose of enhancing the therapeutic effect of the agonist in prostaglandin responsive conditions.

In other embodiments, the 15-PGDH inhibitor can be administered to a subject and/or tissue of the subject to increase tissue stem cells. For example, the 15-PGDH inhibitor can be administered to bone marrow of a subject to increase stem cells in the subject.

In still other embodiments, the 15-PGDH inhibitor can be administered to a tissue graft donor, bone marrow graft donor, and/or a hematopoietic stem cell donor, and/or a tissue graft, and/or a bone marrow graft, and/or a hematopoietic stem cell graft, to increase the fitness of a donor tissue graft, a donor bone marrow graft, and/or a donor hematopoietic stem cell graft. For example, the 15-PGDH inhibitor can be administered to a subject, and/or bone marrow of a subject to increase the fitness of the marrow as a donor graft, and/or to a preparation of hematopoietic stem cells of a subject to increase the fitness of the stem cell preparation as a donor graft, and/or to a preparation of peripheral blood hematopoietic stem cells of a subject to increase the fitness of the stem cell preparation as a donor graft, and/or to a preparation of umbilical cord blood stem cells to increase the fitness of the stem cell preparation as a donor graft, and/or to a preparation of umbilical cord blood stem cells to decrease the number of units of umbilical cord blood required for transplantation.

In other embodiments, the 15-PGDH inhibitor can be administered to a subject to mitigate tissue graft rejection, to enhance tissue and/or bone marrow graft engraftment (e.g., following treatment of the subject or the marrow of the subject with radiation therapy, chemotherapy, or immunosuppressive therapy) to enhance engraftment of a progenitor stem cell graft, hematopoietic stem cell graft, or an umbilical cord blood stem cell graft, to enhance engraftment of a hematopoietic stem cell graft, or an umbilical cord stem cell graft (e.g., following treatment of the subject or the marrow of the subject with radiation therapy, chemotherapy, or immunosuppressive therapy) and/or in order to decrease the number of units of umbilical cord blood required for transplantation into the subject.

In other embodiments, the 15-PGDH inhibitor can be administered to a recipient of a tissue graft transplant, bone marrow transplant, and/or hematopoietic stem cell transplant, or of an umbilical cord stem cell transplant, in order to decrease the administration of other treatments or growth factors.

In some embodiments, the 15-PGDH inhibitor can be administered to a subject or to a tissue graft of a subject to mitigate graft rejection, and/or to enhance graft engraftment (e.g., following treatment of the subject or the marrow of the subject with radiation therapy, chemotherapy, or immunosuppressive therapy).

In other embodiments, the 15-PGDH inhibitor can be administered to a subject or to the bone marrow of a subject to confer resistance to toxic or lethal effects of exposure to radiation, to confer resistance to the toxic effect of Cytoxan, the toxic effect of fludarabine, the toxic effect of chemotherapy, or the toxic effect of immunosuppressive therapy, to decrease pulmonary toxicity from radiation, and/or to decrease infection.

In still other embodiments, the 15-PGDH inhibitor can be administered to a subject to increase neutrophil counts following a hematopoetic cell transplant with bone marrow, hematopoetic stem cells, or umbilical cord blood, to increase neutrophil counts in a subject with neutropia following chemotherapy administration or radiation therapy, to increase neutrophil counts in a subject with aplastic anemia, myelodysplasia, myelofibrosis, neutropenia due to other bone marrow diseases, drug induced neutropenia, autoimmune neutropenia, idiopathic neutropenia, or neutropenia following viral infections, to increase neutrophil counts in a subject with neutropia, to increase platelet counts following a hematopoetic cell transplant with bone marrow, hematopoetic stem cells, or umbilical cord blood, to increase platelet counts in a subject with thrombocytopenia following chemotherapy administration or radiation therapy, to increase platelet counts in a subject with aplastic anemia, myelodysplasia, myelofibrosis, thrombocytopenia due to other bone marrow diseases, drug induced thrombocytopenia, autoimmune thrombocytopenia, idiopathic thrombocytopenic purpura, idiopathic thrombocytopenia, or thrombocytopenia following viral infections, to increase platelet counts in a subject with thrombocytopenia, to increase red blood cell counts, or hematocrit, or hemoglobin level, following a hematopoetic cell transplant with bone marrow, hematopoetic stem cells, or umbilical cord blood, to increase red blood cell counts, or hematocrit, or hemoglobin level in a subject with anemia following chemotherapy administration or radiation therapy, to increase red blood cell counts, or hematocrit, or hemoglobin level counts in a subject with aplastic anemia, myelodysplasia, myelofibrosis, anemia due to other disorder of bone marrow, drug induced anemia, immune mediated anemias, anemia of chronic disease, anemia following viral infections, or anemia of unknown cause, to increase red blood cell counts, or hematocrit, or hemoglobin level in a subject with anemia, to increase bone marrow stem cells, following a hematopoetic cell transplant with bone marrow, hematopoetic stem cells, or umbilical cord blood, to increase bone marrow stem cells in a subject following chemotherapy administration or radiation therapy, and/or to increase bone marrow stem cells in a subject with aplastic anemia, myelodysplasia, myelofibrosis, other disorder of bone marrow, drug induced cytopenias, immune cytopenias, cytopenias following viral infections, or cytopenias.

In other embodiments, the administration of a 15-PGDH inhibitor can be used to modulate hematopoietic stem cells and hematopoiesis. For a 15-PGDH inhibitor can be administered alone or in combination with a cytokine to a subject in need thereof to increase and/or mobilize hematopoietic stem cells and/or neutrophils in the blood, marrow, and/or tissue of the subject.

In some embodiments, the administration of a 15-PGDH inhibitor can be in combination with G-CSF for the purpose of increasing neutrophils.

In other embodiments, the administration of a 15-PGDH inhibitor can be in combination with a hematopoietic cytokine for the purpose of increasing neutrophils.

In still other embodiments, the administration of a 15-PGDH inhibitor can be in combination with G-CSF for the purpose of increasing numbers of and/or of mobilizing peripheral blood hematopoietic stem cells.

In other embodiments, the administration of a 15-PGDH inhibitor can be in combination with a hemopoietic cytokine for the purpose of increasing numbers of and/or of mobilizing peripheral blood hematopoietic stem cells.

In some embodiments, the administration of a 15-PGDH inhibitor can be in combination with a second agent, including Plerixafor, for the purpose of increasing numbers of and/or of mobilizing peripheral blood hematopoietic stem cells.

In other embodiments, the administration of a 15-PGDH inhibitor can be in combination with G-CSF for the purpose of increasing numbers of and/or of mobilizing peripheral blood hematopoietic stem cells for use in hematopoietic stem cell transplantation.

In still other embodiments, the administration of a 15-PGDH inhibitor can be in combination with a hemopoietic cytokine for the purpose of increasing numbers of and/or of mobilizing peripheral blood hematopoietic stem cells for use in hematopoietic stem cell transplantation.

In other embodiments, the administration of a 15-PGDH inhibitor can be in combination with a second agent, including Plerixafor, for the purpose of increasing numbers of and/or of mobilizing peripheral blood hematopoietic stem cells for use in hematopoietic stem cell transplantation.

In still other embodiments, the administration of a 15-PGDH inhibitor can be in combination with G-CSF for the purpose of increasing numbers of hematopoietic stem cells in blood or bone marrow.

In other embodiments, the administration of a 15-PGDH inhibitor can be in combination with a hemopoietic cytokine for the purpose of increasing numbers of hematopoietic stem cells in blood or bone marrow.

In other embodiments, the 15-PGDH inhibitor can be administered to a subject and/or tissue of the subject to increase tissue stem cells. For example, the 15-PGDH inhibitor can be administered to bone marrow of a subject to increase stem cells in the subject.

In still other embodiments, the 15-PGDH inhibitor can be administered to a tissue graft donor, bone marrow graft donor, and/or a hematopoietic stem cell donor, and/or a tissue graft, and/or a bone marrow graft, and/or a hematopoietic stem cell graft, to increase the fitness of a donor tissue graft, a donor bone marrow graft, and/or a donor hematopoietic stem cell graft. For example, the 15-PGDH inhibitor can be administered to a subject, and/or bone marrow of a subject to increase the fitness of the marrow as a donor graft, and/or to a preparation of hematopoietic stem cells of a subject to increase the fitness of the stem cell preparation as a donor graft, and/or to a preparation of peripheral blood hematopoietic stem cells of a subject to increase the fitness of the stem cell preparation as a donor graft, and/or to a preparation of umbilical cord blood stem cells to increase the fitness of the stem cell preparation as a donor graft, and/or to a preparation of umbilical cord blood stem cells to decrease the number of units of umbilical cord blood required for transplantation.

In other embodiments, the 15-PGDH inhibitor can be administered to a recipient of a tissue graft transplant, bone marrow transplant, and/or hematopoietic stem cell transplant, or of an umbilical cord stem cell transplant, in order to decrease the administration of other treatments or growth factors.

In other embodiments, the 15-PGDH inhibitor can be administered to a subject to increase responsiveness to cytokines in the presence of cytopenias including any of: neutropenia, thrombocytopenia, lymphocytopenia and anemia; and with cytokines having increased responsiveness potentiated by the 15-PGDH inhibitor including any of: G-CSF, GM-CSF, EPO, IL-3, IL-6, TPO, TPO-RA (thrombopoietin receptor agonist), and SCF.

In some embodiments, the 15-PGDH inhibitor can be administered to a subject to increase bone density, treat osteoporosis, promote healing of fractures, or promote healing after bone surgery or joint replacement and/or to promote healing of bone to bone implants, bone to artificial implants, dental implants, and bone grafts.

In other embodiments, the 15-PGDH inhibitor can be administered to a subject or to the intestine of a subject to increase stem cells or cell proliferation in the intestine and/or and confer resistance to toxic or lethal effects of exposure to radiation or the toxic, lethal, or mucositis effects resultant from treatment with chemotherapy.

In some embodiments, the 15-PGDH inhibitor can be administered to a subject or to intestine of a subject as a treatment for colitis, ulcerative colitis, or inflammatory bowel disease.

In other embodiments, the 15-PGDH inhibitor can be administered to a subject to increase liver regeneration following liver surgery, following live liver donation, following liver transplantation, or following liver injury by toxins and/or to promote recovery from or resistance to liver toxins, including acetaminophen and related compounds.

In still other embodiments, the 15-PGDH inhibitor can be administered to a subject to treat erectile dysfunction.

In yet other embodiments, the 15-PGDH inhibitor can be administered to inhibit at least one of the growth, proliferation, or metastasis of 15-PGDH expressing cancers.

Still other embodiments described herein relate to a method of treating a subject in need of cell therapy. The method includes administering to the subject a therapeutically effective amount of a preparation comprising human hematopoietic stem cell administered a 15-PGDH inhibitor described herein and/or a therapeutic composition comprising human hematopoietic stem cells and a 15-PGDH inhibitor described herein.

In some embodiments, the subject has received human hematopoietic stem cells and/or has received the preparation and/or the therapeutic composition.

In other embodiments, the subject has acute myelogenous leukemia (AML), acute lymphoblastic leukemia (ALL), chronic myelogenous leukemia (CML), chronic lymphocytic leukemia (CLL), juvenile myelomonocytic leukemia, Hodgkin's lymphoma, non-Hodgkin's lymphoma, multiple myeloma, severe aplastic anemia, Fanconi's anemia, paroxysmal nocturnal hemoglobinuria (PNH), pure red cell aplasia, amegakaryocytosis/congenital thrombocytopenia, severe combined immunodeficiency syndrome (SCID), Wiskott-Aldrich syndrome, β-thalassemia major, sickle cell disease, Hurler's syndrome, adrenoleukodystrophy, metachromatic leukodystrophy, myelodysplasia, refractory anemia, chronic myelomonocytic leukemia, agnogenic myeloid metaplasia, familial erythrophagocytic lymphohistiocytosis, solid tumors, chronic granulomatous disease, mucopolysaccharidoses, or Diamond Blackfan anemia.

Other embodiments relate to a method of treating a subject having at least one symptom associated with an ischemic tissue or a tissue damaged by ischemia. The method includes administering to the subject a therapeutically effective amount of a preparation comprising human hematopoietic stem cells administered a 15-PGDH inhibitor described herein and/or a therapeutic composition comprising human hematopoietic stem cells and a 15-PGDH inhibitor described herein.

In some embodiments, the ischemia can be associated with at least one of acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

Other embodiments relate to methods for treating and/or preventing fibrosis and various fibrotic diseases, disorders or conditions by administration of 15-PGDH inhibitors. In some embodiments, a 15-PGDH inhibitor described herein can be administered to a subject in need thereof to decrease fibrotic symptoms, such as collagen deposition, inflammatory cytokine expression, and inflammatory cell infiltration, and treat and/or prevent various fibrotic diseases, disorders, and conditions characterized, in whole or in part, by the excess production of fibrous material, including excess production of fibrotic material within the extracellular matrix, or the replacement of normal tissue elements by abnormal, non-functional, and/or excessive accumulation of matrix-associated components.

Fibrotic diseases, disorders and conditions characterized, in whole or in part, by excess production of fibrotic material can include systemic sclerosis, multifocal fibrosclerosis, nephrogenic systemic fibrosis, scleroderma (including morphea, generalized morphea, or linear scleroderma), sclerodermatous graft-vs-host-disease, kidney fibrosis (including glomerular sclerosis, renal tubulointerstitial fibrosis, progressive renal disease or diabetic nephropathy), cardiac fibrosis (e.g., myocardial fibrosis), pulmonary fibrosis (e.g., glomerulosclerosis pulmonary fibrosis, idiopathic pulmonary fibrosis, silicosis, asbestosis, interstitial lung disease, interstitial fibrotic lung disease, and chemotherapy/radiation induced pulmonary fibrosis), oral fibrosis, endomyocardial fibrosis, deltoid fibrosis, pancreatitis, inflammatory bowel disease, Crohn's disease, nodular fasciitis, eosinophilic fasciitis, general fibrosis syndrome characterized by replacement of normal muscle tissue by fibrous tissue in varying degrees, retroperitoneal fibrosis, liver fibrosis, liver cirrhosis, chronic renal failure; myelofibrosis (bone marrow fibrosis), drug induced ergotism, glioblastoma in Li-Fraumeni syndrome, sporadic glioblastoma, myleoid leukemia, acute myelogenous leukemia, myelodysplastic syndrome, myeloproliferative syndrome, gynecological cancer, Kaposi's sarcoma, Hansen's disease, collagenous colitis, acute fibrosis, organ specific fibrosis, and the like.

In some embodiments, a method of treating or preventing a fibrotic disease, disorder or condition includes administering to a subject in need thereof a therapeutically effect amount of a 15-PGDH inhibitor.

In some embodiments, the 15-PGDH inhibitors can be used to treat or prevent lung fibrosis. Lung fibrosis, which can be treated, can be selected from the group consisting of pulmonary fibrosis, pulmonary hypertension, chronic obstructive pulmonary disease (COPD), asthma, idiopathic pulmonary fibrosis, sarcoidosis, cystic fibrosis, familial pulmonary fibrosis, silicosis, asbestosis, coal worker's pneumoconiosis, carbon pneumoconiosis, hypersensitivity pneumonitides, pulmonary fibrosis caused by inhalation of inorganic dust, pulmonary fibrosis caused by an infectious agent, pulmonary fibrosis caused by inhalation of noxious gases, aerosols, chemical dusts, fumes or vapors, drug-induced interstitial lung disease, or pulmonary hypertension, and combinations thereof.

In other embodiments, the 15-PGDH inhibitors can be used to treat or prevent kidney fibrosis. The kidney fibrosis can result from dialysis following kidney failure, catheter placement, a nephropathy, glomerulosclerosis, glomerulonephritis, chronic renal insufficiency, acute kidney injury, end stage renal disease or renal failure, or combinations thereof.

In other embodiments, the 15-PGDH inhibitors can be used to treat or prevent liver fibrosis. The liver fibrosis can result from a chronic liver disease, viral induced hepatic cirrhosis, hepatitis B virus infection, hepatitis C virus infection, hepatitis D virus infection, schistosomiasis, primary biliary cirrhosis, alcoholic liver disease or non-alcoholic steatohepatitis (NASH), NASH associated cirrhosis obesity, diabetes, protein malnutrition, coronary artery disease, autoimmune hepatitis, cystic fibrosis, alpha-1-antitrypsin deficiency, primary biliary cirrhosis, drug reaction and exposure to toxins, or combinations thereof.

In some embodiments, the 15-PGDH inhibitors can be used to treat or prevent heart fibrosis, for example, cardiac fibrosis and endomyocardial fibrosis.

In some embodiments, the 15-PGDH inhibitors can be used to treat or prevent systemic sclerosis.

In some embodiments, the 15-PGDH inhibitors can be used to treat or prevent fibrotic diseases, disorders or conditions caused by post-surgical adhesion formation.

In some embodiments, the 15-PGDH inhibitors can be used for reducing or preventing scar formation in a subject.

In other embodiments, the 15-PGDH inhibitors can be used to reduce or prevent scar formation on skin or scleroderma.

In various embodiments, the 15-PGDH inhibitors can be administered at a therapeutically effective amount such that at least one symptom or feature of a fibrotic disease, disorder or condition, or other related diseases, disorders or conditions, is reduced in intensity, severity, or frequency, or has delayed onset.

In other embodiments, the 15-PGDH inhibitors can be used in a method for decreasing or reducing collagen secretion or collagen deposition in a tissue or organ, such as the lung, the liver, the intestines, the colon, the skin or the heart, of a subject. The method can include administering a therapeutically effective amount of the 15-PGDH inhibitors to the subject in need thereof. The subject can have or be at risk of an excessive collagen secretion or collagen deposition in the tissue or organ, such as the kidney, the lung, the liver, the intestines, the colon, the skin or the heart. Usually, the excessive collagen secretion or collagen deposition in an organ results from an injury or an insult. Such injury and insult can be organ-specific. The 15-PGDH inhibitors can be administered over a sufficient period of time to decrease or reduce the level of collagen deposition in the tissue or organ, completely or partially. A sufficient period of time can be during one week, or between 1 week to 1 month, or between 1 to 2 months, or 2 months or more. For chronic condition, the 15-PGDH inhibitors can be advantageously administered for life time period.

In other embodiments, the 15-PGDH inhibitors described herein, can promote neuroprotection in a subject from axonal degeneration, neuronal cell death, and/or glia cell damage after injury, augment neuronal signaling underlying learning and memory, stimulate neuronal regeneration after injury, and/or treat diseases, disorders, and/or conditions of the nervous system.

In some embodiments, the disease, disorder, and/or condition of the nervous system that can be treated with the 15-PGDH inhibitors can include at least one of a neurological disorder, neuropsychiatric disorder, neural injury, neural toxicity disorder, a neuropathic pain, and neural degenerative disorders.

For example, the neurological disorder can include at least one of traumatic or toxic injuries to peripheral or cranial nerves, spinal cord or to the brain, cranial nerves, traumatic brain injury, stroke, cerebral aneurism, and spinal cord injury. The neurological disorder can also include at least one of Alzheimer's disease, dementias related to Alzheimer's disease, Parkinson's, Lewy diffuse body diseases, senile dementia, Huntington's disease, Gilles de la Tourette's syndrome, multiple sclerosis, amyotrophic lateral sclerosis, hereditary motor and sensory neuropathy, diabetic neuropathy, progressive supranuclear palsy, epilepsy, or Jakob-Creutzfieldt disease.

In some embodiments, the neural injury can be caused by or associated with at least one of epilepsy, cerebrovascular diseases, autoimmune diseases, sleep disorders, autonomic disorders, urinary bladder disorders, abnormal metabolic states, disorders of the muscular system, infectious and parasitic diseases neoplasms, endocrine diseases, nutritional and metabolic diseases, immunological diseases, diseases of the blood and blood-forming organs, mental disorders, diseases of the nervous system, diseases of the sense organs, diseases of the circulatory system, diseases of the respiratory system, diseases of the digestive system, diseases of the genitourinary system, diseases of the skin and subcutaneous tissue, diseases of the musculoskeletal system and connective tissue, congenital anomalies, or conditions originating in the perinatal period.

In certain embodiments, the 15-PGDH inhibitors can be administered to a subject or neurons of the subject to promote the survival, growth, development and/or function of the neurons, particularly CNS, brain, cerebral, and hippocampal neurons. In certain embodiments, the 15-PGDH inhibitors can be used stimulate hippocampal neurogenesis, for the treatment of neuropsychiatric and neurodegenerative diseases, including (but not limited to) schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, and abuse of neuro-active drugs, such as alcohol, opiates, methamphetamine, phencyclidine, and cocaine.

DETAILED DESCRIPTION

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g. sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n-1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl)ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and al kylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate. The term sulfoxide refers to a sulfur attached to 2 different carbon atoms and one oxygen and the S—O bond can be graphically represented with a double bond (S=O), a single bond without charges (S—O) or a single bond with charges [S(+)—O(−)].

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—N$^+$C$^-$), cyanato (—O—CN), isocyanato (—ON$^+$C$^-$), isothiocyanato (—S—CN), azido (—N=N$^+$=N$^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The term "neoplasm" refers to any abnormal mass of cells or tissue as a result of neoplasia. The neoplasm may be benign, potentially malignant (precancerous), or malignant (cancerous). An adenoma is an example of a neoplasm.

The terms "adenoma", "colon adenoma" and "polyp" are used herein to describe any precancerous neoplasm of the colon.

The term "colon" as used herein is intended to encompass the right colon (including the cecum), the transverse colon, the left colon and the rectum.

The terms "colorectal cancer" and "colon cancer" are used interchangeably herein to refer to any cancerous neoplasia of the colon (including the rectum, as defined above).

The terms "gene expression" or "protein expression" includes any information pertaining to the amount of gene transcript or protein present in a sample, as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information". Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

The terms "healthy" and "normal" are used interchangeably herein to refer to a subject or particular cell or tissue that is devoid (at least to the limit of detection) of a disease condition.

The term "nucleic acid" refers to polynucleotides such as deoxyribonucleic acid (DNA), and, where appropriate, ribonucleic acid (RNA). The term should also be understood to include analogues of either RNA or DNA made from nucleotide analogues, and, as applicable to the embodiment being described, single-stranded (such as sense or antisense) and double-stranded polynucleotides. In some embodiments, "nucleic acid" refers to inhibitory nucleic acids. Some categories of inhibitory nucleic acid compounds include antisense nucleic acids, RNAi constructs, and catalytic nucleic acid constructs. Such categories of nucleic acids are well-known in the art.

Embodiments described herein relate to compounds and methods of modulating SCD activity (e.g., 15-PGDH activity), modulating tissue prostaglandin levels, and/or treating diseases, disorders, or conditions in which it is desired to modulate 15-PGDH activity and/or prostaglandin levels.

"Inhibitors," "activators," and "modulators" of 15-PGDH expression or of 15-PGDH activity are used to refer to inhibitory, activating, or modulating molecules, respectively, identified using in vitro and in vivo assays for 15-PGDH expression or 15-PGDH activity, e.g., ligands, agonists, antagonists, and their homologs and mimetics. The term "modulator" includes inhibitors and activators. Inhibitors are agents that, e.g., inhibit expression of 15-PGDH or bind to, partially or totally block stimulation, decrease, prevent, delay activation, inactivate, desensitize, or down regulate the activity of 15-PGDH, e.g., antagonists. Activators are agents that, e.g., induce or activate the expression of a 15-PGDH or bind to, stimulate, stabilize, increase, open, activate, facilitate, or enhance activation, sensitize or up regulate the activity of 15-PGDH, e.g., agonists. Modulators include naturally occurring and synthetic ligands, small chemical molecules, and the like.

15-PGDH inhibitors described herein can provide a pharmacologic method for elevating prostaglandin levels in tissue. Known activities of prostaglandins include promoting hair growth, promoting skin pigmentation, and promoting skin darkening or the appearance of skin tanning. Known activities of prostaglandins also include ameliorating pulmonary artery hypertension. 15-PGDH inhibitors described herein may also be utilized to increase tissue stem cell numbers for purposes that would include increasing resistance to tissue damage by radiation, increasing resistance to environmental exposures to radiation, increasing stem cell numbers to increase fitness of bone marrow or other types of transplantation (through either in vivo exposure to 15-PGDH inhibitors described herein to increase stem cell numbers prior to harvest of a transplanted tissue, or through ex vivo exposure of a harvested tissue prior to transplant into a recipient host, or through treatment of the graft recipient). 15-PGDH inhibitors described herein may also be utilized for purposes that would include promoting liver regeneration, including liver regeneration after liver resection, and liver regeneration after toxic insults, which for example may be the toxic insult of acetaminophen overdose. Prostaglandin signaling is also known to promote wound healing, protect the stomach from ulceration, and promote healing of ulcers of stomach and intestines. Additionally, 15-PGDH inhibitors described herein can promote activity of human keratinocytes in "healing" scratches across cultures of keratinocyte cells. Hence, 15-PGDH inhibitors described herein may be utilized to also heal ulcers of other tissues, including, but not limited to skin, and including but not limited to diabetic ulcers. Further, 15-PGDH inhibitors described herein may be utilized for the treatment of erectile dysfunction.

15-PGDH inhibitors described herein can be identified using assays in which putative modulator compounds are applied to cells expressing 15-PGDH and then the functional effects on 15-PGDH activity are determined. Samples or assays comprising 15-PGDH that are treated with a potential activator, inhibitor, or modulator are compared to control samples without the inhibitor, activator, or modulator to examine the extent of effect. Control samples (untreated with modulators) are assigned a relative 15-PGDH activity value of 100%. Inhibition of 15-PGDH is achieved when the 15-PGDH activity value relative to the control is about 80%, optionally 50% or 25%, 10%, 5% or 1%.

Agents tested as modulators of SCD (e.g., 15-PGDH) can be any small chemical molecule or compound. Typically, test compounds will be small chemical molecules, natural products, or peptides. The assays are designed to screen large chemical libraries by automating the assay steps and providing compounds from any convenient source to assays, which are typically run in parallel (e.g., in microtiter formats on microtiter plates in robotic assays). Modulators also include agents designed to increase the level of 15-PGDH mRNA or the level of translation from an mRNA.

In some embodiments, the modulator of SCD can be an SCD inhibitor that can be administered to tissue or blood of a subject at an amount effective to inhibit the activity of a short chain dehydrogenase enzyme. The SCD inhibitor can be a 15-PGDH inhibitor that can be administered to tissue or blood of a subject at an amount effective to increase prostaglandin levels in the tissue or blood. The 15-PGDH inhibitor can include a compound having the formulas (I) or (II):

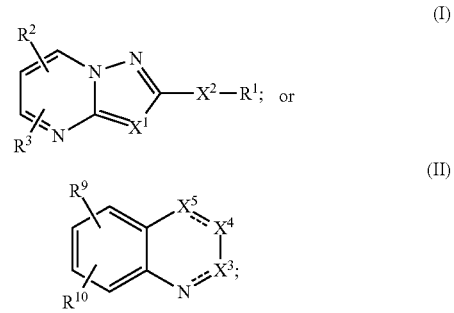

wherein $X^1$ is N or $CR^4$;
$X^2$ is S, S=O, S(=O)$_2$, or C=O;
$X^3$ is $CR^8$ (the compound forming a polycyclic heteroaryl with 10 ring atoms) or absent (the compound forming a polycyclic heteroaryl with 9 ring atoms);
$X^4$ is N, NH, or $CR^7$;
$X^5$ is N, C=O, or $CR^{16}$; and $X^5$ is N if $X^4$ is $CR^7$ or $X^3$ is absent; $X^4$ is NH if $X^5$ is C=O; and $X^5$ is $CR^{16}$ if $X^4$ is N and $X^3$ is $CR^8$;
$R^1$, $R^2$, $R^3$, $R^4$, $R^9$, $R^{10}$, and $R^{16}$ are the same or different and are independently selected from the group consisting of hydrogen, oxygen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-7 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$N (R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof;

R$^7$ and R$^8$ are same or different and are each independently selected from the group consisting of H, a substituted or unsubstituted aryl, a substituted or unsubstituted heteroaryl, a substituted or unsubstituted cycloalkyl, and a substituted or unsubstituted heterocyclyl, and at least one of R$^7$ or R$^8$ is not H; and pharmaceutically acceptable salts thereof.

In some embodiments, at least one of R$^2$ or R$^3$ is not H, and at least one of R$^9$ or R$^{10}$ is not H.

In some embodiments, the 15-PGDH inhibitor can include a compound having the following formula (Ia):

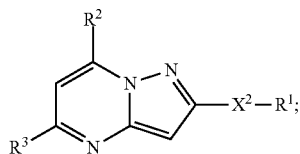

(Ia)

wherein X$^2$ is S, S=O, S(=O)$_2$, or C=O;

each R$^1$, R$^2$, and R$^3$ are the same or different and are independently selected from the group consisting of hydrogen, substituted or unsubstituted C$_1$-C$_{24}$ alkyl, C$_2$-C$_{24}$ alkenyl, C$_2$-C$_{24}$ alkynyl, C$_3$-C$_{20}$ aryl, heterocycloalkenyl containing from 5-7 ring atoms, (wherein from 1-3 of the ring atoms is independently selected from N, NH, N(C$_1$-C$_6$ alkyl), NC(O) (C$_1$-C$_6$ alkyl), O, and S), heteroaryl or heterocyclyl containing from 5-14 ring atoms, (wherein from 1-6 of the ring atoms is independently selected from N, NH, N(C$_1$-C$_3$ alkyl), O, and S), C$_6$-C$_{24}$ alkaryl, C$_6$-C$_{24}$ aralkyl, halo, silyl, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl (including C$_2$-C$_{24}$ alkylcarbonyl (—CO-alkyl) and C$_6$-C$_{20}$ arylcarbonyl (—CO-aryl)), acyloxy (—O-acyl), C$_2$-C$_{24}$ alkoxycarbonyl (—(CO)—O-alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO$^-$), carbamoyl (—(CO)—NH$_2$), C$_1$-C$_{24}$ alkyl-carbamoyl (—(CO)—NH(C$_1$-C$_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), C$_1$-C$_{24}$ alkyl amino, C$_5$-C$_{20}$ aryl amino, C$_2$-C$_{24}$ alkylamido (—NH—(CO)-alkyl), C$_6$-C$_{20}$ arylamido (—NH—(CO)-aryl), sulfanamido (—SO$_2$N(R)$_2$ where R is independently H, alkyl, aryl or heteroaryl), imino (—CR=NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, aralkyl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, combinations thereof, and at least one of R$^2$ or R$^3$ is not H; and pharmaceutically acceptable salts thereof In other embodiments, the 15-PGDH inhibitor can include a compound having the following formula (Ib):

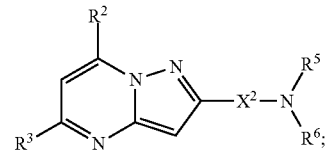

(Ib)

wherein X$^2$ is S, S=O, S(=O)$_2$, or C=O;

R$^2$, R$^3$, R$^5$ and R$^6$ are the same or different and are independently selected from the group consisting of hydrogen, substituted or unsubstituted C$_1$-C$_{24}$ alkyl, C$_2$-C$_{24}$ alkenyl, C$_2$-C$_{24}$ alkynyl, C$_3$-C$_{20}$ aryl, heterocycloalkenyl containing from 5-7 ring atoms, (wherein from 1-3 of the ring atoms is independently selected from N, NH, N(C$_1$-C$_6$ alkyl), NC(O) (C$_1$-C$_6$ alkyl), O, and S), heteroaryl or heterocyclyl containing from 5-14 ring atoms, (wherein from 1-6 of the ring atoms is independently selected from N, NH, N(C$_1$-C$_3$ alkyl), O, and S), C$_6$-C$_{24}$ alkaryl, C$_6$-C$_{24}$ aralkyl, halo, silyl, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl (including C$_2$-C$_{24}$ alkylcarbonyl (—CO-alkyl) and C$_6$-C$_{20}$ arylcarbonyl (—CO-aryl)), acyloxy (—O-acyl), C$_2$-C$_{24}$ alkoxycarbonyl (—(CO)—O-alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO$^-$), carbamoyl (—(CO)—NH$_2$), C$_1$-C$_{24}$ alkyl-carbamoyl (—(CO)—NH(C$_1$-C$_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), C$_1$-C$_{24}$ alkyl amino, C$_5$-C$_{20}$ aryl amino, C$_2$-C$_{24}$ alkylamido (—NH—(CO)-alkyl), C$_6$-C$_{20}$ arylamido (—NH—(CO)-aryl), sulfanamido (—SO$_2$N(R)$_2$ where R is independently H, alkyl, aryl or heteroaryl), imino (—CR=NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, aralkyl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO₂—O⁻), C₁-C₂₄ alkylsulfanyl (—S-alkyl; also termed "alkylthio"), arylsulfanyl (—S-aryl; also termed "arylthio"), C₁-C₂₄ alkylsulfinyl (—(SO)-alkyl), C₅-C₂₀ arylsulfinyl (—(SO)-aryl), C₁-C₂₄ alkylsulfonyl (—SO₂-alkyl), C₅-C₂₀ arylsulfonyl (—SO₂-aryl), sulfonamide (—SO₂—NH₂, —SO₂NY₂ (wherein Y is independently H, aryl or alkyl), phosphono (—P(O)(OH)₂), phosphonato (—P(O)(O⁻)₂), phosphinato (—P(O)(O⁻)), phospho (—PO₂), phosphino (—PH₂), polyalkyl ethers (—[(CH₂)ₙO]ₘ), phosphates, phosphate esters [—OP(O)(OR)₂ where R=H, methyl or other alkyl], groups incorporating amino acids or other moieties expected to bear positive or negative charge at physiological pH, combinations thereof, and at least one of R² or R³ is not H; wherein R⁵ and R⁶ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl; and pharmaceutically acceptable salts thereof.

In other embodiments, the 15-PGDH inhibitor can include a compound having the following formula (Ic):

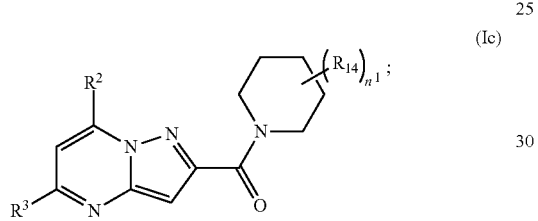

(Ic)

wherein R², R³, and R¹⁴ are the same or different and are independently selected from the group consisting of hydrogen, substituted or unsubstituted C₁-C₂₄ alkyl, C₂-C₂₄ alkenyl, C₂-C₂₄ alkynyl, C₃-C₂₀ aryl, heterocycloalkenyl containing from 5-7 ring atoms, (wherein from 1-3 of the ring atoms is independently selected from N, NH, N(C₁-C₆ alkyl), NC(O) (C₁-C₆ alkyl), O, and S), heteroaryl or heterocyclyl containing from 5-14 ring atoms, (wherein from 1-6 of the ring atoms is independently selected from N, NH, N(C₁-C₃ alkyl), O, and S), C₆-C₂₄ alkaryl, C₆-C₂₄ aralkyl, halo, silyl, hydroxyl, sulfhydryl, C₁-C₂₄ alkoxy, C₂-C₂₄ alkenyloxy, C₂-C₂₄ alkynyloxy, C₅-C₂₀ aryloxy, acyl (including C₂-C₂₄ alkylcarbonyl (—CO-alkyl) and C₆-C₂₀ arylcarbonyl (—CO-aryl)), acyloxy (—O-acyl), C₂-C₂₄ alkoxycarbonyl (—(CO)—O-alkyl), C₆-C₂₀ aryloxycarbonyl (—(CO)—O-aryl), C₂-C₂₄ alkylcarbonato (—O—(CO)—O-alkyl), C₆-C₂₀ arylcarbonato (—O—(CO)—O-aryl), carboxy (—COOH), carboxylato (—COO⁻), carbamoyl (—(CO)—NH₂), C₁-C₂₄ alkyl-carbamoyl (—(CO)—NH(C₁-C₂₄ alkyl)), arylcarbamoyl (—(CO)—NH-aryl), thiocarbamoyl (—(CS)—NH₂), carbamido (—NH—(CO)—NH₂), cyano (—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH₂), C₁-C₂₄ alkyl amino, C₅-C₂₀ aryl amino, C₂-C₂₄ alkylamido (—NH—(CO)-alkyl), C₆-C₂₀ arylamido (—NH—(CO)-aryl), sulfanamido (—SO₂N(R)₂ where R is independently H, alkyl, aryl or heteroaryl), imino (—CR=NH where R is hydrogen, C₁-C₂₄ alkyl, C₅-C₂₀ aryl, C₆-C₂₄ alkaryl, C₆-C₂₄ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO₂), nitroso (—NO), sulfo (—SO₂—OH), sulfonato (—SO₂—O⁻), C₁-C₂₄ alkylsulfanyl (—S-alkyl; also termed "alkylthio"), arylsulfanyl (—S-aryl; also termed "arylthio"), C₁-C₂₄ alkylsulfinyl (—(SO)-alkyl), C₅-C₂₀ arylsulfinyl (—(SO)-aryl), C₁-C₂₄ alkylsulfonyl (—SO₂-alkyl), C₅-C₂₀ arylsulfonyl (—SO₂-aryl), sulfonamide (—SO₂—NH₂, —SO₂NY₂ (wherein Y is independently H, aryl or alkyl), phosphono (—P(O)(OH)₂), phosphonato (—P(O)(O⁻)₂), phosphinato (—P(O)(O⁻)), phospho (—PO₂), phosphino (—PH₂), polyalkyl ethers (—[(CH₂)ₙO]ₘ), phosphates, phosphate esters [—OP(O)(OR)₂ where R=H, methyl or other alkyl], groups incorporating amino acids or other moieties expected to bear positive or negative charge at physiological pH, combinations thereof, at least one of R² or R³ is not H, n¹ is 0-4, and each R¹⁴ is the same or different; and pharmaceutically acceptable salts thereof.

In still other embodiments, the 15-PGDH inhibitor can include a compound having the following formula (Id):

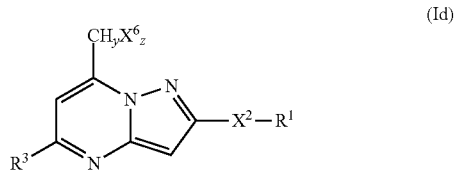

(Id)

wherein X² is S, S=O, S(=O)₂, or C=O;
X⁶ is Cl, Br, or F, and y+z=3;
R¹ and R³ are the same or different and are independently selected from the group consisting of hydrogen, substituted or unsubstituted C₁-C₂₄ alkyl, C₂-C₂₄ alkenyl, C₂-C₂₄ alkynyl, C₃-C₂₀ aryl, heterocycloalkenyl containing from 5-7 ring atoms, (wherein from 1-3 of the ring atoms is independently selected from N, NH, N(C₁-C₆ alkyl), NC(O) (C₁-C₆ alkyl), O, and S), heteroaryl or heterocyclyl containing from 5-14 ring atoms, (wherein from 1-6 of the ring atoms is independently selected from N, NH, N(C₁-C₃ alkyl), O, and S), C₆-C₂₄ alkaryl, C₆-C₂₄ aralkyl, halo, silyl, hydroxyl, sulfhydryl, C₁-C₂₄ alkoxy, C₂-C₂₄ alkenyloxy, C₂-C₂₄ alkynyloxy, C₅-C₂₀ aryloxy, acyl (including C₂-C₂₄ alkylcarbonyl (—CO-alkyl) and C₆-C₂₀ arylcarbonyl (—CO-aryl)), acyloxy (—O-acyl), C₂-C₂₄ alkoxycarbonyl (—(CO)—O-alkyl), C₆-C₂₀ aryloxycarbonyl (—(CO)—O-aryl), C₂-C₂₄ alkylcarbonato (—O—(CO)—O-alkyl), C₆-C₂₀ arylcarbonato (—O—(CO)—O-aryl), carboxy (—COOH), carboxylato (—COO⁻), carbamoyl (—(CO)—NH₂), C₁-C₂₄ alkyl-carbamoyl (—(CO)—NH(C₁-C₂₄ alkyl)), arylcarbamoyl (—(CO)—NH-aryl), thiocarbamoyl (—(CS)—NH₂), carbamido (—NH—(CO)—NH₂), cyano (—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH₂), C₁-C₂₄ alkyl amino, C₅-C₂₀ aryl amino, C₂-C₂₄ alkylamido (—NH—(CO)-alkyl), C₆-C₂₀ arylamido (—NH—(CO)-aryl), sulfanamido (—SO₂N(R)₂ where R is independently H, alkyl, aryl or heteroaryl), imino (—CR=NH where R is hydrogen, C₁-C₂₄ alkyl, C₅-C₂₀ aryl, C₆-C₂₄ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, combinations thereof, and at least one of $R^2$ or $R^3$ is not H; and pharmaceutically acceptable salts thereof.

In yet other embodiments, the 15-PGDH inhibitor can include a compound having the following formula (Ie):

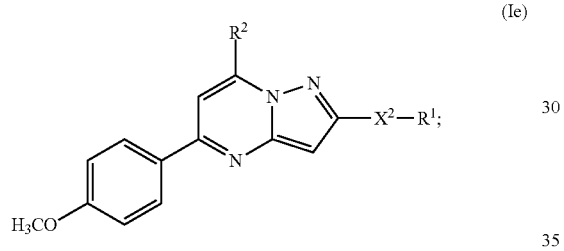

(Ie)

wherein X$^2$ is S, S=O, S(=O)$_2$, or C=O;

$R^1$ and $R^2$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-7 ring atoms, (wherein from 1-3 of the ring atoms is independently selected from N, NH, N(C$_1$-C$_6$ alkyl), NC(O) (C$_1$-C$_6$ alkyl), O, and S), heteroaryl or heterocyclyl containing from 5-14 ring atoms, (wherein from 1-6 of the ring atoms is independently selected from N, NH, N(C$_1$-C$_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH(C$_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, combinations thereof, and at least one of $R^2$ or $R^3$ is not H; and pharmaceutically acceptable salts thereof.

Examples of 15-PGDH inhibitors having formulas (I), (Ia), (Ib), (Ic), (Id), or (Ie) can include the following compounds:

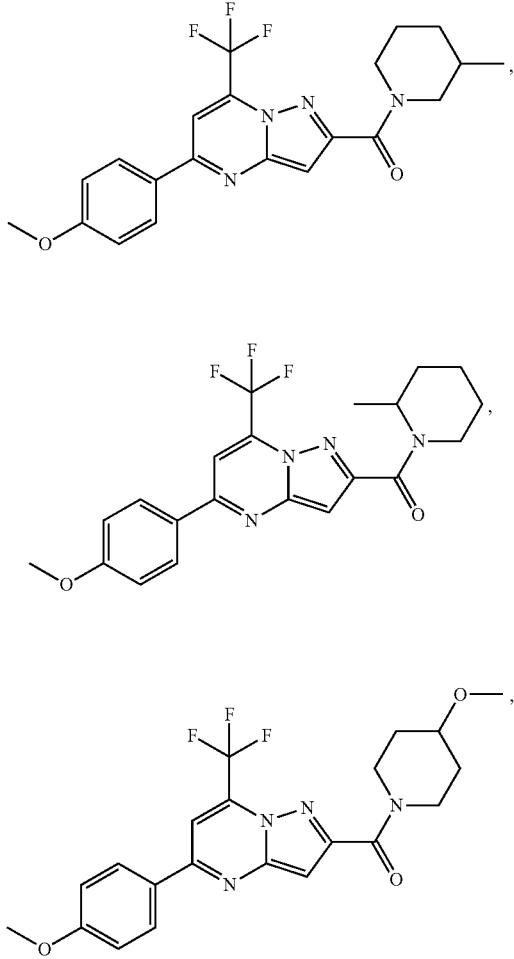

-continued
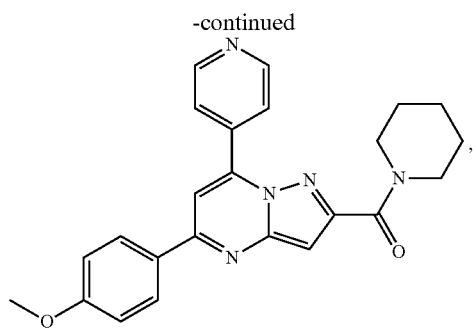
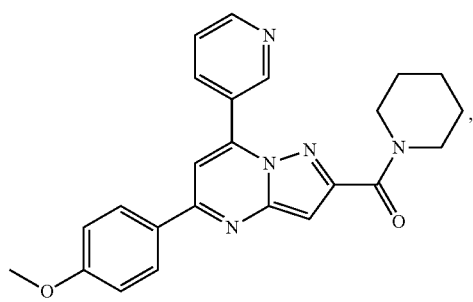
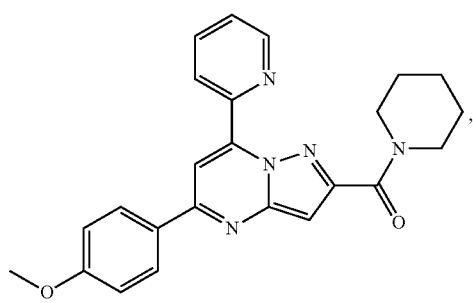
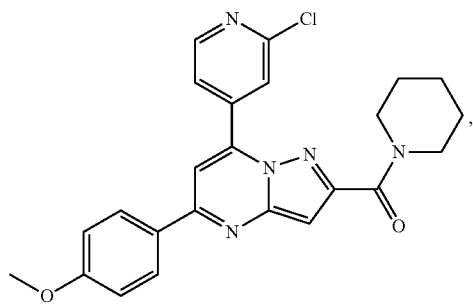
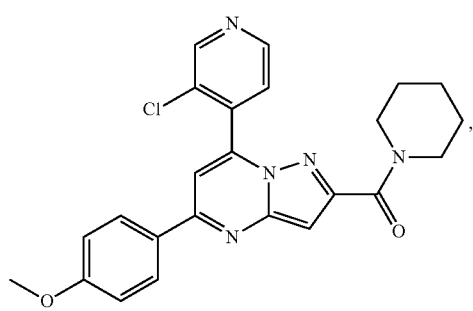
-continued
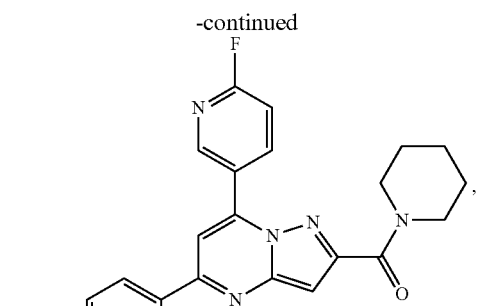
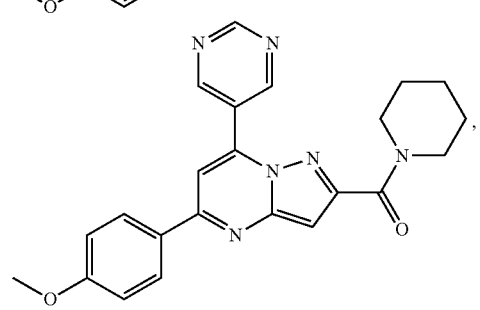
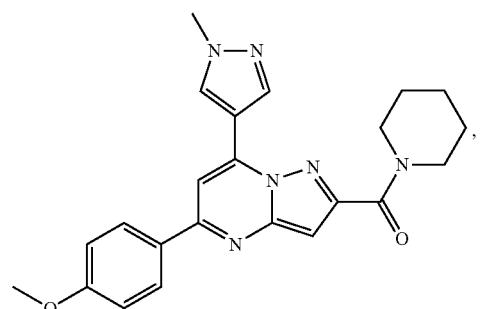
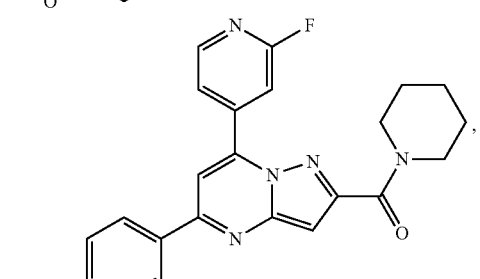
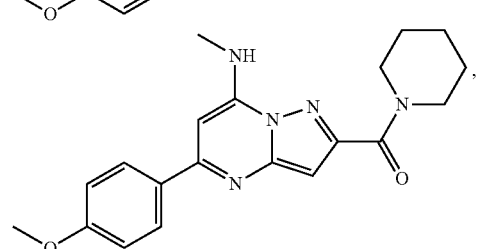
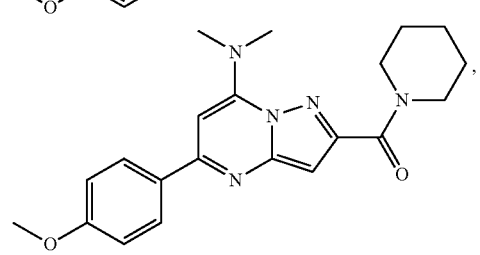

33
-continued
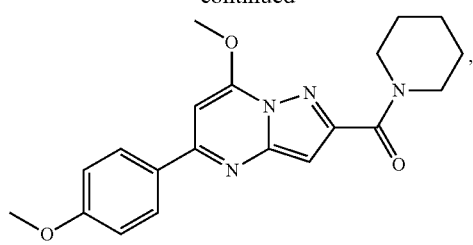
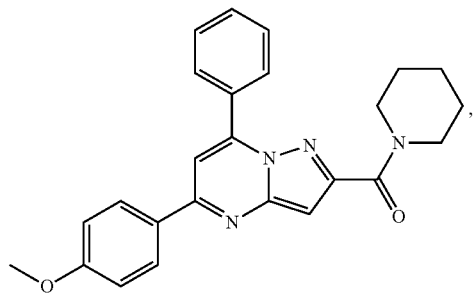
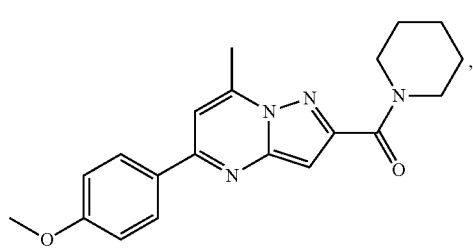
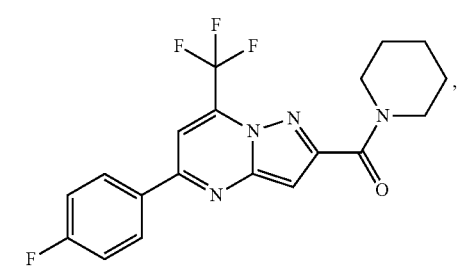
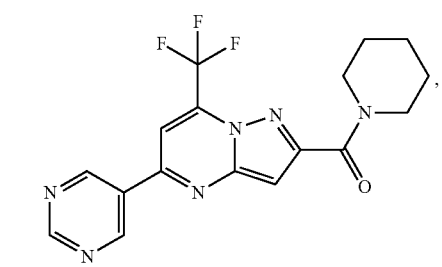
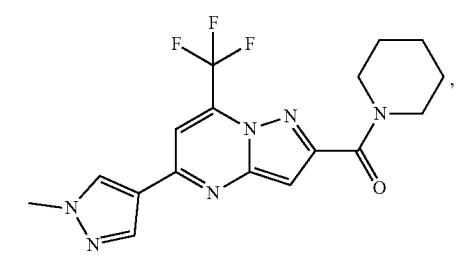
34
-continued
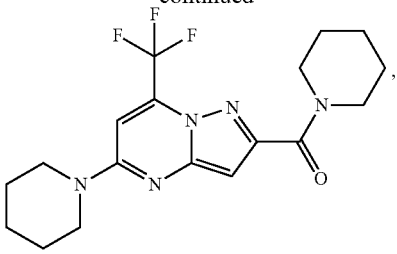
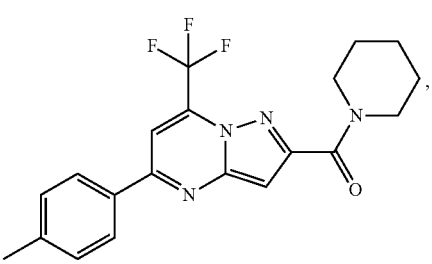
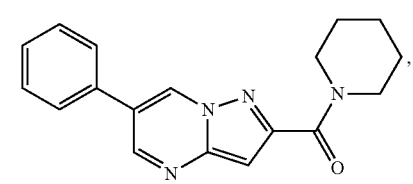
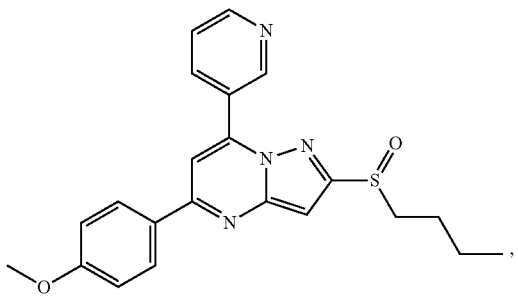
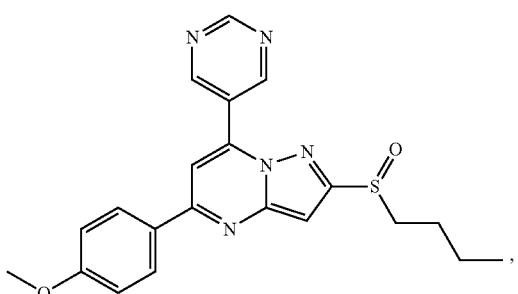
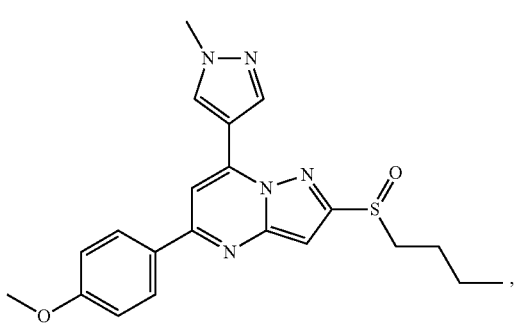

-continued
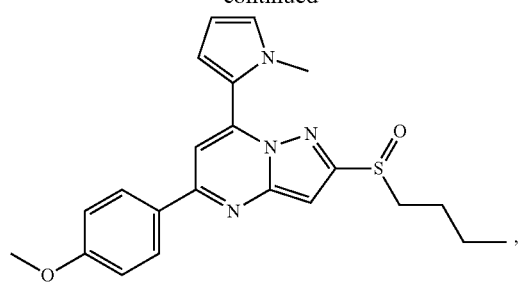
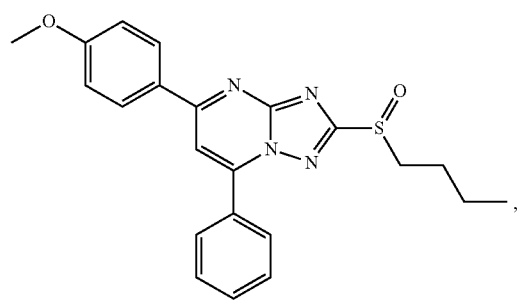
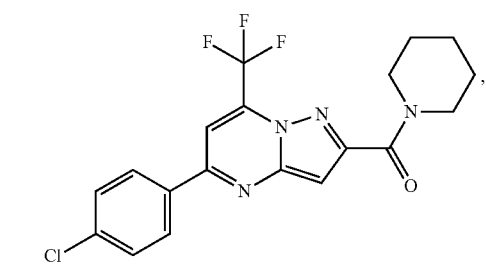
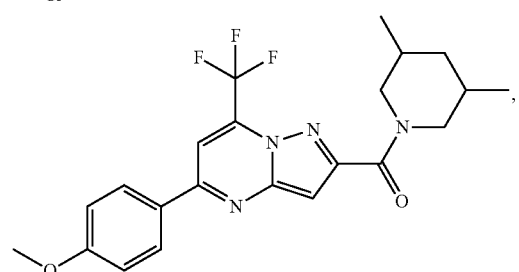
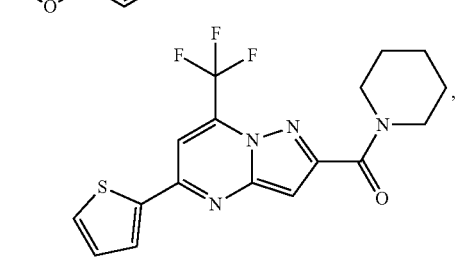
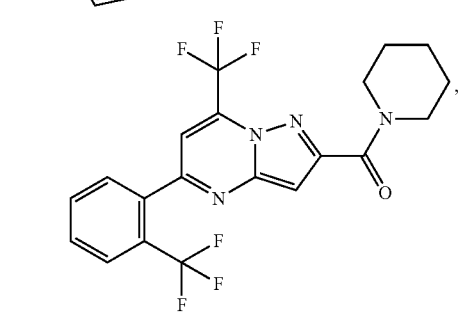
-continued
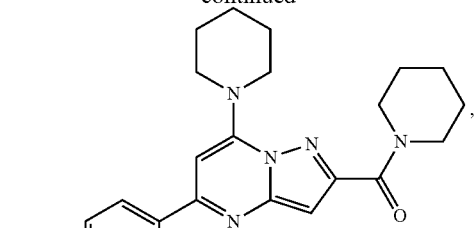
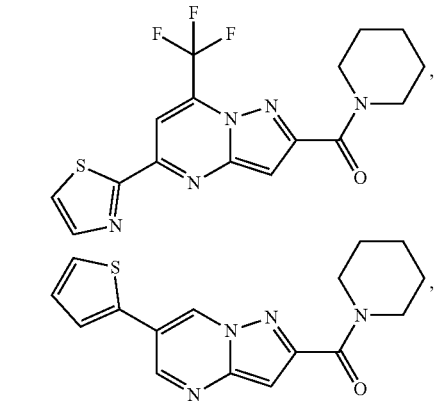

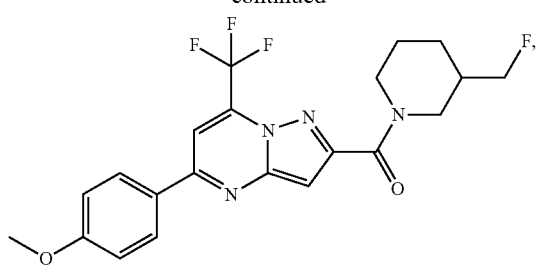
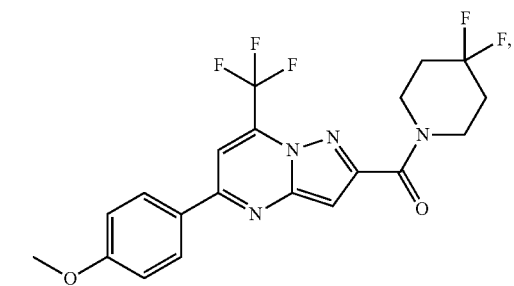
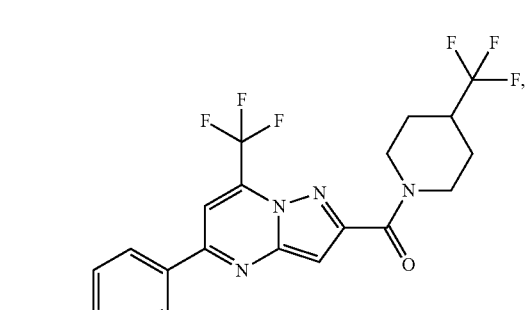
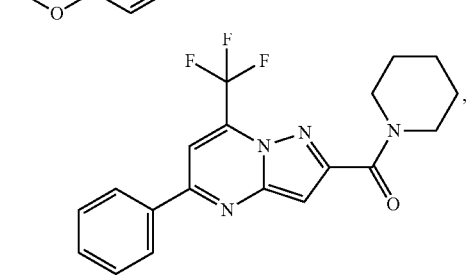
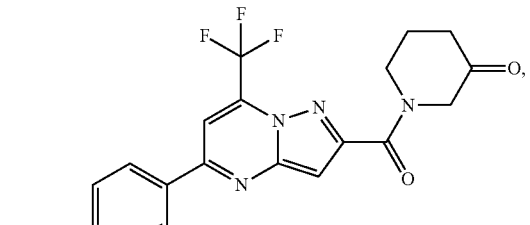
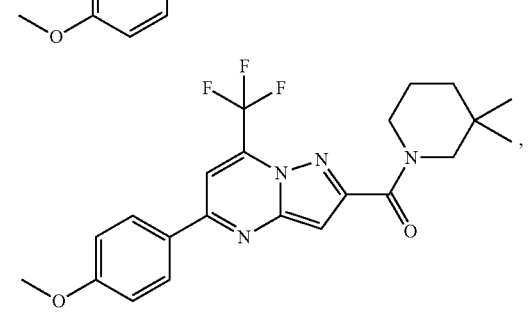
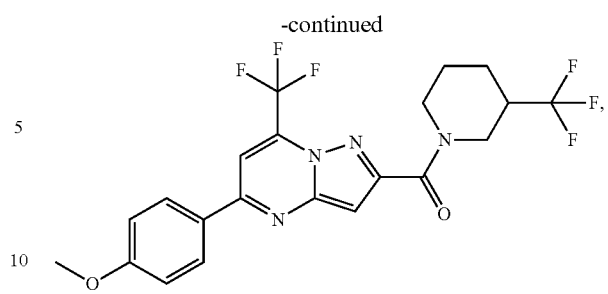
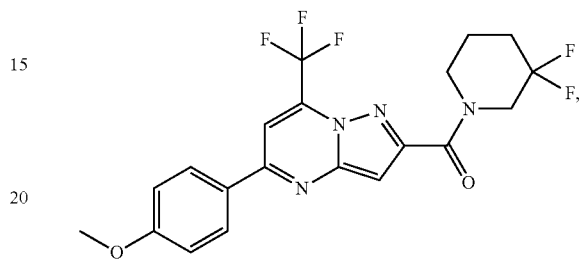
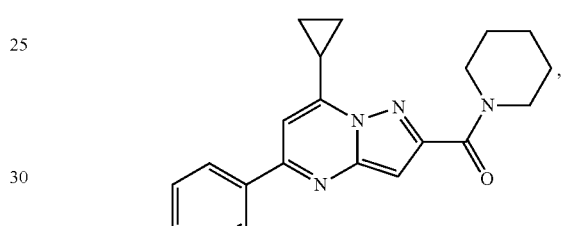
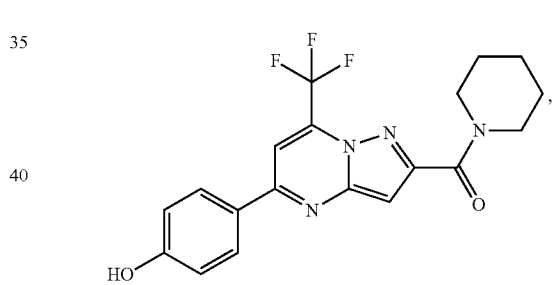
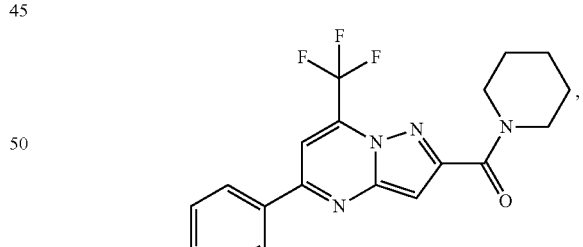
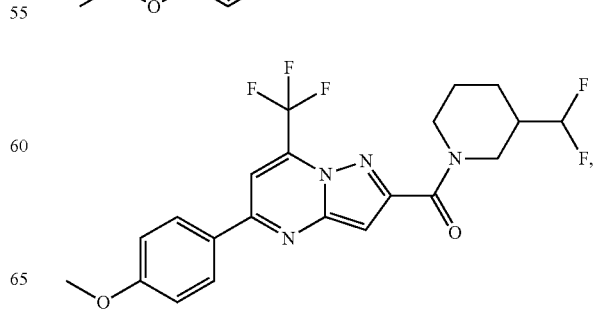

-continued

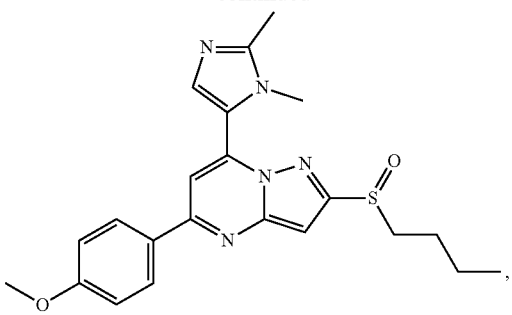

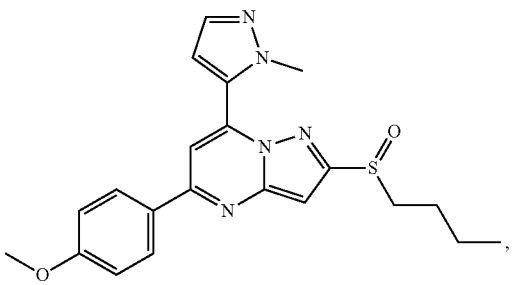

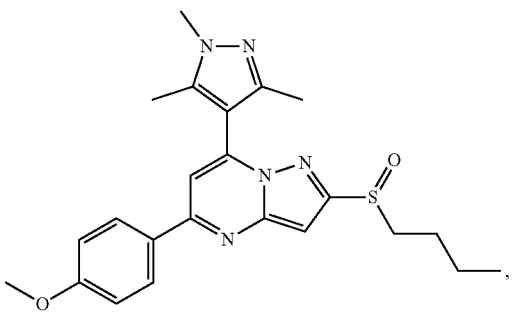

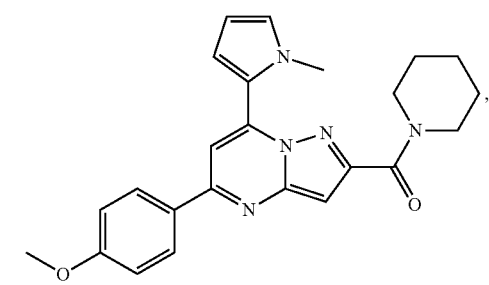

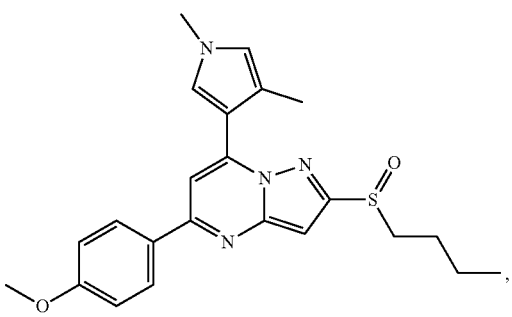

-continued

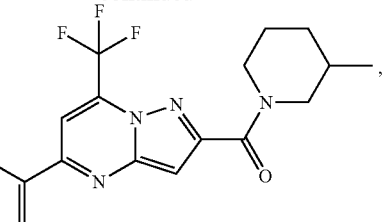

and pharmaceutically acceptable salts thereof.

In other embodiments, the 15-PGDH inhibitor can include a compound having the following formula (IIa):

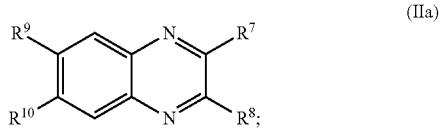

(IIa)

wherein $R^7$ and $R^8$ are same or different and are each independently selected from the group consisting of H, a substituted or unsubstituted aryl, a substituted or unsubstituted heteroaryl, a substituted or unsubstituted cycloalkyl, and a substituted or unsubstituted heterocyclyl, and at least one of $R^7$ or $R^8$ is not H;

$R^9$ and $R^{10}$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-7 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$≡C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), sulfonamide (—$SO_2$—$NH_2$, —$SO_2NY_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—$PO_2$), phosphino (—$PH_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, combinations thereof, and optionally at least one of $R^9$ or $R^{10}$ is not H; and pharmaceutically acceptable salts thereof.

In still other embodiments, the 15-PGDH inhibitor can include a compound having the following formula (IIb):

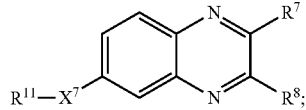

(IIb)

wherein $X^7$ is S, S=O, S(=O)$_2$, or C=O;

$R^7$ and $R^8$ are same or different and are each independently selected from the group consisting of H, a substituted or unsubstituted aryl, a substituted or unsubstituted heteroaryl, a substituted or unsubstituted cycloalkyl, and a substituted or unsubstituted heterocyclyl, and at least one of $R^7$ or $R^8$ is not H;

$R^{11}$ is selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-7 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—$NH_2$), carbamido (—NH—(CO)—$NH_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—$NH_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—$SO_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), sulfonamide (—$SO_2$—$NH_2$, —$SO_2NY_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—$PO_2$), phosphino (—$PH_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, combinations thereof; and pharmaceutically acceptable salts thereof.

In some embodiments, the 15-PGDH inhibitor can include a compound having the following formula (IIc):

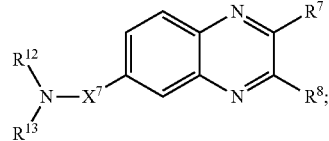

(IIc)

wherein $X^7$ is S, S=O, S(=O)$_2$, or C=O;

$R^7$ and $R^8$ are same or different and are each independently selected from the group consisting of H, a substituted or unsubstituted aryl, a substituted or unsubstituted heteroaryl, a substituted or unsubstituted cycloalkyl, and a substituted or unsubstituted heterocyclyl, and at least one of $R^7$ or $R^8$ is not H;

$R^{12}$ and $R^{13}$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-7 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—$NH_2$), carbamido (—NH—(CO)—$NH_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—$NH_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—$SO_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof; wherein $R^{12}$ and $R^{13}$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl; and pharmaceutically acceptable salts thereof.

In other embodiments, the 15-PGDH inhibitor can include a compound having the following formula (IId):

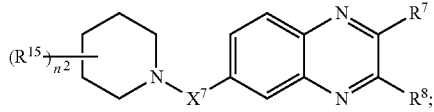

wherein $X^7$ is S, S=O, S(=O)$_2$, or C=O;

$R^7$ and $R^8$ are same or different and are each independently selected from the group consisting of H, a substituted or unsubstituted aryl, a substituted or unsubstituted heteroaryl, a substituted or unsubstituted cycloalkyl, and a substituted or unsubstituted heterocyclyl, and at least one of $R^7$ or $R^8$ is not H;

$R^{15}$ is selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-7 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), iso-cyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, combinations thereof, $n^2$ is 0-4, and each $R^{15}$ is the same or different; and pharmaceutically acceptable salts thereof.

In yet other embodiments, the 15-PGDH inhibitor can include a compound having the following formula (IIe):

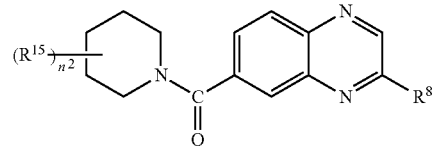

$R^8$ is a substituted or unsubstituted aryl, a substituted or unsubstituted heteroaryl, a substituted or unsubstituted cycloalkyl, and a substituted or unsubstituted heterocyclyl;

$R^{15}$ is selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-7 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), C$_1$-C$_{24}$ alkyl amino, C$_5$-C$_{20}$ aryl amino, C$_2$-C$_{24}$ alkylamido (—NH—(CO)-alkyl), C$_6$-C$_{20}$ arylamido (—NH—(CO)-aryl), sulfanamido (—SO$_2$N(R)$_2$ where R is independently H, alkyl, aryl or heteroaryl), imino (—CR=NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, combinations thereof, n$^2$ is 0-4, and each R$^{15}$ is the same or different; and pharmaceutically acceptable salts thereof.

In yet other embodiments, the 15-PGDH inhibitor can include a compound having the following formula (IIf):

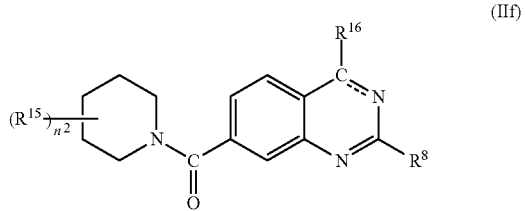

(IIf)

R$^8$ is a substituted or unsubstituted aryl, a substituted or unsubstituted heteroaryl, a substituted or unsubstituted cycloalkyl, and a substituted or unsubstituted heterocyclyl;

R$^{15}$ and R$^{16}$ are the same or different and are independently selected from the group consisting of hydrogen, oxygen, substituted or unsubstituted C$_1$-C$_{24}$ alkyl, C$_2$-C$_{24}$ alkenyl, C$_2$-C$_{24}$ alkynyl, C$_3$-C$_{20}$ aryl, heterocycloalkenyl containing from 5-7 ring atoms, (wherein from 1-3 of the ring atoms is independently selected from N, NH, N(C$_1$-C$_6$ alkyl), NC(O) (C$_1$-C$_6$ alkyl), O, and S), heteroaryl or heterocyclyl containing from 5-14 ring atoms, (wherein from 1-6 of the ring atoms is independently selected from N, NH, N(C$_1$-C$_3$ alkyl), O, and S), C$_6$-C$_{24}$ alkaryl, C$_6$-C$_{24}$ aralkyl, halo, silyl, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl (including C$_2$-C$_{24}$ alkylcarbonyl (—CO-alkyl) and C$_6$-C$_{20}$ arylcarbonyl (—CO-aryl)), acyloxy (—O-acyl), C$_2$-C$_{24}$ alkoxycarbonyl (—(CO)—O-alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO$^-$), carbamoyl (—(CO)—NH$_2$), C$_1$-C$_{24}$ alkyl-carbamoyl (—(CO)—NH(C$_1$-C$_{24}$ alkyl)), aryl-carbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), C$_1$-C$_{24}$ alkyl amino, C$_5$-C$_{20}$ aryl amino, C$_2$-C$_{24}$ alkylamido (—NH—(CO)-alkyl), C$_6$-C$_{20}$ arylamido (—NH—(CO)-aryl), sulfanamido (—SO$_2$N(R)$_2$ where R is independently H, alkyl, aryl or heteroaryl), imino (—CR=NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, combinations thereof, n$^2$ is 0-4, and each R$^{15}$ is the same or different; and pharmaceutically acceptable salts thereof.

Examples of 15-PGDH inhibitors having formulas (II), (IIa), (IIb), (IIc), (IId), (IIe), or (IIf) can include the following compounds:

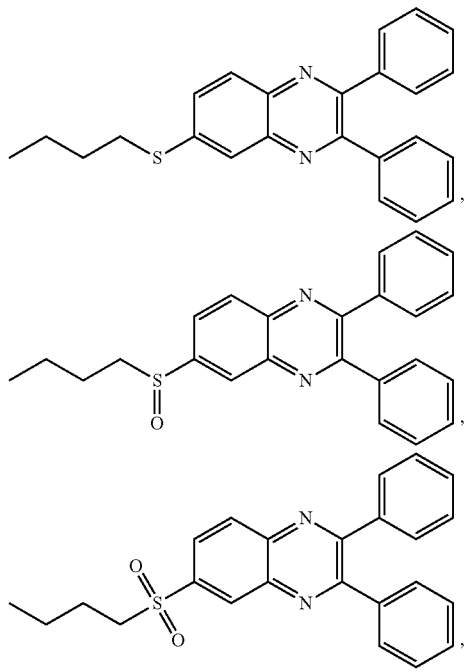

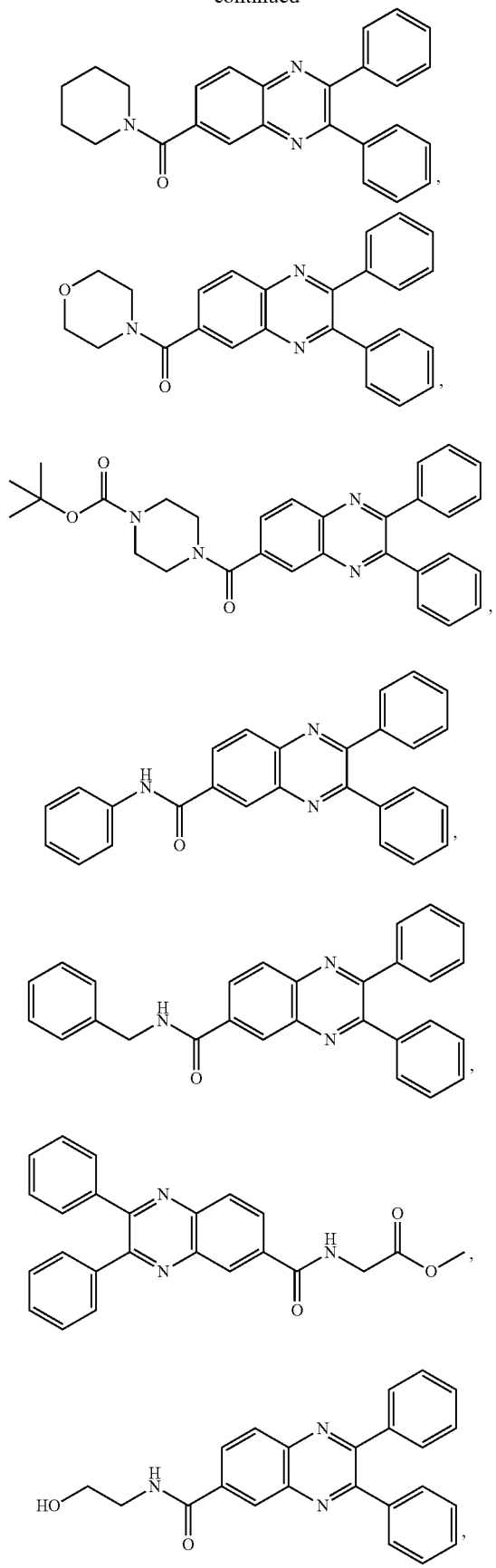
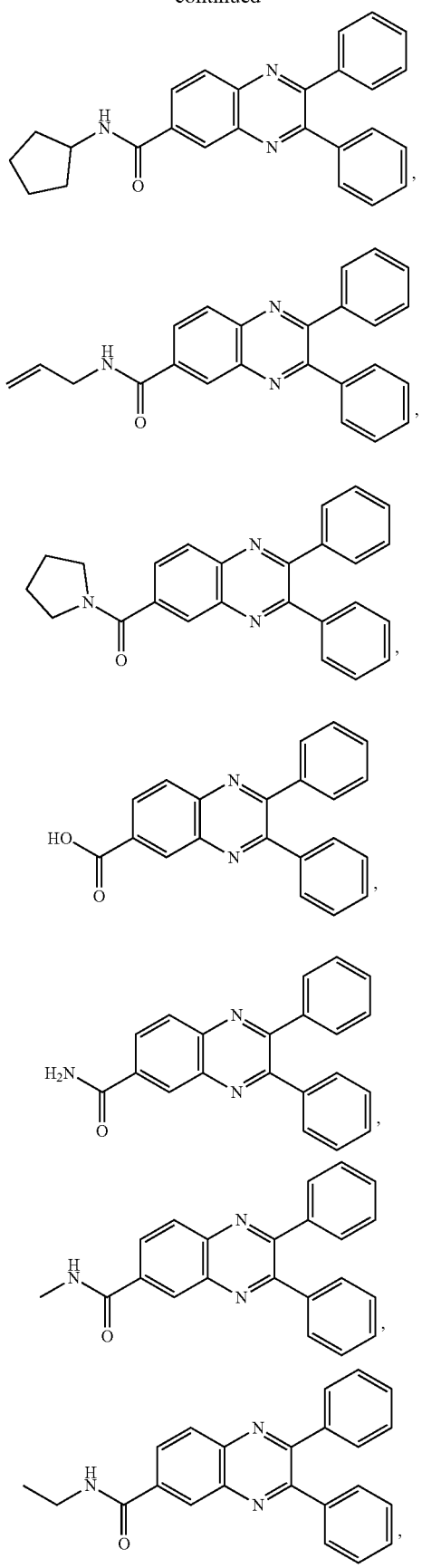

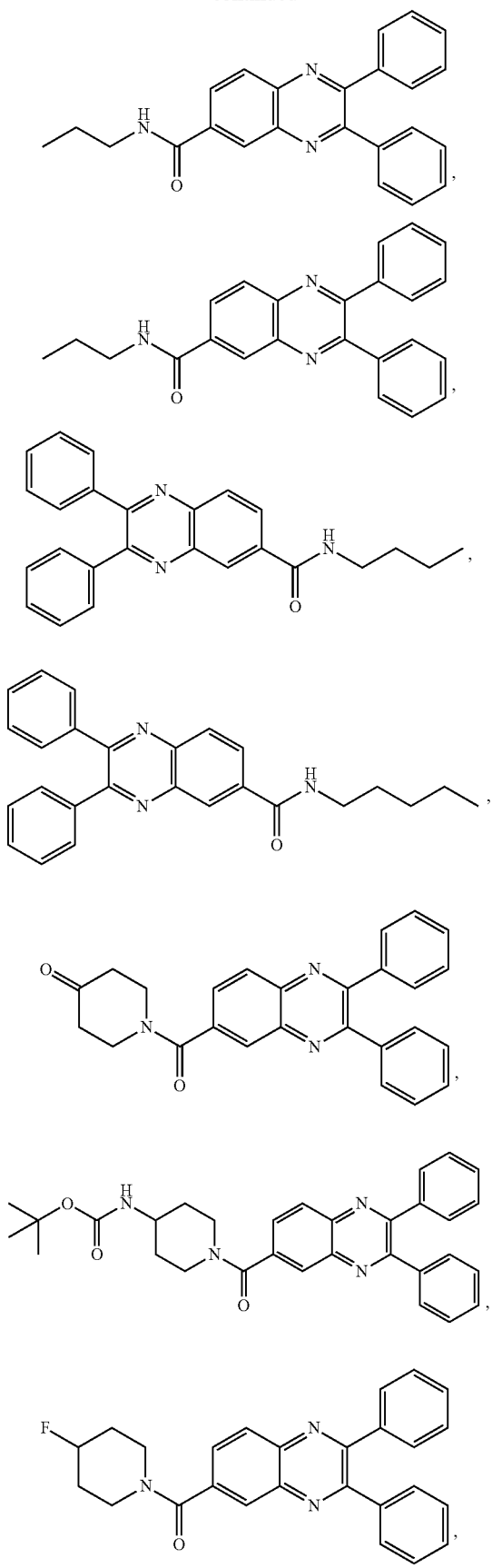
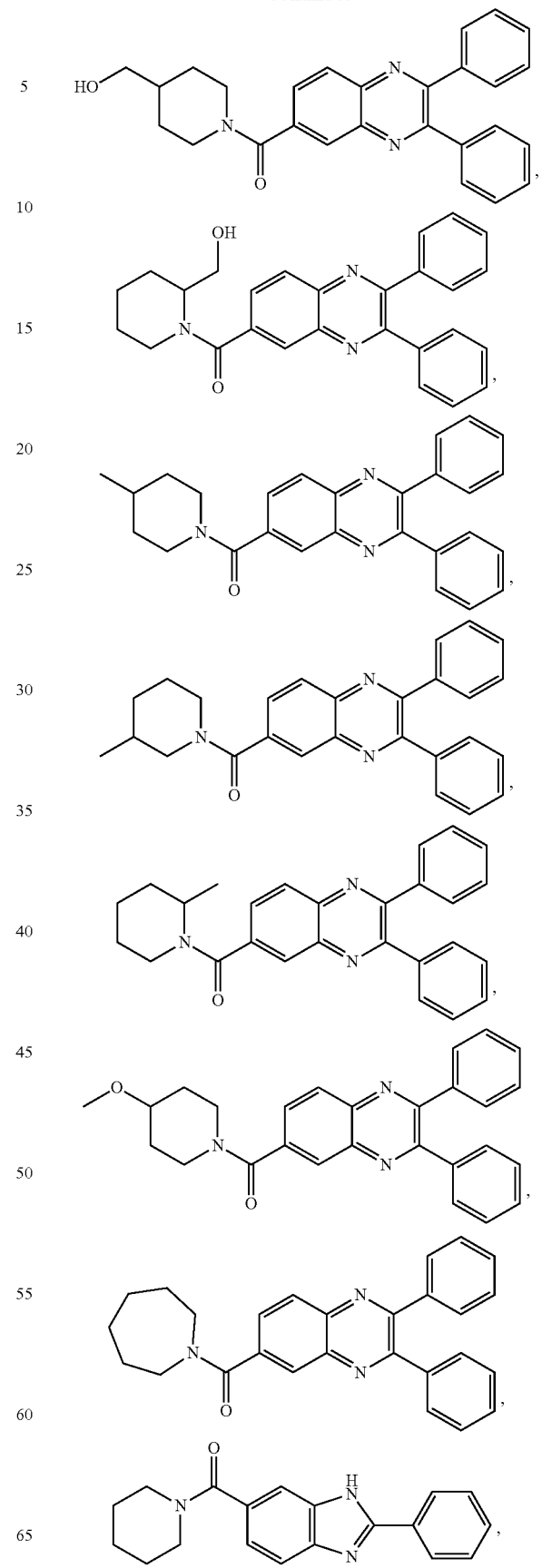

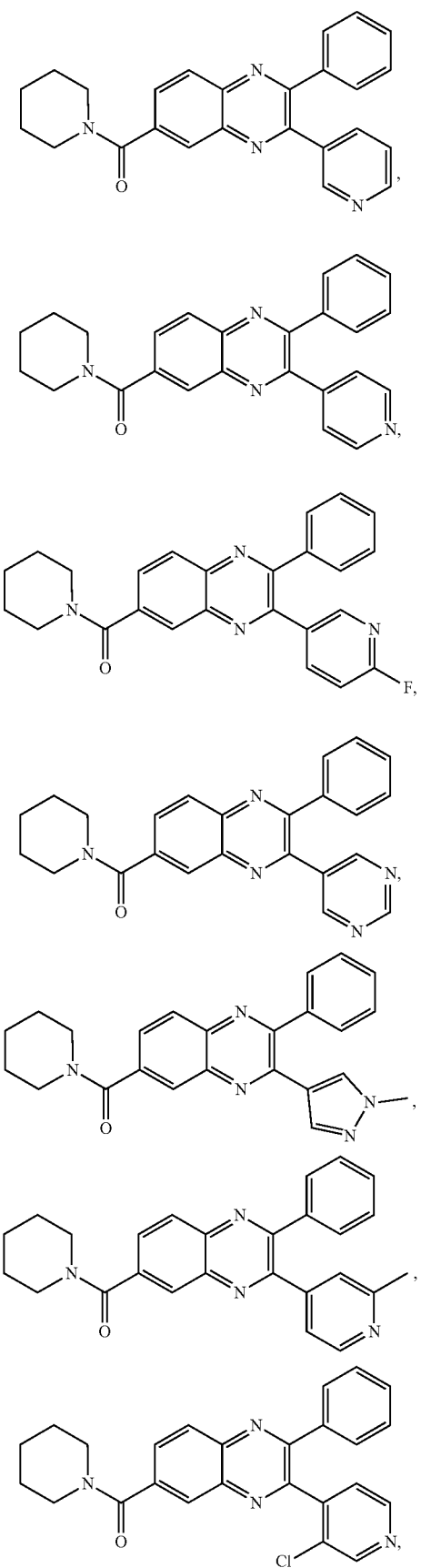
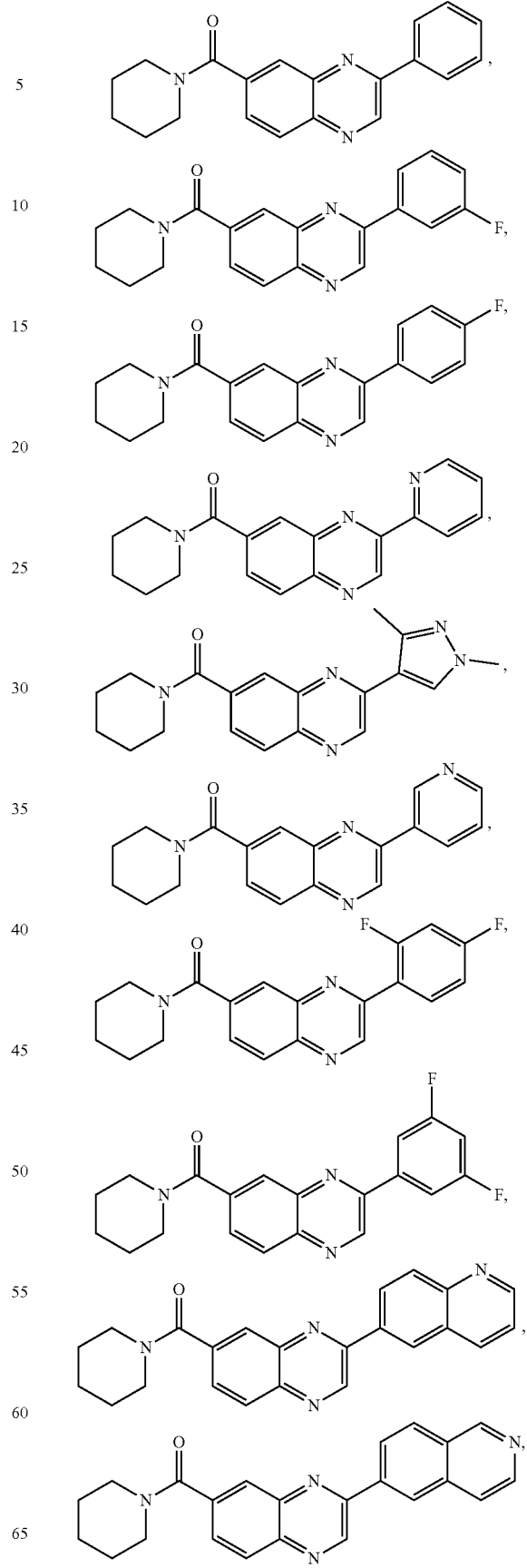

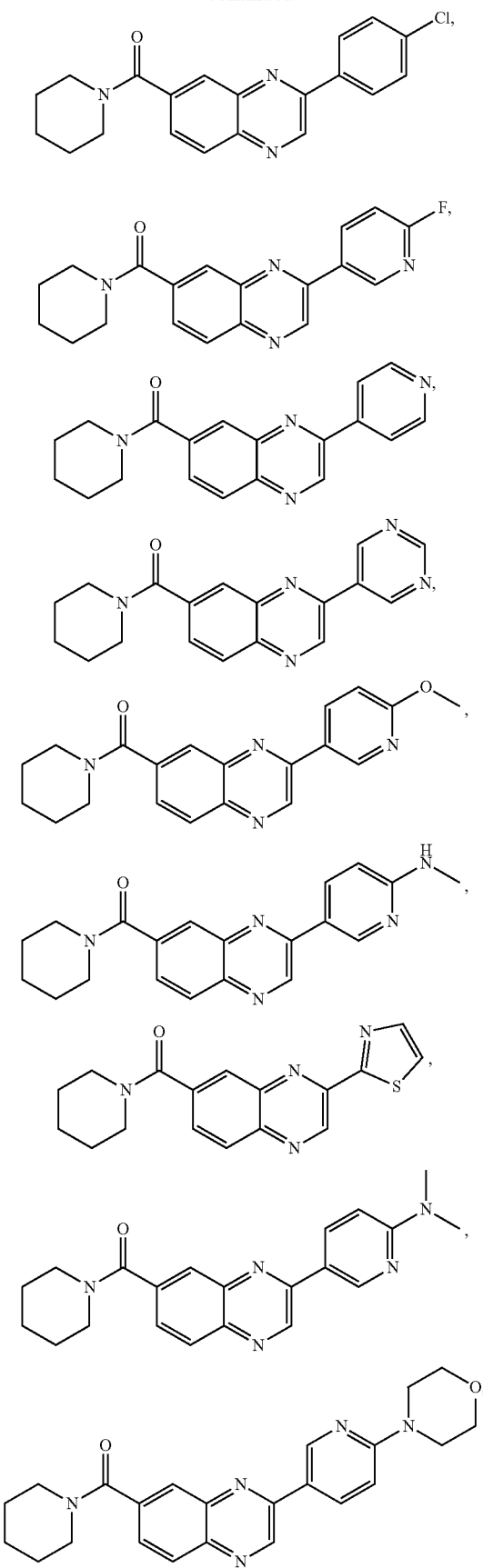
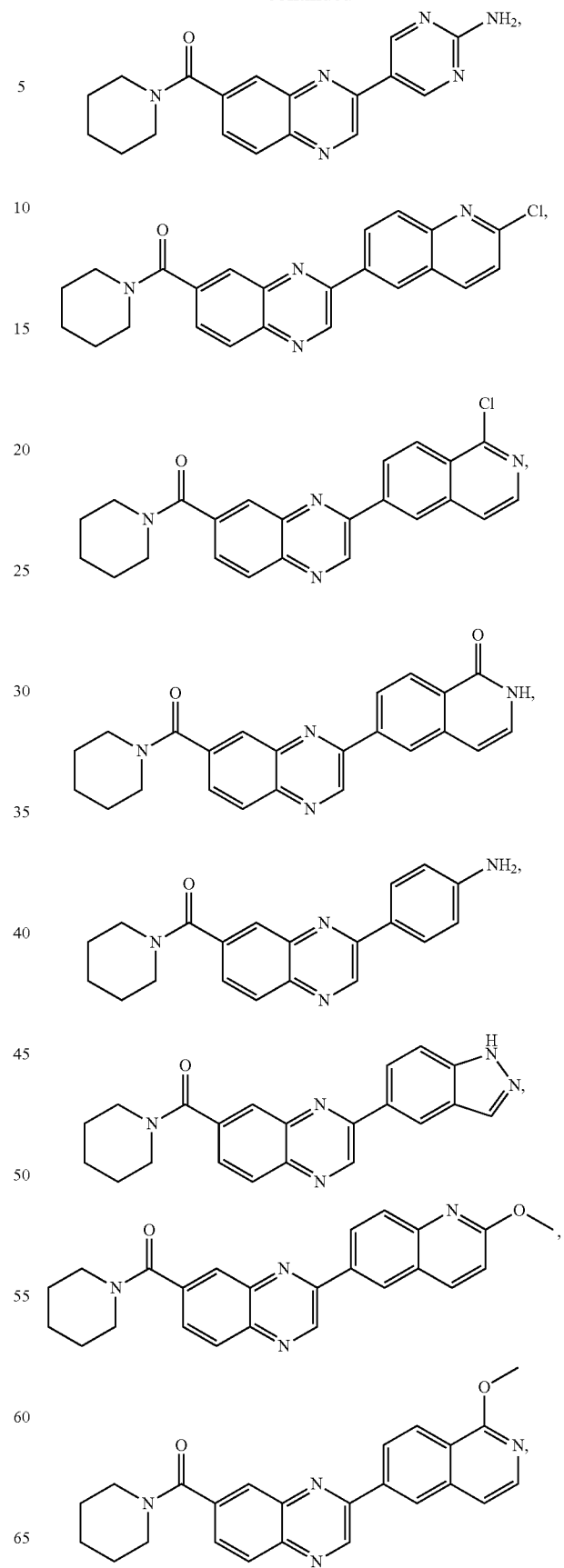

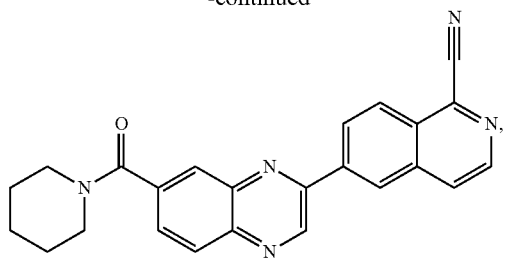
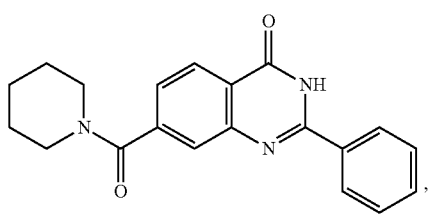
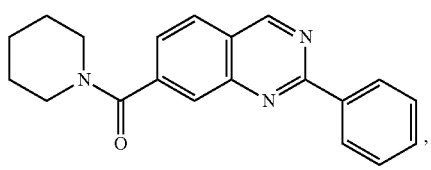
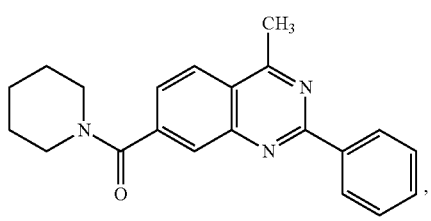
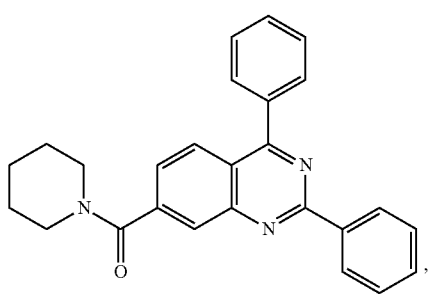
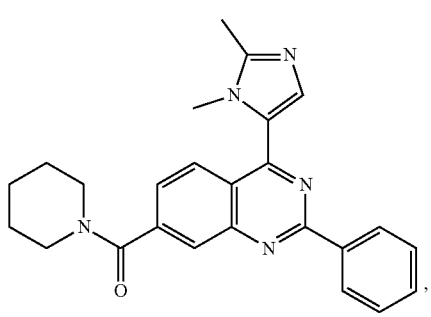
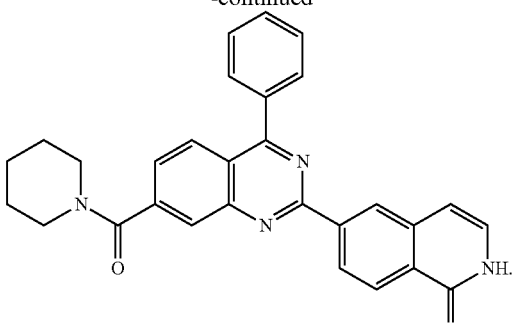
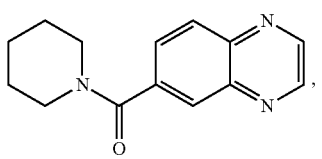
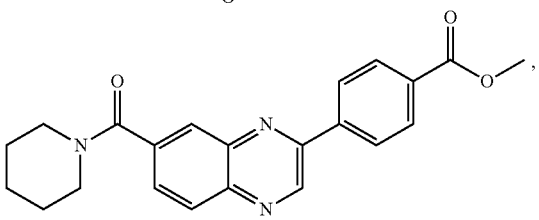
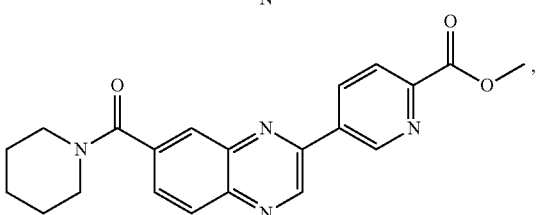
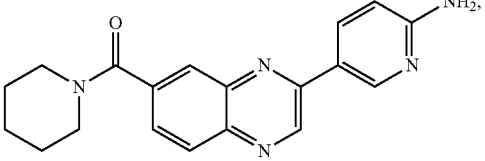
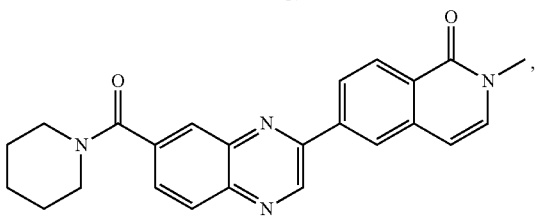
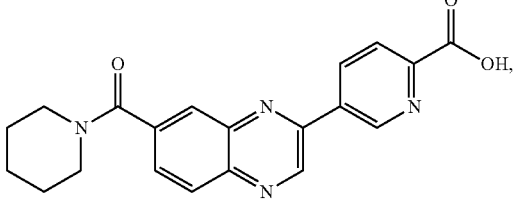
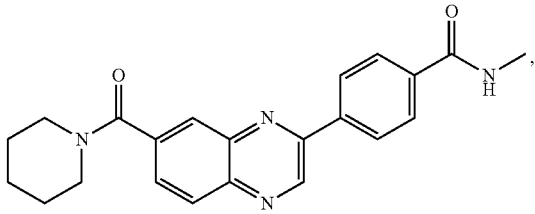

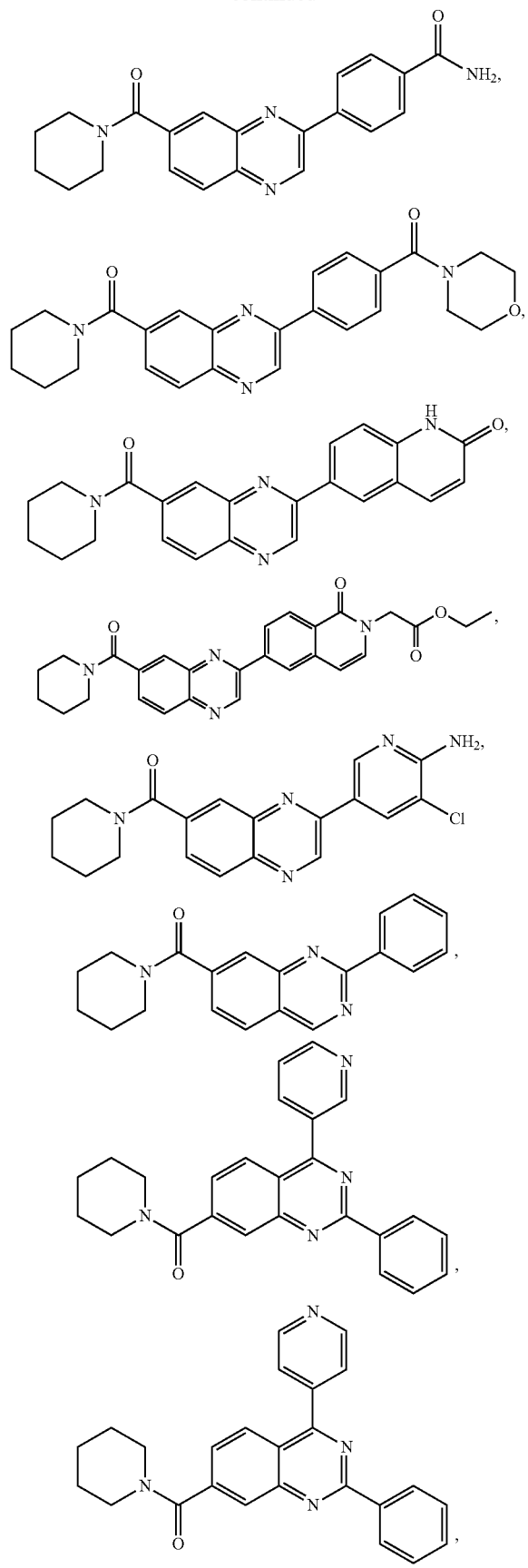

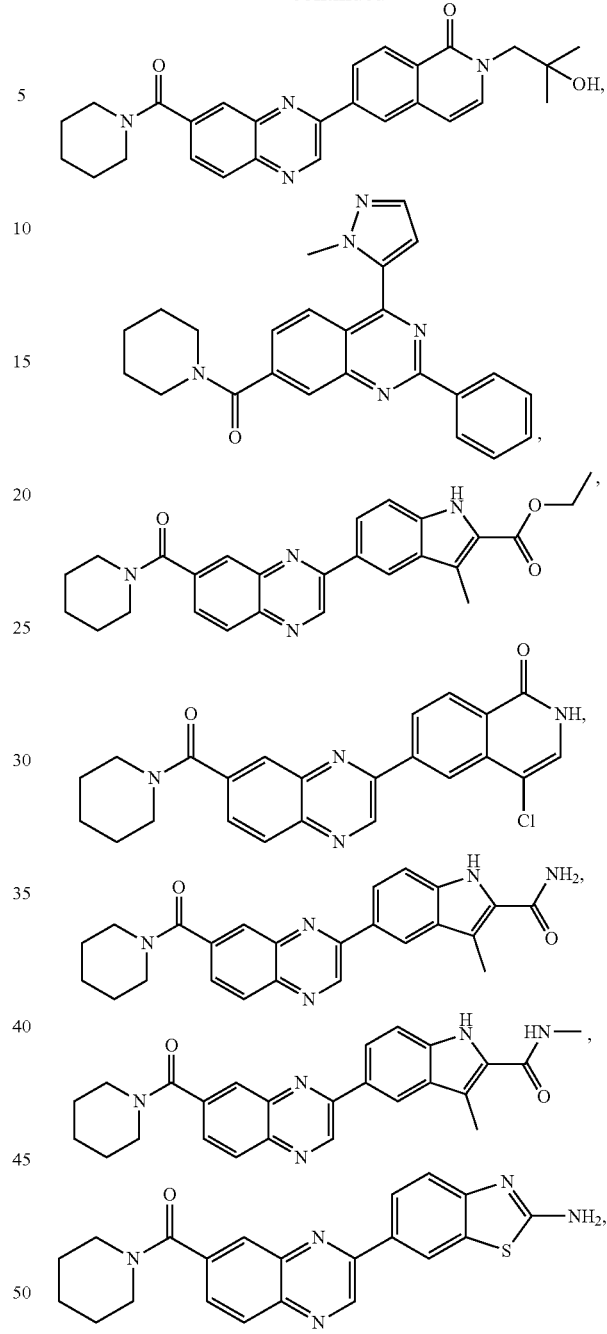

and pharmaceutically acceptable salts thereof.

In certain embodiments, the 15-PGDH inhibitor having formula (I), and (II), can be selected that can ia) at 2.5 μM concentration, stimulate a Vaco503 reporter cell line expressing a 15-PGDH luciferase fusion construct to a luciferase output level of greater than 70 (using a scale on which a value of 100 indicates a doubling of reporter output over baseline); iia) at 2.5 μM concentration stimulate a V9m reporter cell line expressing a 15-PGDH luciferase fusion construct to a luciferase output level of greater than 75; iiia) at 7.5 μM concentration stimulate a LS174T reporter cell line expressing a 15-PGDH luciferase fusion construct to a luciferase output level of greater than 70; and iva) at 7.5 μM concentration, does not activate a negative control V9m cell line expressing TK-renilla luciferase reporter to a level greater than 20; and va) inhibits the enzymatic activity of recombinant 15-PGDH protein at an $IC_{50}$ of less than 1 µM.

In other embodiments, the 15-PGDH inhibitor can ib) at 2.5 µM concentration, stimulate a Vaco503 reporter cell line expressing a 15-PGDH luciferase fusion construct to increase luciferase output; iib) at 2.5 µM concentration stimulate a V9m reporter cell line expressing a 15-PGDH luciferase fusion construct to increase luciferase output; iiib) at 7.5 µM concentration stimulate a LS174T reporter cell line expressing a 15-PGDH luciferase fusion construct to increase luciferase output; ivb) at 7.5 µM concentration, does not activate a negative control V9m cell line expressing TK-renilla luciferase reporter to a luciferase level greater than 20% above background; and vb) inhibits the enzymatic activity of recombinant 15-PGDH protein at an $IC_{50}$ of less than 1 µM.

In other embodiments, the 15-PGDH inhibitor can inhibit the enzymatic activity of recombinant 15-PGDH at an $IC_{50}$ of less than 1 µM, or preferably at an $IC_{50}$ of less than 250 nM, or more preferably at an $IC_{50}$ of less than 50 nM, or more preferably at an $IC_{50}$ of less than 10 nM, or more preferably at an $IC_{50}$ of less than 5 nM at a recombinant 15-PGDH concentration of about 5 nM to about 10 nM.

In other embodiments, the 15-PGDH inhibitor can increase the cellular levels of PGE-2 following stimulation of an A459 cell with an appropriate agent, for example, IL1-β.

The 15-PGDH inhibitors described herein can be used for the prevention or the treatment of diseases that are associated with 15-PGDH and/or decreased prostaglandin levels and/or where it desirable to increase prostaglandin levels in the subject. For example, as discussed above, it is known that prostaglandins play an important role in hair growth. Specifically, internal storage of various types ($A_2$, $F_{2a}$, $E_2$) of prostaglandins in the various compartments of hair follicles or their adjacent skin environments has been shown to be essential in maintaining and increasing hair density (Colombe L et. al, 2007, Exp. Dermatol, 16(9), 762-9). It has been reported that 15-PGDH, which is involved in the degradation of prostaglandins is present in the hair follicle dermal papillae, inactivates prostaglandins, especially, $PGF_{2a}$ and $PGE_2$, to cause scalp damage and alopecia (Michelet J F et. al., 2008, Exp. Dermatol, 17(10), 821-8). Thus, the compounds described herein, which have a suppressive or inhibitory activity against 15-PGDH that degrades prostaglandins, can improve scalp damage, prevent alopecia and promote hair growth and be used in a pharmaceutical composition for the prevention of alopecia and the promotion of hair growth.

In other embodiments, the 15-PGDH inhibitors described herein can be used in a pharmaceutical composition for promoting and/or inducing and/or stimulating pigmentation of the skin and/or skin appendages, and/or as an agent for preventing and/or limiting depigmentation and/or whitening of the skin and/or skin appendages, in particular as an agent for preventing and/or limiting canities.

In some embodiments, the 15-PGDH inhibitor can be applied to skin of a subject, e.g., in a topical application, to promote and/or stimulate pigmentation of the skin and/or hair growth, inhibit hair loss, and/or treat skin damage or inflammation, such as skin damage caused by physical or chemical irritants and/or UV-exposure.

In still other embodiments, the 15-PGDH inhibitors described herein can be used in a pharmaceutical composition for the prevention or the treatment of cardiovascular disease and/or diseases of vascular insufficiency, such as Raynaud's disease, Buerger's disease, diabetic neuropathy, and pulmonary artery hypertension. Prostaglandins including prostaglandin homologues produced in the body have been known to maintain the proper action of the blood vessel wall, especially to contribute to vasodilation for blood flow, preventing platelet aggregation and modulating the proliferation of smooth muscle that surrounds blood vessel walls (Yan. Cheng et. al., 2006, J. Clin., Invest). In addition, the inhibition of prostaglandins production or the loss of their activity causes the degeneration of the endothelium in the blood vessel walls, platelet aggregation and the dysfunction of cellular mechanism in the smooth muscle. Among others, the production of prostaglandins in blood vessels was shown to be decreased in hypertension patients, including pulmonary artery hypertension.

In other embodiments, the 15-PGDH inhibitors described herein can be used in a pharmaceutical composition for the prevention or the treatment of oral, intestinal, and/or gastrointestinal injury or diseases, or inflammatory bowel disease, such as oral ulcers, gum disease, gastritis, colitis, ulcerative colitis, and gastric ulcers. Gastritis and gastric ulcer, representatives of the gastrointestinal diseases, are defined as the conditions where gastrointestinal mucus membrane is digested by gastric acid to form ulcer. In the stomach walls generally consisting of mucosa, submucosa, muscle layer and serosa, gastric ulcer even damages submucosa and muscle layer, while gastritis damages mucosa only. Although the morbidity rates of gastritis and gastric ulcer are relatively high, the causes thereof have not been clarified yet. Until now, they are known to be caused by an imbalance between aggressive factors and defensive factors, that is, the increase in aggressive factors such as the increase in gastric acid or pepsin secretion, or the decrease in defensive factors such as structural or morphological deficit of the gastric mucus membrane, the decrease in mucus and bicarbonate ion secretion, the decrease in prostaglandin production, or the like.

Currently available therapeutic agents for gastritis and gastric ulcer comprise various drugs for strengthening the defensive factors such as an antacid, which does not affect gastric acid secretion but neutralizes gastric acid that has been already produced, an inhibitor of gastric acid secretion, a promoter of prostaglandin secretion, and a coating agent for stomach walls. Especially, prostaglandins are known to be essential in maintaining the mechanism for protecting and defending gastric mucus membrane (Wallace J L., 2008, Physiol Rev., 88(4), 1547-65, S. J. Konturek et al., 2005, Journal of Physiology and Pharmacology, 56(5)). In view of the above, since the 15-PGDH inhibitors described herein show a suppressive or inhibitory activity against 15-PGDH, which degrades prostaglandins that protect gastric mucus membrane, they can be effective for the prevention or the treatment of gastrointestinal diseases, inter alia, gastritis and gastric ulcer.

Moreover, 15-PGDH inhibitors would also be expected to protect from other form of intestinal injury that would include toxicity from radiation, toxicity from chemotherapy, and chemotherapy induced mucositis.

In the kidney, prostaglandins modulate renal blood flow and may serve to regulate urine formation by both renovascular and tubular effects. In clinical studies, $PGE_1$ has been used to improve creatinine clearance in patients with chronic renal disease, to prevent graft rejection and cyclosporine toxicity in renal transplant patients, to reduce the urinary albumin excretion rate and N-acetyl-β-D-glucosaminidase levels in patients with diabetic nephropathy (see Porter, Am., 1989, J. Cardiol., 64: 22E-26E). In addition, U.S. Pat. No.

5,807,895 discloses a method of preventing renal dysfunction by intravenous administration of prostaglandins such as $PGE_1$, $PGE_2$ and $PGI_2$. Furthermore, it has been reported that prostaglandins serve as vasodilators in the kidney, and, thus, the inhibition of prostaglandin production in the kidney results in renal dysfunction (Hao. C M, 2008, Annu Rev Physiol, 70, 357.about.77).

Thus, the 15-PGDH inhibitors described herein, which have a suppressive or inhibitory activity against 15-PGDH that degrades prostaglandins, may be effective in the prevention or the treatment of renal diseases that are associated with renal dysfunction.

The term "renal dysfunction" as used herein includes such manifestations as follows: lower than normal creatinine clearance, lower than normal free water clearance, higher than normal blood urea, nitrogen, potassium and/or creatinine levels, altered activity of kidney enzymes such as gamma glutamyl synthetase, alanine phosphatidase, N-acetyl-β-D-glucosaminidase, or β-w-microglobulin; and increase over normal levels of macroalbuminuria.

Prostaglandins including $PGE_1$, $PGE_2$ and $PGF_{2a}$ have also been shown to stimulate bone resorption and bone formation to increase the volume and the strength of the bone (H. Kawaguchi et. al., Clinical Orthop. Rel. Res., 313, 1995; J. Keller et al., Eur. Jr. Exp. Musculoskeletal Res., 1, 1992, 8692). Considering that 15-PGDH inhibits the activities of prostaglandins as mentioned in the above, the inhibition of 15-PGDH activity may lead to the promotion of bone resorption and bone formation that are inhibited by 15-PGDH. Thus, the
15-PGDH inhibitors described herein can be effective for the promotion of bone resorption and bone formation by inhibiting 15-PGDH activity. 15-PGDH inhibitors can also be used to increase bone density, treat osteoporosis, promote healing of fractures, or promote healing after bone surgery or joint replacement, or to promote healing of bone to bone implants, bone to artificial implants, dental implants, and bone grafts.

In yet other embodiments, the 15-PGDH inhibitors described herein can effective for treating 15-PGDH expressing cancers. Inhibition of 15-PGDH can inhibit the growth, proliferation, and metastasis of 15-PGDH expressing cancers.

In still other embodiments, the 15-PGDH inhibitors described herein can be effective for wound healing. Among various prostaglandins, $PGE_2$ is known to serve as a mediator for wound healing. Therefore, when skin is injured by wounds or burns, the inhibition of 15-PGDH activity can produce the treatment effect of the wounds or the burns by $PGE_2$.

Additionally, as discussed above, increased prostaglandin levels have been shown to stimulate signaling through the Wnt signaling pathway via increased β-catenin mediated transcriptional activity. Wnt signaling is known to be a key pathway employed by tissue stem cells. Hence, 15-PGDH inhibitors described herein may be utilized to increase tissue stem cell numbers for purposes that would include promoting tissue regeneration or repair in organs that would include liver, colon, and bone marrow. In addition, 15-PGDH inhibitors described herein may be utilized to promote tissue regeneration or repair in additional organs that would include but are not limited to brain, eye, cornea, retina, lung, heart, stomach, small intestine, pancreas,
β-cells of the pancreas, kidney, bone, cartilage, peripheral nerve.

Syndromic conditions, traumatic injuries, chronic conditions, medical interventions, or other conditions that cause or are associated with tissue damage and a need for tissue repair, and thus, suitable for treatment or amelioration using the methods described herein, include, but are not limited to, acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetes, diabetic neuropathy, diabetes induced ischemia, disseminated intravascular coagulation (DIC), embolic brain ischemia, graft-versus-host disease, frostbite, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

Other illustrative examples of genetic disorders, syndromic conditions, traumatic injuries, chronic conditions, medical interventions, or other conditions that cause or are associated with tissue damage and a need for tissue repair suitable for treatment or amelioration using the methods of the present invention, include, ischemia resulting from surgery, chemotherapy, radiation therapy, or cell, tissue, or organ transplant or graft.

In various embodiments, the methods of the invention are suitable for treating cerebrovascular ischemia, myocardial ischemia, limb ischemia (CLI), myocardial ischemia (especially chronic myocardial ischemia), ischemic cardiomyopathy, cerebrovascular ischemia, renal ischemia, pulmonary ischemia, intestinal ischemia, and the like.

In some embodiments, the ischemia is associated with at least one of acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

In some embodiments, the 15-PGDH inhibitor can be administered to a preparation of hematopoietic stem cells, such as peripheral blood hematopoietic stem cells or umbilical cord stem cells of the subject, to increase the fitness of the stem cell preparation as a donor graft or to decrease the number of units of umbilical cord blood required for transplantation.

Hematopoietic stem cells are multipotent stem cells that give rise to all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al, U.S. Pat. No. 5,635,387; McGlave, et al, U.S. Pat. No. 5,460,964; Simmons, P., et al, U.S. Pat. No. 5,677,136; Tsukamoto, et al, U.S. Pat. No. 5,750,397; Schwartz, et al, U.S. Pat. No. 5,759,793; DiGuisto, et al, U.S. Pat. No. 5,681,599; Tsukamoto, et al, U.S. Pat. No. 5,716,827). Hematopoietic stem cells (HSCs) give rise to committed hematopoietic progenitor cells (HPCs) that are capable of generating the entire repertoire of mature blood cells over the lifetime of an organism.

Hematopoietic stem cells and hematopoietic progenitor cells are described herein generally as hematopoietic stem cells unless noted otherwise and can refer to cells or populations identified by the presence of the antigenic marker CD34 (CD34$^+$). In some embodiments, the hematopoietic stem cells can be identified by the presence of the antigenic marker CD34 and the absence of lineage (lin) markers and are therefore characterized as CD34$^+$/lin$^-$ cells.

The hematopoietic stem cells used in the methods described herein may be obtained from any suitable source of hematopoietic stem and progenitor cells and can be provided as a high purified population of hematopoietic stem cells or as composition that includes about 0.01% to about 100% of hematopoietic stem cells. For example, hematopoietic stem cells may be provided in compositions, such as unfractionated bone marrow (where the hematopoietic stem cells comprise less than about 1% of the bone marrow cell population), umbilical cord blood, placental blood, placenta, fetal blood, fetal liver, fetal spleen, Wharton's jelly, or mobilized peripheral blood.

Suitable sources of hematopoietic stem cells can be isolated or obtained from an organ of the body containing cells of hematopoietic origin. The isolated cells can include cells that are removed from their original environment. For example, a cell is isolated if it is separated from some or all of the components that normally accompany it in its native state. For example, an "isolated population of cells," an "isolated source of cells," or "isolated hematopoietic stem cells" and the like, as used herein, refer to in vitro or ex vivo separation of one or more cells from their natural cellular environment, and from association with other components of the tissue or organ, i.e., it is not significantly associated with in vivo substances.

Hematopoietic stem cells can be obtained or isolated from bone marrow of adults, which includes femurs, hip, ribs, sternum, and other bones. Bone marrow aspirates containing hematopoietic stem cells can be obtained or isolated directly from the hip using a needle and syringe. Other sources of hematopoietic stem cells include umbilical cord blood, placental blood, mobilized peripheral blood, Wharton's jelly, placenta, fetal blood, fetal liver, or fetal spleen. In particular embodiments, harvesting a sufficient quantity of hematopoietic stem cells for use in therapeutic applications may require mobilizing the stem and progenitor cells in the donor.

"Hematopoietic stem cell mobilization" refers to the release of stem cells from the bone marrow into the peripheral blood circulation for the purpose of leukapheresis, prior to stem cell transplantation. By increasing the number of stem cells harvested from the donor, the number of stem cells available for therapeutic applications can be significantly improved. Hematopoietic growth factors, e.g., granulocyte colony stimulating factor (G-CSF) or chemotherapeutic agents often are used to stimulate the mobilization. Commercial stem cell mobilization drugs exist and can be used in combination with G-CSF to mobilize sufficient quantities of hematopoietic stem and progenitor cells for transplantation into a subject. For example, G-CSF and Mozobil (Genzyme Corporation) can be administered to a donor in order to harvest a sufficient number of hematopoietic cells for transplantation. Other methods of mobilizing hematopoietic stem cells would be apparent to one having skill in the art.

In some embodiments, hematopoietic stem and progenitor cells (HSPCs) are obtained from umbilical cord blood. Cord blood can be harvested according to techniques known in the art (see, e.g., U.S. Pat. Nos. 7,147,626 and 7,131,958, herein incorporated by reference for such methodologies).

In one embodiment, HSPCs can be obtained from pluripotent stem cell sources, e.g., induced pluripotent stem cells (iPSCs) and embryonic stem cells (ESCs). As used herein, the term "induced pluripotent stem cell" or "iPSC" refers to a non-pluripotent cell that has been reprogrammed to a pluripotent state. Once the cells of a subject have been reprogrammed to a pluripotent state, the cells can then be programmed to a desired cell type, such as a hematopoietic stem or progenitor cell. As used herein, the term "reprogramming" refers to a method of increasing the potency of a cell to a less differentiated state. As used herein, the term "programming" refers to a method of decreasing the potency of a cell or differentiating the cell to a more differentiated state.

In some embodiments, the hematopoietic stem cells can be administered or contacted ex vivo with one or more 15-PGDH inhibitors described herein to provide a therapeutic composition. In one embodiment, the therapeutic compositions of the can include a population of hematopoietic stem cells treated ex vivo with a one or more 15-PGDH inhibitor. In certain embodiments, the therapeutic composition comprising the enhanced HSPCs is whole bone marrow, umbilical cord blood, or mobilized peripheral blood.

In particular embodiments, the therapeutic composition includes a population of cells, wherein the population of cells is about 95% to about 100% hematopoietic stem cells. The invention contemplates, in part, that using therapeutic compositions of highly purified hematopoietic stem cells, e.g., a composition comprising a population of cells wherein the cells comprise about 95% hematopoietic stem cells, may improve the efficiency of stem cell therapies. Currently practiced methods of transplantations typically use unfractionated mixtures of cells where hematopoietic stem cells comprise less than 1% of the total cell population.

In some embodiments, the therapeutic composition comprises a population of cells, wherein the population of cells comprises less than about 0.1%, 0.5%, 1%, 2%, 5%, 10%, 15%, 20%, 25%, or 30% hematopoietic stem cells. The population of cells in some embodiments comprises less than about 0.1%, 0.5%, 1%, 2%, 5%, 10%, 15%, 20%, 25%, or 30% hematopoietic stem cells. In other embodiments, the population of cells is about 0.1% to about 1%, about 1% to about 3%, about 3% to about 5%, about 10%-15%, about 15%-20%, about 20%-25%, about 25%-30%, about 35%-40%, about 40%-45%, about 45%-50%, about 60%-70%, about 70%-80%, about 80%-90%, about 90%-95%, or about 95% to about 100% hematopoietic stem cells.

Hematopoietic stem cells in the therapeutic compositions of the invention can be autologous/autogeneic ("self") or non-autologous ("non-self," e.g., allogeneic, syngeneic or xenogeneic) relative to a subject to which the therapeutic composition is to be administered. "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison.

Hematopoietic stem cells for use in the methods of the present invention may be depleted of mature hematopoietic cells such as T cells, B cells, NK cells, dendritic cells, monocytes, granulocytes, erythroid cells, and their committed precursors from bone marrow aspirate, umbilical cord blood, or mobilized peripheral blood (mobilized leukapheresis product). Mature, lineage committed cells are depleted by immunodepletion, for example, by labeling solid substrates with antibodies that bind to a panel of so-called "lineage" antigens: CD2, CD3, CD11b, CD14, CD15, CD16, CD79, CD56, CD123, and CD235a. A subsequent step can be performed to further purify the population of cells, in which a substrate labeled with antibodies that bind to the CD34$^+$ antigen are used to isolate primitive hematopoietic stem cells. Kits are commercially available for purifying stem and progenitor cells from various cell sources and in particular embodiments, these kits are suitable for use with the methods described herein.

In one embodiment, the amount of hematopoietic stem cells in the therapeutic composition is at least $0.1 \times 10^5$ cells, at least $0.5 \times 10^5$ cells, at least $1 \times 10^5$ cells, at least $5 \times 10^5$ cells, at least $10 \times 10^5$ cells, at least $0.5 \times 10^6$ cells, at least $0.75 \times 10^6$ cells, at least $1 \times 10^6$ cells, at least $1.25 \times 10^6$ cells, at least $1.5 \times 10^6$ cells, at least $1.75 \times 10^6$ cells, at least $2 \times 10^6$ cells, at least $2.5 \times 10^6$ cells, at least $3 \times 10^6$ cells, at least $4 \times 10^6$ cells, at least $5 \times 10^6$ cells, at least $10 \times 10^6$ cells, at least $15 \times 10^6$ cells, at least $20 \times 10^6$ cells, at least $25 \times 10^6$ cells, or at least $30 \times 10^6$ cells.

In one embodiment, the amount of hematopoietic stem cells in the therapeutic composition is the amount of HSPCs in a partial or single cord of blood, or is at least $0.1 \times 10^5$ cells/kg of bodyweight, at least $0.5 \times 10^5$ cells/kg of bodyweight, at least $1 \times 10^5$ cells/kg of bodyweight, at least $5 \times 10^5$ cells/kg of bodyweight, at least $10 \times 10^5$ cells/kg of bodyweight, at least $0.5 \times 10^6$ cells/kg of bodyweight, at least $0.75 \times 10^6$ cells/kg of bodyweight, at least $1 \times 10^6$ cells/kg of bodyweight, at least $1.25 \times 10^6$ cells/kg of bodyweight, at least $1.5 \times 10^6$ cells/kg of bodyweight, at least $1.75 \times 10^6$ cells/kg of bodyweight, at least $2 \times 10^6$ cells/kg of bodyweight, at least $2.5 \times 10^6$ cells/kg of bodyweight, at least $3 \times 10^6$ cells/kg of bodyweight, at least $4 \times 10^6$ cells/kg of bodyweight, at least $5 \times 10^6$ cells/kg of bodyweight, at least $10 \times 10^6$ cells/kg of bodyweight, at least $15 \times 10^6$ cells/kg of bodyweight, at least $20 \times 10^6$ cells/kg of bodyweight, at least $25 \times 10^6$ cells/kg of bodyweight, or at least $30 \times 10^6$ cells/kg of bodyweight.

Preparations of hematopoietic stem cells administered one or more 15-PGDH inhibitors and/or therapeutic compositions that include hematopoietic stem cells and one or more 15-PGDH inhibitor can be used for improving hematopoietic stem cell transplants and in treating ischemia or ischemia-damaged tissue, and in reducing further damage to ischemic tissue and/or repairing damage to ischemic tissue through cell recruitment, improving vascularization in ischemic tissue, improving tissue regeneration at sites of ischemia, decreasing ischemic tissue necrosis or apoptosis, and/or increasing cell survival at sites of ischemia. In particular embodiments, the preparations of 15-PGDH inhibitor treated hematopoietic stem cells and/or therapeutic compositions of 15-PGDH inhibitors and hematopoietic stem cells are useful to subjects in need of hematopoietic reconstitution, such as subjects that have undergone or are scheduled to undergo myeloablative therapy.

Subjects, which can be treated with the preparations of 15-PGDH inhibitor treated hematopoietic stem cells and/or therapeutic compositions of 15-PGDH inhibitors and hematopoietic stem cells, can include subjects that have or that have been diagnosed with various types of leukemias, anemias, lymphomas, myelomas, immune deficiency disorders, and solid tumors. A subject also includes a human who is a candidate for stem cell transplant or bone marrow transplantation, such as during the course of treatment for a malignant disease or a component of gene therapy. Subjects may also include individuals or animals that donate stem cells or bone marrow for allogeneic transplantation. In certain embodiments, a subject may have undergone myeloablative irradiation therapy or chemotherapy, or may have experienced an acute radiation or chemical insult resulting in myeloablation. In certain embodiments, a subject may have undergone irradiation therapy or chemotherapy, such as during various cancer treatments. Typical subjects include animals that exhibit aberrant amounts (lower or higher amounts than a "normal" or "healthy" subject) of one or more physiological activities that can be modulated by an agent or a stem cell or marrow transplant.

Subjects, which can be treated with the preparations of 15-PGDH inhibitor treated hematopoietic stem cells and/or therapeutic compositions of 15-PGDH inhibitors and hematopoietic stem cells, can also include subjects undergoing chemotherapy or radiation therapy for cancer, as well as subjects suffering from (e.g., afflicted with) non malignant blood disorders, particularly immunodeficiencies (e.g. SCID, Fanconi's anemia, severe aplastic anemia, or congenital hemoglobinopathies, or metabolic storage diseases, such as Hurler's disease, Hunter's disease, mannosidosis, among others) or cancer, particularly hematological malignancies, such as acute leukemia, chronic leukemia (myeloid or lymphoid), lymphoma (Hodgkin's or non-Hodgkin's), multiple myeloma, myelodysplastic syndrome, or non-hematological cancers such as solid tumors (including breast cancer, ovarian cancer, brain cancer, prostate cancer, lung cancer, colon cancer, skin cancer, liver cancer, or pancreatic cancer).

Subjects may also include subjects suffering from aplastic anemia, an immune disorder (severe combined immune deficiency syndrome or lupus), myelodysplasia, thalassemaia, sickle-cell disease or Wiskott-Aldrich syndrome. In some embodiments, the subject suffers from a disorder that is the result of an undesired side effect or complication of another primary treatment, such as radiation therapy, chemotherapy, or treatment with a bone marrow suppressive drug, such as zidovadine, chloramphenical or gangciclovir. Such disorders include neutropenias, anemias, thrombocytopenia, and immune dysfunction. Other subjects may have disorders caused by an infection (e.g., viral infection, bacterial infection or fungal infection) which causes damage to stem or progenitor cells of the bone marrow.

In addition, subjects suffering from the following conditions can also benefit from treatment using the preparations of 15-PGDH inhibitor treated hematopoietic stem cells and/or therapeutic compositions of 15-PGDH inhibitors and hematopoietic stem cells: lymphocytopenia, lymphorrhea, lymphostasis, erythrocytopenia, erthrodegenerative disorders, erythroblastopenia, leukoerythroblastosis; erythroclasis, thalassemia, myelodysplasia, myelofibrosis, thrombocytopenia, disseminated intravascular coagulation (DIC), immune (autoimmune) thrombocytopenic purpura (ITP), HIV inducted ITP, myelodysplasia; thrombocytotic disease, thrombocytosis, congenital neutropenias (such as Kostmann's syndrome and Schwachman-Diamond syndrome), neoplastic associated neutropenias, childhood and adult cyclic neutropaenia; post-infective neutropaenia; myelodysplastic syndrome; neutropaenia associated with chemotherapy and radiotherapy; chronic granulomatous disease; mucopolysaccharidoses; Diamond Blackfan Anemia; Sickle cell disease; or Beta thalassemia major.

In other embodiments, the preparations of 15-PGDH inhibitor treated hematopoietic stem cells and/or therapeutic compositions or 15-PGDH inhibitors and hematopoietic stem cells can be used in cell-based therapy for treating ischemic tissue or treating or ameliorating one or more symptoms associated with tissue ischemia, including, but not limited to, impaired, or loss of, organ function (including without limitation impairments or loss of brain, kidney, or heart function), cramping, claudication, numbness, tingling, weakness, pain, reduced wound healing, inflammation, skin discoloration, and gangrene.

In one embodiment, the subject exhibits at least one symptom of an ischemic tissue or tissue damaged by ischemia. In particular embodiments, the subject is a human who has or who is at risk of having an ischemic tissue or tissue damaged by ischemia, e.g., a subject that has diabetes, peripheral vascular disease, thromboangiitis obliterans, vasculitis, cardiovascular disease, coronary artery disease or heart failure, or cerebrovascular disease, cardiovascular disease, or cerebrovascular disease.

Illustrative examples of genetic disorders, syndromic conditions, traumatic injuries, chronic conditions, medical interventions, or other conditions that cause or are associated with ischemia, or increase the risk of ischemia in a subject, or cause a subject to exhibit more or more symptoms of ischemia, and thus, suitable for treatment or amelioration using the methods described herein, include, but are not limited to, acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, frostbite, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

Other illustrative examples of genetic disorders, syndromic conditions, traumatic injuries, chronic conditions, medical interventions, or other conditions that cause or are associated with ischemia, or increase the risk of ischemia in a subject, or cause a subject to exhibit more or more symptoms of ischemia suitable for treatment or amelioration using the methods of the present invention, include, ischemia resulting from surgery, chemotherapy, radiation therapy, or cell, tissue, or organ transplant or graft.

In various embodiments, the methods of the invention are suitable for treating cerebrovascular ischemia, myocardial ischemia, critical limb ischemia (CLI), myocardial ischemia (especially chronic myocardial ischemia), ischemic cardiomyopathy, cerebrovascular ischemia, renal ischemia, pulmonary ischemia, intestinal ischemia, and the like.

In various embodiments, the invention contemplates that the therapeutic cell compositions disclosed herein can be used to treat an ischemic tissue in which it is desirable to increase the blood flow, oxygen supply, glucose supply, or supply of nutrients to the tissue.

In some embodiments, the 15-PGDH inhibitor can be administered to a preparation of tissue stem cells, such as neural stem cells, mesenchymal stem cells, or stem cells that can generate other tissues, and/or a preparation of pluripotent stem cells.

In one embodiment, tissue stems cells can be obtained from pluripotent stem cell sources, e.g., induced pluripotent stem cells (iPSCs) and embryonic stem cells (ESCs). As used herein, the term "induced pluripotent stem cell" or "iPSC" refers to a non-pluripotent cell that has been reprogrammed to a pluripotent state. Once the cells of a subject have been reprogrammed to a pluripotent state, the cells can then be programmed to a desired cell type, such as a hematopoietic stem or progenitor cell. As used herein, the term "reprogramming" refers to a method of increasing the potency of a cell to a less differentiated state. As used herein, the term "programming" refers to a method of decreasing the potency of a cell or differentiating the cell to a more differentiated state.

In some embodiments, the tissue stem cells and/or pluripotent stem cells can be administered or contacted ex vivo with one or more 15-PGDH inhibitors described herein to provide a therapeutic composition. In one embodiment, the therapeutic compositions can include a population of tissue stem cells treated ex vivo with a one or more 15-PGDH inhibitor.

In particular embodiments, the therapeutic composition includes a population of cells, wherein the population of cells is about 95% to about 100% tissue stem cells. The invention contemplates, in part, that using therapeutic compositions of highly purified tissue stem cells, e.g., a composition comprising a population of cells wherein the cells comprise about 95% tissue stem cells, may improve the efficiency of stem cell therapies In some embodiments, the therapeutic composition comprises a population of cells, wherein the population of cells comprises less than about 0.1%, 0.5%, 1%, 2%, 5%, 10%, 15%, 20%, 25%, or 30% tissue stem cells. The population of cells in some embodiments comprises less than about 0.1%, 0.5%, 1%, 2%, 5%, 10%, 15%, 20%, 25%, or 30% tissue stem cells. In other embodiments, the population of cells is about 0.1% to about 1%, about 1% to about 3%, about 3% to about 5%, about 5%, about 10%-15%, about 15%-20%, about 20%-25%, about 25%-30%, about 30%-35%, about 35%-40%, about 40%-45%, about 45%-50%, about 60%-70%, about 70%-80%, about 80%-90%, about 90%-95%, or about 95% to about 100% tissue stem cells.

Tissue stem cells in the therapeutic compositions of the invention can be autologous/autogenic ("self") or non-autologous ("non-self," e.g., allogeneic, syngeneic or xenogeneic) relative to a subject to which the therapeutic composition is to be administered. "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison.

Preparations of tissue stem cells administered one or more 15-PGDH inhibitors and/or therapeutic compositions that include tissue stem cells and one or more 15-PGDH inhibitor can be used for improving tissue stem cell transplants and in treating damaged tissue, and in reducing further tissue damage tissue and/or potentiating repair to damaged tissue through stem cell recruitment and/or increasing cell survival at sites of tissue damage.

Syndromic conditions, traumatic injuries, chronic conditions, medical interventions, or other conditions that cause or are associated with tissue damage and a need for tissue repair, and thus, suitable for treatment or amelioration using the methods described herein, include, but are not limited to, acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetes, diabetic neuropathy, diabetes induced ischemia, disseminated intravascular coagulation (DIC), embolic brain ischemia, graft-versus-host disease, frostbite, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

Other illustrative examples of genetic disorders, syndromic conditions, traumatic injuries, chronic conditions, medical interventions, or other conditions that cause or are associated with tissue damage and a need for tissue repair suitable for treatment or amelioration using the methods of the present invention, include, ischemia resulting from surgery, chemotherapy, radiation therapy, or cell, tissue, or organ transplant or graft.

In various embodiments, the methods of the invention are suitable for treating cerebrovascular ischemia, myocardial ischemia, limb ischemia (CLI), myocardial ischemia (especially chronic myocardial ischemia), ischemic cardiomyopathy, cerebrovascular ischemia, renal ischemia, pulmonary ischemia, intestinal ischemia, and the like.

In other embodiments, the 15-PGDH inhibitor can be administered to a bone marrow graft donor or a hematopoietic stem cell donor to increase the fitness of a donor bone marrow graft or a donor hematopoietic stem cell graft.

In other embodiments, the 15-PGDH inhibitor can also be administered to bone marrow of a subject to increase stem cells in the subject or to increase the fitness of the marrow as a donor graft.

In yet other embodiments, the 15-PGDH inhibitor can be administered to a subject to mitigate bone marrow graft rejection, to enhance bone marrow graft engraftment, to enhance engraftment of a hematopoietic stem cell graft, or an umbilical cord blood stem cell graft, to enhance engraftment of a hematopoietic stem cell graft, or an umbilical cord stem cell graft, and/or to decrease the number of units of umbilical cord blood required for transplantation into the subject. The administration can be, for example, following treatment of the subject or the marrow of the subject with radiation therapy, chemotherapy, or immunosuppressive therapy.

In other embodiments, the 15-PGDH inhibitor can be administered to a recipient of a bone marrow transplant, of a hematopoietic stem cell transplant, or of an umbilical cord blood stem cell transplant, in order to decrease the administration of other treatments or growth factors.

In some embodiments, the 15-PGDH inhibitor can be administered to a subject to enhance recovery of neutrophils following bone marrow transplantation, following umbilical cord blood transplantation, following transplantation with hematopoietic stem cells, following conventional chemotherapy, following radiation treatment, and in individuals with neutropenias from diseases that include but are not limited to aplastic anemia, myelodysplasia, myelofibrosis, neutropenias from other bone marrow diseases, drug induced neutropenia, immune neutropenias, idiopathic neutropenia, and following infections with viruses that include, but are not limited to, HIV, CMV, and parvovirus.

In other embodiments, the 15-PGDH inhibitor can be administered to a subject to enhance recovery of platelets following bone marrow transplantation, following umbilical cord blood transplantation, following transplantation with hematopoietic stem cells, following conventional chemotherapy, following radiation treatment, and in individuals with neutropenias from diseases that include but are not limited to aplastic anemia, myelodysplasia, myelofibrosis, thrombocytopenias from other bone marrow diseases, drug induced thrombocytopenia, immune thrombocytopenia, idiopathic thrombocytopenic purpura, idiopathic thrombocytopenia, and following infections with viruses that include, but are not limited to, HIV, CMV, and parvovirus.

In still other embodiments, the 15-PGDH inhibitor can be administered to a subject to enhance recovery of hemoglobin following bone marrow transplantation, following umbilical cord blood transplantation, following transplantation with hematopoietic stem cells, following conventional chemotherapy, following radiation treatment, and in individuals with anemias from diseases that include but are not limited to aplastic anemia, myelodysplasia, myelofibrosis, anemia from other bone marrow diseases, drug induced anemia, immune mediated anemias, anemia of chronic disease, idiopathic anemia, and following infections with viruses that include, but are not limited to, HIV, CMV, and parvovirus.

In some embodiments, the 15-PGDH inhibitor can be administered to a subject to enhance numbers of bone marrow stem cell numbers following bone marrow transplantation, following umbilical cord blood transplantation, following transplantation with hematopoietic stem cells, following conventional chemotherapy, following radiation treatment, in individuals with other bone marrow diseases, in individuals with cytopenias following viral infections, and in individuals with cytopenias.

In other embodiments, the 15-PGDH inhibitor can be administered to a subject to enhance response to cytokines administered to individuals with cytopenias that include but are not limited to neutropenia, thrombocytopenia, lymphocytopenia, and anemia. Cytokines whose responses may be enhanced by SW033291 include, but are not limited to: G-CSF, GM-CSF, EPO, IL-3, IL-6, TPO, SCF, and TPO-RA (thrombopoietin receptor agonist).

In further embodiments, the 15-PGDH inhibitor can be administered to a subject or to a tissue graft of a subject to mitigate graft rejection, to enhance graft engraftment, to enhance graft engraftment following treatment of the subject or the marrow of the subject with radiation therapy, chemotherapy, or immunosuppressive therapy, to confer resistance to toxic or lethal effects of exposure to radiation, confer resistance to the toxic effect of Cytoxan, the toxic effect of fludarabine, the toxic effect of chemotherapy, or the toxic effect of immunosuppressive therapy, to decrease infection, and/or to decrease pulmonary toxicity from radiation.

In other embodiments, the 15-PGDH inhibitor can be administered to a recipient of a tissue stem cell transplant, including but not limited to a transplant with hematopoietic stem cells, neural stem stems, mesenchymal stem cells, or stem cells for other tissues, so as to accelerate tissue regeneration and repair following the transplant.

In some embodiments, the administration of a 15-PGDH inhibitor can be in combination with G-CSF for the purpose of increasing neutrophils.

In other embodiments, the administration of a 15-PGDH inhibitor can be in combination with a hematopoietic cytokine for the purpose of increasing neutrophils.

In still other embodiments, the administration of a 15-PGDH inhibitor can be in combination with G-CSF for the purpose of increasing numbers of and/or of mobilizing peripheral blood hematopoietic stem cells.

In other embodiments, the administration of a 15-PGDH inhibitor can be in combination with a hemopoietic cytokine for the purpose of increasing numbers of and/or of mobilizing peripheral blood hematopoietic stem cells.

In some embodiments, the administration of a 15-PGDH inhibitor can be in combination with a second agent, including Plerixafor, for the purpose of increasing numbers of and/or of mobilizing peripheral blood hematopoietic stem cells.

In other embodiments, the administration of a 15-PGDH inhibitor can be in combination with G-CSF for the purpose of increasing numbers of and/or of mobilizing peripheral blood hematopoietic stem cells for use in hematopoietic stem cell transplantation.

In still other embodiments, the administration of a 15-PGDH inhibitor can be in combination with a hemopoietic cytokine for the purpose of increasing numbers of and/or of mobilizing peripheral blood hematopoietic stem cells for use in hematopoietic stem cell transplantation.

In other embodiments, the administration of a 15-PGDH inhibitor can be in combination with a second agent, including Plerixafor, for the purpose of increasing numbers of and/or of mobilizing peripheral blood hematopoietic stem cells for use in hematopoietic stem cell transplantation.

In still other embodiments, the administration of a 15-PGDH inhibitor can be in combination with G-CSF for the purpose of increasing numbers of hematopoietic stem cells in blood or bone marrow.

In other embodiments, the administration of a 15-PGDH inhibitor can be in combination with a hemopoietic cytokine for the purpose of increasing numbers of hematopoietic stem cells in blood or bone marrow.

In other embodiments, the 15-PGDH inhibitors can be used to treat and/or prevent fibrosis and various fibrotic diseases, disorders or conditions, and decrease fibrotic symptoms, such as collagen deposition, inflammatory cytokine expression, and inflammatory cell infiltration.

In some embodiments, a method of treating or preventing a fibrotic disease, disorder or condition includes administering to a subject in need thereof a therapeutically effect amount of a 15-PGDH inhibitor such that at least one symptom or feature of a fibrotic disease, disorder or condition, or other related diseases, disorders or conditions, is reduced in intensity, severity, or frequency, or has delayed onset.

As used herein, the term "fibrotic" diseases, disorders, or conditions include diseases, disorders, or conditions characterized, in whole or in part, by the excess production of fibrous material, including excess production of fibrotic material within the extracellular matrix, or the replacement of normal tissue elements by abnormal, non-functional, and/or excessive accumulation of matrix-associated components. The fibrotic diseases, disorders, or conditions, can include acute and chronic, clinical or subclinical presentation, in which fibrogenic associated biology or pathology is evident.

Examples of fibrotic diseases, disorders and conditions include systemic sclerosis, multifocal fibrosclerosis, nephrogenic systemic fibrosis, scleroderma (including morphea, generalized morphea, or linear scleroderma), sclerodermatous graft-vs-host-disease, kidney fibrosis (including glomerular sclerosis, renal tubulointerstitial fibrosis, progressive renal disease or diabetic nephropathy), cardiac fibrosis (e.g., myocardial fibrosis), pulmonary fibrosis (e.g., glomerulosclerosis pulmonary fibrosis, idiopathic pulmonary fibrosis, silicosis, asbestosis, interstitial lung disease, interstitial fibrotic lung disease, and chemotherapy/radiation induced pulmonary fibrosis), oral fibrosis, endomyocardial fibrosis, deltoid fibrosis, pancreatitis, inflammatory bowel disease, Crohn's disease, nodular fascilitis, eosinophilic fasciitis, general fibrosis syndrome characterized by replacement of normal muscle tissue by fibrous tissue in varying degrees, retroperitoneal fibrosis, liver fibrosis, liver cirrhosis, chronic renal failure; myelofibrosis (bone marrow fibrosis), drug induced ergotism, glioblastoma in Li-Fraumeni syndrome, sporadic glioblastoma, myleoid leukemia, acute myelogenous leukemia, myelodysplastic syndrome, myeloproferative syndrome, gynecological cancer, Kaposi's sarcoma, Hansen's disease, collagenous colitis, acute fibrosis, organ specific fibrosis, and the like.

Illustrative organ specific fibrotic disorders include, but are not limited to, pulmonary fibrosis, pulmonary hypertension, cystic fibrosis, asthma, chronic obstructive pulmonary disease, liver fibrosis, kidney fibrosis, NASH, and the like. Many fibrotic diseases, disorders or conditions have disordered and/or exaggerated deposition of extracellular matrix in affected tissues. Fibrosis may be associated with inflammation, occur as a symptom of underlying disease, and/or caused by surgical procedure or wound healing process. Unchecked fibrosis can result in destruction of the architecture of the underlying organ or tissue, commonly referred to as scarring.

In some embodiments, the 15-PGDH inhibitors can be used to treat or prevent lung fibrosis. The lung fibrosis can be selected from the group consisting of pulmonary fibrosis, pulmonary hypertension, chronic obstructive pulmonary disease (COPD), asthma, idiopathic pulmonary fibrosis, sarcoidosis, cystic fibrosis, familial pulmonary fibrosis, silicosis, asbestosis, coal worker's pneumoconiosis, carbon pneumoconiosis, hypersensitivity pneumonitides, pulmonary fibrosis caused by inhalation of inorganic dust, pulmonary fibrosis caused by an infectious agent, pulmonary fibrosis caused by inhalation of noxious gases, aerosols, chemical dusts, fumes or vapors, drug-induced interstitial lung disease, or pulmonary hypertension, and combinations thereof.

Pulmonary fibrosis is characterized by progressive scarring of lung tissue accompanied by fibroblast proliferation, excessive accumulation of extracellular matrix proteins, and abnormal alveolar structure. The thickened and stiff tissue makes it difficult for lungs to work properly, leading to breathing problems such as shortness of breath, and can ultimately be fatal. Pulmonary fibrosis may be caused by acute lung injury, viral infection, exposure to toxins, radiation, chronic disease, medications, or may be idiopathic (i.e., an undiscovered underlying cause).

The classic findings in idiopathic pulmonary fibrosis show diffuse peripheral scarring of the lungs with small bubbles (known as bullae) adjacent to the outer lining of the surface of the lung, often at the bases of the lungs. Idiopathic pulmonary fibrosis often has a slow and relentless progression. Early on, patients often complain of a dry unexplained cough. Next, shortness of breath (dyspnea) sets in and worsens over time triggered by less and less activity. Eventually, the shortness of breath becomes disabling, limiting all activity and even occurring while sitting still. In rarer cases, the fibrosis can be rapidly progressive, with dyspnea and disability occurring in weeks to months of onset of the disease. This form of pulmonary fibrosis has been referred to as Hamman-Rich syndrome.

Pulmonary hypertension is marked by an increase in the blood pressure of the lung vasculature, including the pulmonary artery, pulmonary vein, and/or pulmonary capillaries. Abnormally high pressure strains the right ventricle of the heart, causing it to expand. Over time, the right ventricle can weaken and lose its ability to pump enough blood to the lungs, leading to the development of heart failure. Pulmonary hypertension can occur as a result of other medical conditions, such as chronic liver disease and liver cirrhosis; rheumatic disorders such as scleroderma or systemic lupus erythematosus (lupus); and lung conditions including tumors, emphysema, chronic obstructive pulmonary disease (COPD), and pulmonary fibrosis. Pulmonary fibrosis may lead to narrowing of pulmonary vasculature resulting in pulmonary hypertension.

Chronic Obstructive Pulmonary Disease (COPD) is a common lung disease that is often associated with chronic bronchitis or emphysema. Symptoms can often include cough, mucus build up, fatigue, wheezing, and respiratory infection.

Chronic bronchitis and emphysema are diseases of the lungs in which the airways become narrowed. This leads to a limitation of the flow of air to and from the lungs, causing shortness of breath (dyspnea). In clinical practice, COPD is defined by its characteristically low airflow on lung function tests.

Lung damage and inflammation in the large airways results in chronic bronchitis. In the airways of the lung, the hallmark of chronic bronchitis is an increased number (hyperplasia) and increased size (hypertrophy) of the goblet cells and mucous glands of the airway. As a result, there is more mucus than usual in the airways, contributing to narrowing of the airways and causing a cough with sputum. Microscopically there is infiltration of the airway walls with inflammatory cells. Inflammation is followed by scarring and remodeling that thickens the walls and also results in narrowing of the airways. As chronic bronchitis progresses, there is squamous metaplasia (an abnormal change in the tissue lining the inside of the airway) and fibrosis (further thickening and scarring of the airway wall). The consequence of these changes is a limitation of airflow and difficulty breathing.

Asthma is a chronic lung disease characterized by inflammation and constriction of the airways. Asthma causes recurring periods of wheezing, tightness of the chest, shortness of breath, and coughing. Swelling and overproduction of mucus can cause further airway constriction and worsening of symptoms. There is evidence that increased matrix degradation may occur in asthma, and this may contribute to mechanical changes in the airways in asthma (Roberts et al (1995) Chest 107:111 S-117S, incorporated herein by reference in its entirety. Treatment of extracellular matrix degradation may ameliorate symptoms of asthma.

Cystic fibrosis is a recessive multi-system genetic disease characterized by abnormal transport of chloride and sodium across epithelium, leading to thick, viscous secretions in the lungs, pancreas, liver, intestine and reproductive tract. Cystic fibrosis is caused by a mutation in the gene for the protein cystic fibrosis transmembrane conductance regulator (CFTR). Lung disease results from clogging of the airways due to mucus build-up, decreased mucociliary clearance, and resulting inflammation, which can cause fibrotic injury and structural changes to the lungs. The fibrotic lung damage progresses over time leading some cystic fibrosis patients to require lung transplant.

Common symptoms of subjects suffering from cystic fibrosis include, but are not limited to, accumulation of thick mucus, copious phlegm production, frequent chest infections, frequent coughing, frequent shortness of breath, inflammation, decreased ability to exercise, opportunistic infections of the lung and sinus (including but not limited to *Staphylococcus aureus, Haemophilus influenzae, Mycobacterium aviium*, and *Pseudomonas aeruginosa*), pneumonia, tuberculosis, bronchiectasis, hemoptysis, pulmonary hypertension (and resulting heart failure), hypoxia, respiratory failure, allergic bronchopulmonary aspergillosis, mucus in the paranasal sinuses, sinus infection, facial pain, fever, excessive nasal drainage, development of nasal polyps, cardiorespiratory complications, CF-related diabetes, rectal prolapse, pancreatitis, malabsorption, intestinal blockage, exocrine pancreatic insufficiency, bile duct blockage, and liver cirrhosis.

In other embodiments, the 15-PGDH inhibitors can be used to treat or prevent fibrotic diseases, disorders or conditions caused by post-surgical adhesion formation. Post-surgical adhesion formation is a common complication of surgery. The formation of adhesions, from mechanical damage, ischemia, and infections, can increase morbidity and mortality following surgery. Although refined surgical procedures can reduce the magnitude of adhesion formation, adhesions are rarely eviscerated and an effective adjunctive therapy is needed. Reducing the fibrosis associated with this process could reduce pain, obstruction and other complications of surgery and promote healing and recovery.

Wounds (i.e., lacerations, openings) in mammalian tissue result in tissue disruption and coagulation of the microvasculature at the wound face. Repair of such tissue represents an orderly, controlled cellular response to injury. Soft tissue wounds, regardless of size, heal in a similar manner. Tissue growth and repair are biologic systems wherein cellular proliferation and angiogenesis occur in the presence of an oxygen gradient. The sequential morphological and structural changes which occur during tissue repair have been characterized in detail and have in some instances been quantified (see e.g., Hunt, T. K., et al., "Coagulation and macrophage stimulation of angiogenesis and wound healing," in The Surgical Wound, pp. 1-18, ed. F. Dineen & G. Hildrick-Smith (Lea & Febiger, Philadelphia: 1981)). The cellular morphology consists of three distinct zones. The central avascular wound space is oxygen deficient, acidotic and hypercarbic, and has high lactate levels. Adjacent to the wound space is a gradient zone of local anemia (ischemia) which is populated by dividing fibroblasts. Behind the leading zone is an area of active collagen synthesis characterized by mature fibroblasts and numerous newly-formed capillaries (i.e., neovascularization). U.S. Pat. Nos. 5,015,629 and 7,022,675 (each incorporated by reference herein) disclose methods and compositions for increasing the rate of wound repair.

In some embodiments, the 15-PGDH inhibitors can used for reducing or preventing scar formation in a subject by administering to a subject in need of treatment. Scar formation is a natural part of the healing process. Disorderly collagen synthesis and deposition in a wound can result in excessive, thick, or raised scar formation. Generally, the larger the wound, the longer it takes to heal and the greater the chance of a problematic scar.

In other embodiments, the 15-PGDH inhibitors can be used to reduce or prevent scar formation on skin or scleroderma. There are several types of scars on skin. Hypertropic scars are raised, pinkish-red areas located inside the borders of the original injury. They are often described as itchy. In some cases, hypertropic scars shrink and fade on their own. Keloids are raised, deep-red areas that tend to cover much more area than that of the original injury. Even when surgically removed, keloids tend to recur. Atrophic scars are skin depressions, like those that sometimes form from severe acne. They are caused by inflammation that destroys the collagen during the rebuilding process, leaving an area of indentation.

In some embodiments, the 15-PGDH inhibitors can be used to treat or prevent systemic sclerosis. Systemic sclerosis is a systemic connective tissue disease characterized by alterations of the microvasculature, disturbances of the immune system and by massive deposition of collagen and other matrix substances in the connective tissue. Systemic sclerosis is a clinically heterogeneous generalized disorder which affects the connective tissue of the skin and internal organs such as gastrointestinal tract, lungs, heart and kidneys. Reduction of fibrosis resulting from systemic sclerosis may ameliorate symptoms and/or prevent further complications in affected tissues.

In other embodiments, the 15-PGDH inhibitors can be used to treat or prevent liver fibrosis. Liver fibrosis can result from a chronic liver disease, viral induced hepatic cirrhosis, hepatitis B virus infection, hepatitis C virus infection, hepatitis D virus infection, schistosomiasis, primary biliary cirrhosis, alcoholic liver disease or non-alcoholic steatohepatitis (NASH), NASH associated cirrhosis obesity, diabetes, protein malnutrition, coronary artery disease, auto-immune hepatitis, cystic fibrosis, alpha-1-antitrypsin deficiency, primary biliary cirrhosis, drug reaction and exposure to toxins.

Nonalcoholic steatohepatitis (NASH) is a common liver disease. It resembles alcoholic liver disease but occurs in people who drink little or no alcohol. The major feature in NASH is fat in the liver, along with inflammation and damage. Nevertheless, NASH can be severe and can lead to cirrhosis, in which the liver is permanently damaged and scarred and no longer able to work properly.

NASH is usually a silent disease with few or no symptoms. Patients generally feel well in the early stages and only begin to have symptoms—such as fatigue, weight loss, and weakness—once the disease is more advanced or cirrhosis develops. The progression of NASH can take years, even decades. The process can stop and, in some cases may even begin to reverse on its own without specific therapy. Or NASH can slowly worsen, causing scarring or fibrosis to appear and accumulate in the liver. As fibrosis worsens, cirrhosis develops in which the liver becomes seriously scarred, hardened, and unable to function normally. Not every person with NASH develops cirrhosis, but once serious scarring or cirrhosis is present, few treatments can halt the progression. A person with cirrhosis experiences fluid retention, muscle wasting, bleeding from the intestines, and liver failure. Liver transplantation is the only treatment for advanced cirrhosis with liver failure, and transplantation is increasingly performed in people with NASH. NASH ranks as one of the major causes of cirrhosis in America, behind hepatitis C and alcoholic liver disease.

In some embodiments, the 15-PGDH inhibitors can be used to treat or prevent kidney fibrosis. Kidney fibrosis can result from dialysis following kidney failure, catheter placement, a nephropathy, glomerulosclerosis, glomerulonephritis, chronic renal insufficiency, acute kidney injury, end stage renal disease or renal failure.

Kidney (renal) fibrosis results from excessive formation of fibrous connective tissue in the kidney. Kidney fibrosis causes significant morbidity and mortality and leads to a need for dialysis or kidney transplantation. Fibrosis can occur in either the filtering or reabsorptive component of the nephron, the functional unit of the kidney. A number of factors may contribute to kidney scarring, particularly derangements of physiology involved in the autoregulation of glomerular filtration. This in turn leads to replacement of normal structures with accumulated extracellular matrix. A spectrum of changes in the physiology of individual cells leads to the production of numerous peptide and non-peptide fibrogens that stimulate alterations in the balance between extracellular matrix synthesis and degradation to favor scarring.

In some embodiments, the symptoms of fibrosis of a tissue organ can comprise inflammation. In these embodiments, a therapeutically effective amount of the 15-PGDH inhibitor administered to the subject in need thereof can be an amount effective to decrease or reduce inflammatory cell count in the tissue or organ. A relevant sample can be obtained from the subject to determine the decrease or reduction in inflammatory cell count. In a non-limiting embodiment, the beneficial effect may be assessed by demonstrating a reduction in neutrophil count in BAL fluid from the subject with cystic fibrosis. The excessive recruitment of neutrophils into the airways of patients with CF is a significant predictor of lung disease severity in CF and therefore is an important therapeutic target. Methods for measuring such cell counts are well known in the art, including but not limited to FACS techniques. In some embodiments, the method may comprise reducing neutrophil cell count in BAL fluid from the subject compared to control. Any suitable control can be used for comparison, such as cystic fibrosis subjects not treated the 15-PGDH inhibitors. In some embodiments, a decrease in inflammatory cell count, such as neutrophil count, provides a clinical benefit to the subject. In various embodiments, the reduction in inflammatory cell count is at least 5%, 10%, 15%, 20%, 25%, 50%, or more compared to control.

In another embodiment, the beneficial effect of the 15-PGDH inhibitors may be assessed by a reduction in one or more inflammatory biomarkers in a relevant sample from the subject. In various non-limiting embodiments, the inflammatory biomarker may comprise or consist of one or more of cytokines or inflammatory cytokines associated with fibrosis. Such cytokines can include, for example, IL1β, MIP2 (e.g., CCL3 or CCL4), IFNδ, TGFβ, TNFα, IL-6, MCP-1, IL2, and IL-10 in BAL fluid. Methods for measuring the amount of such biomarkers are well known in the art, including but not limited to ELISAs. Thus, in this embodiment, the methods may further comprise the reducing an amount of one or more inflammatory biomarkers in a sample from the subject compared to control.

In other embodiments, the 15-PGDH inhibitors can be used in a method for decreasing or reducing collagen secretion or collagen deposition in a tissue or organ, such as the lung, the liver, the skin or the heart, of a subject. The method can include administering a therapeutically effective amount of the 15-PGDH inhibitors to the subject in need thereof. The subject can have or be at risk of an excessive collagen secretion or collagen deposition in the tissue or organ, such as the kidney, the lung, the liver, the intestines, the colon, the skin or the heart. Usually, the excessive collagen secretion or collagen deposition in an organ results from an injury or an insult. Such injury and insult are organ-specific. The 15-PGDH inhibitors can be administered over a sufficient period of time to decrease or reduce the level of collagen deposition in the tissue or organ, completely or partially. A sufficient period of time can be during one week, or between 1 week to 1 month, or between 1 to 2 months, or 2 months or more. For chronic condition, the 15-PGDH inhibitors can be advantageously administered for life time period.

15-PGDH inhibitors used to treat the fibrotic disease, disorder or condition and/or reduce collagen deposition can be identified using assays in which putative inhibitor compounds are applied to cells expressing 15-PGDH and then the functional effects on 15-PGDH activity are determined. Samples or assays comprising 15-PGDH that are treated with a potential inhibitor are compared to control samples without the inhibitor to examine the extent of effect. Control samples (untreated with modulators) are assigned a relative 15-PGDH activity value of 100%. Inhibition of 15-PGDH is achieved when the 15-PGDH activity value relative to the control is about 80%, optionally 50% or 25%, 10%, 5% or 1%.

Additionally, in a model organism, $PGE_2$ signaling stimulates liver regeneration and increase survival after exposure to hepatoxic agents, such as acetaminophen. Hence, 15-PGDH inhibitors described herein may be utilized to increase liver regeneration after liver resection, in other settings that include after liver surgery, after live liver donation, or after receiving a liver transplant or to increase liver regeneration and increase survival after exposures to hepatoxic agents, including but not limited to acetaminophen and similar compounds.

PGE1 analogues have also been used in the treatment of erectile dysfunction. Accordingly, in some embodiments, 15-PGDH inhibitors described herein can used either alone or combination with a prostaglandin for the treatment of erectile dysfunction.

15-PGDH inhibitors described herein can also be used to promote neuroprotection in a subject from axonal degeneration, neuronal cell death, and/or glia cell damage after injury, augment neuronal signaling underlying learning and memory, stimulate neuronal regeneration after injury, and/or treat diseases, disorders, and/or conditions of the nervous system.

In some embodiments, the disease, disorder, and/or condition of the nervous system that can be treated with the 15-PGDH inhibitors can include at least one of a neurological disorder, neuropsychiatric disorder, neural injury, neural toxicity disorder, a neuropathic pain, and neural degenerative disorders.

In some embodiments, the 15-PGDH inhibitors described herein can be used in methods for treating (e.g., controlling, relieving, ameliorating, alleviating, or slowing the progression of) or methods for preventing (e.g., delaying the onset of or reducing the risk of developing) one or more diseases, disorders, or conditions caused by, or associated with insufficient (e.g., aberrant) neurogenesis or unwanted neuronal cell death in a subject in need thereof. The methods include administering to the subject an effective amount of a 15-PGDH inhibitor described herein (and/or a compound of any of the other formulae described herein) or a salt (e.g., a pharmaceutically acceptable salt) thereof as defined anywhere herein to the subject. The one or more diseases, disorders, or conditions can include neuropathies, nerve trauma, and neurodegenerative diseases.

In some embodiments, the one or more diseases, disorders, or conditions can be diseases, disorders, or conditions caused by, or associated with insufficient neurogenesis (e.g., aberrant hippocampal neurogenesis) as is believed to occur in neuropsychiatric diseases, or aberrant neuronal cell death as is believed to occur in neurodegenerative diseases. Examples of the one or more diseases, disorders, or conditions include, but are not limited to, schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, and abuse of neuro-active drugs, such as alcohol, opiates, methamphetamine, phencyclidine, and cocaine.

In some embodiments, the subject can be a subject in need thereof (e.g., a subject identified as being in need of such treatment, such as a subject having, or at risk of having, one or more of the diseases or conditions described herein). Identifying a subject in need of such treatment can be in the judgment of a subject or a health care professional and can be subjective (e.g., opinion) or objective (e.g., measurable by a test or diagnostic method). In some embodiments, the subject can be a mammal. In certain embodiments, the subject can be a human.

In other embodiments, the 15-PGDH inhibitors can be used to treat diseases, disorders, or condition associated with elements of the nervous system, including the central, somatic, autonomic, sympathetic and parasympathetic components of the nervous system, neurosensory tissues within the eye, ear, nose, mouth or other organs, as well as glial tissues associated with neuronal cells and structures. Neurological disorders may be caused by an injury to a neuron, such as a mechanical injury or an injury due to a toxic compound, by the abnormal growth or development of a neuron, or by the misregulation, such as downregulation, of an activity of a neuron.

Neurological disorders can detrimentally affect nervous system functions such as the sensory function (the ability to sense changes within the body and the outside environment); the integrative function (the ability to interpret the changes); and the motor function (the ability to respond to the interpretation by initiating an action such as a muscular contraction or glandular secretion).

Examples of neurological disorders that can be treated by administration of the 15-PGDH inhibitors to a subject in need thereof include traumatic or toxic injuries to peripheral or cranial nerves, spinal cord or to the brain, cranial nerves, traumatic brain injury, stroke, cerebral aneurism, and spinal cord injury. Other neurological disorders that can be treated by administration of the 15-PGDH inhibitors to a subject in need thereof include cognitive and neurodegenerative disorders such as Alzheimer's disease, dementias related to Alzheimer's disease (such as Pick's disease), Parkinson's and other Lewy diffuse body diseases, senile dementia, Huntington's disease, Gilles de Ia Tourette's syndrome, multiple sclerosis, amyotrophic lateral sclerosis, hereditary motor and sensory neuropathy (Charcot-Marie-Tooth disease), diabetic neuropathy, progressive supranuclear palsy, epilepsy, and Jakob-Creutzfieldt disease. Autonomic function disorders include hypertension and sleep disorders.

Also to be treated with 15-PGDH inhibitors described herein are neuropsychiatric disorders, such as depression, schizophrenia, schizoaffective disorder, Korsakoff's psychosis, mania, anxiety disorders, or phobic disorders, learning or memory disorders (such as amnesia and age-related memory loss), attention deficit disorder, dysthymic disorder, major depressive disorder, mania, obsessive-compulsive disorder, psychoactive substance use disorders, anxiety, phobias, panic disorder, bipolar affective disorder, psychogenic pain syndromes, and eating disorders. Other examples of neurological disorders that can be treated by administration of the 15-PGDH inhibitors to a subject in need thereof include injuries to the nervous system due to an infectious disease (such as meningitis, high fevers of various etiologies, HIV, syphilis, or post-polio syndrome) and injuries to the nervous system due to electricity (including contact with electricity or lightning, and complications from electroconvulsive psychiatric therapy). Neurological disorders associated with ophthalmic conditions include retina and optic nerve damage, glaucoma and age related macular degeneration.

The developing brain is a target for neurotoxicity in the developing central nervous system through many stages of pregnancy as well as during infancy and early childhood, and the 15-PGDH inhibitors described herein may be utilized in preventing or treating neurological deficits in embryos or fetuses in utero, in premature infants, or in children with need of such treatment, including those with neurological birth defects. Further neurological disorders include, for example, those listed in HARRISON'S PRINCIPLES OF INTERNAL MEDICINE (Braunwald et al., McGraw-Hill, 2001) and in the AMERICAN PSYCHIATRIC ASSOCIATION'S DIAGNOSTIC AND STATISTICAL MANUAL OF MENTAL DISORDERS DSM-IV (American Psychiatric Press, 2000).

The 15-PGDH inhibitors described herein can also be used in a method of to treat a medical condition associated with a neural injury. The medical condition can refer to any movement disorders, epilepsy, cerebrovascular diseases, autoimmune diseases, sleep disorders, autonomic disorders, urinary bladder disorders, abnormal metabolic states, disorders of the muscular system, infectious and parasitic diseases neoplasms, endocrine diseases, nutritional and metabolic diseases, immunological diseases, diseases of the blood and blood-forming organs, mental disorders, diseases of the nervous system, diseases of the sense organs, diseases of the circulatory system, diseases of the respiratory system, diseases of the digestive system, diseases of the genitourinary system, diseases of the skin and subcutaneous tissue, diseases of the musculoskeletal system and connective tissue, congenital anomalies, certain conditions originating in the perinatal period, and symptoms, signs, and ill-defined conditions.

Cerebrovascular disease treatable may be caused by conditions including, but not limited to, aneurysms, strokes, arrhythmia, myocardial infarction, ischemia reperfusion injury, and cerebral hemorrhage.

Autoimmune diseases treatable include, but are not limited to, multiple sclerosis.

Sleep disorders treatable by the 15-PGDH inhibitors may be caused by conditions including, but not limited to, sleep apnea and parasomnias.

Autonomic disorders treatable by the 15-PGDH inhibitors may be caused by conditions including, but not limited to, gastrointestinal disorders, including but not limited to gastrointestinal motility disorders, nausea, vomiting, diarrhea, chronic hiccups, gastroesphageal reflux disease, and hypersecretion of gastric acid, autonomic insufficiency; excessive epiphoresis, excessive rhinorrhea; and cardiovascular disorders including, but not limited, to cardiac dysrythmias and arrythmias, hypertension, and carotid sinus disease.

Urinary bladder disorders treatable by the 15-PGDH inhibitors may be caused by conditions including, but not limited to, spinal cord injury and spastic or flaccid bladder Abnormal metabolic states treatable by the 15-PGDH inhibitors may be caused by conditions including, but not limited to, hyperthyroidism or hypothyroidism.

Disorders of the muscular system treatable by the 15-PGDH inhibitors can include, but are not limited to, muscular dystrophy, and spasms of the upper respiratory tract and face.

The 15-PGDH inhibitors can also be used to treat neuropathic pain caused by conditions including, but not limited to, migraine headaches, including migraine headaches with aura, migraine headaches without aura, menstrual migraines, migraine variants, atypical migraines, complicated migraines, hemiplegic migraines, transformed migraines, and chronic daily migraines, episodic tension headaches, chronic tension headaches, analgesic rebound headaches, episodic cluster headaches, chronic cluster headaches, cluster variants, chronic paroxysmal hemicranias, hemicrania continua, post-traumatic headache, post-traumatic neck pain, post-herpetic neuralgia involving the head or face, pain from spine fracture secondary to osteoporosis, arthritis pain in the spine, headache related to cerebrovascular disease and stroke, headache due to vascular disorder, reflex sympathetic dystrophy, cervicalgia (which may be due to various causes, including, but not limited to, muscular, discogenic, or degenerative, including arthritic, posturally related, or metastatic), glossodynia, carotidynia, cricoidynia, otalgia due to middle ear lesion, gastric pain, sciatica, maxillary neuralgia, laryngeal pain, myalgia of neck muscles, trigeminal neuralgia (sometimes also termed tic douloureux), post-lumbar puncture headache, low cerebro-spinal fluid pressure headache, temporomandibular joint disorder, atypical facial pain, ciliary neuralgia, paratrigeminal neuralgia (sometimes also termed Raeder's syndrome); petrosal neuralgia, Eagle's syndrome, idiopathic intracranial hypertension, orofacial pain, myofascial pain syndrome involving the head, neck, and shoulder, chronic migraneous neuralgia, cervical headache, paratrigeminal paralysis, SPG neuralgia (sometimes also termed lower-half headache, lower facial neuralgia syndrome, Sluder's neuralgia, and Sluder's syndrome), carotidynia, vidian neuralgia, causalgia, and/or a combination of the above.

As used herein, the term "headache" can refer to migraines, tension headaches, cluster headaches, trigeminal neuralgia, secondary headaches, tension-type headaches, chronic and epsisodic headaches, medication overuse/rebound headaches, chronic paroxysmal hemicrinia headaches, hemicranias continua, post-traumatic headaches, post-herpetic headaches, vascular headaches, reflex sympathetic dystrophy-related headaches, crvicalgia headaches, caroidynia headaches, sciatica headaches, trigeminal headaches, occipital headaches, maxillary headaches, diary headaches, paratrigeminal headaches, petrosal headaches, Sluder's headache, vidian headaches, low CSF pressure headaches, TMJ headaches, causalgia headaches, myofascial headaches, all primary headaches (e.g., primary stabbing headache, primary cough headache, primary exertional headache, primary headache associated with sexual activity, hypnic headache, and new daily persistent headache), all trigeminal autonomic cephalagias (e.g., episodic paroxysmal hemicranias, SUNCT, all probable TACs, and SUNA), chronic daily headaches, occipital neuralgia, atypical facial pain, neuropathic trigeminal pain, and miscellaneous-type headaches.

In still other embodiments, the 15-PGDH inhibitors can be used to promote neural stem cell or progenitor cell survival, plasticity, and/or growth. The 15-PGDH inhibitors can be administered to the stem cell or progenitor cells ex vivo, in vitro, or in vivo. When administered ex vivo or in vitro to the stem cells or progenitor cells, the stem cell or progenitor can then be transplanted to a subject for therapeutic applications.

For the neural stem/progenitor cell, for example, a method of transplanting a neural stem/progenitor cell(s) to a desired area that is generally used in the field of regenerative medicine may be employed in conjunction with administration of the 15-PGDH inhibitor to the cells or area. More specifically, there can be exemplified, for example, a method of transplanting a neural stem/progenitor cell(s) to an area of interest by: suspending neural stem/progenitor cells in phosphate buffered saline with the 15-PGDH inhibitor; and adding/injecting the resultant cell suspension to the area.

In other embodiments, the 15-PGDH inhibitors described herein can be applied to a nerve graft. The graft can include any tissue intended for implantation within a human or animal. Various types of graft are encompassed within the subject invention, such as autografts, syngrafts, allografts, and xenografts. The size (e.g., length and diameter) of the graft is not critical. For example, the length of the nerve graft can be from about 1 centimeter to about 10 centimeters, or over about 10 centimeters. The diameter of the nerve graft can match that of any injured nerve or part of a nerve, as needed. The nerve graft can be a structurally complete segment of nerve to bridge a gap along the length of the recipient's nerve or to replace the distal end, i.e., for end-to-end grafting. Alternatively, the nerve graft can be a partial nerve segment, or eccentrically-shaped (e.g., a nerve flap), and intended to reconstruct a lacerated nerve that has some structural disruption, but retains its physical continuity.

When the 15-PGDH inhibitors are applied to a nerve graft, the entire graft can be treated. The therapeutic agents can be applied to the entire nerve graft, en bloc. The en bloc treatment can be applied to living (fresh) or previously frozen nerve grafts. The therapeutic agents can also be applied to a nerve graft before, during, or after implantation. The therapeutic agents can be applied to any portion of the graft, such as the end or ends to be joined to the stump of a damaged nerve. If the therapeutic agent is applied to the damaged nerve, the therapeutic agent can be applied to any area of the damaged nerve that promotes repair of the damaged nerve, such as at the site of damage or adjacent to the site of damage.

The 15-PGDH inhibitors can be placed in a culture medium for application to the nerve graft. The culture medium can be undefined medium, defined medium, or defined medium supplemented with serum for example. Embodiments described herein also include storage solutions for storage of nerve grafts prior to implantation. The storage solution contains a culture medium and at least one 15-PGDH inhibitor. The storage solution can also include other biologically active agents, such as the growth factors described below.

It will be appreciated that the other 15-PGDH inhibitors can be used in the methods described described herein. These other 15-PGDH inhibitors can include known 15-PGDH inhibitors including, for example, tetrazole compounds of formulas (I) and (II), 2-alkylideneaminooxyacetamide compounds of formula (I), heterocyclic compounds of formulas (VI) and (VII), and pyrazole compounds of formula (III) described in U.S. Patent Application Publication No. 2006/0034786 and U.S. Pat. No. 7,705,041; benzylidene-1,3-thiazolidine compounds of formula (I) described in U.S. Patent Application Publication No. 2007/0071699; phenylfurylmethylthiazolidine-2,4-dione and phenylthienylmethylthiazolidine-2,4-dione compounds described in U.S. Patent Application Publication No. 2007/0078175; thiazolidenedione derivatives described in U.S. Patent Application Publication No. 2011/0269954; phenylfuran, phenylthiophene, or phenylpyrrazole compounds described in U.S. Pat. No. 7,294,641; 5-(3,5-disubstituted phenylazo)-2-hydroxybenzene-acetic acids and salts; and lactones described in U.S. Pat. No. 4,725,676; azo compounds described in U.S. Pat. No. 4,889,846; and 15-PGHD inhibitors described in PCT/US2014/060761 and US Patent Application Publication No. 2015/0072998A1, all of which are herein incorporated by reference in their entirety.

The 15-PGDH inhibitors described herein can be provided in a pharmaceutical composition or cosmetic composition depending on the pathological or cosmetic condition or disorder being treated. A pharmaceutical composition containing the 15-PGDH inhibitors described herein as an active ingredient may be manufactured by mixing the derivative with a pharmaceutically acceptable carrier(s) or an excipient(s) or diluting the 15-PGDH inhibitors with a diluent in accordance with conventional methods. The pharmaceutical composition may further contain fillers, anti-cohesives, lubricants, wetting agents, flavoring agents, emulsifying agents, preservatives and the like. The pharmaceutical composition may be formulated into a suitable formulation in accordance with the methods known to those skilled in the art so that it can provide an immediate, controlled or sustained release of the 15-PGDH inhibitors after being administered into a mammal.

In some embodiments, the pharmaceutical composition may be formulated into a parenteral or oral dosage form. The solid dosage form for oral administration may be manufactured by adding excipient, if necessary, together with binder, disintegrants, lubricants, coloring agents, and/or flavoring agents, to the 15-PGDH inhibitors and shaping the resulting mixture into the form of tablets, sugar-coated pills, granules, powder or capsules. The additives that can be added in the composition may be ordinary ones in the art. For example, examples of the excipient include lactose, sucrose, sodium chloride, glucose, starch, calcium carbonate, kaolin, microcrystalline cellulose, silicate and the like. Exemplary binders include water, ethanol, propanol, sweet syrup, sucrose solution, starch solution, gelatin solution, carboxymethylcellulose, hydroxypropyl cellulose, hydroxypropyl starch, methylcellulose, ethylcellulose, shellac, calcium phosphonate and polypyrrolidone. Examples of the disintegrant include dry starch, sodium arginate, agar powder, sodium bicarbonate, calcium carbonate, sodium lauryl sulfate, stearic monoglyceride and lactose. Further, purified talc, stearates, sodium borate, and polyethylene glycol may be used as a lubricant; and sucrose, bitter orange peel, citric acid, tartaric acid, may be used as a flavoring agent. In some embodiments, the pharmaceutical composition can be made into aerosol formulations (e.g., they can be nebulized) to be administered via inhalation.

The 15-PGDH inhibitors described herein may be combined with flavoring agents, buffers, stabilizing agents, and the like and incorporated into oral liquid dosage forms such as solutions, syrups or elixirs in accordance with conventional methods. One example of the buffers may be sodium citrate. Examples of the stabilizing agents include tragacanth, acacia and gelatin.

In some embodiments, the 15-PGDH inhibitors described herein may be incorporated into an injection dosage form, for example, for a subcutaneous, intramuscular or intravenous route by adding thereto pH adjusters, buffers, stabilizing agents, relaxants, topical anesthetics. Examples of the pH adjusters and the buffers include sodium citrate, sodium acetate and sodium phosphate. Examples of the stabilizing agents include sodium pyrosulfite, EDTA, thioglycolic acid and thiolactic acid. The topical anesthetics may be procaine HCl, lidocaine HCl and the like. The relaxants may be sodium chloride, glucose and the like.

In other embodiments, the 15-PGDH inhibitors described herein may be incorporated into suppositories in accordance with conventional methods by adding thereto pharmaceutically acceptable carriers that are known in the art, for example, polyethylene glycol, lanolin, cacao butter or fatty acid triglycerides, if necessary, together with surfactants such as Tween.

The pharmaceutical composition may be formulated into various dosage forms as discussed above and then administered through various routes including an oral, inhalational, transdermal, subcutaneous, intravenous or intramuscular route. The dosage can be a pharmaceutically effective amount. The pharmaceutically effective amount can be an amount of the 15-PGDH inhibitor to treat or improve alopecia, cardiovascular disease, gastrointestinal disease, wounds, and renal disease. The pharmaceutically effective amount of the compound will be appropriately determined depending on the kind and the severity of the disease to be treated, age, sex, body weight and the physical condition of the patients to be treated, administration route, duration of therapy and the like. Generally, the effective amount of the compound may be in the range of about 1 to 1,000 mg in the oral administration, about 0.1 to 500 mg in the intravenous administration, about 5 to 1,000 mg in the rectal administration. Generally, the daily dosage for adults is in the range of about 0.1 to 5,000 mg, preferably about to 1,000 mg but cannot be determined uniformly because it depends on age, sex, body weight and the physical condition of the patients to be treated. The formulation may be administered once a day or several times a day with a divided dose.

Cosmetic compositions containing the 15-PGDH inhibitor can include any substance or preparation intended to be brought into contact with the various superficial parts of the human body (epidermis, body hair and hair system, nails, lips and external genital organs) or with the teeth or the buccal mucous membranes for the purpose, exclusively or mainly, of cleansing them, of giving them a fragrance, of modifying their appearance and/or of correcting body odors and/or protecting them or of maintaining them in good condition.

The cosmetic composition can comprise a cosmetically acceptable medium that may be water or a mixture of water and at least one solvent selected from among hydrophilic organic solvents, lipophilic organic solvents, amphiphilic organic solvents, and mixtures thereof.

For topical application, the cosmetic composition can be administered in the form of aqueous, alcoholic, aqueous-alcoholic or oily solutions or suspensions, or of a dispersion of the lotion or serum type, of emulsions that have a liquid or semi-liquid consistency or are pasty, obtained by dispersion of a fatty phase in an aqueous phase (O/W) or vice versa (W/O) or multiple emulsions, of a free or compacted powder to be used as it is or to be incorporated into a physiologically acceptable medium, or else of microcapsules or microparticles, or of vesicular dispersions of ionic and/or nonionic type. It may thus be in the form of a salve, a tincture, milks, a cream, an ointment, a powder, a patch, an impregnated pad, a solution, an emulsion or a vesicular dispersion, a lotion, aqueous or anhydrous gels, a spray, a suspension, a shampoo, an aerosol or a foam. It may be anhydrous or aqueous. It may also comprise solid preparations constituting soaps or cleansing cakes.

The cosmetic compositions may in particular comprise a hair care composition, and in particular a shampoo, a setting lotion, a treating lotion, a styling cream or gel, restructuring lotions for the hair, a mask, etc. The cosmetic compositions can be a cream, a hair lotion, a shampoo or a conditioner. These can be used in particular in treatments using an application that may or may not be followed by rinsing, or else in the form of a shampoo. A composition in the form of a foam, or else in the form of spray or an aerosol, then comprising propellant under pressure, is also intended. It can thus be in the form of a lotion, serum, milk, cream, gel, salve, ointment, powder, balm, patch, impregnated pad, cake or foam.

In particular, the compositions for application to the scalp or the hair can be in the form of a hair care lotion, for example for daily or twice-weekly application, of a shampoo or of a hair conditioner, in particular for twice-weekly or weekly application, of a liquid or solid soap for cleansing the scalp, for daily application, of a hairstyle shaping product (lacquer, hair setting product or styling gel), of a treatment mask, or of a foaming gel or cream for cleansing the hair. These may also be in the form of a hair dye or mascara to be applied with a brush or a comb.

Moreover, for topical application to the eyelashes or body hair, the compositions may be in the form of a pigmented or unpigmented mascara, to be applied with a brush to the eyelashes or alternatively to beard or moustache hair. For a composition administration by injection, the composition may be in the form of an aqueous lotion or an oily suspension. For oral use, the composition may be in the form of capsules, granules, oral syrups or tablets. According to a particular embodiment, the composition is in the form of a hair cream or hair lotion, a shampoo, a hair conditioner or a mascara for the hair or for the eyelashes.

In a known manner, the cosmetic compositions may also contain adjuvants that are normal in the cosmetics field, such as hydrophilic or lipophilic gelling agents, hydrophilic or lipophilic additives, preservatives, antioxidants, solvents, fragrances, fillers, UV-screening agents, odor absorbers and dyestuffs. The amounts of these various adjuvants are those conventionally used in the cosmetics field, and are for example from 0.1% to 20%, in particular less than or equal to 10%, of the total weight of the composition. According to their nature, these adjuvants can be introduced into the fatty phase, into the aqueous phase and/or into the lipid spherules.

In some embodiments, the 15-PGDH inhibitor can be administered in a combinatorial therapy or combination therapy that includes administration of a 15-PGDH inhibitor with one or more additional active agents. The phrase "combinatorial therapy" or "combination therapy" embraces the administration of the 15-PGDH inhibitor, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

In some embodiments, the additional active agent can be chosen in particular from lipoxygenase inhibitors as described in EP 648488, the bradykinin inhibitors described in particular in EP 845700, prostaglandins and their derivatives, in particular those described in WO 98/33497, WO 95/11003, JP 97-100091, JP 96-134242, the agonists or antagonists of the receptors for prostaglandins, and the nonprostanoic analogues of prostaglandins as described in EP 1175891 and EP 1175890, WO 01/74307, WO 01/74313, WO 01/74314, WO 01/74315 or WO 01/72268.

In other embodiments, the 15-PGDH inhibitors can be administered in combination with active agents, such as vasodilators, prostanoid agonists, antiandrogens, cyclosporins and their analogues, antimicrobials, triterpenes, alone or as a mixture. The vasodilators can include potassium channel agonists including minoxidil and its derivatives, aminexil and the compounds described in U.S. Pat. Nos. 3,382,247, 5,756,092, 5,772,990, 5,760,043, 5,466,694, 5,438,058, 4,973,474, chromakalin and diazoxide. The antiandrogens can include 5.alpha.-reductase inhibitors such as finasteride and the compounds described in U.S. Pat. No. 5,516,779, cyproterone acetate, azelaic acid, its salts and its derivatives, and the compounds described in U.S. Pat. No. 5,480,913, flutamide and the compounds described in U.S. Pat. Nos. 5,411,981, 5,565,467 and 4,910,226. The antimicrobial compounds can include selenium derivatives, ketoconazole, triclocarban, triclosan, zinc pyrithione, itraconazole, pyridine acid, hinokitiol, mipirocine, and the compounds described in EP 680745, clinycine hydrochloride, benzoyl or benzyl peroxide and minocycline. The anti-inflammatory agents can include inhibitors specific for Cox-2 such as for example NS-398 and DuP-697 (B. Batistini et al., DN&P 1994; 7(8):501-511) and/or inhibitors of lipoxygenases, in particular 5-lipoxygenase, such as for example zileuton (F. J. Alvarez & R. T. Slade, Pharmaceutical Res. 1992; 9(11): 1465-1473).

Other active compounds, which can be present in pharmaceutical and/or cosmetic compositions can include aminexil and its derivatives, 6O-[(9Z,12Z)octadec-9,12-dienoyl]

hexapyranose, benzalkonium chloride, benzethonium chloride, phenol, oestradiol, chlorpheniramine maleate, chlorophyllin derivatives, cholesterol, cysteine, methionine, benzyl nicotinate, menthol, peppermint oil, calcium pantothenate, panthenol, resorcinol, protein kinase C inhibitors, prostaglandin H synthase 1 or COX-1 activators, or COX-2 activators, glycosidase inhibitors, glycosaminoglycanase inhibitors, pyroglutamic acid esters, hexosaccharidic or acylhexosaccharidic acids, substituted ethylenearyls, N-acylated amino acids, flavonoids, derivatives and analogues of ascomycin, histamine antagonists, triterpenes, such as ursolic acid and the compounds described in U.S. Pat. Nos. 5,529,769, 5,468,888, 5,631,282, saponins, proteoglycanase inhibitors, agonists and antagonists of oestrogens, pseudopterins, cytokines and growth factor promoters, IL-1 or IL-6 inhibitors, IL-10 promoters, TNF inhibitors, vitamins, such as vitamin D, analogues of vitamin B12 and panthotenol, hydroxy acids, benzophenones, esterified fatty acids, and hydantoin.

Pharmaceutical and/or cosmetic compositions including the 15-PGDH inhibitor described herein can additionally contain, for example, at least one compound chosen from prostaglandins, in particular prostaglandin $PGE_1$, $PGE_2$, their salts, their esters, their analogues and their derivatives, in particular those described in WO 98/33497, WO 95/11003, JP 97-100091, JP 96-134242, in particular agonists of the prostaglandin receptors. It may in particular contain at least one compound such as the agonists (in acid form or in the form of a precursor, in particular in ester form) of the prostaglandin $F_2\alpha$ receptor, such as for example latanoprost, fluprostenol, cloprostenol, bimatoprost, unoprostone, the agonists (and their precursors, in particular the esters such as travoprost) of the prostaglandin $E_2$ receptors such as 17-phenyl $PGE_2$, viprostol, butaprost, misoprostol, sulprostone, 16,16-dimethyl $PGE_2$, 11-deoxy $PGE_1$, 1-deoxy $PGE_1$, the agonists and their precursors, in particular esters, of the prostacycline (IP) receptor such as cicaprost, iloprost, isocarbacycline, beraprost, eprostenol, treprostinil, the agonists and their precursors, in particular the esters, of the prostaglandin $D_2$ receptor such as BW245C ((4S)-(3-[(3R,S)-3-cyclohexyl-3-isopropyl]-2,5-dioxo)-4-imidazolidineheptanoic acid), BW246C ((4R)-(3-[(3R,S)-3-cyclohexyl-3-isopropyl]-2,5-dioxo)-4-imidazolidinehept-anoic acid), the agonists and their precursors, in particular the esters, of the receptor for the thromboxanes A2 (TP) such as I-BOP ([1S-[1a,2a(Z), 3b(1E,3S),4a]]-7-[3-[3-hydroxy-4-[4-(iodophenoxy)-1-butenyl]-7-oxabicyclo-[2.2.1]hept-2-yl]-5-heptenoic acid).

Advantageously, the composition can include at least one 15-PGDH inhibitor as defined above and at least one prostaglandin or one prostaglandin derivative such as for example the prostaglandins of series 2 including in particular $PGF_{2\alpha}$ and $PGE_2$ in saline form or in the form of precursors, in particular of the esters (example isopropyl esters), their derivatives such as 16,16-dimethyl $PGE_2$, 17-phenyl $PGE_2$ and 16,16-dimethyl $PGF_{2\alpha}$ 17-phenyl $PGF_{2\alpha}$, prostaglandins of series 1 such as 11-deoxyprostaglandin E1, 1-deoxyprostaglandin E1 in saline or ester form, is their analogues, in particular latanoprost, travoprost, fluprostenol, unoprostone, bimatoprost, cloprostenol, viprostol, butaprost, misoprostol, their salts or their esters.

The invention is further illustrated by the following examples, which is not intended to limit the scope of the claims.

Example 1

Analysis of Activity of 15-PGDH Inhibitors

This Example provides data on two groups (Table 1 and Table 2) of structural analogues of identified 15-PGDH inhibitors. Data provided is the $IC_{50}$ of each compound for inhibiting enzymatic activity of recombinant 15-PGDH in an in vitro assay. Recombinant 15-PGDH is human unless otherwise specified. Additionally, the example provides data for selected compounds on induction of PGE2 in A549 cell culture administered 2.5 µM or 0.1 µM of the selected compound.

TABLE 1

| Structure # | Compound | Enzyme inhibition ($IC_{50}$, nM) | induction of PGE2 in A549 cell culture at 2.5 µM (fold) | induction of PGE2 in A549 cell culture at 0.1 µM (fold) |
|---|---|---|---|---|
| 1a | [structure] | 24 | 1.89 | 1.29 |
| 2a | [structure] | >2.5 uM | | |

TABLE 1-continued

| Structure # | Compound | Enzyme inhibition (IC$_{50}$, nM) | induction of PGE2 in A549 cell culture at 2.5 μM (fold) | induction of PGE2 in A549 cell culture at 0.1 μM (fold) |
|---|---|---|---|---|
| 3a | | 35.5 | 2.13 | 1.45 |
| 4a | | >2.5 uM | | |
| 5a | | 39 | 1.69 | 1.08 |
| 6a | | 59 | | |
| 7a | | >2500 | | |

TABLE 1-continued

| Structure # | Compound | Enzyme inhibition (IC$_{50}$, nM) | induction of PGE2 in A549 cell culture at 2.5 μM (fold) | induction of PGE2 in A549 cell culture at 0.1 μM (fold) |
|---|---|---|---|---|
| 8a | | 100 | | |
| 9a | | >2500 | | |
| 10a | | 100-500 | | |
| 11a | | 18.9 | | |
| 12a | | >2500 | | |

TABLE 1-continued

| Structure # | Compound | Enzyme inhibition (IC$_{50}$, nM) | induction of PGE2 in A549 cell culture at 2.5 µM (fold) | induction of PGE2 in A549 cell culture at 0.1 µM (fold) |
|---|---|---|---|---|
| 13a | | 500-2500 | | |
| 14a | | 100-500 | | |
| 15a | | 42 | | |
| 16a | | <100 | | |
| 17a | | <100 | | |

TABLE 1-continued

| Structure # | Compound | Enzyme inhibition (IC$_{50}$, nM) | induction of PGE2 in A549 cell culture at 2.5 μM (fold) | induction of PGE2 in A549 cell culture at 0.1 μM (fold) |
| --- | --- | --- | --- | --- |
| 18a | | 30.6 | | |
| 19a | | 14.6 | | |
| 20a | | 33 | | |
| 21a | | 100-500 | | |
| 22a | | ~100 | | |

TABLE 1-continued

| Structure # | Compound | Enzyme inhibition (IC$_{50}$, nM) | induction of PGE2 in A549 cell culture at 2.5 μM (fold) | induction of PGE2 in A549 cell culture at 0.1 μM (fold) |
| --- | --- | --- | --- | --- |
| 23a | | ~100 | | |
| 24a | | 20-100 | | |
| 25a | | >100 | | |
| 26a | | ~500 | | |

TABLE 1-continued

| Structure # | Compound | Enzyme inhibition (IC$_{50}$, nM) | induction of PGE2 in A549 cell culture at 2.5 μM (fold) | induction of PGE2 in A549 cell culture at 0.1 μM (fold) |
| --- | --- | --- | --- | --- |
| 27a | | >500 | | |
| 28a | | 100-500 | | |
| 29a | | 20-100 | | |
| 30a | | 20-100 | | |
| 31a | | 20-100 | | |

TABLE 1-continued

| Structure # | Compound | Enzyme inhibition (IC$_{50}$, nM) | induction of PGE2 in A549 cell culture at 2.5 µM (fold) | induction of PGE2 in A549 cell culture at 0.1 µM (fold) |
|---|---|---|---|---|
| 32a | | 33.4 | | |
| 33a | | 20-100 | | |
| 34a | | >500 | | |
| 35a | | 100 | | |
| 36a | | 30.7 | | |

103
104
TABLE 1-continued
| Structure # | Compound | Enzyme inhibition (IC$_{50}$, nM) | induction of PGE2 in A549 cell culture at 2.5 μM (fold) | induction of PGE2 in A549 cell culture at 0.1 μM (fold) |
|---|---|---|---|---|
| 37a | 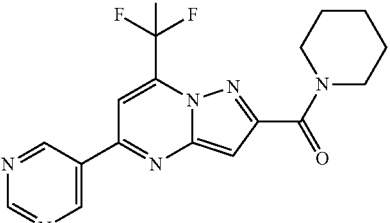 | >2500 | | |
| 38a | 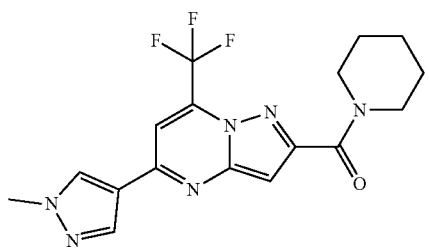 [SMILES: Cn1cc(-c2cc(C(F)(F)F)n3nc(C(=O)N4CCCCC4)cc3n2)cn1] | >2500 | | |
| 39a | 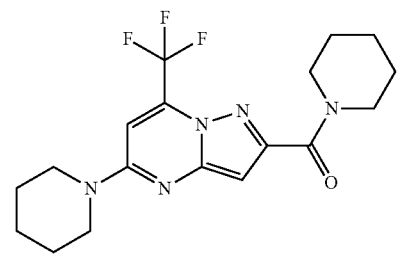 [SMILES: O=C(c1cc2nc(N3CCCCC3)cc(C(F)(F)F)n2n1)N1CCCCC1] | 660 | | |
| 40a | 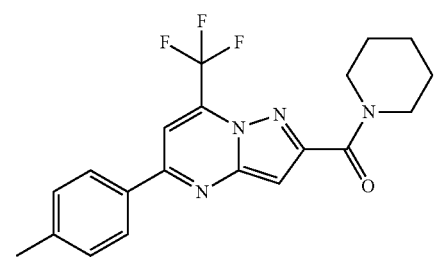 [SMILES: Cc1ccc(-c2cc(C(F)(F)F)n3nc(C(=O)N4CCCCC4)cc3n2)cc1] | 395 | | |
| 41a | 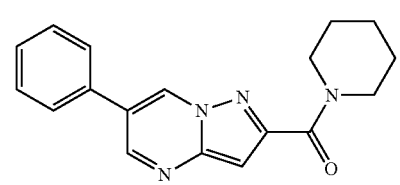 [SMILES: O=C(c1cc2ncc(-c3ccccc3)cn2n1)N1CCCCC1] | 768 | | |
| 42a | 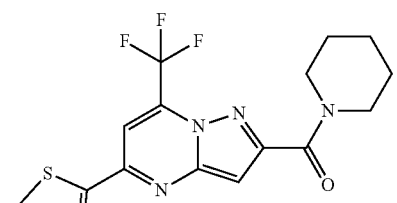 | >2500 | | |

TABLE 1-continued

| Structure # | Compound | Enzyme inhibition (IC$_{50}$, nM) | induction of PGE2 in A549 cell culture at 2.5 μM (fold) | induction of PGE2 in A549 cell culture at 0.1 μM (fold) |
| --- | --- | --- | --- | --- |
| 43a | | >2500 | | |
| 44a | | 500 | | |
| 45a | | 14 | | |
| 46a | | 100 | | |
| 47a | | >2500 | | |

TABLE 1-continued
| Structure # | Compound | Enzyme inhibition (IC$_{50}$, nM) | induction of PGE2 in A549 cell culture at 2.5 μM (fold) | induction of PGE2 in A549 cell culture at 0.1 μM (fold) |
|---|---|---|---|---|
| 48a | 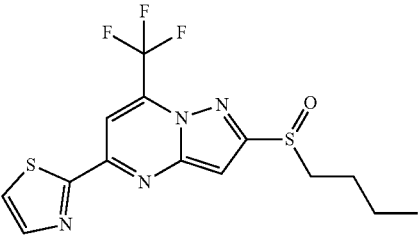 [SMILES: CCCCS(=O)c1cc2nc(-c3nccs3)cc(C(F)(F)F)n2n1] | 20-100 | | |
| 49a | 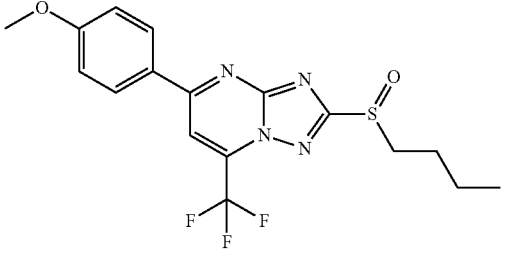 [SMILES: CCCCS(=O)c1nc2nc(-c3ccc(OC)cc3)cc(C(F)(F)F)n2n1] | >2500 | | |
| 50a | 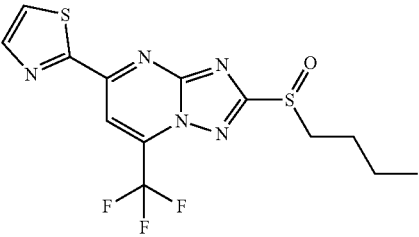 [SMILES: CCCCS(=O)c1nc2nc(-c3nccs3)cc(C(F)(F)F)n2n1] | >2500 | | |
| 51a | 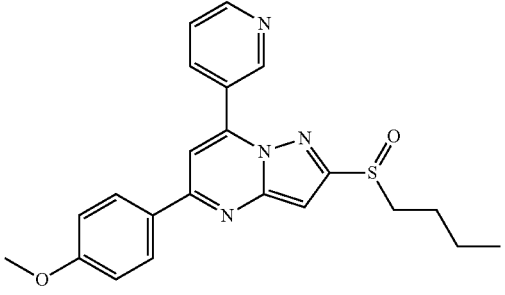 [SMILES: CCCCS(=O)c1cc2nc(-c3ccc(OC)cc3)cc(-c3cccnc3)n2n1] | 500-2500 | | |
| 52a | 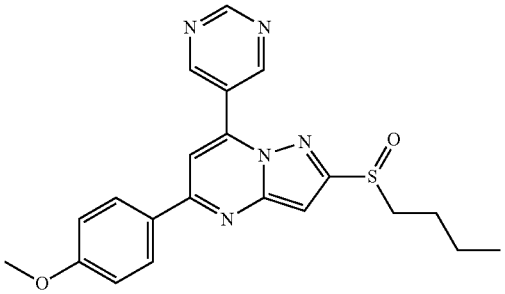 [SMILES: CCCCS(=O)c1cc2nc(-c3ccc(OC)cc3)cc(-c3cncnc3)n2n1] | 2500 | | |

TABLE 1-continued

| Structure # | Compound | Enzyme inhibition (IC$_{50}$, nM) | induction of PGE2 in A549 cell culture at 2.5 μM (fold) | induction of PGE2 in A549 cell culture at 0.1 μM (fold) |
|---|---|---|---|---|
| 53a | | 500-2500 | | |
| 54a | | 4-20 | | |
| 55a | | >2500 | | |
| 56a | | >2500 | | |
| 57a | | 100 | | |

TABLE 1-continued

| Structure # | Compound | Enzyme inhibition (IC$_{50}$, nM) | induction of PGE2 in A549 cell culture at 2.5 μM (fold) | induction of PGE2 in A549 cell culture at 0.1 μM (fold) |
|---|---|---|---|---|
| 58a | | 20-100 | | |
| 59a | | 100-500 | | |
| 60a | | 500-2500 | | |
| 61a | | >2500 | | |
| 62a | | 500-2500 | | |

TABLE 1-continued

| Structure # | Compound | Enzyme inhibition (IC$_{50}$, nM) | induction of PGE2 in A549 cell culture at 2.5 μM (fold) | induction of PGE2 in A549 cell culture at 0.1 μM (fold) |
|---|---|---|---|---|
| 63a | | 4-20 | | |
| 64a | | 100-500 | | |
| 65a | | 100 | | |
| 66a | | 20-100 | | |
| 67a | | 4-20 | | |

TABLE 1-continued
| Structure # | Compound | Enzyme inhibition (IC$_{50}$, nM) | induction of PGE2 in A549 cell culture at 2.5 µM (fold) | induction of PGE2 in A549 cell culture at 0.1 µM (fold) |
|---|---|---|---|---|
| 68a | 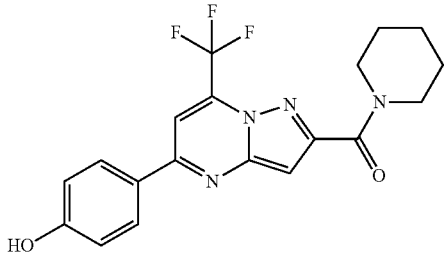 [SMILES: O=C(c1cc2nc(-c3ccc(O)cc3)cc(C(F)(F)F)n2n1)N1CCCCC1] | >2500 | | |
| 69a | 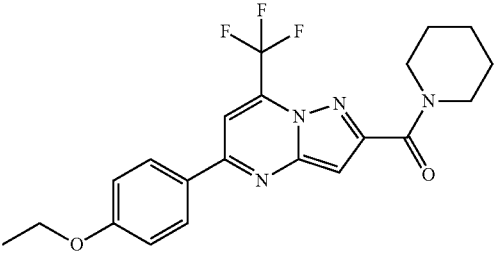 [SMILES: CCOc1ccc(-c2cc(C(F)(F)F)n3nc(C(=O)N4CCCCC4)cc3n2)cc1] | 500-2500 | | |
| 70a | 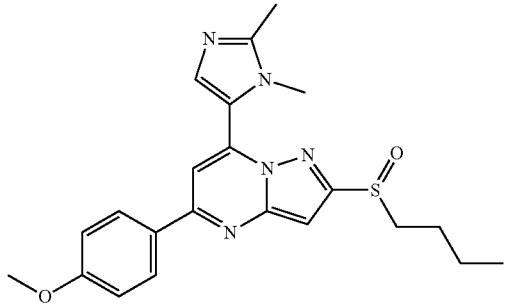 [SMILES: CCCCS(=O)c1cc2nc(-c3ccc(OC)cc3)cc(-c3cnc(C)n3C)n2n1] | 100-500 | | |
| 71a | 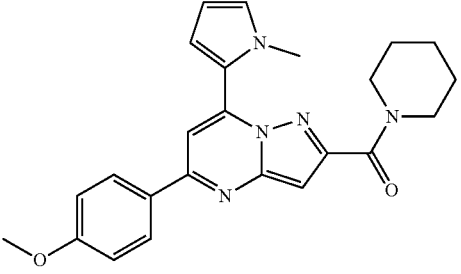 [SMILES: COc1ccc(-c2cc(-c3cccn3C)n3nc(C(=O)N4CCCCC4)cc3n2)cc1] | 20-100 | | |
| 72a | 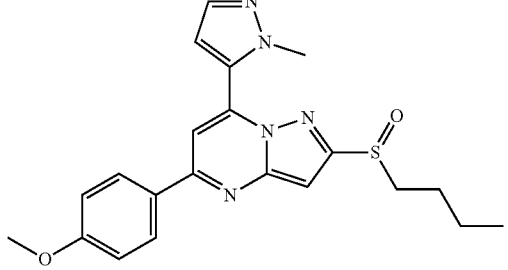 | 4-20 | | |

TABLE 1-continued
| Structure # | Compound | Enzyme inhibition (IC$_{50}$, nM) | induction of PGE2 in A549 cell culture at 2.5 μM (fold) | induction of PGE2 in A549 cell culture at 0.1 μM (fold) |
|---|---|---|---|---|
| 73a | 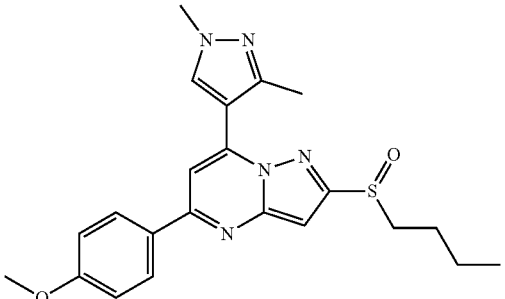 | 500 | | |
| 74a | 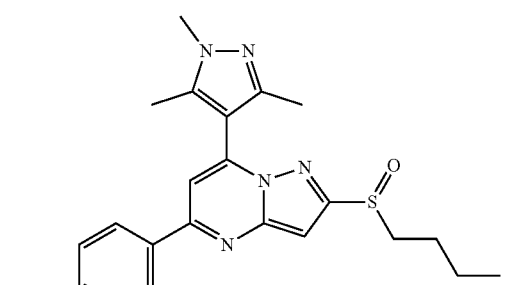 | 20-100 | | |
| 75a | 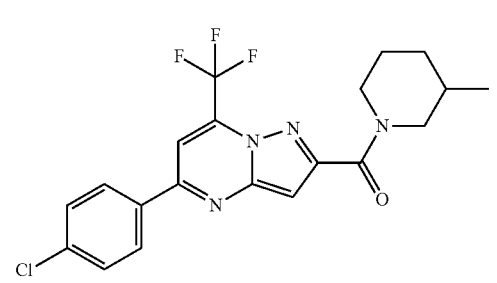 [SMILES: CC1CCCN(C(=O)c2cc3nc(-c4ccc(Cl)cc4)cc(C(F)(F)F)n3n2)C1] | 20-100 | | |
TABLE 2
| 1b | 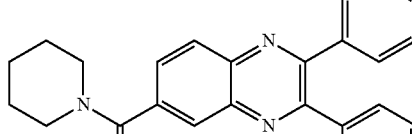 | 17 | 1.87 | 1.11 |
|---|---|---|---|---|
| 2b | 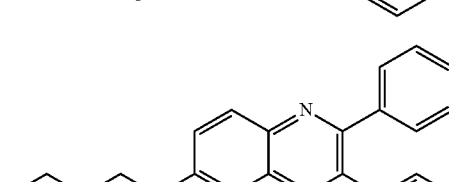 | >2500 | | |

TABLE 2-continued

| | | |
|---|---|---|
| 3b | (butylsulfinyl-substituted 2,3-diphenylquinoxaline) | >2500 |
| 4b | (butylsulfonyl-substituted 2,3-diphenylquinoxaline) | >2500 |
| 5b | (2,3-diphenylquinoxaline-6-carboxamide) | >2500 |
| 6b | (N-methyl 2,3-diphenylquinoxaline-6-carboxamide) | >2500 |
| 7b | (N-ethyl 2,3-diphenylquinoxaline-6-carboxamide) | >2500 |
| 8b | (N-propyl 2,3-diphenylquinoxaline-6-carboxamide) | >2500 |
| 9b | (N-propyl 2,3-diphenylquinoxaline-6-carboxamide) | >2500 |

TABLE 2-continued
| 10b | 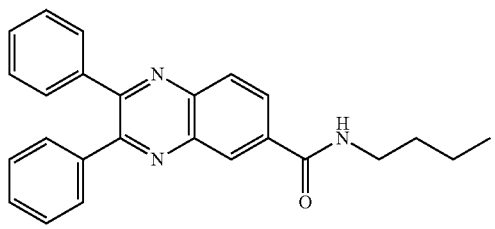 [SMILES: CCCCNC(=O)c1ccc2nc(-c3ccccc3)c(-c3ccccc3)nc2c1] | >2500 |
| 11b | 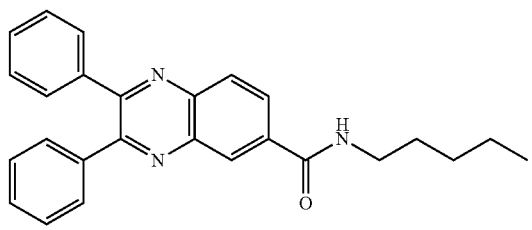 [SMILES: CCCCCNC(=O)c1ccc2nc(-c3ccccc3)c(-c3ccccc3)nc2c1] | >2500 |
| 12b | 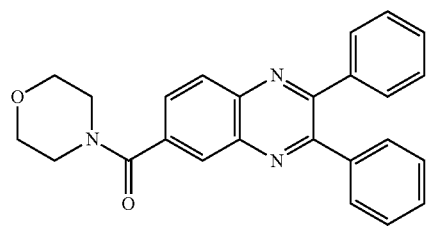 [SMILES: O=C(c1ccc2nc(-c3ccccc3)c(-c3ccccc3)nc2c1)N1CCOCC1] | >2500 |
| 13b | 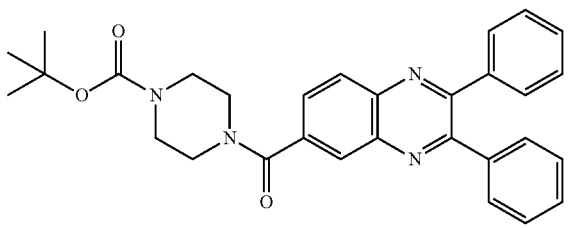 [SMILES: CC(C)(C)OC(=O)N1CCN(C(=O)c2ccc3nc(-c4ccccc4)c(-c4ccccc4)nc3c2)CC1] | >2500 |
| 14b | 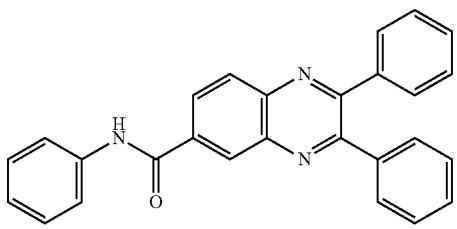 [SMILES: O=C(Nc1ccccc1)c1ccc2nc(-c3ccccc3)c(-c3ccccc3)nc2c1] | >2500 |
| 15b | 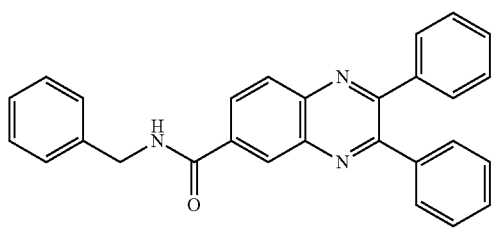 [SMILES: O=C(NCc1ccccc1)c1ccc2nc(-c3ccccc3)c(-c3ccccc3)nc2c1] | >2500 |

TABLE 2-continued
| | | |
|---|---|---|
| 16b | 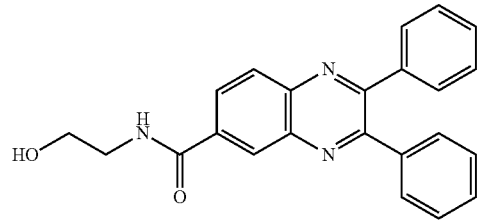 [SMILES: O=C(NCCO)c1ccc2nc(-c3ccccc3)c(-c3ccccc3)nc2c1] | >2500 |
| 17b | 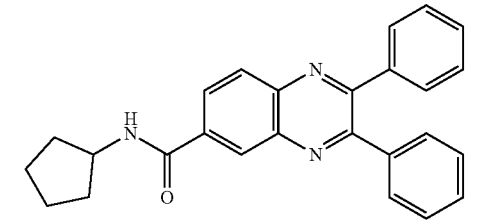 [SMILES: O=C(NC1CCCC1)c1ccc2nc(-c3ccccc3)c(-c3ccccc3)nc2c1] | >2500 |
| 18b | 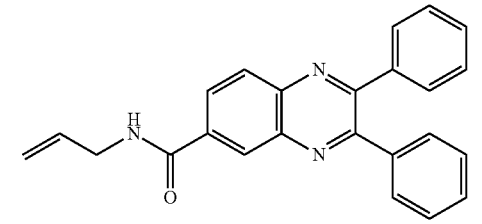 [SMILES: C=CCNC(=O)c1ccc2nc(-c3ccccc3)c(-c3ccccc3)nc2c1] | >2500 |
| 19b | 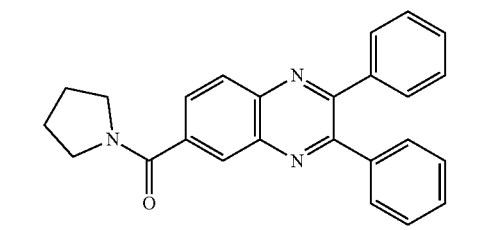 [SMILES: O=C(c1ccc2nc(-c3ccccc3)c(-c3ccccc3)nc2c1)N1CCCC1] | >2500 |
| 20b | 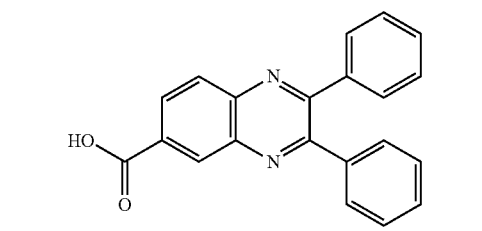 [SMILES: O=C(O)c1ccc2nc(-c3ccccc3)c(-c3ccccc3)nc2c1] | >2500 |
| 21b | 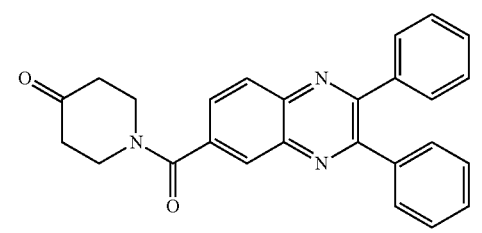 [SMILES: O=C1CCN(C(=O)c2ccc3nc(-c4ccccc4)c(-c4ccccc4)nc3c2)CC1] | >2500 |
| 22b | | 2500 |

TABLE 2-continued

| | | |
|---|---|---|
| 23b | *(structure)* | >2500 |
| 24b | *(structure)* | 34 |
| 25b | *(structure)* | >2500 |
| 26b | *(structure)* | 100-500 |
| 27b | *(structure)* | <20 |
| 28b | *(structure)* | 37 |
| 29b | *(structure)* | 100-500 |

TABLE 2-continued
| | | |
|---|---|---|
| 30b | 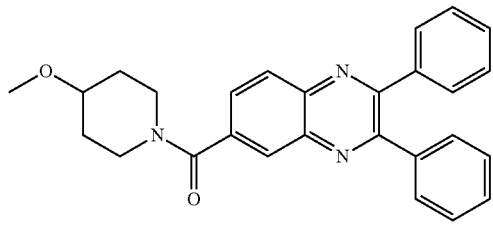 [SMILES: COC1CCN(C(=O)c2ccc3nc(-c4ccccc4)c(-c4ccccc4)nc3c2)CC1] | 100 |
| 31b | 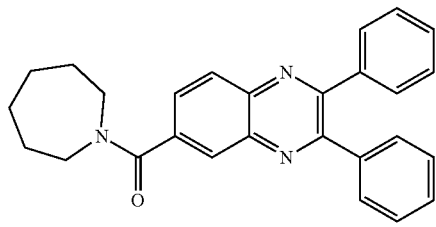 [SMILES: O=C(c1ccc2nc(-c3ccccc3)c(-c3ccccc3)nc2c1)N1CCCCCC1] | <20 |
| 32b | 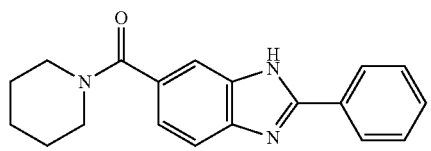 [SMILES: O=C(c1ccc2nc(-c3ccccc3)[nH]c2c1)N1CCCCC1] | 100-500 |
| 33b | 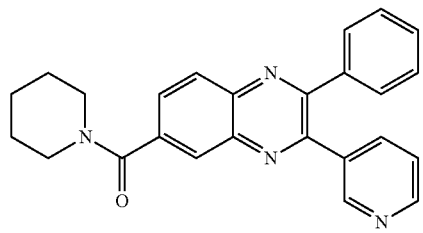 [SMILES: O=C(c1ccc2nc(-c3ccccc3)c(-c3cccnc3)nc2c1)N1CCCCC1] | 20 |
| 34b | 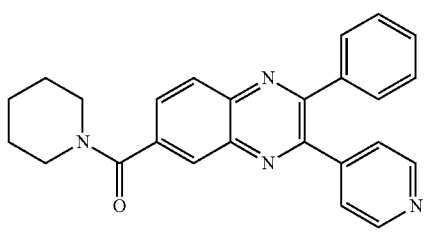 [SMILES: O=C(c1ccc2nc(-c3ccccc3)c(-c3ccncc3)nc2c1)N1CCCCC1] | 20 |
| 35b | 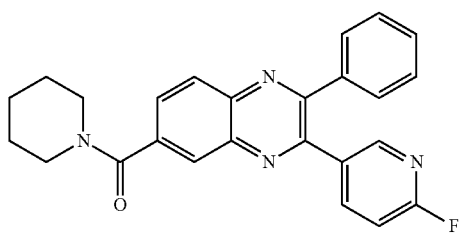 [SMILES: O=C(c1ccc2nc(-c3ccccc3)c(-c3ccc(F)nc3)nc2c1)N1CCCCC1] | 20-100 |
| 36b | 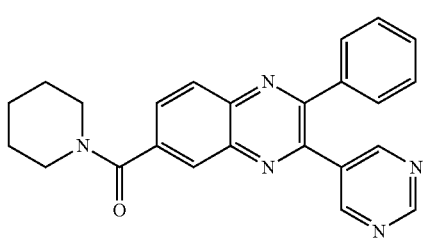 [SMILES: O=C(c1ccc2nc(-c3ccccc3)c(-c3cncnc3)nc2c1)N1CCCCC1] | 20-100 |

TABLE 2-continued
| | | |
|---|---|---|
| 37b | 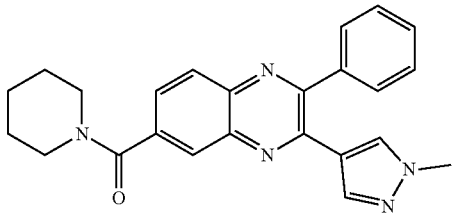 [SMILES: Cn1cc(-c2nc3cc(C(=O)N4CCCCC4)ccc3nc2-c2ccccc2)cn1] | 20-100 |
| 38b | 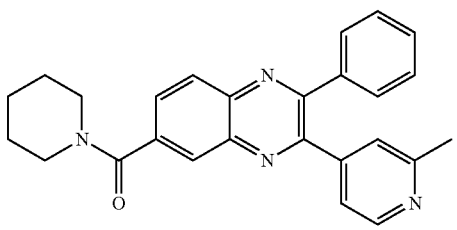 [SMILES: Cc1cc(-c2nc3cc(C(=O)N4CCCCC4)ccc3nc2-c2ccccc2)ccn1] | 20 |
| 39b | 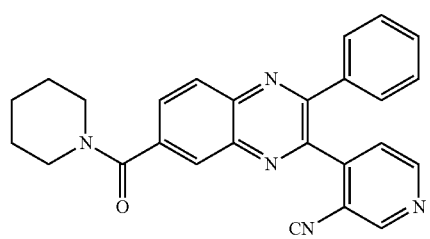 | 10-20 |
| 40b | 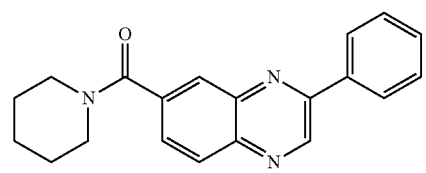 [SMILES: O=C(c1ccc2ncc(-c3ccccc3)nc2c1)N1CCCCC1] | 11 |
| 41b | 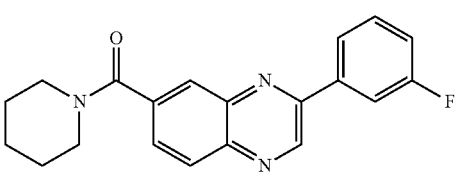 [SMILES: O=C(c1ccc2ncc(-c3cccc(F)c3)nc2c1)N1CCCCC1] | 4-20 |
| 42b | 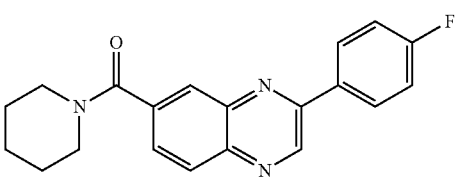 [SMILES: O=C(c1ccc2ncc(-c3ccc(F)cc3)nc2c1)N1CCCCC1] | 4-20 |
| 43b | 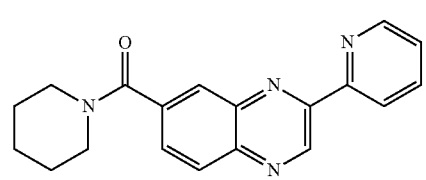 [SMILES: O=C(c1ccc2ncc(-c3ccccn3)nc2c1)N1CCCCC1] | 20-100 |
| 44b | 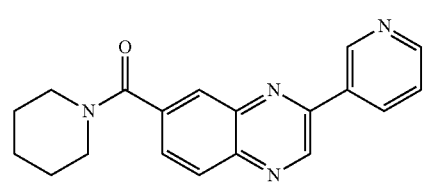 [SMILES: O=C(c1ccc2ncc(-c3cccnc3)nc2c1)N1CCCCC1] | 4 |

TABLE 2-continued

| | | |
|---|---|---|
| 45b | [piperidine-C(=O)-quinoxaline-2-(2,4-difluorophenyl)] | 4 |
| 46b | [piperidine-C(=O)-quinoxaline-2-(1,3-dimethyl-1H-pyrazol-4-yl)] | 100-500 |
| 47b | [piperidine-C(=O)-quinoxaline-2-(3,5-difluorophenyl)] | 16 |
| 48b | [piperidine-C(=O)-quinoxaline-2-(quinolin-6-yl)] | 2.3 |
| 49b | [piperidine-C(=O)-quinoxaline-2-(isoquinolin-6-yl)] | 1.7 |
| 50b | [piperidine-C(=O)-quinoxaline-2-(4-chlorophenyl)] | 20 |
| 51b | [piperidine-C(=O)-quinoxaline-2-(6-fluoropyridin-3-yl)] | 3 |
| 52b | [piperidine-C(=O)-quinoxaline-2-(pyridin-4-yl)] | 4-20 |

TABLE 2-continued
| | | |
|---|---|---|
| 53b | 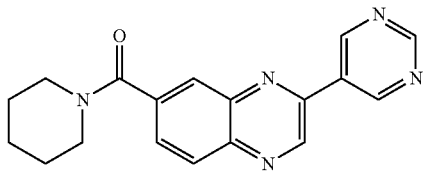 [SMILES: O=C(c1ccc2ncc(-c3cncnc3)nc2c1)N1CCCCC1] | 4-20 |
| 54b | 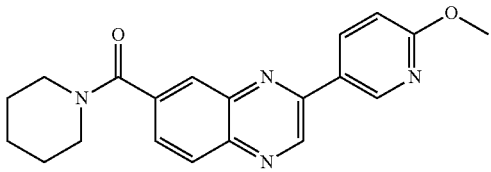 [SMILES: COc1ccc(-c2cnc3ccc(C(=O)N4CCCCC4)cc3n2)cn1] | 3.5 |
| 55b | 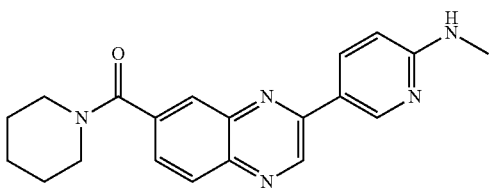 [SMILES: CNc1ccc(-c2cnc3ccc(C(=O)N4CCCCC4)cc3n2)cn1] | 2.88 |
| 56b | 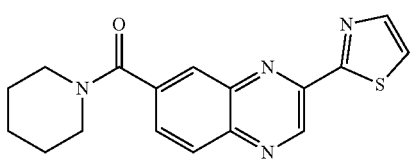 [SMILES: O=C(c1ccc2ncc(-c3nccs3)nc2c1)N1CCCCC1] | 20-100 |
| 57b | 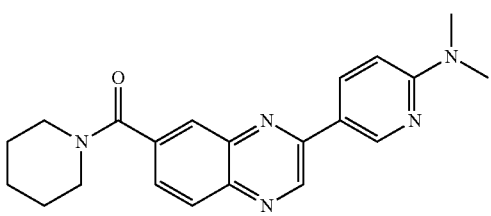 [SMILES: CN(C)c1ccc(-c2cnc3ccc(C(=O)N4CCCCC4)cc3n2)cn1] | 5.6 |
| 58b | 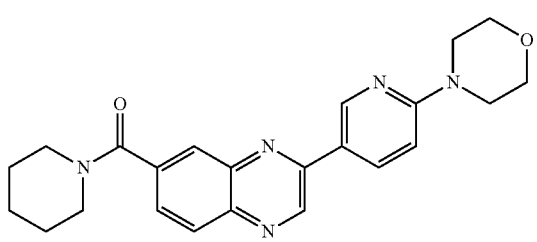 [SMILES: O=C(c1ccc2ncc(-c3ccc(N4CCOCC4)nc3)nc2c1)N1CCCCC1] | 20 |
| 59b | 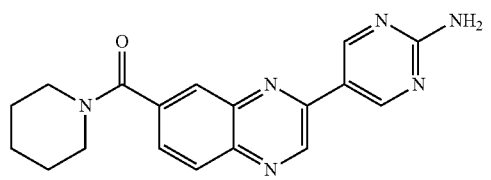 | 1.6 |
| 60b | 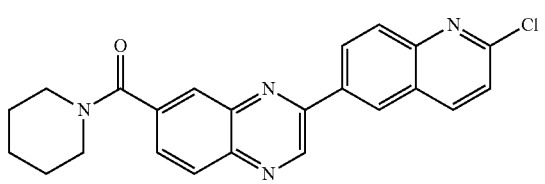 [SMILES: O=C(c1ccc2ncc(-c3ccc4nc(Cl)ccc4c3)nc2c1)N1CCCCC1] | 4.4 |

TABLE 2-continued
| | | |
|---|---|---|
| 61b | 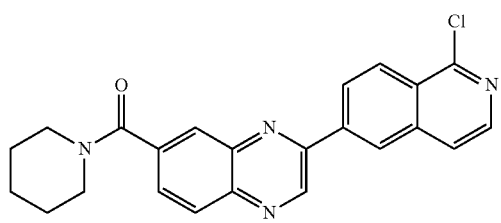 [SMILES: O=C(c1ccc2ncc(-c3ccc4c(Cl)nccc4c3)nc2c1)N1CCCCC1] | 6.4 |
| 62b | 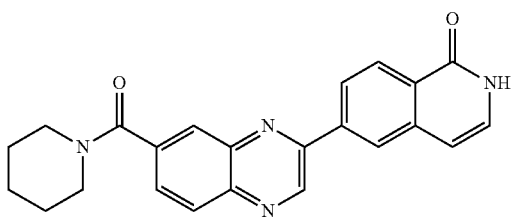 [SMILES: O=C(c1ccc2ncc(-c3ccc4c(=O)[nH]ccc4c3)nc2c1)N1CCCCC1] | 2 |
| 63b | 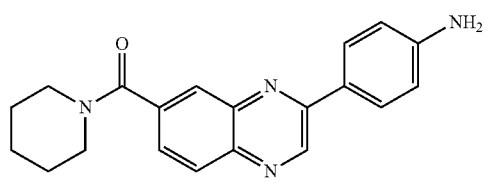 | 4-20 |
| 64b | 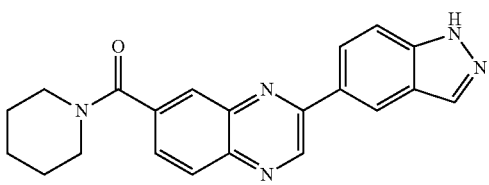 [SMILES: O=C(c1ccc2ncc(-c3ccc4[nH]ncc4c3)nc2c1)N1CCCCC1] | 4.1 |
| 65b | 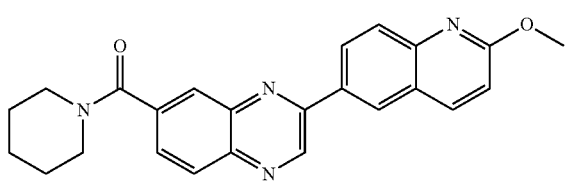 [SMILES: COc1ccc2cc(-c3cnc4ccc(C(=O)N5CCCCC5)cc4n3)ccc2n1] | 4-20 |
| 66b | 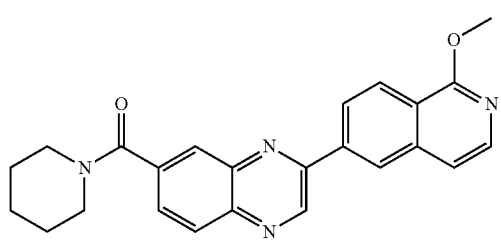 [SMILES: COc1nccc2cc(-c3cnc4ccc(C(=O)N5CCCCC5)cc4n3)ccc12] | 4-20 |
| 67b | 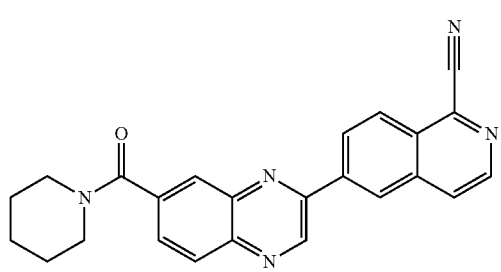 [SMILES: N#Cc1nccc2cc(-c3cnc4ccc(C(=O)N5CCCCC5)cc4n3)ccc12] | 4.0 |

TABLE 2-continued
| | | |
|---|---|---|
| 68b | 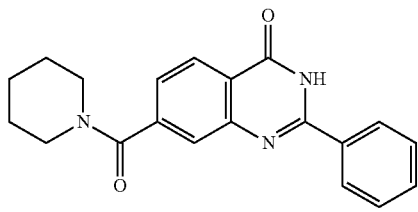 [SMILES: O=C(c1ccc2c(=O)[nH]c(-c3ccccc3)nc2c1)N1CCCCC1] | 100 |
| 69b | 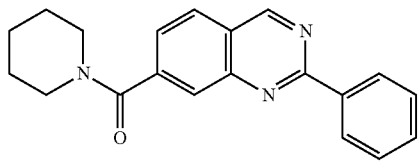 [SMILES: O=C(c1ccc2cnc(-c3ccccc3)nc2c1)N1CCCCC1] | |
| 70b | 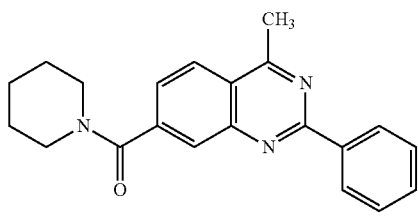 [SMILES: Cc1nc(-c2ccccc2)nc2cc(C(=O)N3CCCCC3)ccc12] | |
| 71b | 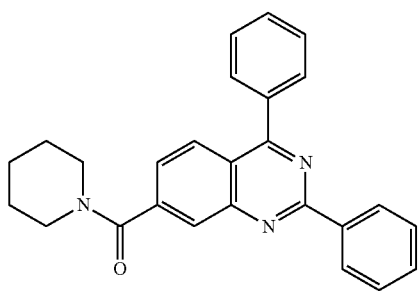 [SMILES: O=C(c1ccc2c(-c3ccccc3)nc(-c3ccccc3)nc2c1)N1CCCCC1] | |
| 72b | 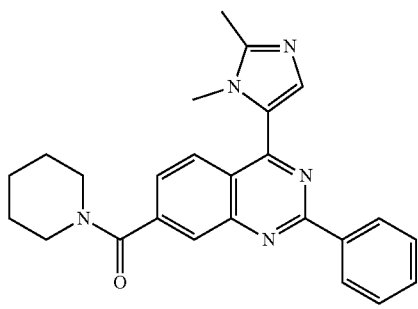 [SMILES: Cc1ncc(-c2nc(-c3ccccc3)nc3cc(C(=O)N4CCCCC4)ccc23)n1C] | |
| 73b | 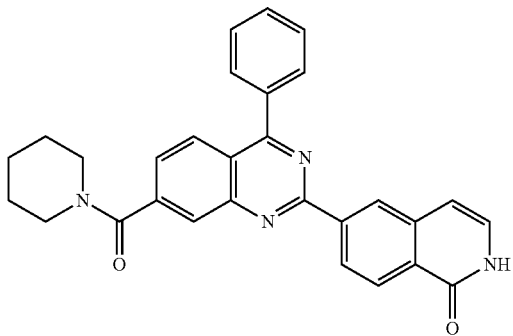 [SMILES: O=C(c1ccc2c(-c3ccccc3)nc(-c3ccc4c(=O)[nH]ccc4c3)nc2c1)N1CCCCC1] | |

TABLE 2-continued
| | | |
|---|---|---|
| 74b | 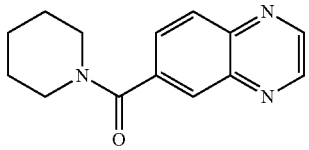 [SMILES: O=C(c1ccc2nccnc2c1)N1CCCCC1] | 100-500 |
| 75b | 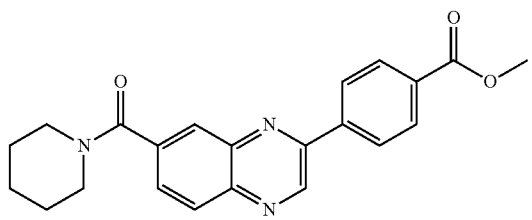 [SMILES: COC(=O)c1ccc(-c2cnc3ccc(C(=O)N4CCCCC4)cc3n2)cc1] | 4-20 |
| 76b | 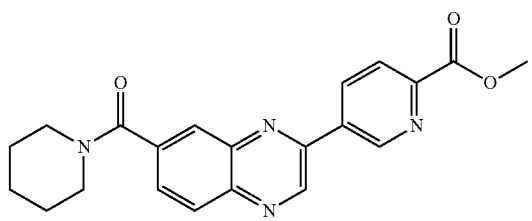 [SMILES: COC(=O)c1ccc(-c2cnc3ccc(C(=O)N4CCCCC4)cc3n2)cn1] | 4-20 |
| 77b | 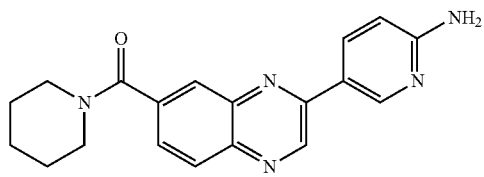 [SMILES: Nc1ccc(-c2cnc3ccc(C(=O)N4CCCCC4)cc3n2)cn1] | 2.3 |
| 78b | 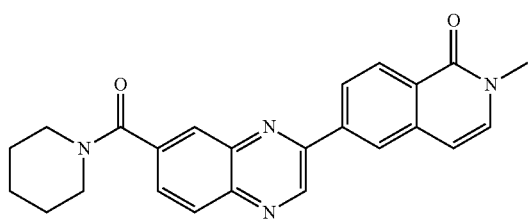 [SMILES: Cn1ccc2cc(-c3cnc4ccc(C(=O)N5CCCCC5)cc4n3)ccc2c1=O] | 3.0 |
| 79b | 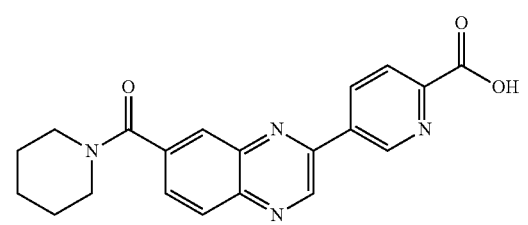 [SMILES: O=C(O)c1ccc(-c2cnc3ccc(C(=O)N4CCCCC4)cc3n2)cn1] | 1.7 |
| 80b | 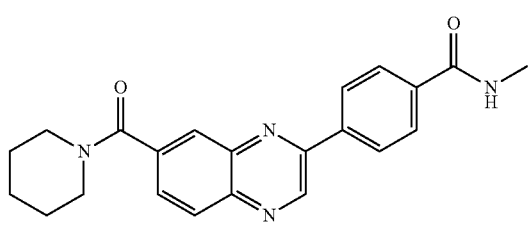 | 4 |

TABLE 2-continued

| | | |
|---|---|---|
| 81b | [structure] | 4 |
| 82b | [structure] | 100 |
| 83b | [structure] | 2.3 |
| 84b | [structure] | 4.8 |
| 85b | [structure] | 2.1 |
| 86b | [structure] | 20-100 |
| 87b | [structure] | ~20 |

TABLE 2-continued
| 88b | 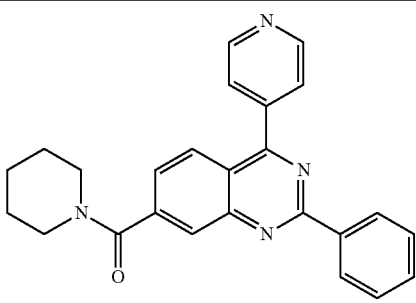 | ~4 |
| 89b | 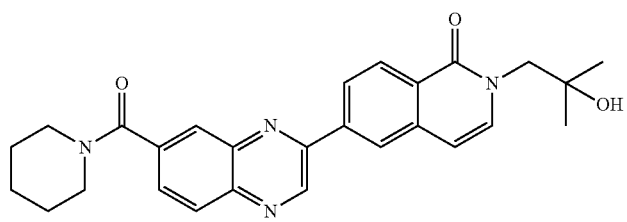 [SMILES: CC(C)(O)Cn1ccc2cc(-c3cnc4ccc(C(=O)N5CCCCC5)cc4n3)ccc2c1=O] | ~4 |
| 90b | 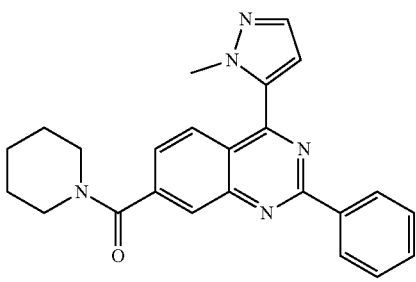 [SMILES: Cn1nccc1-c1nc(-c2ccccc2)nc2cc(C(=O)N3CCCCC3)ccc12] | ~4 |
| 91b | 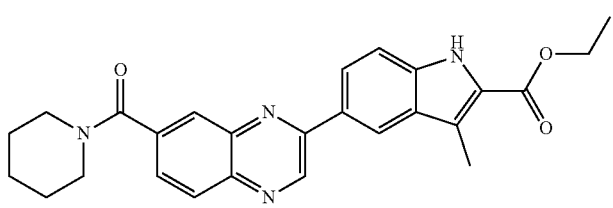 [SMILES: CCOC(=O)c1[nH]c2ccc(-c3cnc4ccc(C(=O)N5CCCCC5)cc4n3)cc2c1C] | ~4 |
| 92b | 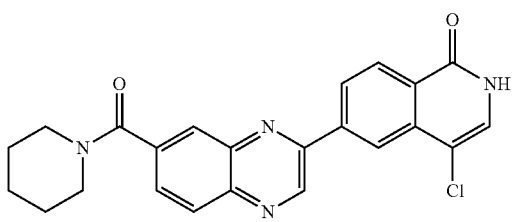 [SMILES: O=C(c1ccc2ncc(-c3ccc4c(=O)[nH]cc(Cl)c4c3)nc2c1)N1CCCCC1] | <4 |
| 93b | 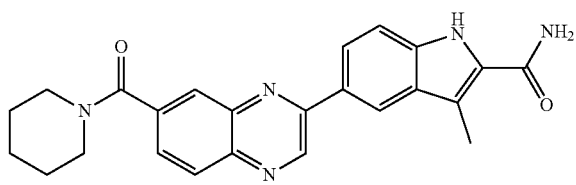 [SMILES: Cc1c(C(N)=O)[nH]c2ccc(-c3cnc4ccc(C(=O)N5CCCCC5)cc4n3)cc12] | <4 |
| 94b | 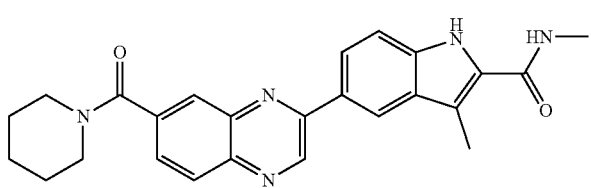 [SMILES: CNC(=O)c1[nH]c2ccc(-c3cnc4ccc(C(=O)N5CCCCC5)cc4n3)cc2c1C] | <4 |

TABLE 2-continued

| | | |
|---|---|---|
| 95b | 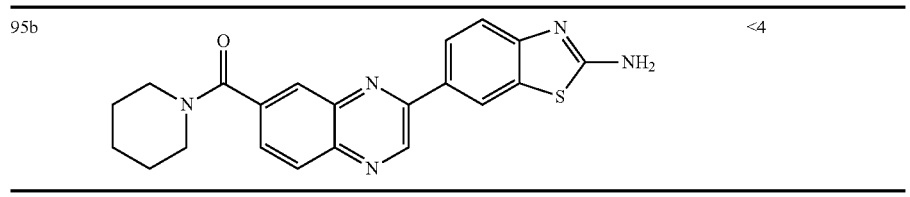 | <4 |

Example 2

The following Example describes the synthesis of at least some analogues described in Tables 1 and 2 as well as provides mass spectrometry and NMR confirmation of the structures.

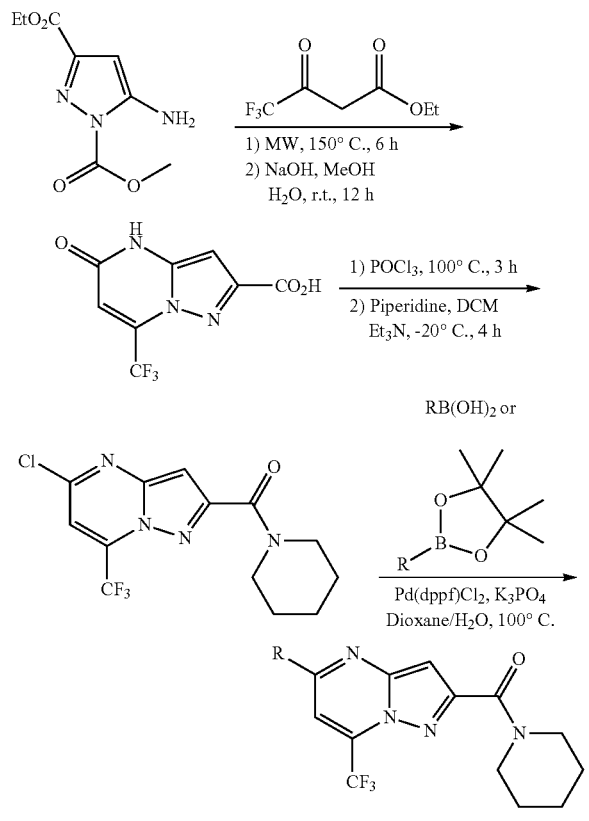

Step 1

3-ethyl 1-methyl 5-amino-1H-pyrazole-1,3-dicarboxylate (426 mg, 2 mmol) and ethyl 4,4,4-trifluoro-3-oxobutanoate (1.84 g, 10 mmol) were placed in a microwave tube. The mixture was heated at 150° C. in a microwave reactor for 6 h and then cooled down to room temperature. The slurry solution was filtered and washed with ether to give a white solid (226 mg, 41% yield). The ester intermediate was taken in MeOH (2 mL) and NaOH aq. (1M, 2 mL), and the solution was stirred at room temperature for 12 h. The solvent was then removed and the residue was acidified by 1M HCl until PH 2. The precipitate was collected by filtration and washed with cold water. The resulting solid was dried to obtain the pure product as a white solid (182 mg, 90% yield). MS (ES+) m/z=248 [M+H]$^+$.

Step 2

POCl$_3$ (0.38 mL, 4 mmol) was added to a 25-mL vial which was charged with 5-oxo-7-(trifluoromethyl)-4,5-dihydropyrazolo[1,5-a]pyrimidine-2-carboxylic acid (99 mg, 0.4 mmol). The mixture was heated at 100° C. for 3 h, and the excess POCl$_3$ was removed under reduced pressure. The resulting crude was dissolved in dichloromethane (2 mL) and Et$_3$N (0.55 mL, 4 mmol), cooled down to −20° C. Piperidine (0.08 mL, 0.8 mmol) was then added to the solution which was allowed to stir at −20° C. for 4 h. After the completion of the reaction, the solvents were removed under reduced pressure and the residue was loaded to a column on silica gel and eluted by hexanes/ethyl acetate=10/1 to give a yellow solid (47 mg, 35% yield). $^1$H NMR (400 MHz, Chloroform-d) δ 11.64 (s, 1H), 7.47 (s, 1H), 3.82 (t, J=5.0 Hz, 2H), 3.29 (t, J=5.2 Hz, 2H), 1.71-1.69 (m, 4H), 1.53-1.47 (m, 2H). m/z (ES+): 333 [M+H]$^+$.

Step 3

Under nitrogen atmosphere, boronic acid or boronic ester (0.11 mmol) was added to a dry tube containing (5-chloro-7-(trifluoromethyl)pyrazolo[1,5-a]pyrimidin-2-yl)(piperidin-1-yl)methanone (33 mg, 0.1 mmol), Pd(dppf)Cl$_2$ (4 mg, 0.5% mmol), K$_3$PO$_4$ (42 mg, 0.2 mmol), 1,4-dioxane (2 mL) and H$_2$O (0.2 mL). The mixture was stirring at 100° C. until the completion of the reaction which was monitored by LC/MS. The reaction mixture was cooled to room temperature, washed with water, extracted with ethyl acetate, dried over anhydrous Na$_2$SO$_4$ and concentrated by rotary evaporation. The crude was purified by flash chromatography on silica gel to give the product.

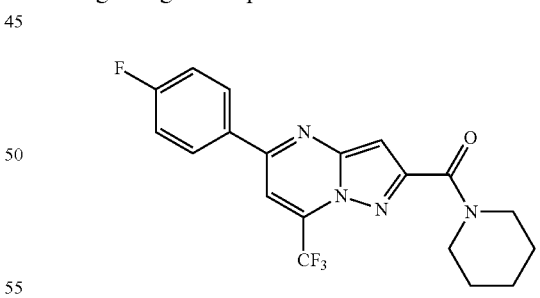

The target compound 36a (81% yield) was obtained by the general procedure described above.

$^1$H NMR (400 MHz, Chloroform-d) δ 12.51 (s, 1H), 8.05-8.01 (m, 2H), 7.77 (s, 1H), 7.20 (t, J=8.3 Hz, 2H), 3.84 (s, 2H), 3.33 (s, 2H), 1.72-1.66 (m, 4H), 1.51-1.49 (m, 2H); $^{13}$C NMR (101 MHz, Chloroform-d) δ 164.3 (d, J=251.4 Hz), 162.5, 157.0, 153.0, 139.4, 133.6 (d, J=3.1 Hz), 132.5 (q, J=35.5 Hz), 129.7 (d, J=8.5 Hz), 122.5 (q, J=273.8 Hz), 116.2 (d, J=21.8 Hz), 112.1 (q, J=4.8 Hz), 106.4, 48.2, 43.0, 26.2, 25.4, 24.5. MS (ES+) m/z=393 [M+H]$^+$.

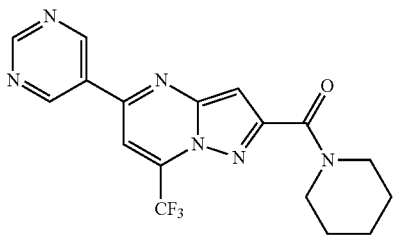 [SMILES: O=C(c1cc2nc(-c3cncnc3)cc(C(F)(F)F)n2n1)N1CCCCC1]

The target compound 37a (85% yield) was obtained by the general procedure described above.

$^1$H NMR (400 MHz, Chloroform-d) δ 13.68 (s, 1H), 9.77 (s, 2H), 9.49 (s, 1H), 7.97 (s, 1H), 3.85 (t, J=4.9 Hz, 2H), 3.39-3.35 (m, 2H), 1.73-1.72 (m, 4H), 1.57-1.52 (m, 2H); $^{13}$C NMR (101 MHz, Chloroform-d) δ 162.1, 158.9, 155.6, 153.4, 151.7, 139.8, 133.4 (q, J=35.8 Hz), 131.4, 122.3 (q, J=274.1 Hz), 111.2 (q, J=5.0 Hz), 107.6, 48.2, 43.0, 26.2, 25.4, 24.5. MS (ES+) m/z=377 [M+H]$^+$.

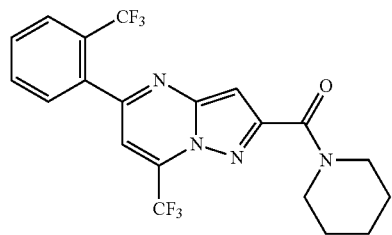

The target compound 43a (51% yield) was obtained by the general procedure described above.

$^1$H NMR (400 MHz, Chloroform-d) δ 12.45 (s, 1H), 7.82 (d, J=7.8 Hz, 1H), 7.68-7.58 (m, 3H), 7.53 (d, J=7.5 Hz, 1H), 3.84-3.81 (m, 2H), 3.37-3.34 (m, 2H), 1.71-1.65 (m, 4H), 1.55-1.49 (m, 2H); $^{13}$C NMR (101 MHz, Chloroform-d) δ 162.2, 158.4, 152.3, 139.5, 137.8 (q, J=2.1 Hz), 132.0 (q, J=35.6 Hz), 131.9, 131.5, 129.5, 128.5 (q, J=31.0 Hz), 126.7 (q, J=5.1 Hz), 123.8 (q, J=275.4 Hz), 122.4 (q, J=275.2 Hz), 115.6 (q, J=2.1 Hz), 106.8 (q, J=1.9 Hz), 48.2, 43.0, 26.2, 25.4, 24.5. MS (ES+) m/z=443 [M+H]$^+$.

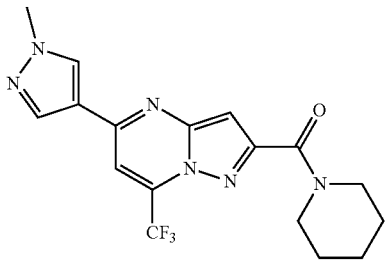 [SMILES: Cn1cc(-c2cc(C(F)(F)F)n3nc(C(=O)N4CCCCC4)cc3n2)cn1]

The target compound 38a (65% yield) was obtained by the general procedure described above.

$^1$H NMR (400 MHz, Chloroform-d) δ 12.55 (s, 1H), 8.33 (s, 1H), 8.17 (s, 1H), 7.56 (s, 1H), 4.02 (s, 3H), 3.83 (t, J=4.8 Hz, 2H), 3.33 (t, J=4.8 Hz, 2H), 1.71 (s, 4H), 1.51 (s, 2H); $^{13}$C NMR (101 MHz, Chloroform-d) δ 162.4, 153.1, 152.6, 139.7, 138.8, 132.4 (q, J=35.6 Hz), 130.2, 122.5 (q, J=273.7 Hz), 122.0, 118.4, 111.9 (q, J=5.0 Hz), 105.7, 48.2, 42.9, 39.4, 26.2, 25.4, 24.5. MS (ES+) m/z=379 [M+H]$^+$.

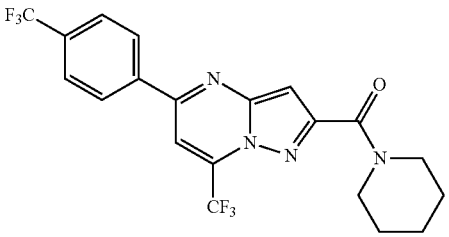

The target compound 47a (66% yield) was obtained by the general procedure described above.

$^1$H NMR (400 MHz, Chloroform-d) δ 11.69 (s, 1H), 8.17 (d, J=8.1 Hz, 2H), 7.88 (s, 1H), 7.78 (d, J=8.1 Hz, 2H), 3.84 (t, J=5.0 Hz, 2H), 3.34 (t, J=5.0 Hz, 2H), 1.75-1.71 (m, 4H), 1.55-1.50 (m, 2H); $^{13}$C NMR (101 MHz, Chloroform-d) δ 162.2, 156.5, 153.0, 140.7, 139.7, 132.7 (q, J=60.5 Hz), 132.3 (q, J=60.3 Hz), 127.9, 126.0 (q, J=3.8 Hz), 123.9 (q, J=274.1 Hz), 122.4 (q, J=273.7 Hz), 112.5 (q, J=4.8 Hz), 106.9, 48.2, 43.0, 26.2, 25.4, 24.5. MS (ES+) m/z=443 [M+H]$^+$.

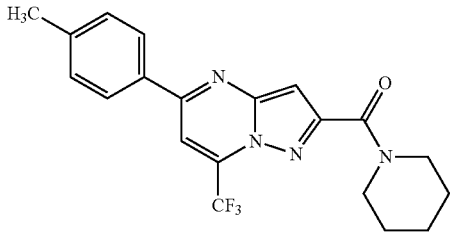 [SMILES: Cc1ccc(-c2cc(C(F)(F)F)n3nc(C(=O)N4CCCCC4)cc3n2)cc1]

The target compound 40a (79% yield) was obtained by the general procedure described above.

$^1$H NMR (400 MHz, Chloroform-d) δ 12.49 (s, 1H), 7.97 (d, J=8.3 Hz, 2H), 7.85 (s, 1H), 7.34 (d, J=7.8 Hz, 2H), 3.84 (t, J=5.1 Hz, 2H), 3.34 (t, J=5.5 Hz, 2H), 2.45 (s, 3H), 1.74-1.67 (m, 4H), 1.54-1.48 (m, 2H); $^{13}$C NMR (101 MHz, Chloroform-d) δ 162.5, 158.3, 153.2, 140.9, 139.4, 134.7, 132.3 (q, J=35.2 Hz), 129.9, 127.6, 122.6 (q, J=273.7 Hz), 112.4 (q, J=4.8 Hz), 106.3, 106.2, 48.2, 43.0, 26.2, 25.4, 24.5, 21.4. MS (ES+) m/z=389 [M+H]$^+$.

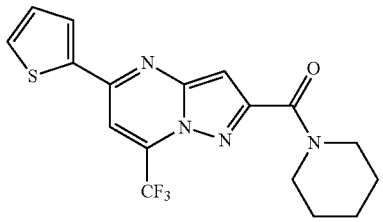 [SMILES: O=C(c1cc2nc(-c3cccs3)cc(C(F)(F)F)n2n1)N1CCCCC1]

The target compound 46a (73% yield) was obtained by the general procedure described above.

$^1$H NMR (400 MHz, Chloroform-d) δ 12.27 (s, 1H), 7.77 (s, 1H), 7.75 (d, J=5.0 Hz, 1H), 7.53 (d, J=5.0 Hz, 1H), 7.17 (t, J=4.2 Hz, 1H), 3.83 (t, J=5.1 Hz, 2H), 3.32 (t, J=5.5 Hz, 2H), 1.74-1.65 (m, 4H), 1.53-1.48 (m, 2H); $^{13}$C NMR (101 MHz, Chloroform-d) δ 162.4, 153.0, 152.7, 142.9, 139.5, 132.4 (q, J=35.4 Hz), 130.0, 128.6, 127.7, 122.4 (q, J=273.8 Hz), 111.3 (q, J=4.9 Hz), 106.2, 48.2, 43.0, 26.1, 25.4, 24.5. MS (ES+) m/z=381 [M+H]$^+$.

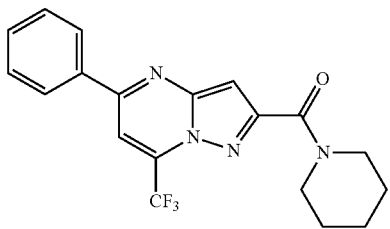 [SMILES: O=C(c1cc2nc(-c3ccccc3)cc(C(F)(F)F)n2n1)N1CCCCC1]

The target compound 61a (82% yield) was obtained by the general procedure described above.

¹H NMR (400 MHz, Chloroform-d) δ 12.25 (s, 1H), 8.07-8.05 (m, 2H), 7.87 (s, 1H), 7.55-7.52 (m, 3H), 3.84 (t, J=5.1 Hz, 2H), 3.34 (t, J=5.4 Hz, 2H), 1.75-1.66 (m, 4H), 1.54-1.49 (m, 2H); ¹³C NMR (101 MHz, Chloroform-d) δ 162.4, 158.3, 153.1, 139.5, 137.5, 132.5 (q, J=35.3 Hz), 130.5, 129.1, 127.7, 122.6 (q, J=273.8 Hz), 112.6 (q, J=4.8 Hz), 106.4, 48.2, 43.0, 26.2, 25.4, 24.5. MS (ES+) m/z=375 [M+H]⁺.

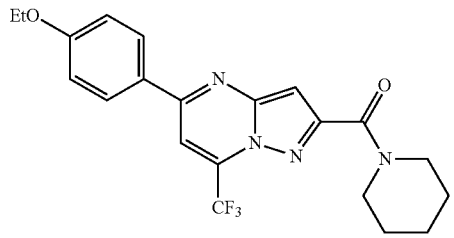

The target compound 69a (86% yield) was obtained by the general procedure described above.

¹H NMR (400 MHz, Chloroform-d) δ 12.63 (s, 1H), 8.01 (d, J=8.0 Hz, 2H), 7.79 (s, 1H), 7.01 (d, J=8.0 Hz, 2H), 4.10 (q, J=7.0 Hz, 2H), 3.83 (t, J=5.1 Hz, 2H), 3.33 (t, J=5.4 Hz, 2H), 1.73-1.65 (m, 4H), 1.53-1.50 (m, 2H), 1.46 (t, J=7.0 Hz, 3H); ¹³C NMR (101 MHz, Chloroform-d) δ 162.6, 161.0, 157.9, 153.2, 139.3, 132.2 (q, J=35.2 Hz), 129.8, 129.2, 122.7 (q, J=273.7 Hz), 115.0, 112.0 (q, J=4.7 Hz), 105.9, 63.7, 48.2, 43.0, 26.2, 25.4, 24.5, 14.8. MS (ES+) m/z=419 [M+H]⁺.

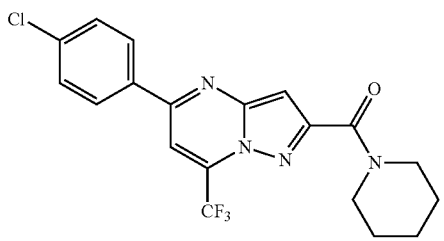 [SMILES: O=C(c1cc2nc(-c3ccc(Cl)cc3)cc(C(F)(F)F)n2n1)N1CCCCC1]

The target compound 56a (53% yield) was obtained by the general procedure described above.

¹H NMR (400 MHz, Chloroform-d) δ 11.01 (s, 1H), 8.05 (d, J=7.1 Hz, 2H), 7.88 (s, 1H), 7.52 (d, J=7.1 Hz, 2H), 3.84-3.82 (m, 2H), 3.35-3.32 (m, 2H), 1.72-1.68 (m, 4H), 1.54-1.50 (m, 2H); ¹³C NMR (101 MHz, Chloroform-d) δ 162.0, 157.1, 153.1, 140.0, 136.9, 135.9, 132.7 (q, J=35.3 Hz), 129.4, 128.8, 122.8 (q, J=273.8 Hz), 112.2, (q, J=4.8 Hz), 106.5, 48.2, 42.9, 26.2, 25.4, 24.5. MS (ES+) m/z=409 [M+H]⁺.

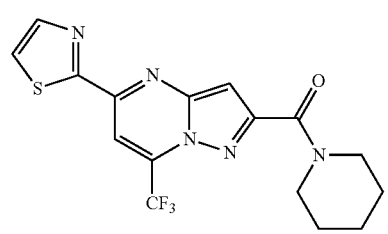

The target compound 45a (50% yield) was obtained by the general procedure described above.

¹H NMR (400 MHz, Chloroform-d) δ 8.16 (s, 1H), 7.99 (d, J=3.0 Hz, 1H), 7.61 (d, J=3.1 Hz, 1H), 7.18 (s, 1H), 3.78-3.76 (m, 4H), 1.70-1.62 (m, 6H); ¹³C NMR (101 MHz, Chloroform-d) δ 165.4, 161.6, 153.2, 150.2, 148.7, 144.8, 134.6 (q, J=38.5 Hz), 124.3, 119.2 (q, J=274.8 Hz), 104.5 (q, J=4.1 Hz), 100.4, 48.4, 43.8, 26.5, 25.7, 24.6. MS (ES+) m/z=382 [M+H]⁺.

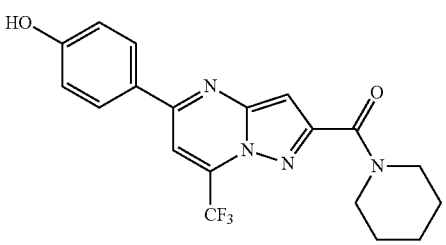 [SMILES: O=C(c1cc2nc(-c3ccc(O)cc3)cc(C(F)(F)F)n2n1)N1CCCCC1]

The target compound 68a (48% yield) was obtained by the general procedure described above.

¹H NMR (400 MHz, DMSO-d₆) δ 10.04 (s, 2H), 8.11 (d, J=8.3 Hz, 2H), 8.03 (s, 1H), 6.91 (d, J=8.3 Hz, 2H), 3.63 (d, J=5.1 Hz, 2H), 3.20 (t, J=5.5 Hz, 2H), 1.61-1.52 (m, 4H), 1.38-1.35 (m, 2H); ¹³C NMR (101 MHz, DMSO-d₆) δ 162.3, 160.3, 157.4, 153.5, 138.8, 130.9 (q, J=34.8 Hz), 129.6, 128.4, 123.2 (q, J=273.6 Hz), 116.3, 111.5 (q, J=5.2 Hz), 104.9, 47.8, 42.4, 26.3, 25.7, 24.4. MS (ES+) m/z=391 [M+H]⁺.

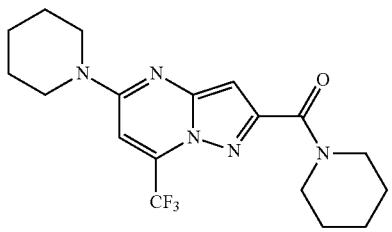 [SMILES: O=C(c1cc2nc(N3CCCCC3)cc(C(F)(F)F)n2n1)N1CCCCC1]

The target compound 39a was obtained by S$_N$Ar reaction of piperidine with chloride intermediate in the general procedure above, which is (5-chloro-7-(trifluoromethyl)pyrazolo[1,5-a]pyrimidin-2-yl)(piperidin-1-yl)methanone.

Piperidine (0.05 mL, 0.5 mmol) was added to a solution of (5-chloro-7-(trifluoromethyl)pyrazolo[1,5-a]pyrimidin-2-yl)(piperidin-1-yl)methanone (33 mg, 0.1 mmol) in 1,4-dioxane (2 mL). The mixture was heated at 90° C. for 3 h and the solvent was removed by reduced pressure. The resulting residue was purified by flash chromatography on silica gel to give the product as a pale yellow solid (31 mg, 81% yield).

¹H NMR (400 MHz, Chloroform-d) δ 11.38 (s, 1H), 6.90 (s, 1H), 3.77 (t, J=5.4 Hz, 2H), 3.73-3.71 (t, J=5.1 Hz, 4H), 3.30 (t, J=5.4 Hz, 2H), 1.74-1.65 (m, 10H), 1.50-1.45 (m, 2H); ¹³C NMR (101 MHz, Chloroform-d) δ 163.1, 158.3, 153.3, 139.6, 132.76 (q, J=34.7 Hz), 122.70 (q, J=273.5 Hz), 102.42 (q, J=5.4 Hz), 99.6, 48.0, 46.8, 42.8, 26.1, 25.6, 25.4, 24.6, 24.5. MS (ES+) m/z=382 [M+H]⁺.

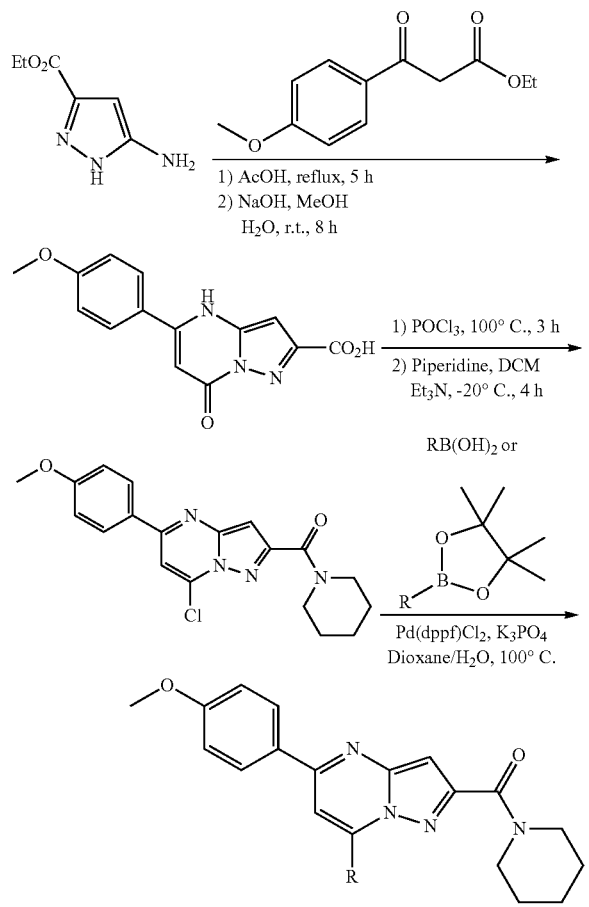

Step 1

To a solution of ethyl 5-amino-1H-pyrazole-3-carboxylate (1.55 g, 10 mmol) in AcOH (20 mL) was added ethyl 3-(4-methoxyphenyl)-3-oxopropanoate (2.44 g, 11 mmol). The mixture was refluxed for 5 h and subsequently cooled down to 0° C. in an ice bath. The precipitate was collected by filtration and washed with ether to give a yellow solid (2.47 g, 79% yield). The ester intermediate was taken in MeOH (20 mL) and NaOH aq. (1M, 20 mL), and the solution was stirred at room temperature for 8 h. The solvent was then removed and the residue was acidified by 1M HCl until PH 2. The precipitate was collected by filtration, and washed with cold water. The resulting solid was dried to obtain the pure product as a yellow solid (2.05 g, 91% yield).

¹H NMR (400 MHz, DMSO-d₆) δ 13.25 (s, 1H), 12.55 (s, 1H), 7.82 (d, J=8.8 Hz, 2H), 7.13 (d, J=8.8 Hz, 2H), 6.50 (s, 1H), 6.12 (s, 1H), 3.84 (s, 3H).

Step 2

POCl₃ (4.69 mL, 50 mmol) was added to a 25-mL vial which was charged with 5-(4-methoxyphenyl)-7-oxo-4,7-dihydropyrazolo[1,5-a]pyrimidine-2-carboxylic acid (1.43 g, 5 mmol). The mixture was heated at 100° C. for 3 h, and the excess POCl₃ was removed under reduced pressure. The resulting crude was dissolved in dichloromethane (10 mL) and Et₃N (6.88 mL, 50 mmol), cooled down to −20° C. Piperidine (1 mL, 10 mmol) was then added to the solution which was allowed to stir at −20° C. for 4 h. After the completion of the reaction, the solvents were removed under reduced pressure and the residue was loaded to a column on silica gel and eluted by hexanes/ethyl acetate=10/1 to give a yellow solid (705 mg, 38% yield).

¹H NMR (400 MHz, Chloroform-d) δ 8.04 (d, J=8.3 Hz, 2H), 7.42 (s, 1H), 7.02 (d, J=8.3 Hz, 2H), 6.97 (s, 1H), 3.89 (s, 3H), 3.77 (t, J=4.5 Hz, 2H), 3.73 (t, J=5.3 Hz, 2H), 1.72-1.69 (m, 4H), 1.63-1.59 (m, 2H).

Step 3

Under nitrogen atmosphere, boronic acid or boronic ester (0.11 mmol) was added to a dry tube containing (7-chloro-5-(4-methoxyphenyl)pyrazolo[1,5-a]pyrimidin-2-yl)(piperidin-1-yl)methanone (37 mg, 0.1 mmol), Pd(dppf)Cl₂ (4 mg, 0.5% mmol), K₃PO₄ (42 mg, 0.2 mmol), 1,4-dioxane (2 mL) and H₂O (0.2 mL). The mixture was stirring at 100° C. until the completion of the reaction which was monitored by LC/MS. The reaction mixture was cooled to room temperature, washed with water, extracted with ethyl acetate, dried over anhydrous Na₂SO₄ and concentrated by rotary evaporation. The crude was purified by flash chromatography on silica gel to give the product.

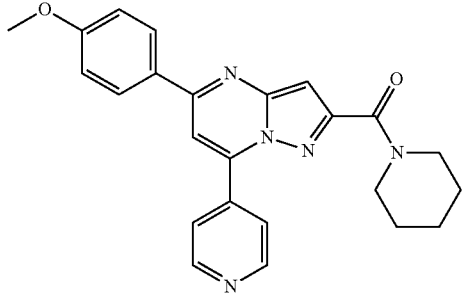 [SMILES: COc1ccc(-c2cc(-c3ccncc3)n3nc(C(=O)N4CCCCC4)cc3n2)cc1]

The target compound 22a (67% yield) was obtained by the general procedure described above.

¹H NMR (400 MHz, Chloroform-d) δ 8.87-8.84 (m, 2H), 8.13-8.08 (m, 2H), 8.01-7.98 (m, 2H), 7.44-7.42 (m, 1H), 7.06-7.00 (m, 3H), 3.90 (s, 3H), 3.78-3.68 (m, 4H), 1.71-1.59 (m, 6H); ¹³C NMR (101 MHz, Chloroform-d) δ 162.8, 161.9, 156.2, 151.8, 150.3, 149.6, 143.6, 138.5, 129.1, 128.8, 123.2, 114.4, 105.9, 98.2, 55.5, 48.4, 43.5, 26.6, 25.6, 24.6. MS (ES+) m/z=414 [M+H]⁺.

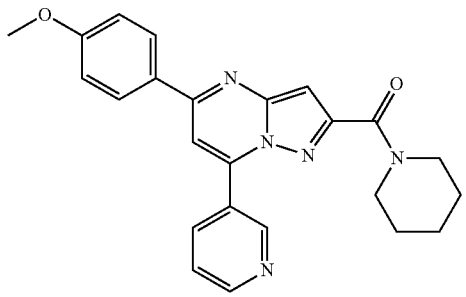 [SMILES: COc1ccc(-c2cc(-c3cccnc3)n3nc(C(=O)N4CCCCC4)cc3n2)cc1]

The target compound 23a (57% yield) was obtained by the general procedure described above.

$^1$H NMR (400 MHz, Chloroform-d) δ 9.21 (s, 1H), 8.77 (d, J=5.0 Hz, 1H), 8.50 (d, J=8.1 Hz, 1H), 8.08 (d, J=8.4 Hz, 2H), 7.49 (dd, J=8.0, 4.9 Hz, 1H), 7.38 (s, 1H), 7.02-6.98 (m, 3H), 3.86 (s, 3H), 3.75-3.68 (m, 4H), 1.68-1.57 (m, 6H); $^{13}$C NMR (400 MHz, Chloroform-d) δ 162.9, 161.9, 156.3, 151.7, 149.6, 143.5, 136.9, 129.3, 128.9, 127.4, 123.2, 114.4, 105.6, 98.1, 55.5, 48.4, 43.5, 26.6, 25.6, 24.6. MS (ES+) m/z=414 [M+H]$^+$.

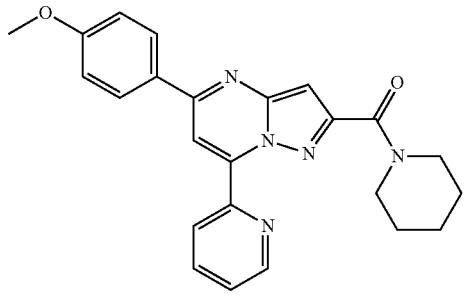 [SMILES: COc1ccc(-c2cc(-c3ccccn3)n3nc(C(=O)N4CCCCC4)cc3n2)cc1]

The target compound 24a (36% yield) was obtained by the general procedure described above.

$^1$H NMR (400 MHz, Chloroform-d) δ 9.13 (d, J=8.0 Hz, 1H), 8.83 (d, J=4.0 Hz, 1H), 8.28 (s, 1H), 8.20 (d, J=7.7 Hz, 2H), 7.92 (t, J=7.8 Hz, 1H), 7.49-7.46 (m, 1H), 7.04 (d, J=7.7 Hz, 2H), 7.00 (s, 1H), 3.90 (s, 3H), 3.81-3.78 (m, 2H), 3.75-3.72 (m, 2H), 1.72 (s, 4H), 1.63 (s, 2H); $^{13}$C NMR (101 MHz, Chloroform-d) δ 163.3, 161.7, 156.4, 151.2, 150.3, 149.9, 148.3, 143.9, 136.6, 129.7, 129.0, 126.2, 125.4, 114.3, 106.2, 97.5, 55.4, 48.4, 43.5, 26.7, 25.7, 24.7. MS (ES+) m/z=414 [M+H]$^+$.

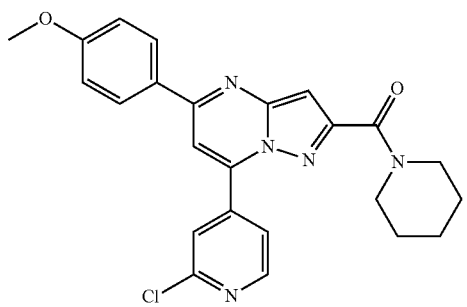 [SMILES: COc1ccc(-c2cc(-c3ccnc(Cl)c3)n3nc(C(=O)N4CCCCC4)cc3n2)cc1]

The target compound 25a (53% yield) was obtained by the general procedure described above.

$^1$H NMR (400 MHz, Chloroform-d) δ 8.63-8.61 (m, 1H), 8.12-8.08 (m, 3H), 7.94-7.92 (m, 1H), 7.43 (s, 1H), 7.06-7.03 (m, 3H), 3.90 (s, 3H), 3.78-3.71 (m, 4H), 1.72-1.70 (m, 4H), 1.65-1.63 (m, 2H); $^{13}$C NMR (101 MHz, Chloroform-d) δ 162.6, 162.1, 156.2, 152.2, 152.0, 150.2, 149.6, 142.2, 141.3, 128.9, 128.9, 124.0, 121.9, 114.5, 106.1, 98.6, 55.5, 48.4, 43.6, 26.6, 25.7, 24.6. MS (ES+) m/z=448 [M+H]$^+$.

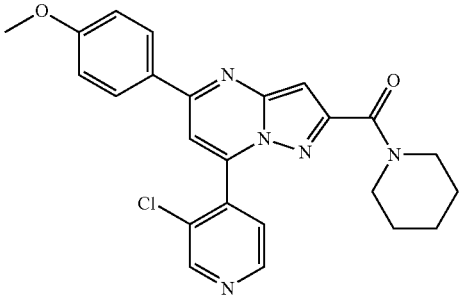 [SMILES: COc1ccc(-c2cc(-c3ccncc3Cl)n3nc(C(=O)N4CCCCC4)cc3n2)cc1]

The target compound 26a (45% yield) was obtained by the general procedure described above.

$^1$H NMR (400 MHz, Chloroform-d) δ 8.80 (s, 1H), 8.69-8.67 (m, 1H), 8.07 (d, J=8.5 Hz, 2H), 7.56-7.54 (m, 1H), 7.32 (s, 1H), 7.02-6.98 (m, 3H), 3.86 (s, 3H), 3.70-3.61 (m, 4H), 1.64 (s, 4H), 1.50 (s, 2H); $^{13}$C NMR (101 MHz, Chloroform-d) δ 162.8, 162.0, 155.9, 152.0, 150.2, 149.0, 148.1, 141.6, 140.9, 137.9, 131.1, 131.0, 129.0, 128.9, 125.0, 114.4, 113.1, 107.1, 98.2, 55.5, 48.4, 43.5, 26.5, 25.6, 24.6. MS (ES+) m/z=448 [M+H]$^+$.

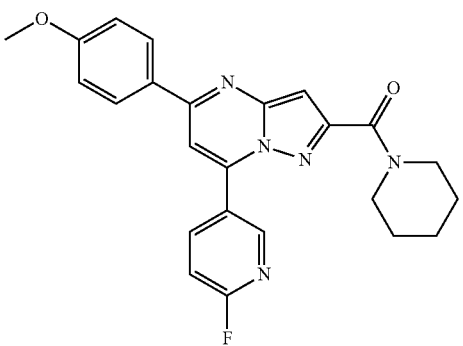 [SMILES: COc1ccc(-c2cc(-c3ccc(F)nc3)n3nc(C(=O)N4CCCCC4)cc3n2)cc1]

The target compound 27a (65% yield) was obtained by the general procedure described above.

$^1$H NMR (400 MHz, Chloroform-d) δ 8.88 (s, 1H), 8.67 (t, J=8.0 Hz, 1H), 8.11 (d, J=8.7 Hz, 2H), 7.39 (s, 1H), 7.15 (dt, J=8.7, 2.5 Hz, 1H), 7.05 (d, J=8.7 Hz, 2H), 6.99 (s, 1H), 3.90 (s, 3H), 3.76 (s, 2H), 3.68 (s, 2H), 1.70 (s, 4H), 1.59 (s, 2H); $^{13}$C NMR (101 MHz, Chloroform-d) δ 164.5 (d, J=244.8 Hz), 162.9, 161.9, 156.3, 151.7, 149.6, 148.5 (d, J=15.8 Hz), 142.4 (d, J=6.4 Hz), 142.3, 129.1, 128.8, 125.4 (d, J=4.7 Hz), 114.4, 109.5 (d, J=37.5 Hz), 105.4, 98.1, 55.5, 48.4, 43.5, 26.6, 25.6, 24.6. MS (ES+) m/z=432 [M+H]$^+$.

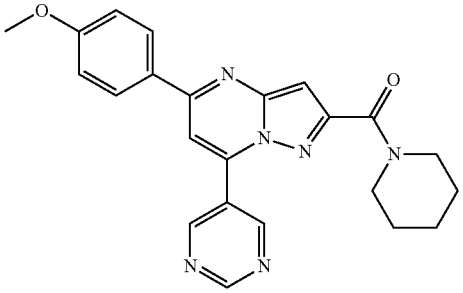 [SMILES: COc1ccc(-c2cc(-c3cncnc3)n3nc(C(=O)N4CCCCC4)cc3n2)cc1]

The target compound 28a (72% yield) was obtained by the general procedure described above.

¹H NMR (400 MHz, Chloroform-d) δ 9.48 (s, 2H), 9.40 (s, 1H), 8.11 (d, J=8.8 Hz, 2H), 7.43 (s, 1H), 7.05 (d, J=8.7 Hz, 2H), 7.03 (s, 1H), 3.90 (s, 3H), 3.77 (t, J=5.3 Hz, 2H), 3.71 (t, J=5.5 Hz, 2H), 1.71-1.70 (m, 4H), 1.62-1.60 (m, 2H); ¹³C NMR (101 MHz, Chloroform-d) δ 162.6, 162.0, 159.9, 156.8, 156.2, 152.0, 149.4, 140.5, 128.9, 128.9, 125.8, 114.4, 105.6, 98.5, 55.5, 48.4, 43.6, 26.6, 25.6, 24.6. MS (ES+) m/z=415 [M+H]⁺.

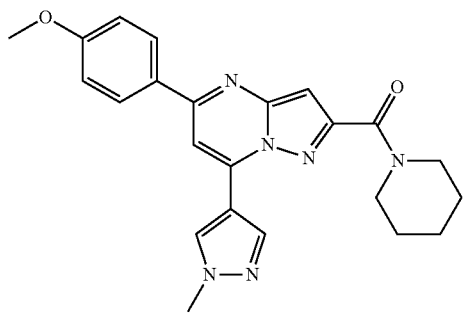 [SMILES: COc1ccc(-c2cc(-c3cnn(C)c3)n3nc(C(=O)N4CCCCC4)cc3n2)cc1]

The target compound 29a (64% yield) was obtained by the general procedure described above.

¹H NMR (400 MHz, Chloroform-d) δ 8.83 (s, 1H), 8.27 (s, 1H), 8.04 (d, J=8.7 Hz, 2H), 7.46 (s, 1H), 6.97 (d, J=8.7 Hz, 2H), 6.85 (s, 1H), 3.98 (s, 3H), 3.83 (s, 3H), 3.78 (t, J=5.4 Hz, 2H), 3.71 (t, J=5.4 Hz, 2H), 1.70 (s, 4H), 1.61 (s, 2H); ¹³C NMR (101 MHz, Chloroform-d) δ 163.6, 161.5, 156.0, 151.1, 149.6, 139.2, 139.1, 136.8, 133.6, 129.8, 128.7, 126.5, 114.2, 112.7, 101.0, 96.9, 55.4, 48.4, 43.4, 39.4, 26.8, 25.7, 24.7. MS (ES+) m/z=417 [M+H]⁺.

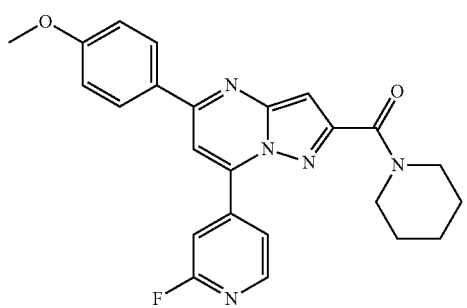

The target compound 30a (61% yield) was obtained by the general procedure described above.

¹H NMR (400 MHz, Chloroform-d) δ 8.46-8.45 (m, 1H), 8.11 (d, J=8.5 Hz, 2H), 7.89-7.87 (m, 1H), 7.74 (s, 1H), 7.45 (s, 1H), 7.06-7.02 (m, 3H), 3.90 (s, 3H), 3.77 (s, 2H), 3.71 (s, 2H), 1.71 (s, 4H), 1.62 (s, 2H); ¹³C NMR (101 MHz, Chloroform-d) δ 163.9 (d, J=239.5 Hz), 162.7, 162.0, 156.2, 151.9, 149.6, 148.3 (d, J=15.1 Hz), 143.6, 143.5, 142.2 (d, J=3.6 Hz), 128.9, 121.0 (d, J=4.5 Hz), 114.4, 109.9 (d, J=40.1 Hz), 106.1, 98.4, 55.5, 48.4, 43.6, 26.6, 25.6, 24.6. MS (ES+) m/z=432 [M+H]⁺.

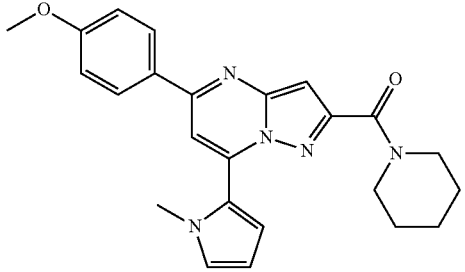 [SMILES: COc1ccc(-c2cc(-c3cccn3C)n3nc(C(=O)N4CCCCC4)cc3n2)cc1]

The target compound 71a (73% yield) was obtained by the general procedure described above.

¹H NMR (400 MHz, Chloroform-d) δ 8.07 (d, J=8.8 Hz, 2H), 7.24 (s, 1H), 7.03 (d, J=8.8 Hz, 2H), 6.95 (s, 1H), 6.94-6.91 (m, 2H), 6.33 (dd, J=3.8, 2.7 Hz, 1H), 3.88 (s, 3H), 3.78 (s, 3H), 3.76-3.71 (m, 4H), 1.70-1.68 (m, 4H), 1.61-1.56 (m, 2H); ¹³C NMR (101 MHz, Chloroform-d) δ 163.3, 161.6, 155.9, 151.6, 149.7, 139.4, 129.8, 128.8, 127.7, 123.8, 115.8, 114.3, 109.1, 106.0, 97.7, 55.5, 48.3, 43.4, 36.4, 26.6, 25.6, 24.7. MS (ES+) m/z=416 [M+H]⁺.

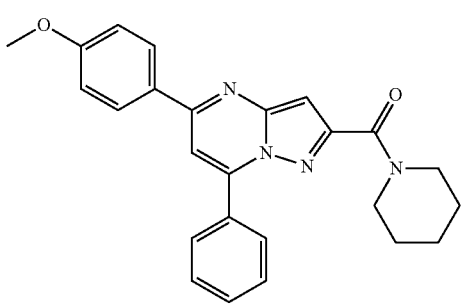

The target compound 34a (85% yield) was obtained by the general procedure described above.

¹H NMR (400 MHz, Chloroform-d) δ 8.10-8.06 (m, 4H), 7.57-7.53 (m, 3H), 7.35 (s, 1H), 7.02-6.99 (m, 3H), 3.87 (s, 3H), 3.74 (t, J=5.4 Hz, 4H), 1.69-1.68 (m, 4H), 1.63-1.59 (m, 2H); ¹³C NMR (101 MHz, Chloroform-d) δ 163.2, 161.7, 156.3, 151.5, 149.8, 146.5, 131.0, 129.6, 129.3, 128.8, 128.6, 114.3, 105.6, 97.8, 55.4, 48.4, 43.5, 26.6, 25.7, 24.7. MS (ES+) m/z=413 [M+H]⁺.

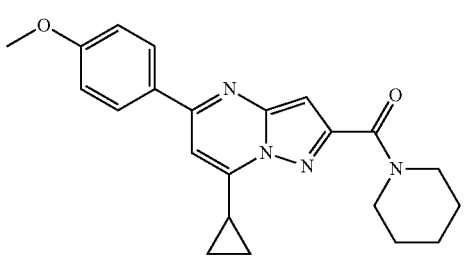 [SMILES: COc1ccc(-c2cc(C3CC3)n3nc(C(=O)N4CCCCC4)cc3n2)cc1]

The target compound 67a (35% yield) was obtained by the general procedure described above.

¹H NMR (400 MHz, Chloroform-d) δ 8.00 (d, J=8.8 Hz, 2H), 6.99 (d, J=8.8 Hz, 2H), 6.85 (s, 1H), 6.76 (s, 1H), 3.87 (s, 3H), 3.78-3.71 (m, 4H), 2.91-2.84 (m, 1H), 1.71-1.69 (m, 4H), 1.62-1.60 (m, 2H), 1.36-1.31 (m, 2H), 1.17-1.13 (m, 2H); ¹³C NMR (101 MHz, Chloroform-d) δ 163.6, 161.5, 156.3, 152.0, 151.2, 148.8, 129.9, 128.8, 114.2, 99.5, 97.1, 55.4, 48.4, 43.4, 26.7, 25.6, 24.7, 10.7, 9.5. MS (ES+) m/z=377 [M+H]⁺.

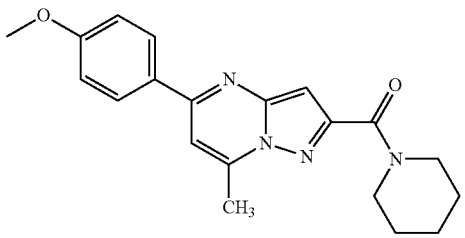 [SMILES: COc1ccc(-c2cc(C)n3nc(C(=O)N4CCCCC4)cc3n2)cc1]

The target compound 35a (40% yield) was obtained by the general procedure described above.

¹H NMR (400 MHz, Chloroform-d) δ 8.02 (d, J=8.4 Hz, 2H), 7.12 (s, 1H), 6.98 (d, J=8.4 Hz, 2H), 6.84 (s, 1H), 3.85 (s, 3H), 3.76 (s, 2H), 3.69 (t, J=5.5 Hz, 2H), 2.79 (s, 3H), 1.68 (s, 4H), 1.58 (s, 2H); ¹³C NMR (101 MHz, Chloroform-d) δ 163.5, 161.6, 156.0, 151.2, 148.7, 145.9, 129.6, 128.8, 114.2, 105.5, 97.2, 55.4, 48.4, 43.4, 26.6, 25.6, 24.6, 17.4. MS (ES+) m/z=351 [M+H]⁺.

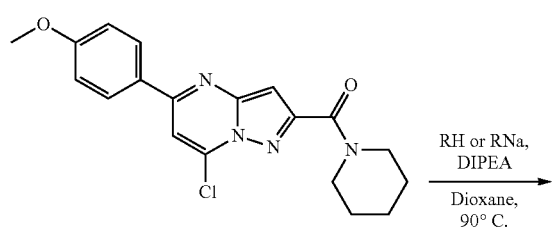

Target compounds were also obtained through S$_N$Ar reaction of chloride intermediate with nucleophiles.

Amine or NaOMe (0.2 mmol) was added to a solution of (7-chloro-5-(4-methoxyphenyl)pyrazolo[1,5-a]pyrimidin-2-yl)(piperidin-1-yl)methanone (37 mg, 0.1 mmol) in 1,4-dioxane (2 mL). The mixture was heated at 90° C. until the completion of the reaction which was monitored by LC/MS and the solvent was removed by reduced pressure. The resulting residue was purified by flash chromatography on silica gel to give the product.

The target compound 31a (81% yield) was obtained through S$_N$Ar reaction described above.

¹H NMR (400 MHz, Chloroform-d) δ 7.99 (d, J=7.5 Hz, 2H), 6.98 (d, J=7.5 Hz, 2H), 6.63 (s, 1H), 6.38 (q, J=5.3 Hz, 1H), 6.31 (s, 1H), 3.86 (s, 3H), 3.75 (t, J=4.6 Hz, 2H), 3.64 (t, J=4.6 Hz, 2H), 3.14 (d, J=5.0 Hz, 3H), 1.68 (s, 4H), 1.57 (s, 2H); ¹³C NMR (101 MHz, Chloroform-d) δ 163.8, 161.1, 157.9, 150.3, 148.9, 147.5, 131.1, 128.7, 114.0, 95.8, 82.2, 55.4, 48.4, 43.3, 28.6, 26.7, 25.6, 24.6. MS (ES+) m/z=366 [M+H]⁺.

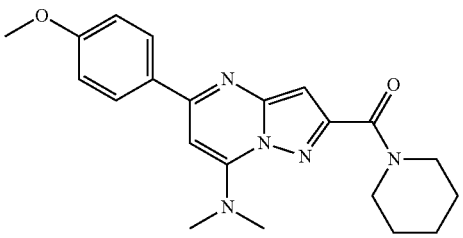 [SMILES: COc1ccc(-c2cc(N(C)C)n3nc(C(=O)N4CCCCC4)cc3n2)cc1]

The target compound 32a (82% yield) was obtained through S$_N$Ar reaction described above.

¹H NMR (400 MHz, Chloroform-d) δ 7.97 (d, J=8.8 Hz, 2H), 6.97 (d, J=8.8 Hz, 2H), 6.74 (s, 1H), 6.36 (s, 1H), 3.85 (s, 3H), 3.76-3.71 (m, 4H), 3.36 (s, 6H), 1.69-1.68 (m, 4H), 1.63-1.59 (m, 2H); ¹³C NMR (101 MHz, Chloroform-d) δ 163.5, 161.2, 157.2, 151.3, 150.8, 150.2, 130.8, 128.7, 114.0, 96.1, 89.1, 55.4, 48.3, 43.4, 41.2, 26.7, 25.7, 24.7. MS (ES+) m/z=380 [M+H]⁺.

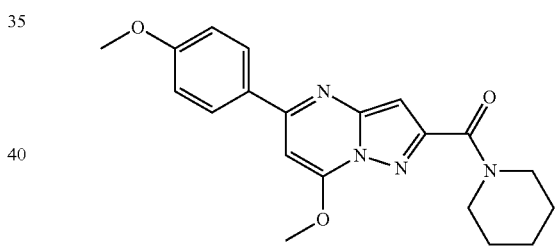

The target compound 33a (68% yield) was obtained through S$_N$Ar reaction described above.

¹H NMR (400 MHz, Chloroform-d) δ 8.01 (d, J=8.8 Hz, 2H), 6.99 (d, J=8.8 Hz, 2H), 6.77 (s, 1H), 6.58 (s, 1H), 4.24 (s, 3H), 3.86 (s, 3H), 3.74-3.72 (m, 2H), 3.64-3.61 (m, 2H), 1.68-1.65 (m, 4H), 1.58-1.52 (m, 2H); ¹³C NMR (101 MHz, Chloroform-d) δ 163.4, 161.6, 158.5, 155.8, 152.1, 150.5, 130.0, 128.8, 114.2, 96.7, 84.1, 57.0, 55.4, 48.3, 43.2, 26.6, 25.5, 24.6. MS (ES+) m/z=367 [M+H]⁺.

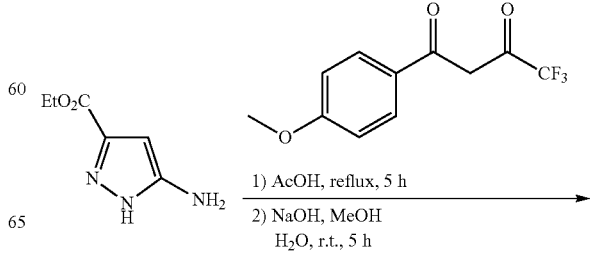

-continued

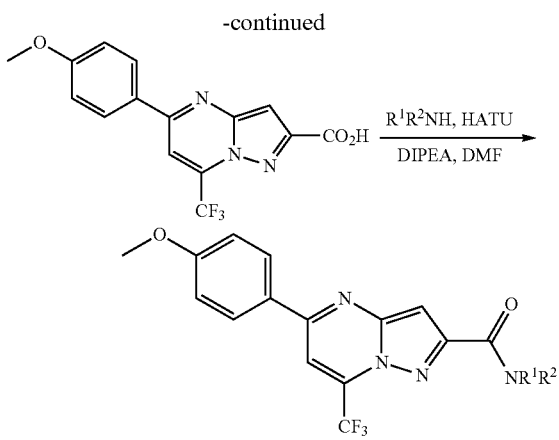

Step 1

To a solution of ethyl 5-amino-1H-pyrazole-3-carboxylate (1.55 g, 10 mmol) in AcOH (20 mL) was added 4,4,4-trifluoro-1-(4-methoxyphenyl)butane-1,3-dione (2.71 g, 11 mmol). The mixture was refluxed for 5 h and subsequently cooled down to 0° C. in an ice bath. The precipitate was collected by filtration and recrystallized by hexanes/ethyl acetate to give a yellow solid. The solid was taken in MeOH (20 mL) and NaOH aq. (1M, 20 mL), and the solution was stirred at room temperature for 5 h. The solvent was then removed and the residue was acidified by 1M HCl until PH 2. The precipitate was collected by filtration, and washed with cold water. The resulting solid was dried to obtain the pure product as a pale yellow solid (1.55 g, 92% yield). $^1$H NMR (400 MHz, DMSO-$d_6$) δ 13.57 (s, 1H), 8.26-8.22 (m, 3H), 7.39 (d, J=7.9 Hz, 2H), 7.32 (s, 1H), 2.39 (s, 3H).

Step 3

To a solution of 5-(4-methoxyphenyl)-7-(trifluoromethyl)pyrazolo[1,5-a]pyrimidine-2-carboxylic acid (34 mg, 0.1 mmol), HATU (42 mg, 0.11 mmol), DIPEA (0.035 mL, 0.2 mmol) in DMF (2 mL) was added amine (0.12 mmol). The mixture was stirred at room temperature until the completion of the reaction which was monitored by LC/MS. Water was added to the solution, and the mixture was extracted with ethyl acetate, washed with brine, dried over anhydrous Na$_2$SO$_4$ and concentrated by rotary evaporation. The crude was purified by flash chromatography on silica gel to give the product.

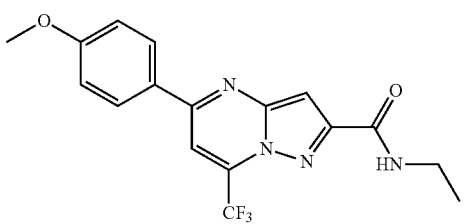 [SMILES: CCNC(=O)c1cc2nc(-c3ccc(OC)cc3)cc(C(F)(F)F)n2n1]

The target compound 7a (81% yield) was obtained by the general procedure described above.

$^1$H NMR (400 MHz, Chloroform-d) δ 8.09 (d, J=8.7 Hz, 2H), 7.65 (s, 1H), 7.32 (s, 1H), 7.18 (t, J=5.9 Hz, 1H), 7.05 (d, J=8.7 Hz, 2H), 3.90 (s, 3H), 3.59-3.52 (m, 2H), 1.31 (t, J=7.2 Hz, 3H); $^{13}$C NMR (101 MHz, Chloroform-d) δ 162.4, 160.9, 155.4, 151.6, 150.3, 134.0 (q, J=37.4 Hz), 128.9, 128.1, 119.3 (q, J=274.7 Hz), 114.5, 104.9 (q, J=4.1 Hz), 98.4, 55.5, 34.3, 14.9. MS (ES+) m/z=365 [M+H]$^+$.

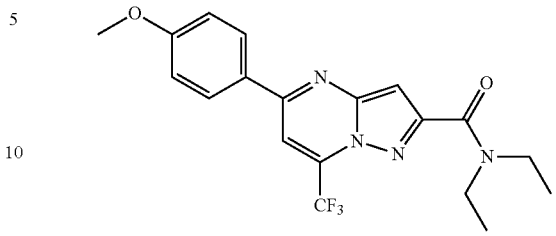

The target compound 8a (85% yield) was obtained by the general procedure described above.

$^1$H NMR (400 MHz, Chloroform-d) δ 8.06 (d, J=8.8 Hz, 2H), 7.58 (s, 1H), 7.15 (s, 1H), 7.01 (d, J=8.8 Hz, 2H), 3.87 (s, 3H), 3.68 (q, J=7.0 Hz, 2H), 3.58 (q, J=7.1 Hz, 2H), 1.32-1.26 (m, 6H); $^{13}$C NMR (101 MHz, Chloroform-d) δ 162.8, 162.3, 155.5, 153.1, 149.3, 134.2 (q, J=37.3 Hz), 129.0, 128.4, 119.4 (q, J=274.5 Hz), 114.5, 104.4 (q, J=4.1 Hz), 99.7, 55.5, 43.6, 41.2, 14.5, 12.8. MS (ES+) m/z=393 [M+H]$^+$.

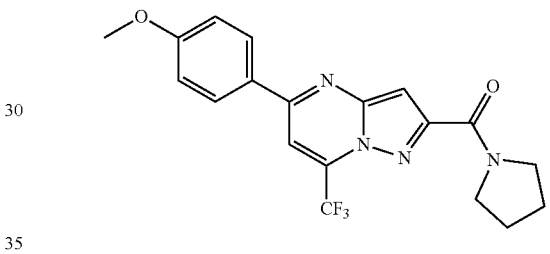

The target compound 9a (84% yield) was obtained by the general procedure described above.

$^1$H NMR (400 MHz, Chloroform-d) δ 8.09 (d, J=7.3 Hz, 2H), 7.62 (s, 1H), 7.29 (s, 1H), 7.04 (d, J=7.3 Hz, 2H), 4.01 (t, J=6.6 Hz, 2H), 3.90 (s, 3H), 3.73 (t, J=6.6 Hz, 2H), 2.04-1.93 (m, 4H); $^{13}$C NMR (101 MHz, Chloroform-d) δ 162.3, 161.0, 155.4, 153.2, 149.2, 134.2 (q, J=37.3 Hz), 128.9, 128.3, 119.4 (q, J=274.5 Hz), 114.5, 104.5 (q, J=4.1 Hz), 99.9, 55.5, 48.9=47.2, 26.6, 23.9. MS (ES+) m/z=391 [M+H]$^+$.

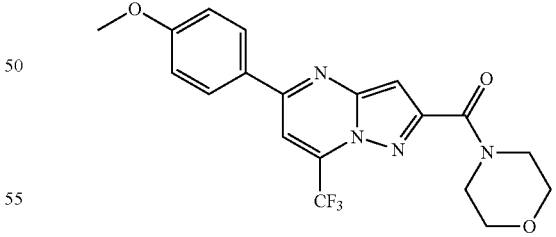

The target compound 10a (88% yield) was obtained by the general procedure described above.

$^1$H NMR (400 MHz, Chloroform-d) δ 8.09 (d, J=7.7 Hz, 2H), 7.63 (s, 1H), 7.18 (s, 1H), 7.04 (d, J=7.8 Hz, 2H), 4.08-4.06 (m, 2H), 3.90 (s, 3H), 3.86-3.82 (m, 4H), 3.77-3.75 (m, 2H); $^{13}$C NMR (101 MHz, Chloroform-d) δ 162.4, 161.9, 155.7, 152.0, 149.4, 134.1 (q, J=37.5 Hz), 129.0, 128.2, 119.3 (q, J=274.9 Hz), 114.5, 104.7 (q, J=4.0 Hz), 100.1, 67.1, 66.8, 55.5, 47.8, 43.1. MS (ES+) m/z=407 [M+H]$^+$.

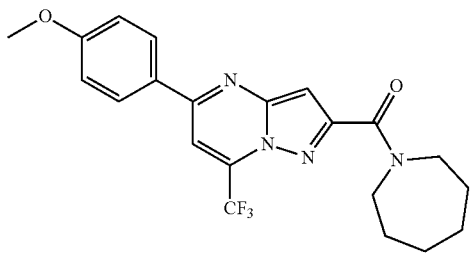 [SMILES: COc1ccc(-c2cc(C(F)(F)F)n3nc(C(=O)N4CCCCCC4)cc3n2)cc1]

The target compound 11a (80% yield) was obtained by the general procedure described above.

$^1$H NMR (400 MHz, Chloroform-d) δ 8.09 (d, J=7.4 Hz, 2H), 7.61 (s, 1H), 7.15 (s, 1H), 7.05 (d, J=7.4 Hz, 2H), 3.90 (s, 3H), 3.80 (t, J=5.5 Hz, 2H), 3.75 (t, J=5.5 Hz, 2H), 1.90-1.81 (m, 4H), 1.69-1.65 (m, 2H); $^{13}$C NMR (101 MHz, Chloroform-d) δ 163.4, 162.3, 155.5, 153.1, 149.4, 134.2 (q, J=37.2 Hz), 129.0, 128.3, 119.4 (q, J=274.5 Hz), 114.5, 104.3 (q, J=4.1 Hz), 99.4, 55.5, 49.4, 47.5, 29.7, 27.2, 27.0, 26.8. MS (ES+) m/z=419 [M+H]$^+$.

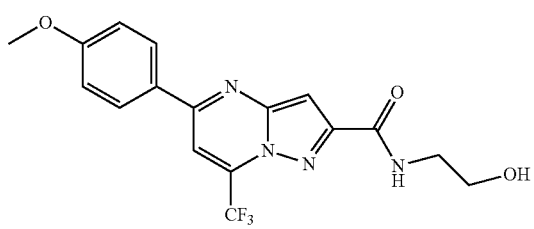 [SMILES: COc1ccc(-c2cc(C(F)(F)F)n3nc(C(=O)NCCO)cc3n2)cc1]

The target compound 12a (72% yield) was obtained by the general procedure described above.

$^1$H NMR (400 MHz, DMSO-d$_6$) δ 8.31-8.27 (m, 3H), 8.19 (s, 1H), 7.21 (s, 1H), 7.09 (d, J=8.5 Hz, 2H), 4.82 (t, J=5.0 Hz, 1H), 3.84 (s, 3H), 3.56-3.52 (m, 2H), 3.41-3.37 (m, 2H); $^{13}$C NMR (101 MHz, DMSO-d$_6$) δ 162.5, 161.0, 155.9, 151.9, 149.9, 133.4 (q, J=37.0 Hz), 129.9, 128.2, 119.9 (q, J=274.6 Hz), 114.9, 106.6 (q, J=4.1 Hz), 97.9, 60.0, 55.9, 42.1. MS (ES+) m/z=381 [M+H]$^+$.

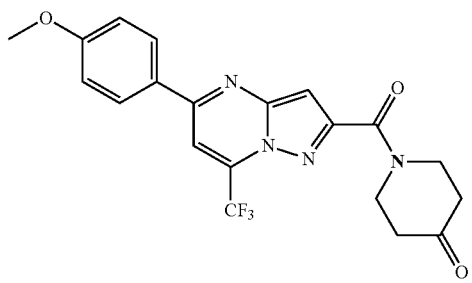 [SMILES: COc1ccc(-c2cc(C(F)(F)F)n3nc(C(=O)N4CCC(=O)CC4)cc3n2)cc1]

The target compound 13a (89% yield) was obtained by the general procedure described above.

$^1$H NMR (400 MHz, Chloroform-d) δ 8.11 (d, J=8.7 Hz, 2H), 7.66 (s, 1H), 7.23 (s, 1H), 7.06 (d, J=8.7 Hz, 2H), 4.27 (t, J=5.7 Hz, 2H), 4.10 (t, J=5.7 Hz, 2H), 3.91 (s, 3H), 2.66-2.62 (m, 4H); $^{13}$C NMR (101 MHz, Chloroform-d) δ 207.1, 162.5, 162.2, 155.9, 151.7, 149.5, 134.13 (q, J=37.7 Hz), 129.0, 128.1, 119.33 (q, J=274.6 Hz), 114.6, 104.89 (q, J=4.0 Hz), 100.1, 55.5, 45.8, 42.1, 41.7, 40.9. MS (ES+) m/z=419 [M+H]$^+$.

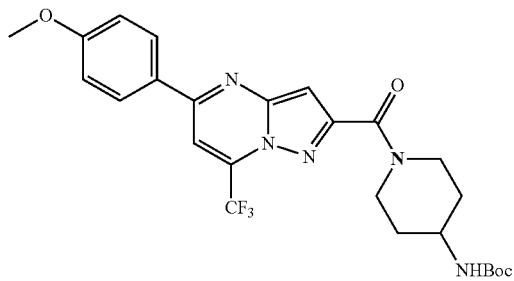 [SMILES: COc1ccc(-c2cc(C(F)(F)F)n3nc(C(=O)N4CCC(NC(=O)OC(C)(C)C)CC4)cc3n2)cc1]

The target compound 14a (87% yield) was obtained by the general procedure described above.

$^1$H NMR (400 MHz, Chloroform-d) δ 8.09 (d, J=8.7 Hz, 2H), 7.63 (s, 1H), 7.26 (d, J=3.1 Hz, 1H), 7.12 (s, 1H), 7.05 (d, J=8.7 Hz, 2H), 4.69-4.50 (m, 2H), 3.91 (s, 3H), 3.78-3.69 (m, 1H), 3.28 (t, J=12.5 Hz, 1H), 3.04-2.96 (m, 1H), 2.11-2.01 (m, 2H), 1.66-1.61 (m, 2H), 1.46 (s, 9H); $^{13}$C NMR (101 MHz, Chloroform-d) δ 162.4, 162.1, 155.7, 155.1, 152.3, 149.5, 134.1 (q, J=37.4 Hz), 129.0, 128.2, 119.3 (q, J=274.8 Hz), 114.6, 104.6 (q, J=4.1 Hz), 99.5, 55.5, 54.8, 47.9, 46.1, 41.7, 33.1, 32.2, 28.4.

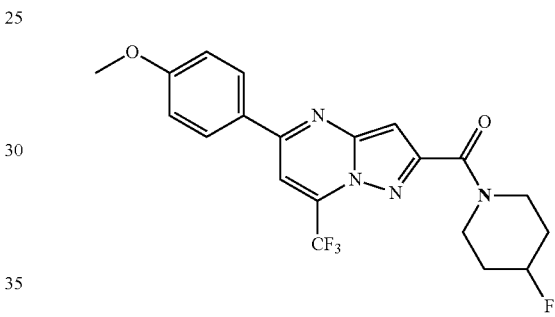

The target compound 15a (85% yield) was obtained by the general procedure described above.

$^1$H NMR (400 MHz, Chloroform-d) δ 8.10 (d, J=8.4 Hz, 2H), 7.63 (s, 1H), 7.15 (s, 1H), 7.05 (d, J=8.4 Hz, 2H), 5.04-4.89 (m, 1H), 4.17-4.08 (m, 2H), 3.91 (s, 3H), 3.90-3.85 (m, 1H), 3.72-3.65 (m, 1H), 2.05-1.95 (m, 4H); $^{13}$C NMR (101 MHz, Chloroform-d) δ 162.4, 162.1, 155.7, 152.2, 149.5, 134.2 (q, J=37.5 Hz), 129.0, 128.2, 119.4 (q, J=274.5 Hz), 114.6, 104.6 (q, J=4.1 Hz), 99.6, 87.8 (d, J=171.0 Hz), 55.5, 43.1 (d, J=4.8 Hz), 38.8 (d, J=4.7 Hz), 31.9 (d, J=20.1 Hz), 31.0 (d, J=20.2 Hz). MS (ES+) m/z=423 [M+H]$^+$.

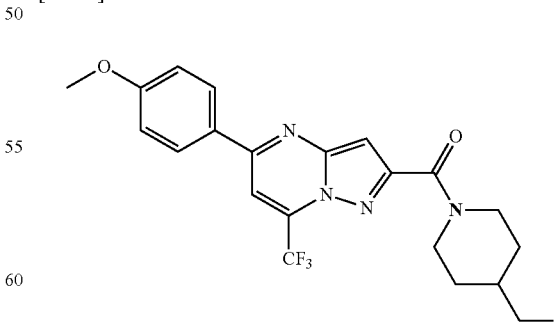

The target compound 16a (71% yield) was obtained by the general procedure described above.

$^1$H NMR (400 MHz, Chloroform-d) δ 8.04 (d, J=8.6 Hz, 2H), 7.58 (s, 1H), 7.07 (s, 1H), 7.00 (d, J=8.9 Hz, 2H), 4.77

(d, J=13.1 Hz, 1H), 4.55 (d, J=13.3 Hz, 1H), 3.86 (s, 3H), 3.55-3.48 (m, 2H), 3.12 (t, J=12.3 Hz, 1H), 2.81 (t, J=11.9 Hz, 1H), 2.27 (s, 1H), 1.89-1.77 (m, 3H), 1.37-1.28 (m, 2H); $^{13}$C NMR (101 MHz, Chloroform-d) δ 162.4, 162.2, 155.6, 152.6, 149.5, 134.2 (q, J=37.4 Hz), 129.0, 128.3, 119.4 (q, J=274.6 Hz), 114.5, 104.5 (q, J=4.1 Hz), 99.3, 67.2, 55.5, 47.3, 42.7, 38.9, 29.4, 28.5. MS (ES+) m/z=435 [M+H]$^+$.

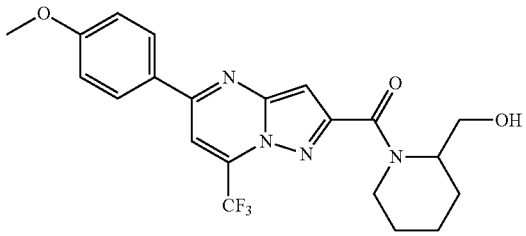 [SMILES: COc1ccc(-c2cc(C(F)(F)F)n3nc(C(=O)N4CCCCC4CO)cc3n2)cc1]

The target compound 17a (55% yield) was obtained by the general procedure described above.

$^1$H NMR (400 MHz, Chloroform-d) δ 8.06 (d, J=7.9 Hz, 2H), 7.62 (s, 1H), 7.17 (s, 1H), 7.02 (d, J=7.9 Hz, 2H), 4.76-4.72 (m, 1H), 4.62-4.59 (m, 1H), 4.11-4.01 (m, 1H), 3.88 (s, 3H), 3.69-3.64 (m, 1H), 2.98-2.91 (m, 1H), 1.81-1.60 (m, 6H); $^{13}$C NMR (101 MHz, Chloroform-d) δ 162.8, 162.5, 156.0, 152.7, 149.6, 133.9 (q, J=37.6 Hz), 129.1, 129.0, 128.1, 119.3 (q, J=274.7 Hz), 114.6, 104.7, 100.3, 60.7, 55.5, 38.6, 37.6, 26.4, 25.2, 19.8. MS (ES+) m/z=435 [M+H]$^+$.

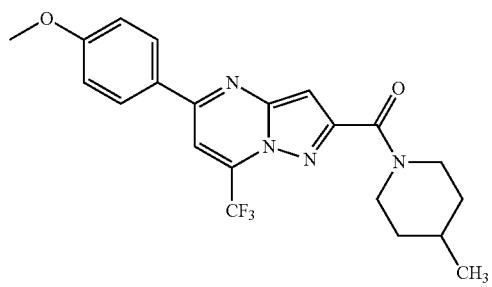

The target compound 18a (85% yield) was obtained by the general procedure described above.

$^1$H NMR (400 MHz, Chloroform-d) δ 8.09 (d, J=8.7 Hz, 2H), 7.61 (s, 1H), 7.10-7.03 (m, 3H), 4.73 (d, J=12.9 Hz, 1H), 4.47 (d, J=13.4 Hz, 1H), 3.90 (s, 3H), 3.12 (t, J=12.8 Hz, 1H), 2.83 (t, J=12.7 Hz, 1H), 1.77-1.65 (m, 3H), 1.35-1.22 (m, 2H), 0.99 (d, J=5.9 Hz, 3H); $^{13}$C NMR (101 MHz, Chloroform-d) δ 162.3, 162.1, 155.5, 152.8, 149.5, 134.2 (q, J=37.4 Hz), 129.0, 128.3, 119.4 (d, J=274.6 Hz), 114.5, 104.4 (q, J=4.3 Hz), 99.2, 55.5, 47.6, 43.1, 34.7, 33.8, 31.2, 21.7. MS (ES+) m/z=419 [M+H]$^+$.

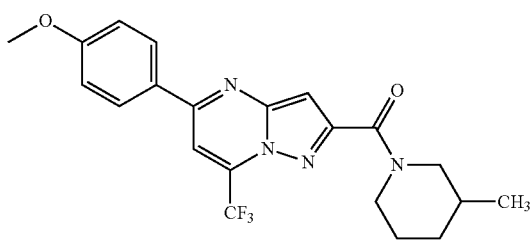

The target compound 19a (88% yield) was obtained by the general procedure described above.

Mixture of Rotamers $^1$H NMR (400 MHz, Chloroform-d) δ 8.07 (d, J=8.6 Hz, 2H), 7.60 (s, 1H), 7.11 and 7.08 (2 s, 1H), 7.02 (d, J=8.6 Hz, 2H), 4.62-4.58 (m, 1H), 4.43-4.37 (m, 1H), 3.88 (s, 3H), 3.13-3.06 (m, 1H), 2.89-2.75 (m, 1H), 2.52-2.47 (m, 1H), 1.91-1.57 (m, 4H), 1.27-1.15 (m, 1H), 0.97 and 0.87 (2 d, J=6.5 Hz, 3H); $^{13}$C NMR (101 MHz, Chloroform-d) δ 162.35, 162.05, 161.87, 155.52, 152.88, 152.84, 149.51, 149.46, 134.21 (q, J=37.6 Hz), 128.98, 128.38, 128.37, 119.40 (q, J=274.9 Hz), 114.56, 104.39, 104.34, 104.30, 99.55, 99.26, 55.49, 54.62, 50.02, 47.88, 43.40, 33.22, 32.09, 31.22, 26.03, 25.03, 19.15, 18.58. MS (ES+) m/z=419 [M+H]$^+$.

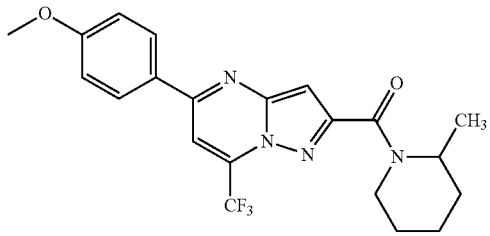

The target compound 20a (61% yield) was obtained by the general procedure described above.

$^1$H NMR (400 MHz, Chloroform-d) δ 8.04 (d, J=8.6 Hz, 2H), 7.57 (s, 1H), 7.03-6.97 (m, 3H), 5.05 and 4.58 (2 s, 1H), 4.65 and 4.24 (2 d, J=13.8 Hz, 1H), 3.86 (s, 3H), 3.23-2.89 (m, 1H), 1.77-1.51 (m, 6H), 1.35-1.30 (m, 3H); $^{13}$C NMR (101 MHz, Chloroform-d) δ 162.6, 162.3, 155.5, 153.1, 149.5, 134.2 (q, J=37.2 Hz), 128.9, 128.3, 119.4 (q, J=274.5 Hz), 114.5, 104.2 (q, J=4.6 Hz), 99.0, 98.7, 55.5, 50.2, 44.9, 42.3, 37.1, 30.9, 30.0, 26.2, 25.6, 19.0, 16.9, 15.6. MS (ES+) m/z=419 [M+H]$^+$.

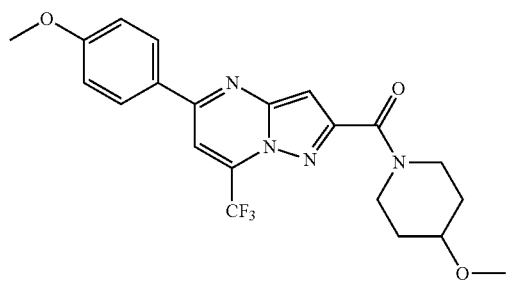

The target compound 21a (87% yield) was obtained by the general procedure described above.

$^1$H NMR (400 MHz, Chloroform-d) δ 8.09 (d, J=8.6 Hz, 2H), 7.62 (s, 1H), 7.12 (s, 1H), 7.05 (d, J=8.5 Hz, 2H), 4.16-4.05 (m, 2H), 3.90 (s, 3H), 3.70-3.50 (m, 3H), 3.39 (s, 3H), 2.04-1.92 (m, 2H), 1.78-1.64 (m, 2H); $^{13}$C NMR (101 MHz, Chloroform-d) δ 162.4, 162.1, 155.6, 152.5, 149.5, 134.2 (q, J=37.4 Hz), 129.0, 128.3, 119.4 (q, J=274.5 Hz), 114.5, 104.5 (q, J=4.1 Hz), 99.4, 75.4, 55.8, 55.5, 44.3, 39.9, 31.3, 30.3. MS (ES+) m/z=435 [M+H]$^+$.

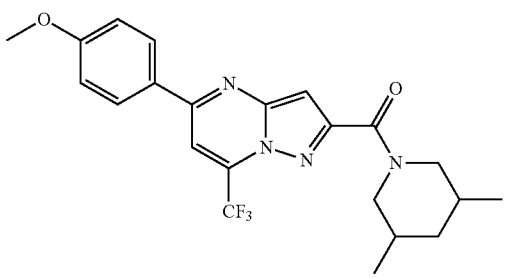

The target compound 57a (86% yield) was obtained by the general procedure described above.
Mixture of Cis and Trans ¹H NMR (400 MHz, Chloroform-d) δ 8.08 (d, J=8.8 Hz, 2H), 7.61 (s, 1H), 7.11 (s, 1H), 7.03 (d, J=8.8 Hz, 2H), 4.76-4.50 (m, 2H), 3.92-3.88 and 3.82-3.78 (2 m, 1H), 3.89 (s, 3H), 3.59-3.29 (m, 1H), 2.58-2.52 (m, 1H), 2.28-2.22 (m, 2H), 2.07-1.76 (m, 2H), 0.97 (d, J=6.6 Hz, 3H), 0.85 (d, J=6.6 Hz, 3H); ¹³C NMR (101 MHz, Chloroform-d) δ 162.68, 162.35, 161.66, 155.53, 155.50, 152.93, 152.87, 149.48, 134.22 (q, J=37.4 Hz), 128.99, 128.41, 119.41 (q, J=274.6 Hz), 114.57, 104.38 (q, J=4.2 Hz), 99.63, 99.56, 55.51, 54.34, 53.39, 49.85, 49.38, 42.57, 39.61, 32.31, 31.31, 28.05, 27.09, 19.20, 18.67, 18.35, 17.60. MS (ES+) m/z=433 [M+H]⁺.

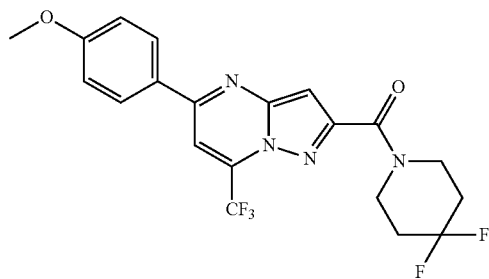 [SMILES: COc1ccc(-c2cc(C(F)(F)F)n3nc(C(=O)N4CCC(F)(F)CC4)cc3n2)cc1]

The target compound 59a (89% yield) was obtained by the general procedure described above.

¹H NMR (400 MHz, Chloroform-d) δ 8.07 (d, J=7.7 Hz, 2H), 7.63 (s, 1H), 7.16 (s, 1H), 7.02 (d, J=7.7 Hz, 2H), 4.09 (t, J=5.1 Hz, 2H), 3.93 (t, J=5.1 Hz, 2H), 3.89 (s, 3H), 2.17-2.06 (m, 4H); ¹³C NMR (101 MHz, Chloroform-d) δ 162.5, 162.0, 155.8, 151.8, 149.5, 134.2 (q, J=37.5 Hz), 129.0, 128.2, 122.9 (t, J=242.2 Hz), 119.3 (q, J=274.6 Hz), 114.6, 104.8 (q, J=4.1 Hz), 100.1, 55.5, 44.0 (t, J=5.5 Hz), 39.8 (t, J=5.3 Hz), 34.8 (t, J=23.3 Hz), 34.0 (t, J=23.4 Hz). MS (ES+) m/z=441 [M+H]⁺.

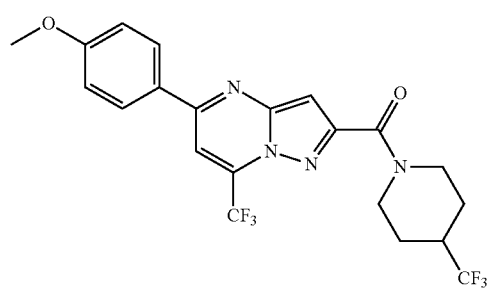 [SMILES: COc1ccc(-c2cc(C(F)(F)F)n3nc(C(=O)N4CCC(C(F)(F)F)CC4)cc3n2)cc1]

The target compound 60a (89% yield) was obtained by the general procedure described above.

¹H NMR (400 MHz, Chloroform-d) δ 8.07 (d, J=7.3 Hz, 2H), 7.62 (s, 1H), 7.14 (s, 1H), 7.02 (d, J=7.3 Hz, 2H), 4.86 (t, J=15.4 Hz, 2H), 3.88 (s, 3H), 3.14 (t, J=12.8 Hz, 1H), 2.81 (t, J=12.6 Hz, 1H), 2.41-2.31 (m, 1H), 2.04-1.86 (m, 2H), 1.76-1.63 (m, 2H); ¹³C NMR (101 MHz, Chloroform-d) δ 162.4, 162.0, 155.7, 152.1, 149.5, 134.20 (d, J=37.4 Hz), 129.0, 128.2, 127.0 (q, J=278.4 Hz), 119.3 (q, J=274.5 Hz), 114.6, 104.65 (q, J=4.2 Hz), 99.9, 55.5, 46.1, 41.7, 40.6 (q, J=27.5 Hz), 38.6, 25.2 (q, J=1.6 Hz), 24.4 (q, J=1.8 Hz). MS (ES+) m/z=473 [M+H]⁺.

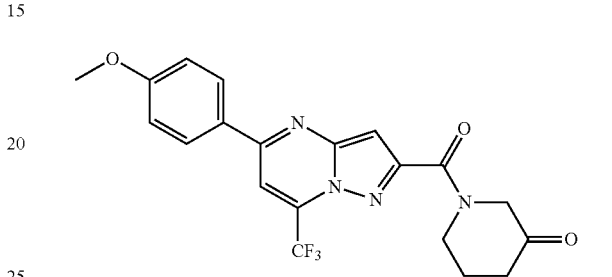

The target compound 62a (81% yield) was obtained by the general procedure described above.
Mixture of Rotamers ¹H NMR (400 MHz, Chloroform-d) δ 8.09 (d, J=8.4 Hz, 2H), 7.65 (s, 1H), 7.20 and 7.17 (2 s, 1H), 7.05 (d, J=8.4 Hz, 2H), 4.63 and 4.60 (2 s, 2H), 4.15 and 3.98 (2 t, J=5.6 Hz, 2H), 3.90 (s, 3H), 2.63-2.56 (m, 2H), 2.18-2.13 (m, 2H); ¹³C NMR (101 MHz, Chloroform-d) δ 205.0, 204.9, 162.5, 162.4, 155.8, 151.9, 151.7, 149.5, 129.1, 128.2, 119.4 (q, J=274.6 Hz), 114.6, 104.9 (q, J=4.2 Hz), 100.3, 57.1, 55.5, 54.0, 45.8, 41.8, 38.4, 38.2, 23.0, 21.5. MS (ES+) m/z=419 [M+H]⁺.

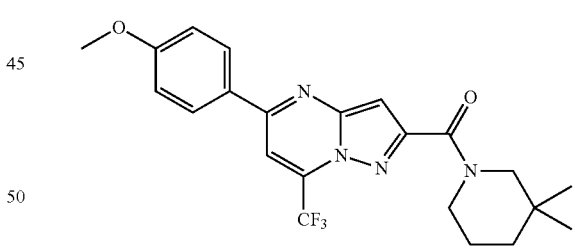

The target compound 63a (86% yield) was obtained by the general procedure described above.
Mixture of Rotamers ¹H NMR (400 MHz, Chloroform-d) δ 8.07 (d, J=8.9 Hz, 2H), 7.60 (s, 1H), 7.10 (s, 1H), 7.03 (d, J=8.9 Hz, 2H), 3.88 (s, 3H), 3.75-3.71 (m, 2H), 3.56 and 3.48 (2 s, 2H), 1.74-1.67 (m, 2H), 1.50-1.44 (m, 2H), 1.02 (s, 3H), 0.93 (s, 3H); ¹³C NMR (101 MHz, Chloroform-d) δ 162.6, 162.4, 162.3, 155.5, 155.5, 152.9, 152.9, 149.5, 149.4, 134.2 (q, J=37.4 Hz), 129.0, 128.4, 119.4 (q, J=274.7 Hz), 114.6, 104.3 (q, J=4.2 Hz), 99.7, 99.3, 58.0, 55.5, 54.1, 48.0, 43.3, 38.1, 31.9, 31.7, 26.0, 25.7, 22.7, 21.6. MS (ES+) m/z=433 [M+H]⁺.

167

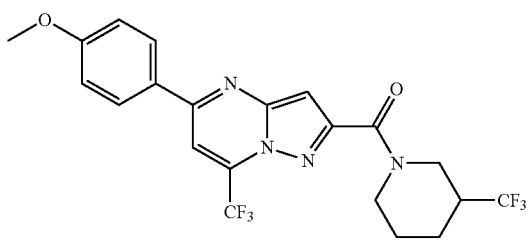 [SMILES: COc1ccc(-c2cc(C(F)(F)F)n3nc(C(=O)N4CCCC(C(F)(F)F)C4)cc3n2)cc1]

The target compound 64a (88% yield) was obtained by the general procedure described above.

Mixture of Rotamers $^1$H NMR (400 MHz, Chloroform-d) δ 8.08 (d, J=8.6 Hz, 2H), 7.63 (s, 1H), 7.19 and 7.13 (2 s, 1H), 7.03 (d, J=8.6 Hz, 2H), 5.09-4.96 (m, 1H), 4.80-4.65 (m, 1H), 3.89 (s, 3H), 3.10 (t, J=12.2 Hz, 1H), 2.86-2.74 (m, 1H), 2.60-2.39 (m, 1H), 2.17-2.12 (m, 1H), 1.94-1.83 (m, 1H), 1.69-1.62 (m, 2H); $^{13}$C NMR (101 MHz, Chloroform-d) δ 162.4, 162.4, 161.9, 155.8, 155.7, 152.1, 149.5, 134.3 (q, J=37.1 Hz), 134.2 (q, J=37.1 Hz), 129.0, 126.3 (q, J=278.3 Hz), 126.4 (q, J=278.3 Hz), 119.2 (q, J=274.6 Hz), 119.3 (q, J=274.6 Hz), 114.6, 104.7 (q, J=4.2 Hz), 100.3, 99.8, 55.5, 47.5, 46.3 (q, J=3.9 Hz), 43.2, 41.8 (q, J=3.9 Hz), 41.2 (q, J=26.4 Hz), 40.3 (q, J=26.8 Hz), 24.6, 23.8, 23.7, 23.6. MS (ES+) m/z=473 [M+H]$^+$.

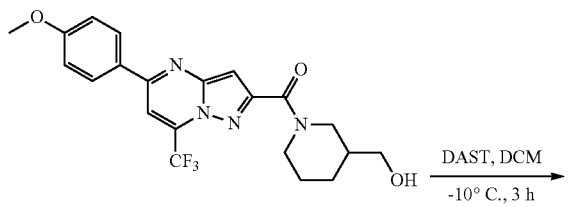

168
-continued

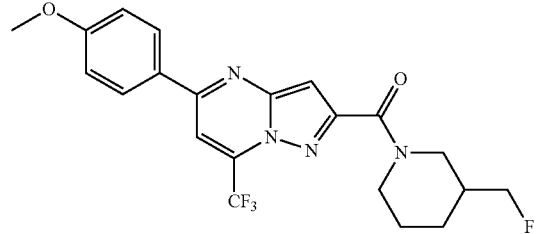

The compound (3-(hydroxymethyl)piperidin-1-yl)(5-(4-methoxyphenyl)-7-(trifluoromethyl)pyrazolo[1,5-a]pyrimidin-2-yl)methanone was obtained through the general procedure described above.

$^1$H NMR (400 MHz, Chloroform-d) δ 8.09 (d, J=8.5 Hz, 2H), 7.63 (s, 1H), 7.15 and 7.13 (2 s, 1H), 7.05 (d, J=8.5 Hz, 2H), 4.17-3.99 (m, 2H), 3.90 (s, 3H), 3.79-3.45 (m, 5H), 2.36-2.18 (m, 1H), 2.00-1.78 (m, 3H), 1.52-1.46 (m, 1H).

To a solution of (3-(hydroxymethyl)piperidin-1-yl)(5-(4-methoxyphenyl)-7-(trifluoromethyl)pyrazolo[1,5-a]pyrimidin-2-yl)methanone (22 mg, 0.05 mmol) was added DAST (16 mg, 0.1 mmol) slowly at –10° C. The mixture was stirred at the same temperature for 3 h. Water was added to quench the reaction, and the solution was extracted with dichloromethane. The combined extracts were washed with brine, dried over anhydrous Na$_2$SO$_4$ and concentrated by rotary evaporation. The crude was purified by flash chromatography on silica gel to give the target product 58a as a pale yellow solid (12 mg, 56% yield).

$^1$H NMR (400 MHz, Chloroform-d) δ 8.09 (d, J=8.6 Hz, 2H), 7.62 (s, 1H), 7.15 and 7.12 (s, 1H), 7.05 (d, J=8.6 Hz, 2H), 4.70-4.24 (m, 4H), 3.90 (s, 3H), 3.21 and 3.13 (t, J=12.4 Hz, 1H), 2.97 and 2.86 (t, J=12.0 Hz, 1H), 2.17-2.03 (m, 1H), 1.94-1.68 (m, 3H), 1.55-1.45 (m, 1H); $^{13}$C NMR (101 MHz, Chloroform-d) δ 162.4, 162.3, 162.1, 155.6, 152.5, 152.5, 149.5, 134.2 (q, J=37.1 Hz), 129.0, 128.4, 119.4 (q, J=274.6 Hz), 114.6, 104.5 (q, J=3.1 Hz), 99.8, 99.5, 85.5 (d, J=169.0 Hz), 85.3 (d, J=169.0 Hz), 55.5, 49.7 (d, J=6.3 Hz), 47.9, 44.9 (d, J=6.7 Hz), 43.5, 37.8 (d, J=18.4 Hz), 37.0 (d, J=18.7 Hz), 26.3 (d, J=5.4 Hz), 26.2 (d, J=6.0 Hz), 25.2, 24.3. MS (ES+) m/z=437 [M+H]$^+$.

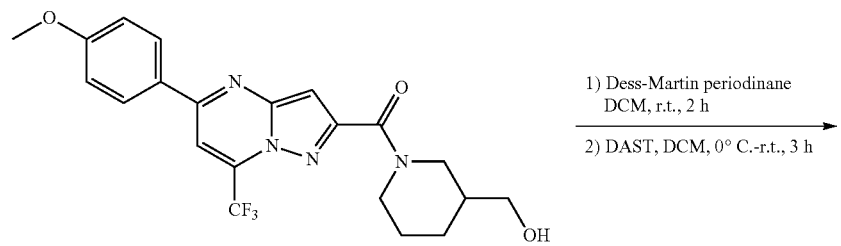

1) Dess-Martin periodinane DCM, r.t., 2 h
2) DAST, DCM, 0° C.-r.t., 3 h

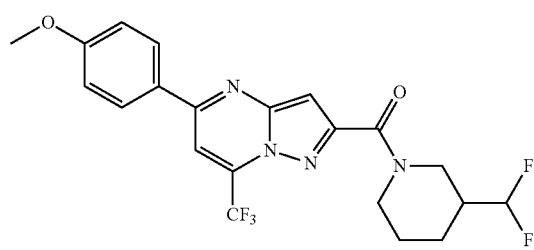

To a solution of (3-(hydroxymethyl)piperidin-1-yl)(5-(4-methoxyphenyl)-7-(trifluoromethyl)pyrazolo[1,5-a]pyrimidin-2-yl)methanone (43 mg, 0.1 mmol) in anhydrous methylene chloride (2 mL) were added Dess-Martin periodinane (64 mg, 0.15 mmol). The reaction was stirred at room temperature for 2 h. After removal of the solvent, the residue was diluted in ethyl acetate, washed with a solution of sodium thiosulfate (1.0 M in saturated sodium bicarbonate), saturated sodium bicarbonate, and brine, and dried over anhydrous sodium sulfate. Filtration and concentration gave the desired product and it was used for the next step without purification. The crude was taken in dichloromethane (2 mL) in an ice-bath and DAST (64 mg, 0.4 mmol) was added slowly. After the addition of DAST, the mixture was allowed to warm up to room temperature and continue to stir for an additional 3 h. Water was added to quench the reaction, and the solution was extracted with dichloromethane. The combined extracts were washed with brine, dried over anhydrous $Na_2SO_4$ and concentrated by rotary evaporation. The crude was purified by flash chromatography on silica gel to give the target product 66 as a pale yellow solid (19 mg, 42% yield over two steps).

Mixture of Rotamers $^1$H NMR (400 MHz, Chloroform-d) δ 8.09 (d, J=8.8 Hz, 2H), 7.63 (s, 1H), 7.17 and 7.13 (2 s, 1H), 7.05 (d, J=8.8 Hz, 2H), 5.90-5.53 (m, 1H), 4.83-4.51 (m, 2H), 3.90 (s, 3H), 3.23-3.10 (m, 1H), 2.91-2.85 (m, 1H), 2.31-2.14 (m, 1H), 2.05-2.1 (m, 1H), 1.93-1.80 (m, 1H), 1.72-1.54 (m, 2H); $^{13}$C NMR (101 MHz, Chloroform-d) δ 162.43, 162.37, 162.02, 155.74, 155.70, 152.27, 149.52, 134.26 (q, J=36.8 Hz), 129.05, 128.33, 118.67 (q, J=274.4 Hz), 118.15 (d, J=242.2 Hz), 114.61, 104.63 (q, J=4.2 Hz), 100.08, 99.71, 47.86, 46.63 (t, J=6.3 Hz), 43.49, 42.17 (t, J=6.4 Hz), 40.82 (t, J=19.7 Hz), 39.94 (t, J=19.9 Hz), 24.81, 24.02, 23.70 (t, J=4.4 Hz), 23.38 (t, J=4.2 Hz). MS (ES+) m/z=455 [M+H]$^+$.

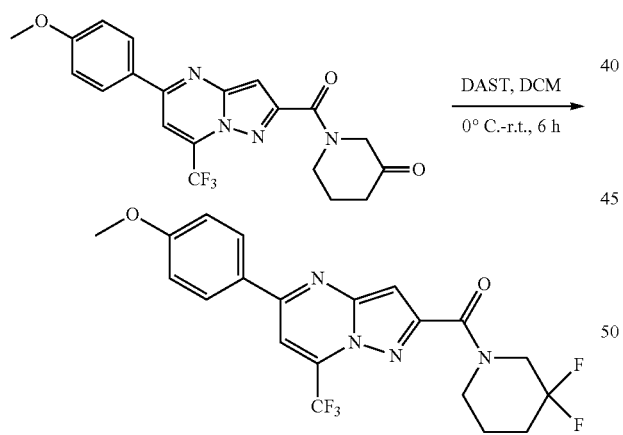

To a solution of 1-(5-(4-methoxyphenyl)-7-(trifluoromethyl)pyrazolo[1,5-a]pyrimidine-2-carbonyl)piperidin-3-one (42 mg, 0.1 mmol) was added DAST (64 mg, 0.4 mmol) slowly at 0° C. After the addition of DAST, the mixture was allowed to warm up to room temperature and continue to stir for an additional 3 h. Water was added to quench the reaction, and the solution was extracted with dichloromethane. The combined extracts were washed with brine, dried over anhydrous $Na_2SO_4$ and concentrated by rotary evaporation. The crude was purified by flash chromatography on silica gel to give the target product 65a as a pale yellow solid (22 mg, 51% yield).

Mixture of rotamers. $^1$H NMR (400 MHz, Chloroform-d) δ 8.10 (d, J=8.9 Hz, 2H), 7.64 (s, 1H), 7.20 (s, 1H), 7.05 (d, J=8.9 Hz, 2H), 4.27 (t, J=11.3 Hz, 1H), 4.06 (t, J=11.7 Hz, 1H), 4.01 (t, J=5.4 Hz, 1H), 3.91 (s, 3H), 3.81 (t, J=5.6 Hz, 1H), 2.17-2.05 (m, 2H), 1.93-1.87 (m, 2H); $^{13}$C NMR (101 MHz, Chloroform-d) δ 162.72, 162.47, 155.84, 155.76, 151.85, 151.67, 149.54, 149.46, 134.27 (q, J=30.6 Hz), 120.38 (q, J=217.4 Hz), 119.34 (q, J=274.5 Hz), 117.95 (t, J=243.5 Hz), 129.07, 128.29, 128.26, 114.62, 104.80 (q, J=3.5 Hz), 100.43, 100.40, 55.52, 52.40 (t, J=32.8 Hz), 48.25 (t, J=32.9 Hz), 46.50, 42.23, 32.92 (t, J=22.6 Hz), 32.70 (t, J=22.6 Hz), 22.76 (t, J=4.2 Hz), 21.51 (t, J=4.1 Hz). MS (ES+) m/z=441 [M+H]$^+$.

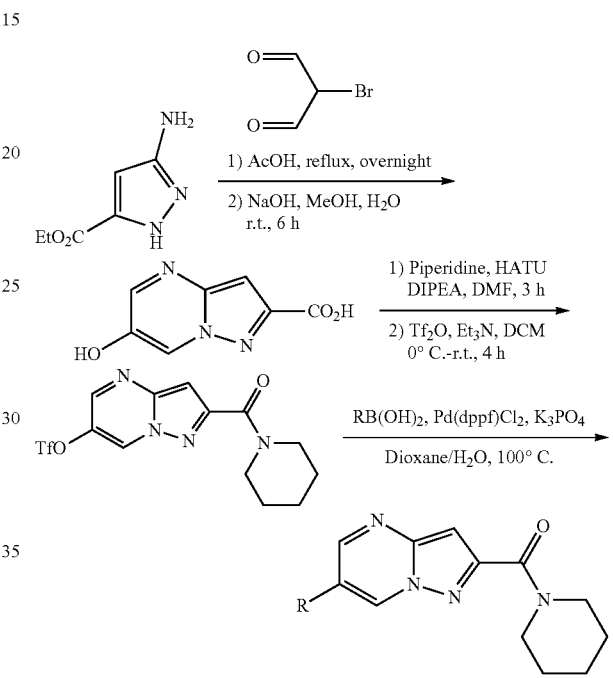

Step 1

To a solution of ethyl 5-amino-1H-pyrazole-3-carboxylate (1.55 g, 10 mmol) in AcOH (20 mL) was added 2-bromomalonaldehyde (1.66 g, 11 mmol). The mixture was refluxed for overnight and the solvent was removed by reduced pressure. The ester crude was taken in MeOH (20 mL) and NaOH aq. (1M, 20 mL), and the solution was stirred at room temperature for 8 h. The solvent was then removed and the residue was acidified by 1M HCl until PH 2. The precipitate was collected by filtration, and washed with cold water. The resulting solid was dried to obtain the pure product as a white solid (1.27 g, 71% yield). $^1$H NMR (400 MHz, DMSO-d$_6$) δ 13.10 (s, 1H), 10.58 (s, 1H), 8.54 (d, J=2.6 Hz, 1H), 8.47 (d, J=2.6 Hz, 1H), 7.04 (s, 1H).

Step 2

To a solution of 7-(piperidine-1-carbonyl)quinoxalin-2(1H)-one (1.25 g, 7 mmol), HATU (3.05 g, 8 mmol), DIPEA (2.45 mL, 14 mmol) in DMF (14 mL) was added piperidine (0.79 mL, 8 mmol). The mixture was stirred at room temperature for 3 h. Water was added to the solution, and the mixture was extracted with ethyl acetate, washed with brine, dried over anhydrous $Na_2SO_4$ and concentrated by rotary evaporation. The crude was dissolved in dichloromethane (14 mL). The mixture was placed in an ice-bath and Et$_3$N (1.96 mL, 14 mmol) and Tf$_2$O (1.77 mL, 10.5 mmol) were added to the solution slowly. After the addition of Tf$_2$O, the reaction was stirred at 0° C. for 2 h, and then the ice-bath was removed. The mixture continued to stir at room temperature for an additional 2 h. The solvent was removed and the resulting residue was purified by flash chromatography on silica gel to give the product as pale yellow oil (2.17 g, 82% yield). $^1$H NMR (400 MHz, Chloroform-d) δ 8.78 (d, J=2.6 Hz, 1H), 8.53 (d, J=2.6 Hz, 1H), 7.09 (s, 1H), 3.77 (d, J=5.2 Hz, 2H), 3.70 (t, J=5.5 Hz, 2H), 1.72-1.70 (m, 4H), 1.62-1.60 (m, 2H).

Step 3

Under nitrogen atmosphere, boronic acid (0.11 mmol) was added to a dry tube containing 2-(piperidine-1-carbonyl)pyrazolo[1,5-a]pyrimidin-6-yl trifluoromethanesulfonate (38 mg, 0.1 mmol), Pd(dppf)Cl$_2$ (4 mg, 0.5% mmol), K$_3$PO$_4$ (42 mg, 0.2 mmol), 1,4-dioxane (2 mL) and H$_2$O (0.2 mL). The mixture was stirring at 100° C. until the completion of the reaction which was monitored by LC/MS. The reaction mixture was cooled to room temperature, washed with water, extracted with ethyl acetate, dried over anhydrous Na$_2$SO$_4$ and concentrated by rotary evaporation. The crude was purified by flash chromatography on silica gel to give the product.

d) δ 162.8, 152.1, 150.1, 147.4, 133.6, 131.8, 129.5, 128.8, 126.9, 123.5, 97.9, 48.3, 43.5, 26.7, 25.6, 24.6. MS (ES+) m/z=307 [M+H]$^+$.

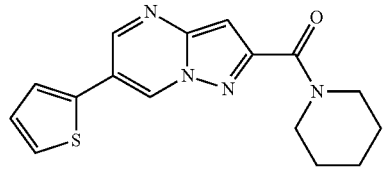

The target compound 46a (88% yield) was obtained by the general procedure described above.

$^1$H NMR (400 MHz, Chloroform-d) δ 8.81 (d, J=2.3 Hz, 1H), 8.78 (d, J=2.3 Hz, 1H), 7.41 (d, J=5.1 Hz, 1H), 7.37 (d, J=3.5 Hz, 1H), 7.16 (dd, J=5.1, 3.7 Hz, 1H), 6.97 (s, 1H), 3.78-3.72 (m, 4H), 1.71-1.70 (m, 4H), 1.62-1.59 (m, 2H); $^{13}$C NMR (101 MHz, Chloroform-d) δ 162.7, 152.1, 149.0, 147.2, 135.8, 130.4, 128.6, 128.5, 126.5, 125.1, 117.9, 98.5, 48.3, 43.5, 26.7, 25.6, 24.6. MS (ES+) m/z=313 [M+H]$^+$.

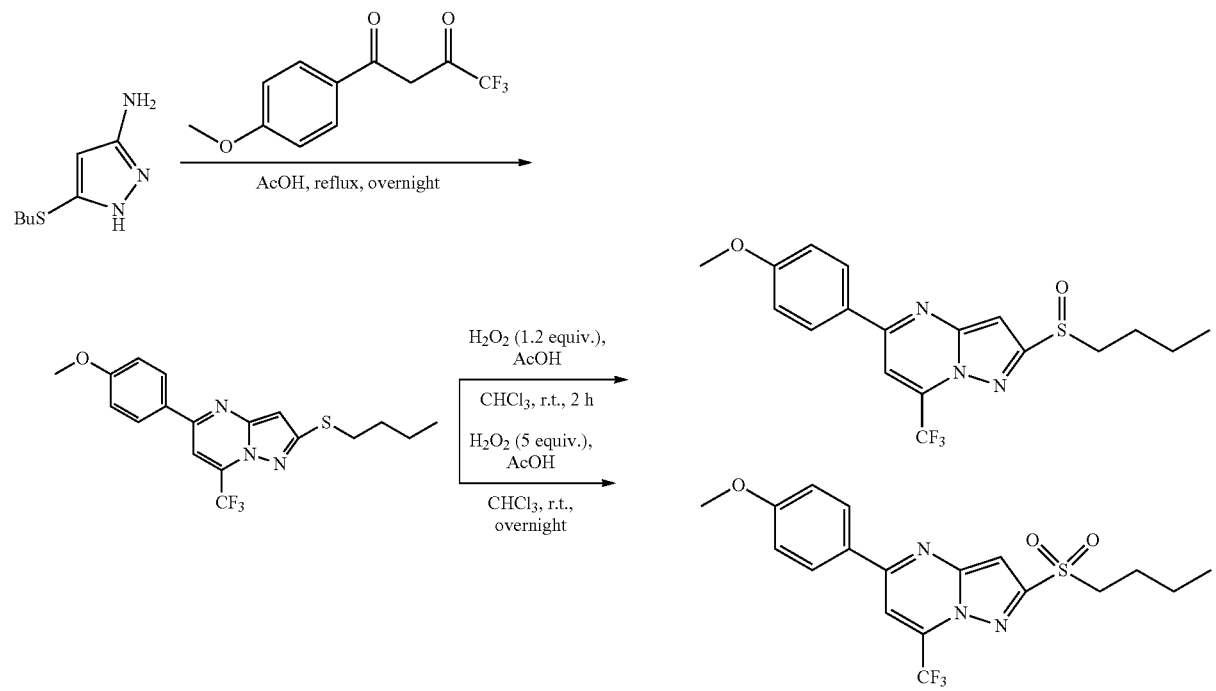

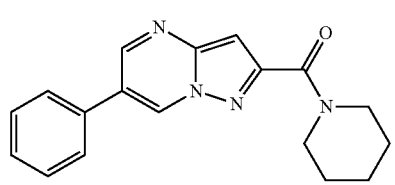 [SMILES: O=C(c1cc2ncc(-c3ccccc3)cn2n1)N1CCCCC1]

The target compound 41a (88% yield) was obtained by the general procedure described above.

$^1$H NMR (400 MHz, Chloroform-d) δ 8.80 (d, J=2.3 Hz, 2H), 7.59 (d, J=7.4 Hz, 2H), 7.53 (t, J=7.5 Hz, 2H), 7.46 (t, J=7.2 Hz, 1H), 6.97 (s, 1H), 3.78-3.72 (m, 4H), 1.7-1.70 (m, 4H), 1.63-1.60 (m, 2H); $^{13}$C NMR (101 MHz, Chloroform- Step 1

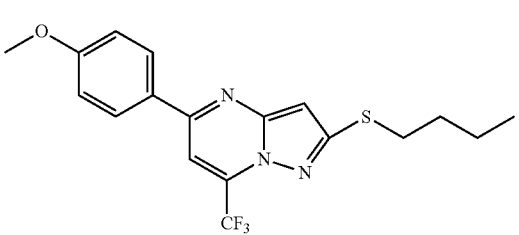 [SMILES: CCCCSc1cc2nc(-c3ccc(OC)cc3)cc(C(F)(F)F)n2n1]

To a solution of 5-(butylthio)-1H-pyrazol-3-amine (1.71 g, 10 mmol) in AcOH (20 mL) was added 4,4,4-trifluoro- 1-(4-methoxyphenyl)butane-1,3-dione (2.71 g, 11 mmol). The mixture was refluxed overnight and subsequently cooled down to 0° C. in an ice bath. The precipitate was collected by filtration and recrystallized by hexanes/ethyl acetate to give the product 2a as a yellow solid (2.4 g, 63% yield).

$^1$H NMR (400 MHz, Chloroform-d) δ 8.04 (d, J=8.2 Hz, 2H), 7.42 (s, 1H), 7.02 (d, J=8.5 Hz, 2H), 6.63 (s, 1H), 3.89 (s, 3H), 3.18 (t, J=7.3 Hz, 2H), 1.82-1.74 (m, 2H), 1.54-1.44 (m, 2H), 0.95 (t, J=7.3 Hz, 3H); $^{13}$C NMR (101 MHz, Chloroform-d) δ 162.07, 156.67, 154.97, 150.40, 133.09 (q, J=37.0 Hz), 128.72, 128.57, 120.86 (q, J=274.7 Hz), 114.37, 101.74 (q, J=4.2 Hz), 96.29, 55.40, 31.65, 31.52, 21.95, 13.59. MS (ES+) m/z=382 [M+H]$^+$.

Step 2

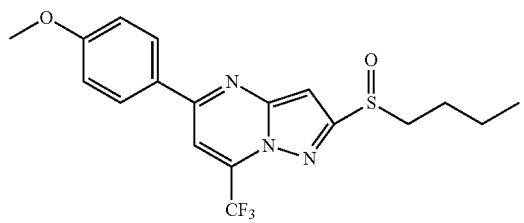 [SMILES: CCCCS(=O)c1cc2nc(-c3ccc(OC)cc3)cc(C(F)(F)F)n2n1]

To a solution of 2-(butylthio)-5-(4-methoxyphenyl)-7-(trifluoromethyl)pyrazolo[1,5-a]pyrimidine (38 mg, 0.1 mmol) in chloroform (2 mL) were added H$_2$O$_2$ (3.7 μL, 0.12 mmol) and AcOH (0.5 mL). The reaction was monitored by LC/MS. After the completion of the reaction, NaHCO$_3$ aq was added to quench the reaction. The mixture was extracted with dichloromethane, washed with brine, dried over anhydrous Na$_2$SO$_4$ and concentrated by rotary evaporation. The crude was purified by flash chromatography on silica gel to give the product 3a as a yellow solid (35 mg, 90% yield).

$^1$H NMR (400 MHz, Chloroform-d) δ 8.11 (d, J=7.4 Hz, 2H), 7.66 (s, 1H), 7.27 (s, 1H), 7.05 (d, J=7.4 Hz, 2H), 3.91 (s, 3H), 3.23-3.11 (m, 2H), 1.94-1.83 (m, 1H), 1.77-1.65 (m, 1H), 1.57-1.44 (m, 2H), 0.95 (t, J=6.8 Hz, 3H); $^{13}$C NMR (101 MHz, Chloroform-d) δ 162.68, 162.57, 155.97, 150.12, 134.20 (q, J=37.7 Hz), 129.07, 127.92, 119.22 (q, J=274.7 Hz), 114.58, 104.66 (q, J=3.8 Hz), 97.19, 55.49, 55.10, 23.88, 21.86, 13.63. MS (ES+) m/z=398 [M+H]$^+$.

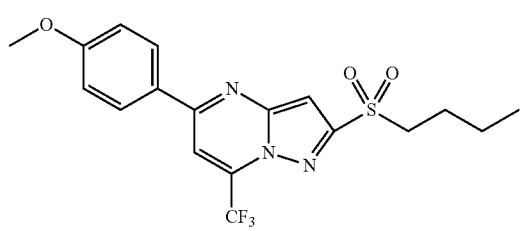 [SMILES: CCCCS(=O)(=O)c1cc2nc(-c3ccc(OC)cc3)cc(C(F)(F)F)n2n1]

The target compound 4a was obtained through the general procedure described above by using 5 equiv. of H$_2$O$_2$ instead.

$^1$H NMR (400 MHz, Chloroform-d) δ 8.10 (d, J=8.3 Hz, 2H), 7.75 (s, 1H), 7.26 (s, 1H), 7.04 (d, J=7.4 Hz, 2H), 3.90 (s, 3H), 3.41 (t, J=7.3 Hz, 2H), 1.88-1.80 (m, 2H), 1.51-1.41 (m, 2H), 0.92 (t, J=7.2 Hz, 3H); $^{13}$C NMR (101 MHz, Chloroform-d) δ 162.88, 156.82, 156.20, 149.71, 134.73 (q, J=37.9 Hz), 129.26, 127.66, 118.82 (q, J=274.4 Hz), 114.74, 106.18 (q, J=4.0 Hz), 98.80, 55.57, 54.56, 24.25, 21.51, 13.46. MS (ES+) m/z=414 [M+H]$^+$.

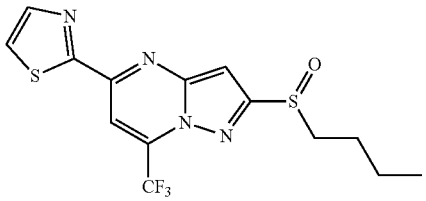 [SMILES: CCCCS(=O)c1cc2nc(-c3nccs3)cc(C(F)(F)F)n2n1]

The target compound 48a was prepared analogously to 3a by using 4,4,4-trifluoro-1-(thiazol-2-yl)butane-1,3-dione instead.

$^1$H NMR (400 MHz, Chloroform-d) δ 8.51 (s, 1H), 8.11 (d, J=3.0 Hz, 1H), 7.77 (d, J=3.0 Hz, 1H), 3.44-3.32 (m, 2H), 1.98-1.87 (m, 1H), 1.80-1.69 (m, 1H), 1.60-1.48 (m, 2H), 0.96 (t, J=7.3 Hz, 3H). MS (ES+) m/z=375 [M+H]$^+$.

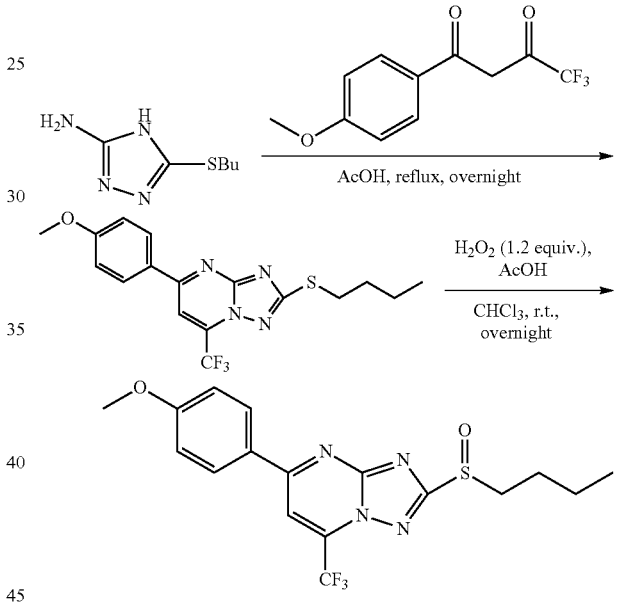

Step 1

To a solution of 5-(butylthio)-4H-1,2,4-triazol-3-amine (1.72 g, 10 mmol) in AcOH (20 mL) was added 4,4,4-trifluoro-1-(4-methoxyphenyl)butane-1,3-dione (2.71 g, 11 mmol). The mixture was refluxed overnight and subsequently cooled down to 0° C. in an ice bath. The precipitate was collected by filtration and recrystallized by hexanes/ethyl acetate to give the product as a yellow solid (2.33 g, 61% yield). $^1$H NMR (400 MHz, Chloroform-d) δ 8.19 (d, J=9.1 Hz, 2H), 7.68 (s, 1H), 7.04 (d, J=9.1 Hz, 2H), 3.91 (s, 3H), 3.33 (t, J=7.4 Hz, 2H), 1.85-1.78 (m, 2H), 1.56-1.47 (m, 2H), 0.96 (t, J=7.4 Hz, 3H).

Step 2

To a solution of 2-(butylthio)-5-(4-methoxyphenyl)-7-(trifluoromethyl)-[1,2,4]triazolo[1,5-a]pyrimidine (38 mg, 0.1 mmol) in chloroform (2 mL) were added H$_2$O$_2$ (3.7 μL, 0.12 mmol) and AcOH (0.5 mL). The reaction was stirred overnight, and NaHCO$_3$ aq was added to quench the reaction. The mixture was extracted with dichloromethane, washed with brine, dried over anhydrous Na$_2$SO$_4$ and concentrated by rotary evaporation. The crude was purified by flash chromatography on silica gel to give the product 49a as a yellow solid (34 mg, 85% yield).

$^1$H NMR (400 MHz, Chloroform-d) δ 8.15 (d, J=8.5 Hz, 2H), 7.87 (s, 1H), 6.98 (d, J=8.5 Hz, 2H), 3.86 (s, 3H), 3.39-3.26 (m, 2H), 1.92-1.81 (m, 1H), 1.76-1.65 (m, 1H), 1.56-1.42 (m, 2H), 0.92 (t, J=7.4 Hz, 3H); $^{13}$C NMR (101 MHz, Chloroform-d) δ 171.5, 163.7, 162.5, 156.6, 135.64 (q, J=39.1 Hz), 130.0, 126.8, 118.51 (q, J=275.3 Hz), 114.8, 106.11 (q, J=3.8 Hz), 55.6, 53.4, 24.0, 21.8, 13.6.

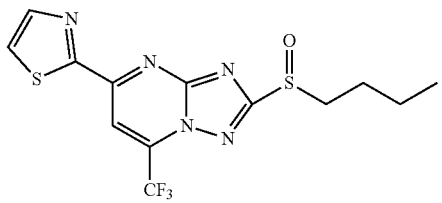 [SMILES: CCCCS(=O)c1nc2nc(-c3nccs3)cc(C(F)(F)F)n2n1]

The target compound 51a was prepared analogously to 50a by using 4,4,4-trifluoro-1-(thiazol-2-yl)butane-1,3-dione instead.

$^1$H NMR (400 MHz, Chloroform-d) δ 8.51 (s, 1H), 8.11 (d, J=3.0 Hz, 1H), 7.77 (d, J=3.0 Hz, 1H), 3.44-3.32 (m, 2H), 1.98-1.87 (m, 1H), 1.80-1.69 (m, 1H), 1.60-1.48 (m, 2H), 0.96 (t, J=7.3 Hz, 3H).

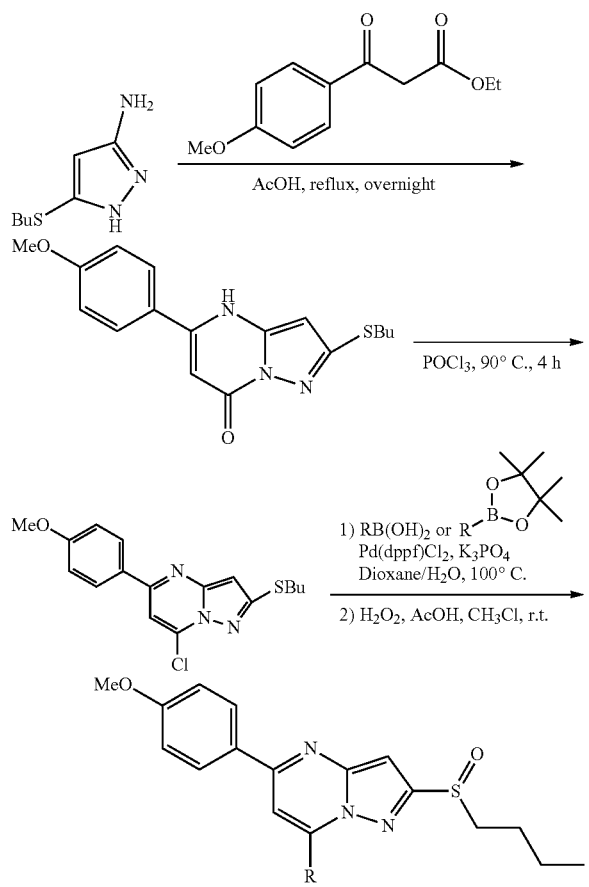

Step 1

To a solution of 5-(butylthio)-1H-pyrazol-3-amine (1.71 g, 10 mmol) in AcOH (20 mL) was added ethyl 3-(4-methoxyphenyl)-3-oxopropanoate (2.44 g, 11 mmol). The mixture was refluxed overnight and then cooled down to 0° C. in an ice bath. The precipitate was collected by filtration and recrystallized by hexanes/ethyl acetate to give a yellow solid (2.11 g, 64% yield). $^1$H NMR (400 MHz, DMSO-d$_6$) δ 12.30 (s, 1H), 7.78 (d, J=8.6 Hz, 2H), 7.10 (d, J=8.7 Hz, 2H), 6.10 (s, 1H), 5.97 (s, 1H), 3.83 (s, 3H), 3.08 (t, J=7.2 Hz, 2H), 1.67-1.59 (m, 2H), 1.45-1.36 (m, 2H), 0.89 (t, J=7.3 Hz, 3H). MS (ES+) m/z=330 [M+H]$^+$.

Step 2

POCl$_3$ (5.63 mL, 60 mmol) was added to a 25-mL vial which was charged with 2-(butylthio)-5-(4-methoxyphenyl)pyrazolo[1,5-a]pyrimidin-7(4H)-one (1.98 g, 6 mmol). The mixture was heated at 90° C. for 4 h, and the excess POCl$_3$ was removed under reduced pressure. Cold NaHCO$_3$ aq was added to the crude slowly which was cooled in an ice bath and the resulting solution was extracted with ethyl acetate. The combined organic extracts were washed with brine, dried over anhydrous Na$_2$SO$_4$ and concentrated by rotary evaporation. The crude was purified by flash chromatography on silica gel to give the product as a yellow solid (1.73 mg, 83% yield). $^1$H NMR (400 MHz, Chloroform-d) δ 8.14 (d, J=9.1 Hz, 2H), 7.48 (s, 1H), 7.02 (d, J=9.1 Hz, 2H), 3.90 (s, 3H), 3.34 (t, J=7.4 Hz, 2H), 1.83-1.77 (m, 2H), 1.56-1.47 (m, 2H), 0.96 (t, J=7.4 Hz, 3H). MS (ES+) m/z=349 [M+H]$^+$.

Step 3

Under nitrogen atmosphere, boronic acid or boronic ester (0.11 mmol) was added to a dry tube containing 2-(butylthio)-7-chloro-5-(4-methoxyphenyl)pyrazolo[1,5-a]pyrimidine (35 mg, 0.1 mmol), Pd(dppf)Cl$_2$ (4 mg, 0.5% mmol), K$_3$PO$_4$ (42 mg, 0.2 mmol), 1,4-dioxane (2 mL) and H$_2$O (0.2 mL). The mixture was stirring at 100° C. until the completion of the reaction which was monitored by LC/MS. The reaction mixture was cooled to room temperature, washed with water, extracted with ethyl acetate, dried over anhydrous Na$_2$SO$_4$ and concentrated by rotary evaporation. The crude was dissolved in chloroform (2 mL), and H$_2$O$_2$ (3.7 μL, 0.12 mmol) and AcOH (0.5 mL) were added. The reaction was monitored by LC/MS. After the completion of the reaction, NaHCO$_3$ aq was added to quench the reaction. The mixture was extracted with dichloromethane, washed with brine, dried over anhydrous Na$_2$SO$_4$ and concentrated by rotary evaporation. The crude was purified by flash chromatography on silica gel to give the product.

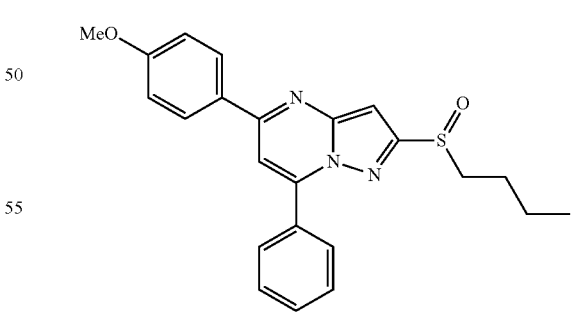

The target compound 5a (89% yield) was obtained by the general procedure described above.

$^1$H NMR (400 MHz, Chloroform-d) δ 8.09 (d, J=8.6 Hz, 2H), 8.03-8.01 (m, 2H), 7.57-7.55 (m, 3H), 7.37 (s, 1H), 7.17 (s, 1H), 7.00 (d, J=8.7 Hz, 2H), 3.86 (s, 3H), 3.12 (t, J=7.6 Hz, 2H), 1.90-1.79 (m, 1H), 1.77-1.66 (m, 1H), 1.55-1.40 (m, 2H), 0.93 (t, J=7.3 Hz, 3H); $^{13}$C NMR (101

MHz, Chloroform-d) δ 161.9, 160.7, 156.8, 150.4, 146.7, 131.3, 130.7, 129.3, 129.2, 128.9, 128.7, 114.4, 106.0, 95.9, 55.5, 55.0, 24.1, 21.9, 13.7. MS (ES+) m/z=406 [M+H]$^+$.

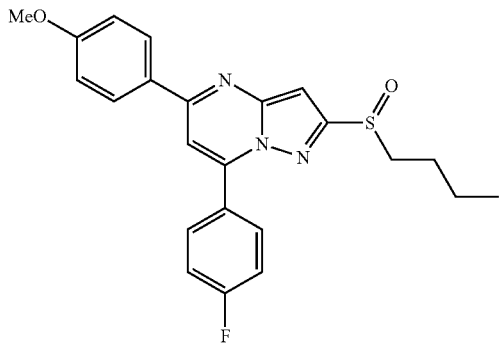 [SMILES: CCCCS(=O)c1cc2nc(-c3ccc(OC)cc3)cc(-c3ccc(F)cc3)n2n1]

The target compound 6a (86% yield) was obtained by the general procedure described above.

$^1$H NMR (400 MHz, Chloroform-d) δ 8.09-8.04 (m, 4H), 7.35 (s, 1H), 7.27-7.22 (m, 2H), 7.16 (s, 1H), 7.01 (d, J=8.7 Hz, 2H), 3.87 (s, 3H), 3.11 (t, J=7.7 Hz, 2H), 1.90-1.78 (m, 1H), 1.77-1.66 (m, 1H), 1.55-1.40 (m, 2H), 0.93 (t, J=7.2 Hz, 3H); $^{13}$C NMR (101 MHz, Chloroform-d) δ 164.29 (d, J=253.1 Hz), 161.95, 160.74, 156.76, 150.43, 145.62, 131.58 (d, J=8.6 Hz), 129.13, 128.92, 126.75 (d, J=3.4 Hz), 115.94 (d, J=21.9 Hz), 114.38, 105.83, 95.99, 55.45, 54.97, 24.10, 21.92, 13.71. MS (ES+) m/z=424 [M+H]$^+$.

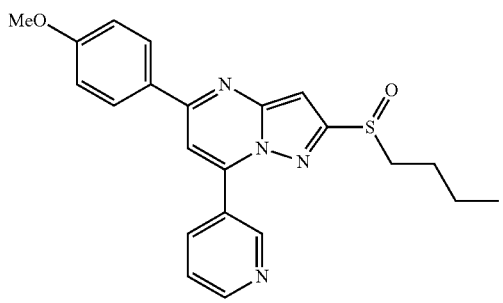 [SMILES: CCCCS(=O)c1cc2nc(-c3ccc(OC)cc3)cc(-c3cccnc3)n2n1]

The target compound 51a (54% yield) was obtained by the general procedure described above.

$^1$H NMR (400 MHz, Chloroform-d) δ 9.20 (s, 1H), 8.81 (d, J=3.3 Hz, 1H), 8.47 (dt, J=8.1, 1.9 Hz, 1H), 8.11 (d, J=8.9 Hz, 2H), 7.53 (dd, J=8.2, 5.0 Hz, 1H), 7.43 (s, 1H), 7.19 (s, 1H), 7.04 (d, J=8.9 Hz, 2H), 3.89 (s, 3H), 3.12 (t, J=7.8 Hz, 2H), 1.93-1.79 (m, 1H), 1.76-1.65 (m, 1H), 1.53-1.42 (m, 2H), 0.93 (t, J=7.3 Hz, 3H); $^{13}$C NMR (101 MHz, Chloroform-d) δ 162.1, 161.0, 156.8, 151.9, 150.3, 149.6, 143.7, 136.9, 129.0, 128.9, 123.3, 114.5, 106.1, 96.4, 55.5, 55.0, 24.1, 21.9, 13.7. MS (ES+) m/z=407 [M+H]$^+$.

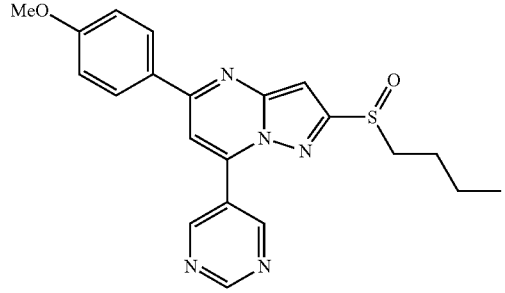 [SMILES: CCCCS(=O)c1cc2nc(-c3ccc(OC)cc3)cc(-c3cncnc3)n2n1]

The target compound 52a (81% yield) was obtained by the general procedure described above.

$^1$H NMR (400 MHz, Chloroform-d) δ 9.44 (s, 2H), 9.40 (s, 1H), 8.10 (d, J=7.9 Hz, 2H), 7.46 (s, 1H), 7.21 (s, 1H), 7.03 (d, J=7.9 Hz, 2H), 3.89 (s, 3H), 3.12 (t, J=7.7 Hz, 2H), 1.90-1.79 (m, 1H), 1.75-1.64 (m, 1H), 1.53-1.42 (m, 2H), 0.93 (t, J=7.3 Hz, 3H); $^{13}$C NMR (101 MHz, Chloroform-d) δ 162.3, 161.4, 160.1, 156.8, 156.7, 150.1, 140.7, 129.0, 128.6, 125.6, 114.6, 106.1, 96.9, 55.5, 55.0, 24.0, 21.9, 13.7. MS (ES+) m/z=408 [M+H]$^+$.

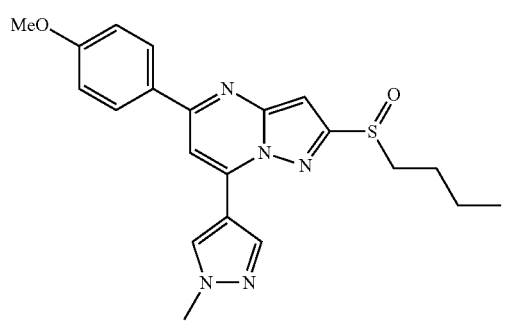 [SMILES: CCCCS(=O)c1cc2nc(-c3ccc(OC)cc3)cc(-c3cnn(C)c3)n2n1]

The target compound 53a (75% yield) was obtained by the general procedure described above.

$^1$H NMR (400 MHz, Chloroform-d) δ 8.81 (s, 1H), 8.28 (s, 1H), 8.07 (d, J=8.8 Hz, 2H), 7.52 (s, 1H), 7.07 (s, 1H), 7.01 (d, J=8.8 Hz, 2H), 4.04 (s, 3H), 3.87 (s, 3H), 3.23-3.10 (m, 2H), 1.89-1.81 (m, 1H), 1.78-1.70 (m, 1H), 1.55-1.44 (m, 2H), 0.94 (t, J=7.3 Hz, 3H); $^{13}$C NMR (101 MHz, Chloroform-d) δ 161.7, 160.0, 156.5, 150.3, 139.5, 139.1, 133.6, 129.5, 128.9, 114.3, 112.4, 101.4, 95.4, 55.4, 55.1, 39.5, 24.2, 22.0, 13.7. MS (ES+) m/z=410 [M+H]$^+$.

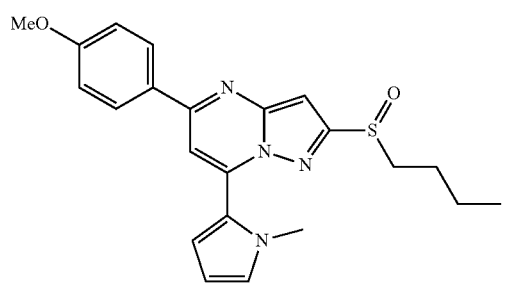 [SMILES: CCCCS(=O)c1cc2nc(-c3ccc(OC)cc3)cc(-c3cccn3C)n2n1]

The target compound 54a (69% yield) was obtained by the general procedure described above.

$^1$H NMR (400 MHz, Chloroform-d) δ 8.08 (d, J=8.9 Hz, 2H), 7.29 (s, 1H), 7.16 (s, 1H), 7.03 (d, J=8.9 Hz, 2H), 6.96-6.95 (m, 1H), 6.92-6.90 (m, 1H), 6.35 (t, J=3.1 Hz, 1H), 3.89 (s, 3H), 3.75 (s, 3H), 3.12 (t, J=7.3 Hz, 2H), 1.89-1.65 (m, 2H), 1.55-1.42 (m, 2H), 0.93 (t, J=7.3 Hz, 3H); $^{13}$C NMR (101 MHz, Chloroform-d) δ 161.9, 160.7, 156.4, 150.3, 139.5, 129.4, 128.9, 128.0, 123.4, 116.0, 114.4, 109.3, 106.4, 96.0, 55.5, 55.0, 36.4, 24.1, 21.9, 13.7. MS (ES+) m/z=409 [M+H]$^+$.

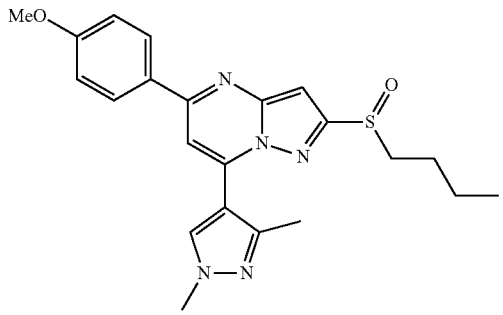 [SMILES: CCCCS(=O)c1cc2nc(-c3ccc(OC)cc3)cc(-c3cn(C)nc3C)n2n1]

The target compound 73a (62% yield) was obtained by the general procedure described above.

$^1$H NMR (400 MHz, Chloroform-d) δ 8.78 (s, 1H), 8.07 (d, J=8.4 Hz, 2H), 7.47 (s, 1H), 7.10 (s, 1H), 7.04 (d, J=8.4 Hz, 2H), 3.98 (s, 3H), 3.89 (s, 3H), 3.21-3.09 (m, 2H), 2.64 (s, 3H), 1.90-1.75 (m, 2H), 1.56-1.44 (m, 2H), 0.94 (t, J=7.2 Hz, 3H); $^{13}$C NMR (101 MHz, Chloroform-d) δ 161.8, 159.7, 156.4, 150.4, 148.3, 140.5, 135.1, 129.7, 128.8, 114.4, 109.6, 103.2, 95.6, 55.5, 55.1, 39.2, 24.2, 22.0, 15.2, 13.7. MS (ES+) m/z=424 [M+H]$^+$.

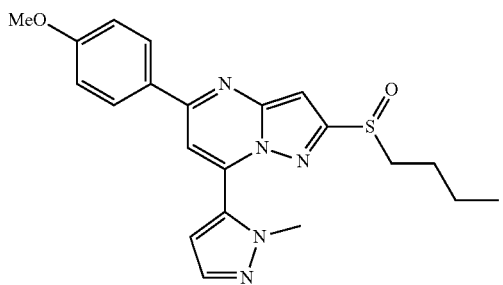 [SMILES: CCCCS(=O)c1cc2nc(-c3ccc(OC)cc3)cc(-c3ccnn3C)n2n1]

The target compound 72a (65% yield) was obtained by the general procedure described above.

$^1$H NMR (400 MHz, Chloroform-d) δ 8.09 (d, J=8.9 Hz, 2H), 7.66 (d, J=2.0 Hz, 1H), 7.37 (s, 1H), 7.21 (s, 1H), 7.03 (d, J=8.9 Hz, 2H), 6.79 (d, J=1.9 Hz, 1H), 3.94 (s, 3H), 3.89 (s, 3H), 3.10 (t, J=7.8 Hz, 2H), 1.90-1.79 (m, 1H), 1.73-1.62 (m, 1H), 1.54-1.41 (m, 2H), 0.92 (t, J=7.3 Hz, 3H); $^{13}$C NMR (101 MHz, Chloroform-d) δ 162.2, 161.5, 156.3, 150.0, 139.1, 137.1, 133.0, 129.0, 128.7, 114.5, 110.4, 107.8, 96.7, 55.5, 55.0, 39.0, 24.0, 21.9, 13.7. MS (ES+) m/z=410 [M+H]$^+$.

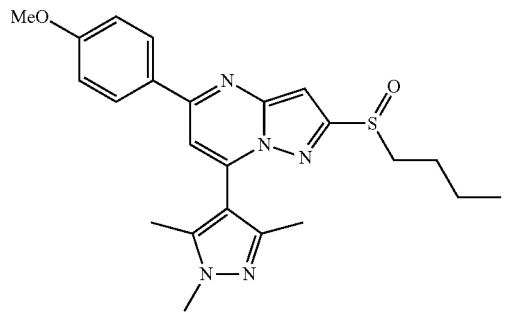 [SMILES: CCCCS(=O)c1cc2nc(-c3ccc(OC)cc3)cc(-c3c(C)nn(C)c3C)n2n1]

The target compound 74a (45% yield) was obtained by the general procedure described above.

$^1$H NMR (400 MHz, Chloroform-d) δ 8.07 (d, J=8.0 Hz, 2H), 7.16 (s, 1H), 7.15 (s, 1H), 7.03 (d, J=8.2 Hz, 2H), 3.89 (s, 3H), 3.84 (s, 3H), 3.11 (t, J=7.8 Hz, 2H), 2.28 (s, 3H), 2.27 (s, 3H), 1.87-1.78 (m, 1H), 1.74-1.63 (m, 1H), 1.54-1.39 (m, 2H), 0.92 (t, J=7.2 Hz, 3H); $^{13}$C NMR (101 MHz, Chloroform-d) δ 161.9, 160.5, 156.4, 150.1, 146.8, 141.7, 140.1, 129.4, 128.9, 114.4, 109.5, 107.5, 96.0, 55.5, 55.0, 36.3, 24.0, 21.9, 13.7, 13.2, 11.6. MS (ES+) m/z=438 [M+H]$^+$.

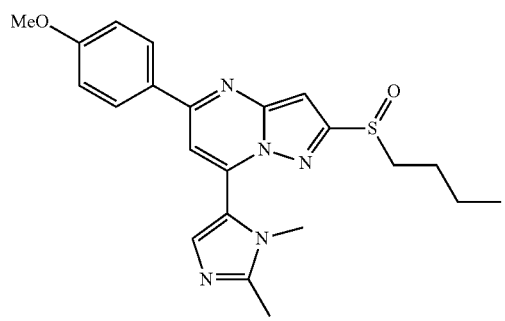 [SMILES: CCCCS(=O)c1cc2nc(-c3ccc(OC)cc3)cc(-c3cnc(C)n3C)n2n1]

The target compound 70a (46% yield) was obtained by the general procedure described above.

$^1$H NMR (400 MHz, Chloroform-d) δ 8.09 (d, J=8.8 Hz, 2H), 7.55 (s, 1H), 7.32 (s, 1H), 7.17 (s, 1H), 7.04 (d, J=8.8 Hz, 2H), 3.90 (s, 3H), 3.61 (s, 3H), 3.11 (t, J=7.8 Hz, 2H), 2.54 (s, 3H), 1.87-1.80 (m, 1H), 1.73-1.65 (m, 1H), 1.53-1.42 (m, 2H), 0.93 (t, J=7.3 Hz, 3H); $^{13}$C NMR (101 MHz, Chloroform-d) δ 162.1, 160.9, 156.6, 150.1, 149.6, 137.3, 132.6, 129.1, 129.0, 123.8, 114.5, 106.9, 96.3, 55.5, 55.1, 33.1, 24.1, 21.9, 13.7, 13.7. MS (ES+) m/z=424 [M+H]$^+$.

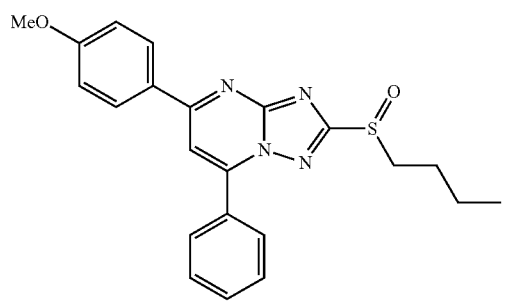

The target compound 55a was obtained analogously to SW218511 by using 5-(butylthio)-4H-1,2,4-triazol-3-amine.

¹H NMR (400 MHz, Chloroform-d) δ 8.24 (d, J=8.8 Hz, 2H), 8.14-8.12 (m, 2H), 7.67 (s, 1H), 7.63-7.58 (m, 3H), 7.04 (d, J=8.8 Hz, 2H), 3.90 (s, 3H), 3.44-3.34 (m, 2H), 1.95-1.87 (m, 1H), 1.79-1.69 (m, 1H), 1.59-1.47 (m, 2H), 0.95 (t, J=7.3 Hz, 3H); ¹³C NMR (101 MHz, Chloroform-d) δ 170.1, 162.8, 162.2, 156.9, 148.4, 132.1, 129.7, 129.5, 129.4, 129.1, 128.2, 114.5, 106.8, 55.5, 53.2, 24.0, 21.9, 13.7. MS (ES+) m/z=407 [M+H]⁺.

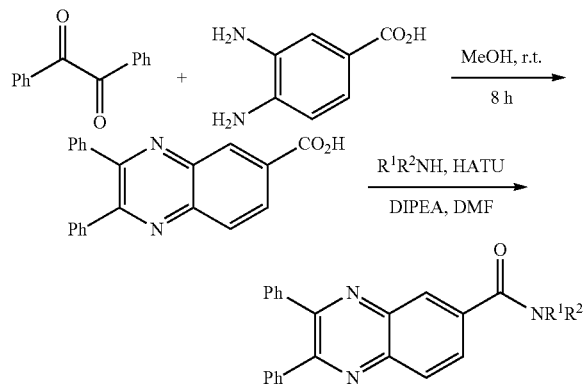

Step 1

To a solution of benzil (2.1 g, 10 mmol) in MeOH (20 mL) was added 3,4-diaminobenzoic acid (1.52 g, 10 mmol). The slurry was stirred at room temperature for 8 h. The solid in solution was collected by filtration and crystallized by MeOH/EtOAc to afford the product as a pale yellow solid (2.93 g, 90% yield). ¹H NMR (400 MHz, DMSO-d₆) δ 13.31 (s, 1H), 8.64 (d, J=1.8 Hz, 1H), 8.30 (dd, J=8.8, 1.8 Hz, 1H), 8.22 (d, J=8.7 Hz, 1H), 7.50-7.47 (m, 4H), 7.42-7.34 (m, 6H).

Step 2

To a solution of 2,3-diphenylquinoxaline-6-carboxylic acid (33 mg, 0.1 mmol), HATU (42 mg, 0.11 mmol), DIPEA (0.035 mL, 0.2 mmol) in DMF (2 mL) was added amine (0.12 mmol). The mixture was stirred at room temperature until the completion of the reaction which was monitored by LC/MS. Water was added to the solution, and the mixture was extracted with ethyl acetate, washed with brine, dried over anhydrous Na₂SO₄ and concentrated by rotary evaporation. The crude was purified by flash chromatography on silica gel to give the product.

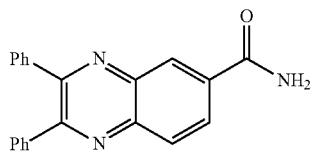 [SMILES: NC(=O)c1ccc2nc(-c3ccccc3)c(-c3ccccc3)nc2c1]

The target compound 5b (57% yield) was obtained by the general procedure described above.

¹H NMR (400 MHz, DMSO-d₆) δ 8.70 (s, 1H), 8.37 (s, 1H), 8.29 (d, J=8.7 Hz, 1H), 8.18 (d, J=8.7 Hz, 1H), 7.70 (s, 1H), 7.48 (d, J=7.2 Hz, 4H), 7.41-7.33 (m, 6H); ¹³C NMR (101 MHz, DMSO-d₆) δ 167.3, 154.7, 154.3, 142.0, 140.3, 138.99, 138.96, 135.8, 130.2, 130.1, 129.5, 129.4, 129.2, 128.6, 128.54, 128.52, (missing 1 signal due to overlap). MS (ES+) m/z=326 [M+H]⁺.

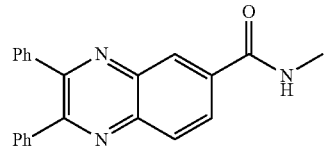 [SMILES: CNC(=O)c1ccc2nc(-c3ccccc3)c(-c3ccccc3)nc2c1]

The target compound 6b (67% yield) was obtained by the general procedure described above.

¹H NMR (400 MHz, DMSO-d₆) δ 8.87-8.84 (m, 1H), 8.63 (s, 1H), 8.26 (d, J=8.7 Hz, 1H), 8.20 (d, J=8.7 Hz, 1H), 7.48 (d, J=7.6 Hz, 4H), 7.42-7.33 (m, 6H), 2.86 (d, J=3.8 Hz, 3H); ¹³C NMR (101 MHz, DMSO-d₆) δ 166.0, 154.6, 154.3, 141.9, 140.3, 139.0, 136.0, 130.2, 130.1, 129.5, 129.4, 129.3, 129.1, 128.54, 128.52, 128.1, 27.0, (missing 1 signal due to overlap). MS (ES+) m/z=340 [M+H]⁺.

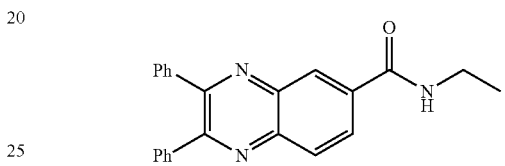

The target compound 7b (66% yield) was obtained by the general procedure described above.

¹H NMR (400 MHz, DMSO-d₆) δ 8.88 (t, J=5.5 Hz, 1H), 8.66 (s, 1H), 8.27 (d, J=8.6 Hz, 1H), 8.20 (d, J=8.8 Hz, 1H), 7.48 (d, J=7.3 Hz, 4H), 7.42-7.33 (m, 6H), 3.40-3.34 (m, 2H), 1.18 (t, J=7.2 Hz, 3H); ¹³C NMR (101 MHz, DMSO-d₆) δ 165.3, 154.6, 154.3, 141.9, 140.3, 139.0, 136.2, 130.2, 130.1, 129.5, 129.4, 129.3, 129.2, 128.54, 128.51, 128.1, 34.8, 15.1, (missing 1 signal due to overlap). MS (ES+) m/z=354 [M+H]⁺.

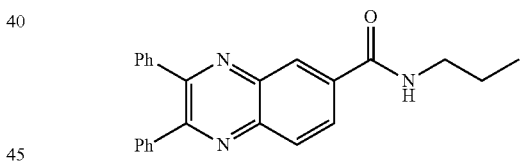

The target compound 8b (73% yield) was obtained by the general procedure described above.

¹H NMR (400 MHz, DMSO-d₆) δ 8.86 (d, J=5.7 Hz, 1H), 8.66 (s, 1H), 8.27 (d, J=8.6 Hz, 1H), 8.20 (d, J=8.4 Hz, 1H), 7.48 (d, J=7.3 Hz, 4H), 7.42-7.34 (m, 6H), 3.32-3.27 (m, 2H), 1.64-1.54 (m, 2H), 0.92 (t, J=7.1 Hz, 3H); ¹³C NMR (101 MHz, DMSO-d₆) δ 165.5, 154.6, 154.3, 141.9, 140.2, 138.98, 138.96, 136.2, 130.2, 130.1, 129.5, 129.4, 129.3, 128.5, 128.1, 41.7, 22.8, 12.0, (missing 2 signals due to overlap). MS (ES+) m/z=368 [M+H]⁺.

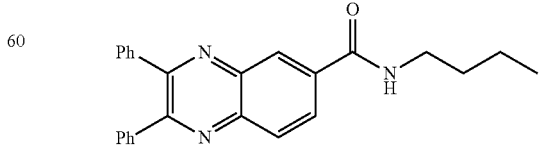

The target compound 10b (76% yield) was obtained by the general procedure described above.

¹H NMR (400 MHz, DMSO-d₆) δ 8.85 (t, J=5.5 Hz, 1H), 8.66 (s, 1H), 8.26 (d, J=8.9 Hz, 1H), 8.19 (d, J=8.7 Hz, 1H), 7.48 (d, J=7.3 Hz, 4H), 7.42-7.33 (m, 6H), 3.35-3.31 (m, 2H), 1.59-1.52 (m, 2H), 1.41-1.31 (m, 2H), 0.91 (t, J=7.3 Hz, 3H); ¹³C NMR (101 MHz, DMSO-d₆) δ 165.4, 154.6, 154.3, 141.9, 140.2, 138.97, 138.95, 136.2, 130.2, 130.1, 129.5, 129.4, 129.2, 128.5, 128.1, 39.6, 31.6, 20.2, 14.2, (missing 2 signals due to overlap). MS (ES+) m/z=382 [M+H]⁺.

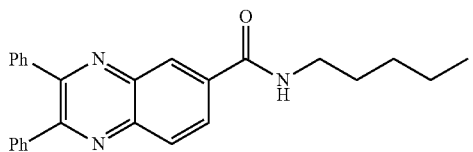 [SMILES: CCCCCNC(=O)c1ccc2nc(-c3ccccc3)c(-c3ccccc3)nc2c1]

The target compound 11b (78% yield) was obtained by the general procedure described above.

¹H NMR (400 MHz, DMSO-d₆) δ 8.86 (t, J=5.4 Hz, 1H), 8.66 (s, 1H), 8.27 (d, J=8.8 Hz, 1H), 8.20 (d, J=8.7 Hz, 1H), 7.48 (d, J=7.2 Hz, 4H), 7.42-7.34 (m, 6H), 3.33-3.30 (m, 2H), 1.61-1.54 (m, 2H), 1.34-1.26 (m, 4H), 0.87 (t, J=6.4 Hz, 3H); ¹³C NMR (101 MHz, DMSO-d₆) δ 165.4, 154.6, 154.3, 141.9, 140.2, 138.97, 138.95, 136.2, 130.2, 130.1, 129.5, 129.4, 129.3, 128.5, 128.1, 29.2, 29.1, 22.4, 14.4, (missing 2 signals due to overlap). MS (ES+) m/z=396 [M+H]⁺.

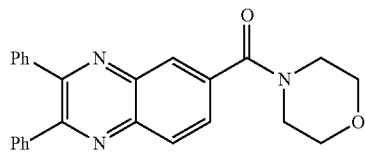 [SMILES: O=C(c1ccc2nc(-c3ccccc3)c(-c3ccccc3)nc2c1)N1CCOCC1]

The target compound 12b (86% yield) was obtained by the general procedure described above.

¹H NMR (400 MHz, DMSO-d₆) δ 8.21 (d, J=8.5 Hz, 1H), 8.15 (s, 1H), 7.86 (d, J=8.5 Hz, 1H), 7.47 (d, J=7.0 Hz, 4H), 7.42-7.33 (m, 6H), 3.69-3.58 (m, 6H), 3.42 (s, 2H); ¹³C NMR (101 MHz, DMSO-d₆) δ 168.3, 154.4, 141.0, 140.2, 138.9, 137.6, 130.2, 130.1, 129.8, 129.5, 129.43, 129.40, 128.5, 127.5, 66.5, 48.2, 42.6, (missing 3 signals due to overlap). MS (ES+) m/z=396 [M+H]⁺.

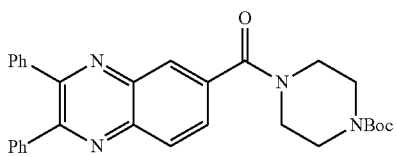 [SMILES: CC(C)(C)OC(=O)N1CCN(C(=O)c2ccc3nc(-c4ccccc4)c(-c4ccccc4)nc3c2)CC1]

The target compound 13b (83% yield) was obtained by the general procedure described above.

¹H NMR (400 MHz, DMSO-d₆) δ 8.21 (d, J=8.5 Hz, 1H), 8.15 (s, 1H), 7.86 (d, J=8.5 Hz, 1H), 7.47 (d, J=5.7 Hz, 4H), 7.42-7.33 (m, 6H), 3.66 (s, 2H), 3.47-3.36 (m, 6H), 1.40 (s, 9H); ¹³C NMR (101 MHz, DMSO-d₆) δ 168.4, 154.41, 154.39, 154.2, 141.0, 140.3, 139.0, 137.8, 130.2, 130.1, 129.8, 129.4, 128.5, 127.4, 79.7, 47.4, 42.0, 28.5, (missing 3 signals due to overlap).

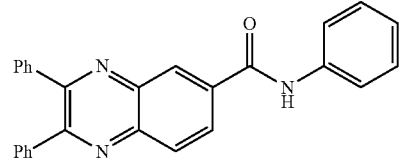 [SMILES: O=C(Nc1ccccc1)c1ccc2nc(-c3ccccc3)c(-c3ccccc3)nc2c1]

The target compound 14b (53% yield) was obtained by the general procedure described above.

¹H NMR (400 MHz, DMSO-d₆) δ 10.62 (s, 1H), 8.84 (s, 1H), 8.36 (d, J=8.6 Hz, 1H), 8.25 (d, J=8.7 Hz, 1H), 7.86 (d, J=8.1 Hz, 2H), 7.50 (d, J=7.3 Hz, 4H), 7.42-7.34 (m, 8H), 7.13 (t, J=7.4 Hz, 1H); ¹³C NMR (101 MHz, DMSO-d₆) δ 164.8, 154.9, 154.5, 142.2, 140.2, 139.4, 138.94, 138.91, 136.3, 130.2, 130.1, 129.54, 129.47, 129.1, 128.8, 128.57, 128.55, 124.4, 120.9, (missing 3 signals due to overlap). MS (ES+) m/z=402 [M+H]⁺.

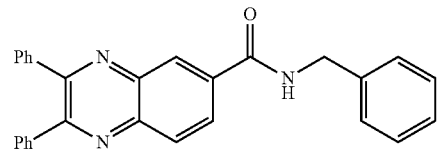 [SMILES: O=C(NCc1ccccc1)c1ccc2nc(-c3ccccc3)c(-c3ccccc3)nc2c1]

The target compound 15b (74% yield) was obtained by the general procedure described above.

¹H NMR (400 MHz, DMSO-d₆) δ 9.47 (t, J=6.0 Hz, 1H), 8.72 (s, 1H), 8.31 (d, J=8.7 Hz, 1H), 8.21 (d, J=8.7 Hz, 1H), 7.48 (d, J=7.2 Hz, 4H), 7.41-7.32 (m, 10H), 7.26-7.22 (m, 1H), 4.56 (d, J=6.0 Hz, 2H); ¹³C NMR (101 MHz, DMSO-d₆) δ 165.6, 154.7, 154.3, 142.0, 140.3, 139.9, 139.0, 138.9, 135.9, 130.2, 130.1, 129.5, 129.43, 129.39, 129.3, 128.8, 128.5, 128.3, 127.8, 127.3, 43.4, (missing 1 signal due to overlap). MS (ES+) m/z=416 [M+H]⁺.

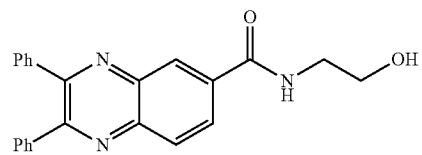 [SMILES: O=C(NCCO)c1ccc2nc(-c3ccccc3)c(-c3ccccc3)nc2c1]

The target compound 17b (86% yield) was obtained by the general procedure described above.

¹H NMR (400 MHz, DMSO-d₆) δ 8.85 (t, J=5.3 Hz, 1H), 8.68 (s, 1H), 8.28 (d, J=8.6 Hz, 1H), 8.20 (d, J=8.5 Hz, 1H), 7.49 (d, J=7.2 Hz, 4H), 7.42-7.33 (m, 6H), 4.80-4.77 (m, 1H), 3.59-3.54 (m, 2H), 3.43-3.38 (m, 2H); ¹³C NMR (101 MHz, DMSO-d₆) δ 165.7, 154.6, 154.3, 141.9, 140.2, 139.0, 136.1, 130.2, 130.1, 129.5, 129.4, 129.3, 128.5, 128.3, 60.1, 42.9, (missing 3 signals due to overlap). MS (ES+) m/z=370 [M+H]⁺.

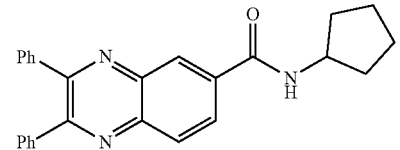 [SMILES: O=C(NC1CCCC1)c1ccc2nc(-c3ccccc3)c(-c3ccccc3)nc2c1]

The target compound 18b (86% yield) was obtained by the general procedure described above.

¹H NMR (400 MHz, DMSO-d₆) δ 8.72-8.69 (m, 2H), 8.27 (dd, J=8.9, 1.9 Hz, 1H), 8.18 (d, J=8.7 Hz, 1H), 7.49-7.47 (m, 4H), 7.41-7.33 (m, 6H), 4.32-4.25 (m, 1H), 1.97-1.87 (m, 2H), 1.75-1.68 (m, 2H), 1.64-1.50 (m, 4H); ¹³C NMR (101 MHz, DMSO-d₆) δ 165.2, 154.5, 154.2, 141.9, 140.2, 139.0, 136.2, 130.2, 130.1, 129.5, 129.43, 129.40, 129.1, 128.5, 128.2, 51.7, 32.6, 24.2, (missing 2 signals due to overlap). MS (ES+) m/z=394 [M+H]⁺.

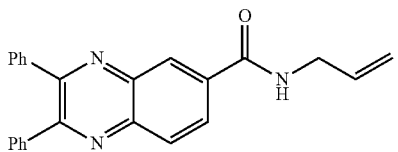 [SMILES: C=CCNC(=O)c1ccc2nc(-c3ccccc3)c(-c3ccccc3)nc2c1]

The target compound 19b (86% yield) was obtained by the general procedure described above.

¹H NMR (400 MHz, DMSO-d₆) δ 9.08 (s, 1H), 8.69 (s, 1H), 8.28 (d, J=8.8 Hz, 1H), 8.20 (d, J=8.8 Hz, 1H), 7.48 (d, J=7.3 Hz, 4H), 7.42-7.33 (m, 6H), 5.99-5.89 (m, 1H), 5.22 (d, J=17.2 Hz, 1H), 5.12 (d, J=10.3 Hz, 1H), 3.99-3.97 (m, 2H); ¹³C NMR (101 MHz, DMSO-d₆) δ 165.4, 154.7, 154.3, 142.0, 140.3, 138.97, 138.95, 135.9, 135.6, 130.2, 130.1, 129.5, 129.4, 129.3, 129.2, 128.6, 128.5, 128.3, 115.9, 42.2. MS (ES+) m/z=366 [M+H]⁺.

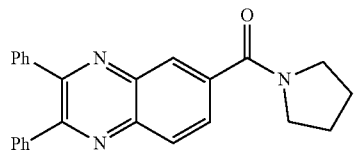 [SMILES: O=C(c1ccc2nc(-c3ccccc3)c(-c3ccccc3)nc2c1)N1CCCC1]

The target compound 20b (86% yield) was obtained by the general procedure described above.

¹H NMR (400 MHz, Chloroform-d) δ 8.28 (s, 1H), 8.20 (d, J=8.6 Hz, 1H), 7.94 (d, J=9.2 Hz, 1H), 7.51 (d, J=6.8 Hz, 4H), 7.38-7.30 (m, 6H), 3.72 (t, J=6.9 Hz, 2H), 3.55 (t, J=6.6 Hz, 2H), 2.04-1.97 (m, 2H), 1.94-1.87 (m, 2H); ¹³C NMR (101 MHz, Chloroform-d) δ 168.3, 154.4, 154.2, 141.5, 140.4, 138.7, 138.3, 129.8, 129.8, 129.6, 129.1, 129.04, 129.03, 128.3, 127.7, 49.7, 46.4, 26.5, 24.5, (missing 2 signals due to overlap). MS (ES+) m/z=380 [M+H]⁺.

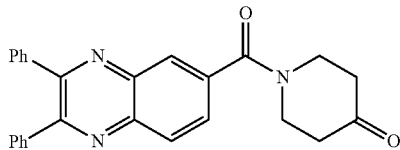 [SMILES: O=C1CCN(C(=O)c2ccc3nc(-c4ccccc4)c(-c4ccccc4)nc3c2)CC1]

The target compound 22b (86% yield) was obtained by the general procedure described above.

¹H NMR (400 MHz, Chloroform-d) δ 8.27-8.25 (m, 2H), 7.87 (d, J=8.5 Hz, 1H), 7.55-7.51 (m, 4H), 7.40-7.33 (m, 6H), 4.13-3.86 (m, 4H), 2.66-2.46 (m, 4H); ¹³C NMR (101 MHz, Chloroform-d) δ 206.3, 169.6, 154.7, 154.6, 141.6, 140.4, 138.53, 138.51, 136.2, 130.2, 129.82, 129.79, 129.23, 129.21, 128.5, 128.4, 127.6, 46.6, 41.2, (missing 1 signal due to overlap). MS (ES+) m/z=408 [M+H]⁺.

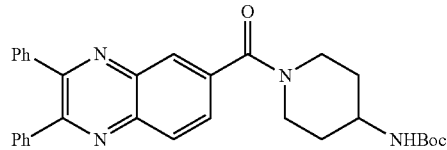 [SMILES: CC(C)(C)OC(=O)NC1CCN(C(=O)c2ccc3nc(-c4ccccc4)c(-c4ccccc4)nc3c2)CC1]

The target compound 23b (86% yield) was obtained by the general procedure described above.

¹H NMR (400 MHz, Chloroform-d) δ 8.19 (d, J=8.6 Hz, 1H), 8.14 (d, J=1.9 Hz, 1H), 7.77 (dd, J=8.6, 1.9 Hz, 1H), 7.51-7.48 (m, 4H), 7.37-7.29 (m, 6H), 4.73-4.64 (m, 2H), 3.80-3.68 (m, 2H), 3.18-3.00 (m, 2H), 2.00-1.93 (m, 2H), 1.47-1.34 (m, 2H), 1.42 (s, 9H); ¹³C NMR (101 MHz, Chloroform-d) δ 169.1, 155.1, 154.40, 154.36, 141.4, 140.5, 138.7, 138.6, 137.1, 129.9, 129.8, 129.10, 129.08, 128.6, 128.3, 127.3, 79.5, 47.8, 46.7, 41.3, 33.1, 32.2, 28.4, (missing 2 signals due to overlap).

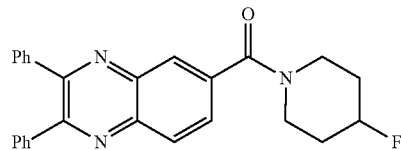 [SMILES: O=C(c1ccc2nc(-c3ccccc3)c(-c3ccccc3)nc2c1)N1CCC(F)CC1]

The target compound 24b (86% yield) was obtained by the general procedure described above.

¹H NMR (400 MHz, Chloroform-d) δ 8.22 (d, J=8.6 Hz, 1H), 8.17 (d, J=1.8 Hz, 1H), 7.80 (dd, J=8.5, 1.9 Hz, 1H), 7.53-7.50 (m, 4H), 7.38-7.30 (m, 6H), 5.00-4.84 (m, 1H), 4.13-4.07 (m, 1H), 3.69-3.50 (m, 3H), 1.99-1.80 (m, 4H); ¹³C NMR (101 MHz, Chloroform-d) δ 169.2, 154.44, 154.39, 141.4, 140.5, 138.7, 138.6, 137.0, 130.0, 129.82, 129.80, 129.1, 129.1, 128.6, 128.3, 127.3, 87.4 (d, J=171.6 Hz), 43.6, 38.2, 31.6, 31.0, (missing 1 signal due to overlap). MS (ES+) m/z=412 [M+H]⁺.

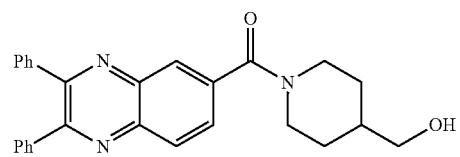 [SMILES: O=C(c1ccc2nc(-c3ccccc3)c(-c3ccccc3)nc2c1)N1CCC(CO)CC1]

The target compound 25b (86% yield) was obtained by the general procedure described above.

¹³C NMR (101 MHz, Chloroform-d) δ 169.0, 154.4, 154.3, 141.3, 140.5, 138.7, 138.6, 137.5, 129.81, 129.80, 129.10, 129.08, 128.7, 128.3, 127.2, 67.0, 47.9, 42.4, 36.5, 29.5, 28.4, (missing 2 signals due to overlap). MS (ES+) m/z=424 [M+H]⁺.

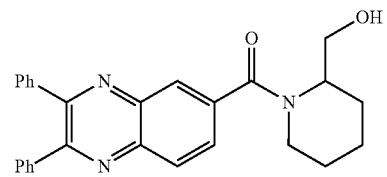 [SMILES: O=C(c1ccc2nc(-c3ccccc3)c(-c3ccccc3)nc2c1)N1CCCCC1CO]

The target compound 26b (86% yield) was obtained by the general procedure described above.

¹H NMR (400 MHz, Chloroform-d) δ 8.20-8.18 (m, 2H), 7.82 (d, J=8.3 Hz, 1H), 7.52-7.50 (m, 4H), 7.39-7.31 (m, 6H), 5.11-4.91 (m, 1H), 4.09-3.51 (m, 4H), 3.35-3.07 (m, 1H), 1.82-1.55 (m, 6H); ¹³C NMR (101 MHz, Chloroform-d) δ 154.3, 154.2, 141.3, 140.5, 138.70, 138.68, 129.9, 129.8, 129.8, 129.1, 128.9, 128.3, 127.3, 61.8, 51.9, 44.4, 37.8, 25.7, 19.8, (missing 4 signals due to overlap). MS (ES+) m/z=424 [M+H]⁺.

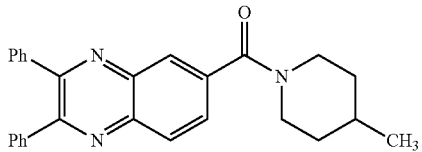 [SMILES: CC1CCN(C(=O)c2ccc3nc(-c4ccccc4)c(-c4ccccc4)nc3c2)CC1]

The target compound 27b (86% yield) was obtained by the general procedure described above.
¹H NMR (400 MHz, Chloroform-d) δ 8.21 (d, J=8.5 Hz, 1H), 8.16 (s, 1H), 7.80 (d, J=8.6 Hz, 1H), 7.52-7.50 (m, 4H), 7.38-7.30 (m, 6H), 4.77-4.73 (m, 1H), 3.82-3.79 (m, 1H), 3.10-2.79 (m, 2H), 1.82-1.58 (m, 3H), 1.31-1.15 (m, 2H), 0.98 (d, J=6.4 Hz, 3H); ¹³C NMR (101 MHz, Chloroform-d) δ 169.0, 154.3, 141.3, 140.5, 138.7, 137.7, 129.82, 129.79, 129.0, 128.8, 128.3, 127.2, 48.2, 42.7, 34.8, 33.9, 31.1, 21.7, (missing 5 signals due to overlap). MS (ES+) m/z=408 [M+H]⁺.

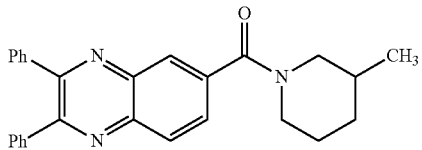 [SMILES: CC1CCCN(C(=O)c2ccc3nc(-c4ccccc4)c(-c4ccccc4)nc3c2)C1]

The target compound 28b (86% yield) was obtained by the general procedure described above.
Mixture of Rotamers
¹H NMR (400 MHz, Chloroform-d) δ 8.21 (d, J=8.6 Hz, 1H), 8.15 (s, 1H), 7.79 (d, J=8.6 Hz, 1H), 7.51 (d, J=7.3 Hz, 4H), 7.38-7.29 (m, 6H), 4.63-4.59 (m, 1H), 3.76-3.65 (m, 1H), 3.06-2.86 (m, 1H), 2.77-2.50 (m, 1H), 1.90-1.49 (m, 4H), 1.24-1.14 (m, 1H), 1.00-0.76 (m, 3H); ¹³C NMR (101 MHz, Chloroform-d) δ 168.9, 154.3, 141.3, 140.5, 138.7, 137.8, 129.8, 129.0, 128.7, 128.3, 127.2, 55.2, 49.6, 48.4, 42.8, 33.0, 32.0, 31.1, 26.1, 24.8, 19.1, 18.8, (missing 6 signals due to overlap). MS (ES+) m/z=408 [M+H]⁺.

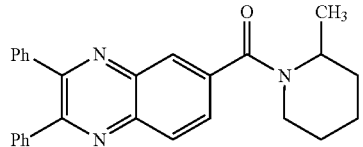 [SMILES: CC1CCCCN1C(=O)c1ccc2nc(-c3ccccc3)c(-c3ccccc3)nc2c1]

The target compound 29b (86% yield) was obtained by the general procedure described above.
Mixture of Rotamers
¹H NMR (400 MHz, Chloroform-d) δ 8.21 (d, J=8.5 Hz, 1H), 8.14 (s, 1H), 7.77 (d, J=8.5 Hz, 1H), 7.52 (d, J=6.6 Hz, 4H), 7.39-7.31 (m, 6H), 5.03-4.18 (m, 2H), 3.09-2.94 (m, 1H), 1.81-1.67 (m, 4H), 1.58-1.51 (m, 2H), 1.30-1.25 (m, 3H); ¹³C NMR (101 MHz, Chloroform-d) δ 169.1, 154.23, 154.16, 141.2, 140.6, 138.7, 138.3, 129.84, 129.81, 129.0, 128.4, 128.3, 126.7, 50.2, 43.4, 37.2, 30.3, 26.1, 18.8, 16.3, (missing 4 signals due to overlap). MS (ES+) m/z=408 [M+H]⁺.

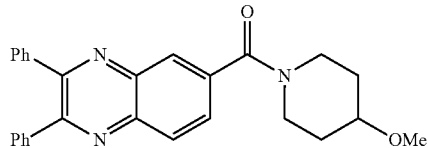 [SMILES: COC1CCN(C(=O)c2ccc3nc(-c4ccccc4)c(-c4ccccc4)nc3c2)CC1]

The target compound 30b (86% yield) was obtained by the general procedure described above.
¹H NMR (400 MHz, Chloroform-d) δ 8.20 (d, J=8.6 Hz, 1H), 8.16 (d, J=1.9 Hz, 1H), 7.79 (dd, J=8.5, 1.8 Hz, 1H), 7.51 (d, J=7.9 Hz, 4H), 7.37-7.29 (m, 6H), 4.10-4.04 (m, 1H), 3.65 (br s, 2H), 3.52-3.47 (m, 1H), 3.37-3.30 (m, 4H), 1.97-1.58 (m, 4H); ¹³C NMR (101 MHz, Chloroform-d) δ 169.0, 154.32, 154.30, 141.3, 140.5, 138.69, 138.67, 137.4, 129.9, 129.8, 129.1, 128.7, 128.3, 127.3, 75.1, 55.8, 44.8, 39.3, 31.3, 30.2, (missing 3 signals due to overlap). MS (ES+) m/z=424 [M+H]⁺.

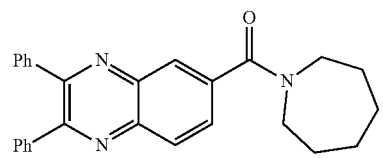 [SMILES: O=C(c1ccc2nc(-c3ccccc3)c(-c3ccccc3)nc2c1)N1CCCCCC1]

The target compound 31b (86% yield) was obtained by the general procedure described above.
¹H NMR (400 MHz, Chloroform-d) δ 8.21 (d, J=8.6 Hz, 1H), 8.16 (s, 1H), 7.78 (d, J=8.5 Hz, 1H), 7.52 (d, J=6.1 Hz, 4H), 7.39-7.30 (m, 6H), 3.75 (t, J=5.9 Hz, 2H), 3.45 (t, J=5.5 Hz, 2H), 1.92-1.86 (m, 2H), 1.70-1.59 (m, 6H); ¹³C NMR (101 MHz, Chloroform-d) δ 170.3, 154.23, 154.17, 141.1, 140.6, 138.8, 138.7, 138.6, 129.82, 129.76, 129.0, 128.5, 128.3, 126.8, 49.9, 46.4, 29.5, 27.8, 27.3, 26.5, (missing 3 signals due to overlap). MS (ES+) m/z=408 [M+H]⁺.

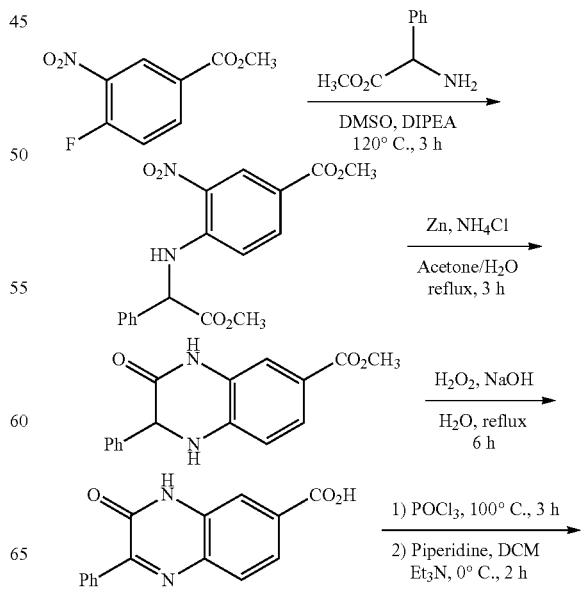

-continued

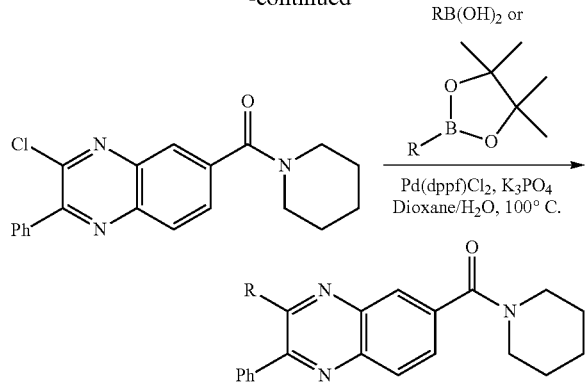

Step 1

To a solution of methyl 4-fluoro-3-nitrobenzoate (1.99 g, 10 mmol) in DMSO (20 mL) was added methyl 2-amino-2-phenylacetate (1.65 g, 10 mmol) and DIPEA (2.09 mL, 12 mmol) at room temperature, and the mixture was then heated at 120° C. for 3 h. The solution was cooled in an ice bath and cold water (30 mL) was added. The precipitate was filtered and washed with water. The resulting solid was dried to obtain the pure product as a yellow solid (3.13 g, 91% yield). $^1$H NMR (400 MHz, DMSO-$d_6$) δ 9.32 (d, J=6.1 Hz, 1H), 8.63 (s, 1H), 7.88 (d, J=9.0 Hz, 1H), 7.50 (d, J=7.2 Hz, 2H), 7.41-7.31 (m, 3H), 6.89 (d, J=9.1 Hz, 1H), 5.82 (d, J=6.1 Hz, 1H), 3.79 (s, 3H), 3.71 (s, 3H).

Step 2

To a solution of methyl 4-((2-methoxy-2-oxo-1-phenylethyl)amino)-3-nitrobenzoate (2.75 g, 8 mmol) in acetone (16 mL) was added Zn powder (2.6 g, 40 mmol), ammonium chloride (2.14 g, 40 mmol) and water (2 mL). The mixture was refluxed for 3 h, then filtered and concentrated. The residue was diluted with water and extracted with ethyl acetate. The combined organic extracts were washed with brine, dried over anhydrous $Na_2SO_4$ and concentrated by reduced pressure. The crude was purified by flash chromatography on silica gel to give the product as a white solid (2.01 g, 89% yield). $^1$H NMR (400 MHz, DMSO-$d_6$) δ 10.62 (s, 1H), 7.45-7.43 (m, 2H), 7.37 (d, J=1.9 Hz, 1H), 7.35-7.25 (m, 5H), 6.77 (d, J=8.3 Hz, 1H), 5.08 (s, 1H), 3.74 (s, 3H).

Step 3

NaOH (1.12 g, 28 mmol) in $H_2O$ (4 mL) and $H_2O_2$ (0.86 mL, 28 mmol, 30% w/w) was added to a solution of methyl 3-oxo-2-phenyl-1,2,3,4-tetrahydroquinoxaline-6-carboxylate (1.97 g, 7 mmol) in $H_2O$ (20 mL). The reaction was refluxed for 6 h, then cooled in an ice bath and acidified by 1 M HCl until PH 2. The precipitate was collected by filtration, and washed with cold water. The resulting solid was dried to obtain the pure product as a pale yellow solid (1.02 g, 55% yield). $^1$H NMR (400 MHz, DMSO-$d_6$) δ 13.17 (s, 1H), 12.71 (s, 1H), 8.31 (d, J=7.4 Hz, 2H), 7.91 (s, 1H), 7.90 (d, J=9.2 Hz, 1H), 7.81 (d, J=8.4 Hz, 1H), 7.55-7.48 (m, 3H).

Step 4

$POCl_3$ (2.86 mL, 30 mmol) was added to a 25-mL vial which was charged with 3-oxo-2-phenyl-3,4-dihydroquinoxaline-6-carboxylic acid (798 mg, 3 mmol). The mixture was heated at 100° C. for 3 h, and the excess $POCl_3$ was removed under reduced pressure. The resulting crude was dissolved in dichloromethane (10 mL) and $Et_3N$ (4.12 mL, 30 mmol), cooled down to 0° C. Piperidine (0.6 mL, 6 mmol) was then added to the solution which was allowed to stir at 0° C. for 2 h. After the completion of the reaction, the solvents were removed under reduced pressure and the residue was loaded to a column on silica gel and eluted by hexanes/ethyl acetate=10/1 to give a pale yellow solid (600 mg, 57% yield). $^1$H NMR (400 MHz, Chloroform-d) δ 8.19 (d, J=8.6 Hz, 1H), 8.04 (d, J=1.9 Hz, 1H), 7.89-7.81 (m, 3H), 7.56-7.54 (m, 3H), 3.79 (s, 2H), 3.40 (s, 2H), 1.73 (s, 4H), 1.58 (s, 2H).

Step 5

Under nitrogen atmosphere, boronic acid or boronic ester (0.11 mmol) was added to a dry tube containing (3-chloro-2-phenylquinoxalin-6-yl)(piperidin-1-yl)methanone (35 mg, 0.1 mmol), Pd(dppf)$Cl_2$ (4 mg, 0.5% mmol), $K_3PO_4$ (42 mg, 0.2 mmol), 1,4-dioxane (2 mL) and $H_2O$ (0.2 mL). The mixture was stirring at 100° C. until the completion of the reaction which was monitored by LC/MS. The reaction mixture was cooled to room temperature, washed with water, extracted with ethyl acetate, dried over anhydrous $Na_2SO_4$ and concentrated by rotary evaporation. The crude was purified by flash chromatography on silica gel to give the product.

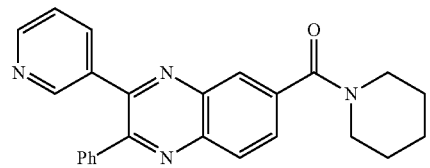 [SMILES: O=C(c1ccc2nc(-c3ccccc3)c(-c3cccnc3)nc2c1)N1CCCCC1]

The target compound 33b (46% yield) was obtained by the general procedure described above.

$^1$H NMR (400 MHz, Chloroform-d) δ 8.76 (s, 1H), 8.59 (s, 1H), 8.22-8.16 (m, 2H), 7.81 (d, J=8.3 Hz, 2H), 7.49 (d, J=7.1 Hz, 2H), 7.37-7.35 (m, 3H), 3.77 (s, 2H), 3.42 (s, 2H), 1.70 (s, 4H), 1.56 (s, 2H); $^{13}$C NMR (101 MHz, Chloroform-d) δ 168.8, 154.1, 151.2, 150.5, 149.8, 141.4, 140.6, 138.1, 137.1, 134.6, 129.9, 129.8, 129.4, 129.3, 128.7, 127.2, 123.0, 48.9, 43.3, 26.6, 25.6, 24.5 (missing 1 signal due to overlap). MS (ES+) m/z=395 [M+H]$^+$.

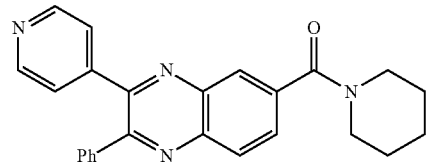 [SMILES: O=C(c1ccc2nc(-c3ccccc3)c(-c3ccncc3)nc2c1)N1CCCCC1]

The target compound 34b (52% yield) was obtained by the general procedure described above.

$^1$H NMR (400 MHz, Chloroform-d) δ 8.60 (s, 2H), 8.23 (d, J=8.6 Hz, 1H), 8.17 (s, 1H), 7.85 (d, J=8.6 Hz, 1H), 7.50 (d, J=7.5 Hz, 2H), 7.44-7.35 (m, 5H), 3.79 (s, 2H), 3.43 (s, 2H), 1.72 (s, 4H), 1.57 (s, 2H); $^{13}$C NMR (101 MHz, Chloroform-d) δ 168.7, 153.9, 151.5, 149.9, 146.4, 141.6, 140.5, 138.2, 137.8, 129.9, 129.8, 129.63, 129.55, 128.6, 127.3, 124.1, 48.9, 43.3, 26.6, 25.6, 24.5. MS (ES+) m/z=395 [M+H]$^+$.

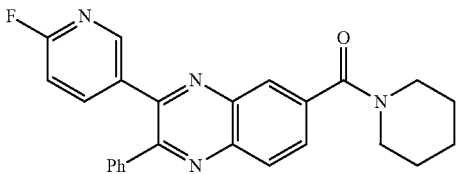 [SMILES: O=C(c1ccc2nc(-c3ccccc3)c(-c3ccc(F)nc3)nc2c1)N1CCCCC1]

The target compound 35b (58% yield) was obtained by the general procedure described above.

¹H NMR (400 MHz, Chloroform-d) δ 8.40 (d, J=2.5 Hz, 1H), 8.21 (d, J=8.6 Hz, 1H), 8.15 (s, 1H), 7.92 (td, J=8.1, 2.5 Hz, 1H), 7.82 (dd, J=8.6, 1.8 Hz, 1H), 7.51-7.49 (m, 2H), 7.43-7.37 (m, 3H), 6.89 (dd, J=8.5, 2.9 Hz, 1H), 3.78 (s, 2H), 3.43 (s, 2H), 1.71 (s, 4H), 1.57 (s, 2H); ¹³C NMR (101 MHz, Chloroform-d) δ 168.7, 163.6 (d, J=242.4 Hz), 153.9, 150.0, 149.0 (d, J=15.4 Hz), 142.4 (d, J=8.3 Hz), 141.4, 140.6, 138.2, 138.0, 132.6 (d, J=4.7 Hz), 129.9, 129.7, 129.6, 129.4, 128.8, 127.2, 109.09 (d, J=37.5 Hz), 48.9, 43.3, 26.6, 25.6, 24.5. MS (ES+) m/z=413 [M+H]⁺.

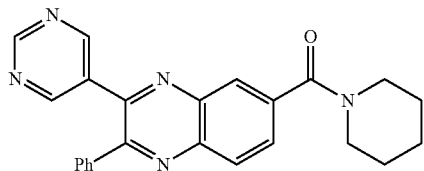 [SMILES: O=C(c1ccc2nc(-c3ccccc3)c(-c3cncnc3)nc2c1)N1CCCCC1]

The target compound 36b (69% yield) was obtained by the general procedure described above.

¹H NMR (400 MHz, Chloroform-d) δ 9.18 (s, 1H), 8.87 (s, 2H), 8.21 (d, J=8.6 Hz, 1H), 8.16 (s, 1H), 7.84 (dd, J=8.6, 1.8 Hz, 1H), 7.50-7.48 (m, 2H), 7.43-7.38 (m, 3H), 3.77 (s, 2H), 3.42 (s, 2H), 1.71 (s, 4H), 1.56 (s, 2H); ¹³C NMR (101 MHz, Chloroform-d) δ 168.5, 158.3, 157.3, 153.9, 148.1, 141.6, 140.7, 138.4, 137.5, 132.6, 129.9, 129.84, 129.82, 129.7, 129.0, 127.3, 48.9, 43.3, 26.6, 25.6, 24.5. MS (ES+) m/z=396 [M+H]⁺.

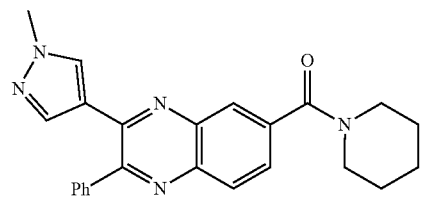 [SMILES: Cn1cc(-c2nc3cc(C(=O)N4CCCCC4)ccc3nc2-c2ccccc2)cn1]

The target compound 37b (52% yield) was obtained by the general procedure described above.

¹H NMR (400 MHz, Chloroform-d) δ 8.10 (d, J=8.9 Hz, 1H), 8.05 (s, 1H), 7.70 (d, J=8.5 Hz, 1H), 7.59-7.48 (m, 5H), 7.42 (d, J=6.8 Hz, 2H), 3.83 (s, 3H), 3.78 (s, 2H), 3.42 (s, 2H), 1.71 (s, 4H), 1.57 (s, 2H); ¹³C NMR (101 MHz, Chloroform-d) δ 169.1, 153.8, 147.2, 140.9, 140.3, 140.2, 139.1, 137.8, 131.5, 129.6, 129.4, 129.0, 128.8, 127.8, 126.7, 121.2, 48.9, 43.3, 39.1, 26.6, 25.6, 24.5. MS (ES+) m/z=398 [M+H]⁺.

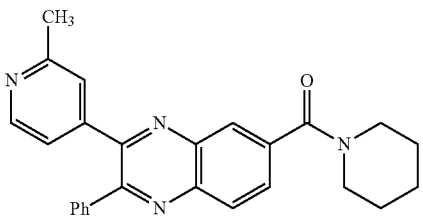 [SMILES: Cc1cc(-c2nc3cc(C(=O)N4CCCCC4)ccc3nc2-c2ccccc2)ccn1]

The target compound 38b (52% yield) was obtained by the general procedure described above.

¹H NMR (400 MHz, Chloroform-d) δ 8.43 (d, J=5.1 Hz, 1H), 8.22 (d, J=8.6 Hz, 1H), 8.17 (s, 1H), 7.84 (d, J=8.6 Hz, 1H), 7.50 (d, J=8.1 Hz, 2H), 7.44-7.35 (m, 4H), 7.11 (d, J=5.2 Hz, 1H), 3.79 (s, 2H), 3.43 (s, 2H), 2.56 (s, 3H), 1.72 (s, 4H), 1.56 (s, 2H); ¹³C NMR (101 MHz, Chloroform-d) δ 168.7, 158.9, 153.9, 151.8, 149.0, 146.7, 141.6, 140.4, 138.1, 137.9, 129.9, 129.8, 129.54, 129.50, 128.5, 127.2, 123.6, 121.3, 48.9, 45.5, 43.3, 26.6, 25.6, 24.5. MS (ES+) m/z=409 [M+H]⁺.

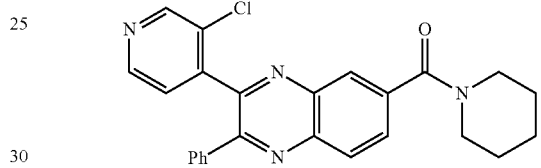

The target compound 39b (32% yield) was obtained by the general procedure described above.

¹H NMR (400 MHz, Chloroform-d) δ 8.60 (d, J=4.9 Hz, 1H), 8.57 (s, 1H), 8.27 (d, J=8.6 Hz, 1H), 8.16 (s, 1H), 7.88 (dd, J=8.6, 1.8 Hz, 1H), 7.50-7.46 (m, 3H), 7.37 (d, J=7.2 Hz, 1H), 7.32 (t, J=7.2 Hz, 2H), 3.78 (s, 2H), 3.44 (s, 2H), 1.71 (s, 4H), 1.57 (s, 2H); ¹³C NMR (101 MHz, Chloroform-d) δ 168.6, 153.9, 150.2, 150.0, 147.9, 145.7, 142.0, 140.0, 138.3, 137.3, 130.5, 130.0, 129.9, 129.6, 129.3, 128.4, 127.3, 125.3, 48.9, 43.3, 26.6, 25.6, 24.5. MS (ES+) m/z=429 [M+H]⁺.

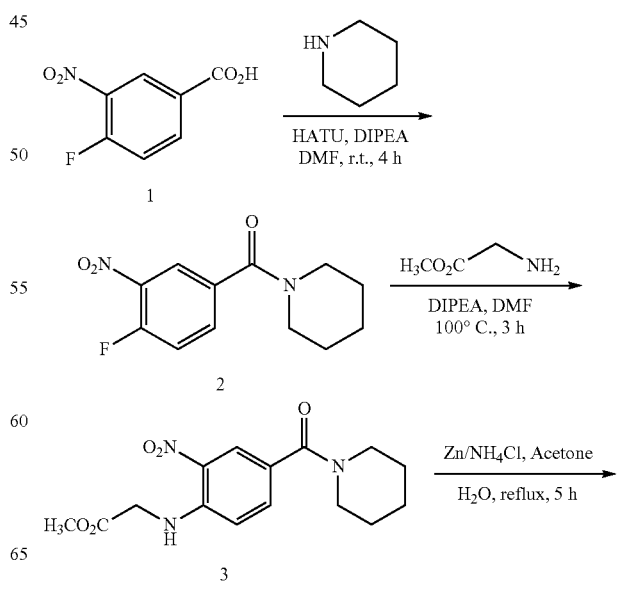

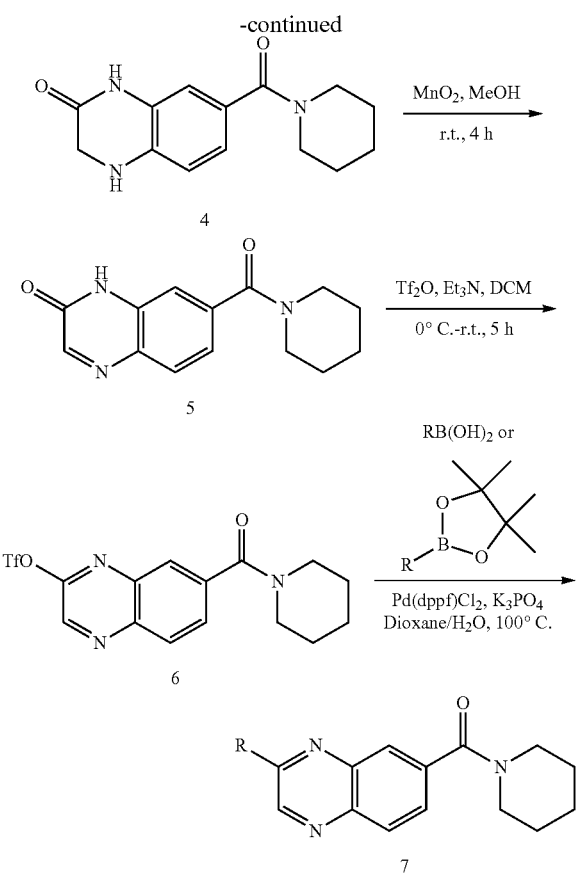

Step 1

To a solution of 4-fluoro-3-nitrobenzoic acid (1.85 g, 10 mmol), HATU (4.2 g, 11 mmol), DIPEA (3.5 mL, 20 mmol) in DMF (20 mL) was added amine (11 mmol). The mixture was stirred at room temperature for 4 h. Water was added to the solution, and the mixture was extracted with ethyl acetate, washed with brine, dried over anhydrous Na$_2$SO$_4$ and concentrated by rotary evaporation. The crude was purified by flash chromatography on silica gel to give the product as yellow oil (2.32 g, 92% yield). MS (ES+) m/z=253 [M+H]$^+$.

Step 2

To a solution of (4-fluoro-3-nitrophenyl)(piperidin-1-yl) methanone (2.27 g, 9 mmol) in DMSO (18 mL) was added methyl glycinate (801 mg, 9 mmol) and DIPEA (1.91 mL, 11 mmol) at room temperature, and the mixture was then heated at 100° C. for 3 h. The solution was cooled in an ice bath and cold water (30 mL) was added. The precipitate was filtered and washed with water. The resulting solid was dried to obtain the pure product as a yellow solid (2.60 g, 90% yield). $^1$H NMR (400 MHz, DMSO-d$_6$) δ 8.52 (t, J=5.9 Hz, 1H), 8.09 (d, J=2.1 Hz, 1H), 7.54 (dd, J=8.8, 2.1 Hz, 1H), 6.95 (d, J=8.9 Hz, 1H), 4.31 (d, J=5.8 Hz, 2H), 3.69 (s, 3H), 3.44 (s, 4H), 1.60-1.57 (m, 2H), 1.49 (s, 4H). MS (ES+) m/z=322 [M+H]$^+$.

Step 3

To a solution of methyl (2-nitro-4-(piperidine-1-carbonyl) phenyl)glycinate (2.57 g, 8 mmol) in acetone (16 mL) was added Zn powder (2.6 g, 40 mmol), ammonium chloride (2.14 g, 40 mmol) and water (2 mL). The mixture was refluxed for 3 h, then filtered and concentrated. The residue was diluted with water and extracted with ethyl acetate. The combined organic extracts were washed with brine, dried over anhydrous Na$_2$SO$_4$ and concentrated by reduced pressure. The crude was purified by flash chromatography on silica gel to give the product as a white solid (1.7 g, 82% yield). MS (ES+) m/z=260 [M+H]$^+$.

Step 4

MnO$_2$ (2.61 g, 30 mmol) was added to a 50-mL flask which was charged with 7-(piperidine-1-carbonyl)-3,4-dihydroquinoxalin-2(1H)-one (1.55 g, 6 mmol) in dichloromethane (20 mL). The mixture was stirred at room temperature for 4 h, then filtered and concentrated. The resulting residue was purified by flash chromatography on silica gel to give the product as brown oil (1.28 g, 83% yield). MS (ES+) m/z=258 [M+H]$^+$.

Step 5

7-(piperidine-1-carbonyl)quinoxalin-2(1H)-one (1.03 g, 4 mmol) was placed in a 20-mL vial and dissolved in dichloromethane (10 mL). The mixture was placed in an ice-bath and Et$_3$N (1.12 mL, 8 mmol) and Tf$_2$O (1.01 mL, 6 mmol) were added to the solution slowly. After the addition of Tf$_2$O, the reaction was stirred at 0° C. for 2 h, and then the ice-bath was removed. The mixture continued to stir at room temperature for an additional 3 h. The solvent was removed and the resulting residue was purified by flash chromatography on silica gel to give the product as brown oil (949 mg, 61% yield). MS (ES+) m/z=390 [M+H]$^+$.

Step 6

Under nitrogen atmosphere, boronic acid or boronic ester (0.11 mmol) was added to a dry tube containing 7-(piperidine-1-carbonyl)quinoxalin-2-yl trifluoromethanesulfonate (39 mg, 0.1 mmol), Pd(dppf)Cl$_2$ (4 mg, 0.5% mmol), K$_3$PO$_4$ (42 mg, 0.2 mmol), 1,4-dioxane (2 mL) and H$_2$O (0.2 mL). The mixture was stirring at 100° C. until the completion of the reaction which was monitored by LC/MS. The reaction mixture was cooled to room temperature, washed with water, extracted with ethyl acetate, dried over anhydrous Na$_2$SO$_4$ and concentrated by rotary evaporation. The crude was purified by flash chromatography on silica gel to give the product

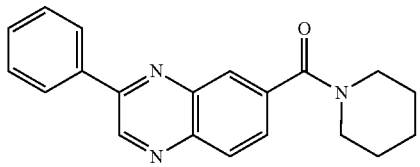 [SMILES: O=C(c1ccc2ncc(-c3ccccc3)nc2c1)N1CCCCC1]

The target compound 40b (89% yield) was obtained by the general procedure described above.

$^1$H NMR (400 MHz, Chloroform-d) δ 9.36 (s, 1H), 8.22-8.15 (m, 4H), 7.77 (d, J=8.5 Hz, 1H), 7.61-7.52 (m, 3H), 3.79 (s, 2H), 3.42 (s, 2H), 1.72 (s, 4H), 1.57 (s, 2H); $^{13}$C NMR (101 MHz, Chloroform-d) δ 168.9, 152.6, 144.1, 141.7, 141.6, 138.2, 136.4, 130.5, 129.7, 129.2, 128.2, 127.6, 48.9, 43.3, 26.6, 25.6, 24.5. (missing 1 signal due to overlap). MS (ES+) m/z=318 [M+H]$^+$.

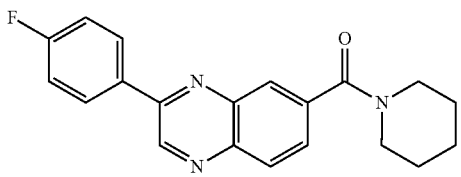 [SMILES: O=C(c1ccc2ncc(-c3ccc(F)cc3)nc2c1)N1CCCCC1]

The target compound 42b (87% yield) was obtained by the general procedure described above.

$^1$H NMR (400 MHz, Chloroform-d) δ 9.31 (s, 1H), 8.22-8.11 (m, 4H), 7.75 (d, J=8.6 Hz, 1H), 7.25 (t, J=8.6 Hz, 2H), 3.78 (s, 2H), 3.41 (s, 2H), 1.71 (s, 4H), 1.56 (s, 2H); $^{13}$C NMR (101 MHz, Chloroform-d) δ 168.8, 164.4 (d, J=251.4 Hz), 151.4, 143.7, 141.6, 141.5, 138.4, 132.55 (d, J=3.3 Hz), 129.7, 129.6 (d, J=8.6 Hz), 128.2, 127.5, 116.3 (d, J=21.9 Hz), 48.8, 43.3, 26.6, 25.6, 24.5. MS (ES+) m/z=336 [M+H]$^+$.

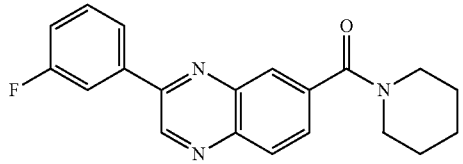 [SMILES: O=C(c1ccc2ncc(-c3cccc(F)c3)nc2c1)N1CCCCC1]

The target compound 41b (85% yield) was obtained by the general procedure described above.

$^1$H NMR (400 MHz, Chloroform-d) δ 9.33 (s, 1H), 8.17-8.14 (m, 2H), 7.97-7.93 (m, 2H), 7.78 (d, J=8.5 Hz, 1H), 7.56-7.51 (m, 1H), 7.22 (t, J=8.3 Hz, 1H), 3.79 (s, 2H), 3.42 (s, 2H), 1.72 (s, 4H), 1.57 (s, 2H); $^{13}$C NMR (101 MHz, Chloroform-d) δ 168.8, 163.4 (d, J=247.1 Hz), 151.1 (d, J=2.7 Hz), 143.7, 141.8, 141.6, 138.6 (d, J=7.6 Hz), 138.4, 130.8 (d, J=8.1 Hz), 129.8, 128.6, 127.6, 123.1 (d, J=3.0 Hz), 117.4 (d, J=21.3 Hz), 114.5 (d, J=23.1 Hz), 48.9, 43.3, 26.6, 25.6, 24.5. MS (ES+) m/z=336 [M+H]$^+$.

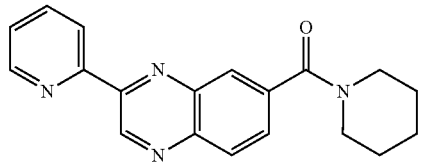 [SMILES: O=C(c1ccc2ncc(-c3ccccn3)nc2c1)N1CCCCC1]

The target compound 43b (37% yield) was obtained by the general procedure described above.

$^1$H NMR (400 MHz, Chloroform-d) δ 9.99 (s, 1H), 8.79 (d, J=4.7 Hz, 1H), 8.59 (d, J=8.0 Hz, 1H), 8.20-8.17 (m, 2H), 7.91 (t, J=7.7 Hz, 1H), 7.79 (d, J=8.5 Hz, 1H), 7.43 (dd, J=7.5, 4.9 Hz, 1H), 3.80 (s, 2H), 3.43 (s, 2H), 1.73-1.58 (m, 6H); $^{13}$C NMR (101 MHz, Chloroform-d) δ 168.9, 154.2, 150.9, 149.5, 145.0, 142.6, 141.2, 138.1, 137.2, 129.9, 128.6, 127.7, 124.9, 122.2, 48.9, 43.3, 26.6, 25.6, 24.5. MS (ES+) m/z=319 [M+H]$^+$.

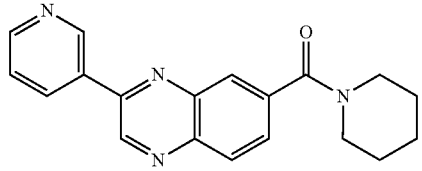 [SMILES: O=C(c1ccc2ncc(-c3cccnc3)nc2c1)N1CCCCC1]

The target compound 44b (46% yield) was obtained by the general procedure described above.

$^1$H NMR (400 MHz, Chloroform-d) δ 9.43 (s, 1H), 9.38 (s, 1H), 8.78 (d, J=4.6 Hz, 1H), 8.54 (d, J=8.0 Hz, 1H), 8.20-8.17 (m, 2H), 7.81 (dd, J=8.5, 1.8 Hz, 1H), 7.53 (dd, J=8.0, 4.8 Hz, 1H), 3.80 (s, 2H), 3.43 (s, 2H), 1.74-1.62 (m, 6H); $^{13}$C NMR (101 MHz, Chloroform-d) δ 168.7, 151.2, 150.2, 148.7, 143.5, 141.9, 141.8, 138.6, 135.0, 132.2, 129.9, 128.8, 127.6, 124.0, 48.9, 43.3, 26.6, 25.6, 24.5. MS (ES+) m/z=319 [M+H]$^+$.

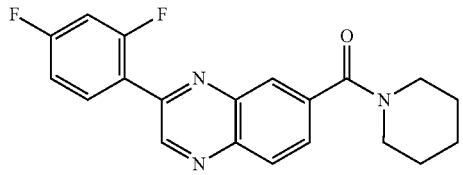 [SMILES: O=C(c1ccc2ncc(-c3ccc(F)cc3F)nc2c1)N1CCCCC1]

The target compound 45b (78% yield) was obtained by the general procedure described above.

$^1$H NMR (400 MHz, Chloroform-d) δ 9.30 (d, J=3.0 Hz, 1H), 8.18-8.12 (m, 3H), 7.78 (d, J=8.5 Hz, 1H), 7.08 (td, J=8.3, 2.4 Hz, 1H), 6.99 (dt, J=8.5, 2.4 Hz, 1H), 3.77 (s, 2H), 3.40 (s, 2H), 1.70 (s, 4H), 1.55 (s, 2H); $^{13}$C NMR (101 MHz, Chloroform-d) δ 168.7, 164.3 (dd, J=253.8, 12.0 Hz), 161.1 (dd, J=253.8, 12.1 Hz), 149.0 (d, J=3.6 Hz), 146.3 (d, J=12.0 Hz), 141.9, 141.4, 138.3, 132.77 (dd, J=9.9, 4.5 Hz), 129.8, 128.7, 127.5, 121.0 (dd, J=12.7, 3.8 Hz), 112.7 (dd, J=21.4, 3.5 Hz), 104.7 (t, J=26.1 Hz), 48.8, 43.3, 26.6, 25.6, 24.5. MS (ES+) m/z=354 [M+H]$^+$.

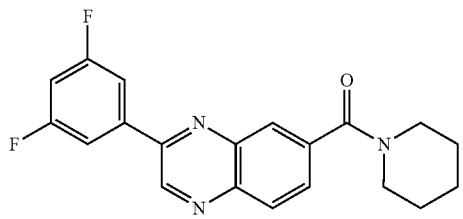 [SMILES: O=C(c1ccc2ncc(-c3cc(F)cc(F)c3)nc2c1)N1CCCCC1]

The target compound 47b (79% yield) was obtained by the general procedure described above.

$^1$H NMR (400 MHz, Chloroform-d) δ 9.29 (s, 1H), 8.17 (d, J=8.5 Hz, 1H), 8.14 (s, 1H), 7.81-7.74 (m, 3H), 6.97 (td, J=8.7, 2.2 Hz, 1H), 3.79 (s, 2H), 3.41 (s, 2H), 1.72 (s, 4H), 1.57 (s, 2H).

$^{13}$C NMR (101 MHz, Chloroform-d) δ 168.6, 163.6 (d, J=248.3 Hz), 163.5 (d, J=248.6 Hz), 149.9 (t, J=3.2 Hz), 143.3, 142.0, 141.5, 139.6 (t, J=9.4 Hz), 138.7, 129.8, 129.0, 127.6, 110.4 (dd, J=26.8, 7.6 Hz), 105.8 (t, J=25.4 Hz), 48.8, 43.3, 26.6, 25.6, 24.5. MS (ES+) m/z=354 [M+H]$^+$.

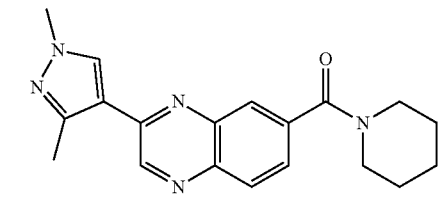 [SMILES: Cc1nn(C)cc1-c1cnc2ccc(C(=O)N3CCCCC3)cc2n1]

The target compound 46b (38% yield) was obtained by the general procedure described above.

$^1$H NMR (400 MHz, Chloroform-d) δ 9.02 (s, 1H), 8.06 (d, J=8.3 Hz, 1H), 8.02 (s, 1H), 8.00 (s, 1H), 7.66 (d, J=8.3 Hz, 1H), 3.94 (s, 3H), 3.77 (s, 2H), 3.40 (s, 2H), 2.67 (s, 3H), 1.71 (s, 4H), 1.55 (s, 2H); $^{13}$C NMR (101 MHz, Chloroform-d) δ 169.1, 149.1, 148.7, 144.4, 141.9, 140.4, 138.1, 131.1, 129.6, 127.1, 127.0, 117.7, 48.8, 43.2, 39.0, 26.6, 25.6, 24.5, 14.5. MS (ES+) m/z=336 [M+H]$^+$.

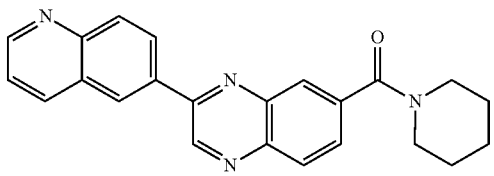 [SMILES: O=C(c1ccc2ncc(-c3ccc4ncccc4c3)nc2c1)N1CCCCC1]

The target compound 48 (77% yield) was obtained by the general procedure described above.

¹H NMR (400 MHz, Chloroform-d) δ 9.52 (s, 1H), 9.00 (s, 1H), 8.67 (s, 1H), 8.61 (dd, J=8.8, 2.0 Hz, 1H), 8.34 (d, J=8.3 Hz, 1H), 8.30 (d, J=8.9 Hz, 1H), 8.20 (s, 1H), 8.18 (d, J=5.6 Hz, 1H), 7.80 (d, J=8.7 Hz, 1H), 7.51 (dd, J=8.3, 4.1 Hz, 1H), 3.80 (s, 2H), 3.44 (s, 2H), 1.73 (s, 4H), 1.58 (s, 2H); ¹³C NMR (101 MHz, Chloroform-d) δ 168.8, 151.7, 151.6, 149.0, 144.0, 141.8, 141.7, 138.5, 137.0, 134.5, 130.6, 129.8, 128.6, 128.1, 127.6, 127.4, 122.0, 121.9, 48.9, 43.3, 26.6, 25.6, 24.5. MS (ES+) m/z=369 [M+H]⁺.

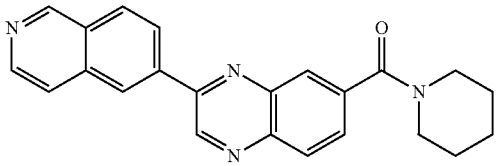 [SMILES: O=C(c1ccc2ncc(-c3ccc4cnccc4c3)nc2c1)N1CCCCC1]

The target compound 49b (76% yield) was obtained by the general procedure described above.

¹H NMR (400 MHz, Chloroform-d) δ 9.51 (s, 1H), 9.35 (s, 1H), 8.63 (s, 1H), 8.62 (d, J=6.1 Hz, 1H), 8.49 (dd, J=8.6, 1.7 Hz, 1H), 8.20-8.16 (m, 3H), 7.83-7.80 (m, 2H), 3.80 (s, 2H), 3.43 (s, 2H), 1.73 (s, 4H), 1.58 (s, 2H); ¹³C NMR (101 MHz, Chloroform-d) δ 168.7, 152.5, 151.4, 144.1, 144.0, 141.9, 141.7, 138.6, 138.0, 135.8, 129.8, 128.92, 128.85, 128.7, 127.7, 126.02, 125.98, 121.1, 48.9, 43.3, 26.6, 25.6, 24.5. MS (ES+) m/z=369 [M+H]⁺.

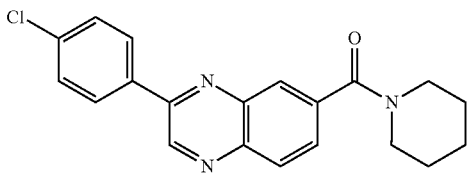 [SMILES: O=C(c1ccc2ncc(-c3ccc(Cl)cc3)nc2c1)N1CCCCC1]

The target compound 50b (56% yield) was obtained by the general procedure described above.

¹H NMR (400 MHz, Chloroform-d) δ 9.33 (s, 1H), 8.18-8.14 (m, 3H), 7.78 (d, J=8.5 Hz, 1H), 7.56 (d, J=8.2 Hz, 2H), 7.26 (s, 1H), 3.80 (s, 2H), 3.43 (s, 2H), 1.73 (s, 4H), 1.58 (s, 2H); ¹³C NMR (101 MHz, Chloroform-d) δ 168.8, 151.3, 143.6, 141.7, 138.4, 136.9, 134.8, 129.8, 129.5, 129.1, 128.8, 128.4, 127.6, 48.8, 43.3, 26.6, 25.6, 24.5. MS (ES+) m/z=352 [M+H]⁺.

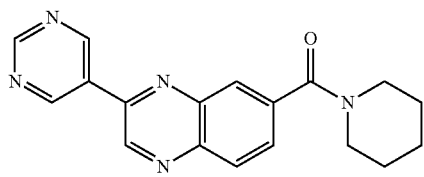 [SMILES: O=C(c1ccc2ncc(-c3cncnc3)nc2c1)N1CCCCC1]

The target compound 53b (61% yield) was obtained by the general procedure described above.

¹H NMR (400 MHz, Chloroform-d) δ 9.55 (s, 2H), 9.38 (s, 2H), 8.22-8.18 (m, 2H), 7.85 (dd, J=8.6, 1.8 Hz, 1H), 3.80 (s, 2H), 3.42 (s, 2H), 1.73 (s, 4H), 1.59 (s, 2H); ¹³C NMR (101 MHz, Chloroform-d) δ 168.4, 159.6, 155.6, 147.5, 142.8, 142.2, 141.8, 139.0, 130.0, 129.4, 127.7, 48.9, 43.3, 26.6, 25.6, 24.5. MS (ES+) m/z=320 [M+H]⁺.

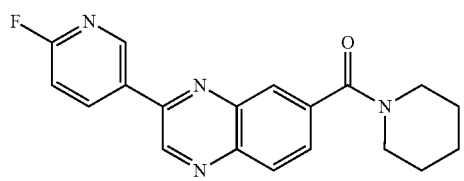 [SMILES: O=C(c1ccc2ncc(-c3ccc(F)nc3)nc2c1)N1CCCCC1]

The target compound 51b (52% yield) was obtained by the general procedure described above.

¹H NMR (400 MHz, Chloroform-d) δ 9.35 (s, 1H), 9.05 (d, J=2.5 Hz, 1H), 8.68 (td, J=8.1, 2.6 Hz, 1H), 8.20-8.15 (m, 2H), 7.81 (dd, J=8.6, 1.8 Hz, 1H), 7.16 (dd, J=8.6, 3.0 Hz, 1H), 3.80 (s, 2H), 3.42 (s, 2H), 1.74 (s, 4H), 1.58 (s, 2H); ¹³C NMR (101 MHz, Chloroform-d) δ 168.6, 164.7 (d, J=243.5 Hz), 149.0, 147.0 (d, J=15.7 Hz), 143.0, 141.8, 141.6, 140.4 (d, J=8.6 Hz), 138.7, 130.4 (d, J=4.7 Hz), 129.8, 128.8, 127.5, 110.3 (d, J=37.7 Hz), 48.8, 43.3, 26.6, 25.6, 24.5. MS (ES+) m/z=337 [M+H]⁺.

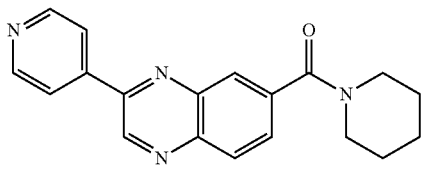 [SMILES: O=C(c1ccc2ncc(-c3ccncc3)nc2c1)N1CCCCC1]

The target compound 52b (47% yield) was obtained by the general procedure described above.

¹H NMR (400 MHz, Chloroform-d) δ 9.38 (s, 1H), 8.84 (d, J=5.3 Hz, 2H), 8.18 (d, J=9.0 Hz, 1H), 8.17 (s, 1H), 8.09 (d, J=5.7 Hz, 2H), 7.82 (dd, J=8.5, 1.8 Hz, 1H), 3.79 (s, 2H), 3.41 (s, 2H), 1.72 (s, 4H), 1.57 (s, 2H); ¹³C NMR (101 MHz, Chloroform-d) δ 168.6, 150.8, 149.9, 143.5, 143.4, 142.4, 141.7, 138.7, 129.9, 129.3, 127.8, 121.4, 48.8, 43.3, 26.6, 25.6, 24.5. MS (ES+) m/z=319 [M+H]⁺.

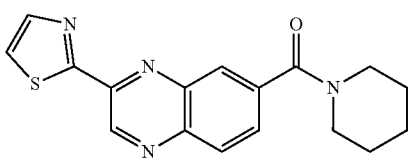 [SMILES: O=C(c1ccc2ncc(-c3nccs3)nc2c1)N1CCCCC1]

The target compound 58b (45% yield) was obtained by the general procedure described above.

¹H NMR (400 MHz, Chloroform-d) δ 9.77 (s, 1H), 8.18 (d, J=8.5 Hz, 1H), 8.13 (s, 1H), 8.07 (d, J=2.9 Hz, 1H), 7.80 (d, J=8.5 Hz, 1H), 7.60 (d, J=3.0 Hz, 1H), 3.80 (s, 2H), 3.42 (s, 2H), 1.73 (s, 4H), 1.59 (s, 2H); ¹³C NMR (101 MHz, Chloroform-d) δ 168.6, 166.6, 146.5, 144.8, 143.4, 142.8, 141.2, 138.6, 130.0, 129.0, 127.3, 123.1, 48.9, 43.3, 29.7, 26.6, 24.5. MS (ES+) m/z=325 [M+H]⁺.

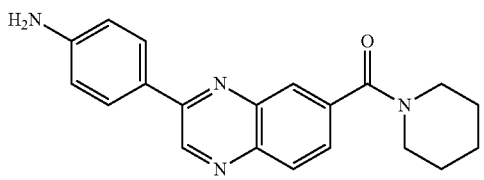 [SMILES: Nc1ccc(-c2cnc3ccc(C(=O)N4CCCCC4)cc3n2)cc1]

The target compound 63b (74% yield) was obtained by the general procedure described above.

$^1$H NMR (400 MHz, Chloroform-d) δ 9.27 (s, 1H), 8.09-8.04 (m, 4H), 7.68 (d, J=8.5 Hz, 1H), 6.81 (d, J=8.2 Hz, 2H), 3.78 (s, 2H), 3.41 (s, 2H), 1.71 (s, 4H), 1.56 (s, 2H); $^{13}$C NMR (101 MHz, Chloroform-d) δ 169.1, 152.4, 148.9, 143.8, 141.8, 141.0, 137.9, 129.6, 129.0, 127.2, 127.2, 126.2, 115.2, 48.8, 43.2, 26.6, 25.6, 24.5. MS (ES+) m/z=333 [M+H]$^+$.

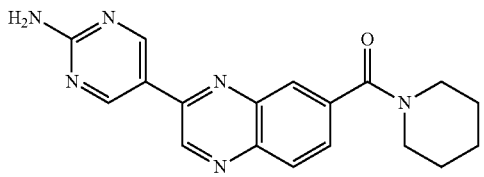 [SMILES: Nc1ncc(-c2cnc3ccc(C(=O)N4CCCCC4)cc3n2)cn1]

The target compound 59 (52% yield) was obtained by the general procedure described above.

$^1$H NMR (400 MHz, Chloroform-d) δ 9.24 (s, 1H), 9.15 (s, 2H), 8.14 (d, J=8.5 Hz, 1H), 8.10 (s, 1H), 7.75 (d, J=8.5 Hz, 1H), 5.60 (s, 2H), 3.79 (s, 2H), 3.42 (s, 2H), 1.72 (s, 4H), 1.58 (s, 2H); $^{13}$C NMR (101 MHz, Chloroform-d) δ 168.8, 163.4, 157.6, 148.5, 142.3, 141.7, 141.6, 138.5, 129.8, 128.1, 127.3, 120.6, 48.8, 43.3, 26.6, 25.6, 24.5. MS (ES+) m/z=335 [M+H]$^+$.

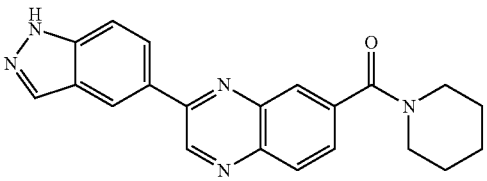 [SMILES: O=C(c1ccc2ncc(-c3ccc4[nH]ncc4c3)nc2c1)N1CCCCC1]

The target compound 64b (51% yield) was obtained by the general procedure described above.

$^1$H NMR (400 MHz, DMSO-d$_6$) δ 13.33 (s, 1H), 9.68 (d, J=1.5 Hz, 1H), 8.81 (s, 1H), 8.37 (d, J=8.9 Hz, 1H), 8.25 (s, 1H), 8.13 (d, J=7.9 Hz, 1H), 8.03 (s, 1H), 7.76-7.72 (m, 2H), 3.65 (s, 2H), 3.33 (s, 2H), 1.61 (s, 4H), 1.48 (s, 2H); $^{13}$C NMR (101 MHz, DMSO-d$_6$) δ 168.1, 152.7, 145.1, 141.4, 141.1, 141.1, 138.8, 135.4, 129.7, 128.8, 128.2, 127.0, 125.9, 123.8, 121.4, 111.4, 48.5, 42.9, 26.4, 25.7, 24.5. MS (ES+) m/z=358 [M+H]$^+$.

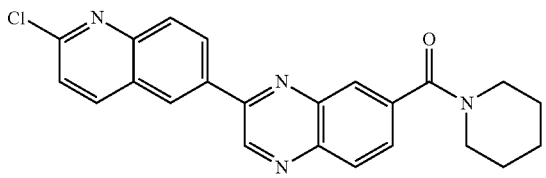 [SMILES: O=C(c1ccc2ncc(-c3ccc4nc(Cl)ccc4c3)nc2c1)N1CCCCC1]

The target compound 60 (77% yield) was obtained by the general procedure described above.

$^1$H NMR (400 MHz, Chloroform-d) δ 9.50 (s, 1H), 8.67 (s, 1H), 8.64 (d, J=9.0 Hz, 1H), 8.29 (d, J=8.5 Hz, 1H), 8.23-8.19 (m, 3H), 7.81 (d, J=8.9 Hz, 1H), 7.49 (d, J=8.6 Hz, 1H), 3.81 (s, 2H), 3.44 (s, 2H), 1.74 (s, 4H), 1.59 (s, 2H); $^{13}$C NMR (101 MHz, Chloroform-d) δ 168.7, 152.0, 151.1, 148.6, 143.8, 141.7, 141.7, 139.5, 138.6, 134.8, 129.8, 129.6, 129.2, 128.7, 127.6, 127.0, 126.8, 123.3, 48.9, 43.3, 26.6, 25.6, 24.5. MS (ES+) m/z=403 [M+H]$^+$.

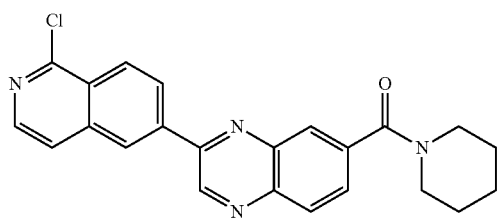 [SMILES: O=C(c1ccc2ncc(-c3ccc4c(Cl)nccc4c3)nc2c1)N1CCCCC1]

The target compound 61 (75% yield) was obtained by the general procedure described above.

$^1$H NMR (400 MHz, Chloroform-d) δ 9.52 (s, 1H), 8.67 (s, 1H), 8.58-8.51 (m, 2H), 8.38 (d, J=5.6 Hz, 1H), 8.22-8.20 (m, 2H), 7.84 (d, J=8.7 Hz, 1H), 7.78 (d, J=5.6 Hz, 1H), 3.81 (s, 2H), 3.44 (s, 2H), 1.74 (s, 4H), 1.59 (s, 2H); $^{13}$C NMR (101 MHz, cdcl$_3$) δ 168.6, 151.6, 150.7, 143.8, 142.4, 141.9, 141.7, 138.7, 138.7, 137.8, 129.8, 129.0, 127.7, 127.5, 127.3, 127.2, 126.2, 121.3, 48.9, 43.3, 26.6, 25.6, 24.5. MS (ES+) m/z=403 [M+H]$^+$.

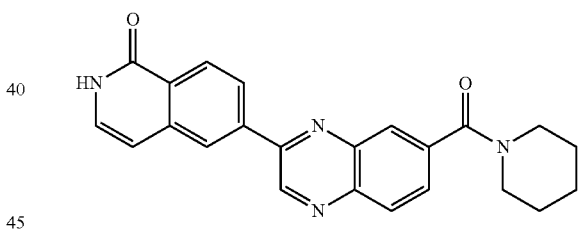

The target compound 62 (60% yield) was obtained by the general procedure described above.

$^1$H NMR (400 MHz, DMSO-d$_6$) δ 11.40 (s, 1H), 9.73 (s, 1H), 8.64 (s, 1H), 8.41 (d, J=7.7 Hz, 1H), 8.36 (d, J=8.4 Hz, 1H), 8.20 (d, J=8.5 Hz, 1H), 8.11 (s, 1H), 7.83 (d, J=8.5 Hz, 1H), 7.26 (t, J=6.4 Hz, 1H), 6.71 (d, J=7.2 Hz, 1H), 3.66 (s, 2H), 3.27 (s, 2H), 1.62 (s, 4H), 1.49 (s, 2H); $^{13}$C NMR (101 MHz, DMSO-d$_6$) δ 167.9, 162.0, 151.4, 145.2, 141.7, 141.3, 139.5, 139.1, 138.8, 130.3, 129.9, 129.2, 128.1, 127.5, 127.3, 126.1, 125.4, 105.3, 48.5, 42.9, 26.4, 25.7, 24.5. MS (ES+) m/z=385 [M+H]$^+$.

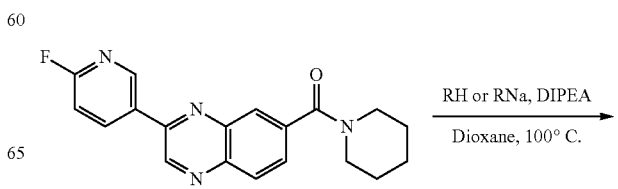

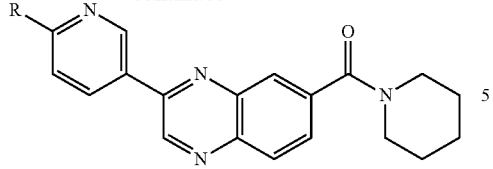

RH or RNa (0.3 mmol) was added to a solution of (3-(6-fluoropyridin-3-yl)quinoxalin-6-yl)(piperidin-1-yl)methanone (34 mg, 0.1 mmol) in 1,4-dioxane (2 mL). The mixture was heated at 100° C. until the completion of the reaction which was monitored by LC/MS and the solvent was removed by reduced pressure. The resulting residue was purified by flash chromatography on silica gel to give the product.

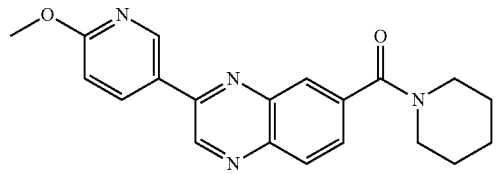 [SMILES: COc1ccc(-c2cnc3ccc(C(=O)N4CCCCC4)cc3n2)cn1]

The target compound 54b (63% yield) was obtained by the general procedure described above.

$^1$H NMR (400 MHz, Chloroform-d) δ 9.30 (s, 1H), 8.98 (d, J=1.8 Hz, 1H), 8.46 (dd, J=8.7, 2.5 Hz, 1H), 8.13 (d, J=8.5 Hz, 1H), 8.10 (d, J=1.3 Hz, 1H), 7.74 (dd, J=8.5, 1.8 Hz, 1H), 6.93 (d, J=9.1 Hz, 1H), 4.03 (s, 3H), 3.78 (s, 2H), 3.41 (s, 2H), 1.72 (s, 4H), 1.56 (s, 2H); $^{13}$C NMR (101 MHz, Chloroform-d) δ 168.8, 165.5, 150.3, 146.5, 143.2, 141.8, 141.5, 138.4, 137.7, 129.7, 128.1, 127.4, 125.7, 111.7, 53.9, 48.8, 43.3, 26.6, 25.6, 24.5. MS (ES+) m/z=349 [M+H]$^+$.

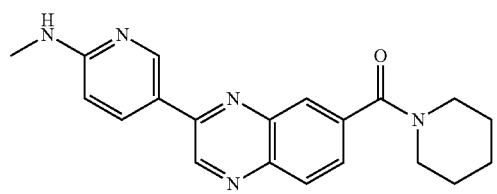 [SMILES: CNc1ccc(-c2cnc3ccc(C(=O)N4CCCCC4)cc3n2)cn1]

The target compound 55b (71% yield) was obtained by the general procedure described above.

$^1$H NMR (400 MHz, Chloroform-d) δ 9.25 (s, 1H), 8.93 (s, 1H), 8.31 (d, J=8.9 Hz, 1H), 8.08 (d, J=8.4 Hz, 1H), 8.05 (s, 1H), 7.67 (d, J=8.5 Hz, 1H), 6.53 (d, J=8.8 Hz, 1H), 5.15 (d, J=4.3 Hz, 1H), 3.77 (s, 2H), 3.40 (s, 2H), 3.00 (d, J=4.3 Hz, 3H), 1.70 (s, 4H), 1.55 (s, 2H); $^{13}$C NMR (101 MHz, Chloroform-d) δ 169.0, 160.4, 150.9, 148.0, 143.1, 141.9, 141.1, 138.1, 136.3, 129.6, 127.3, 127.2, 121.3, 106.7, 48.8, 43.2, 29.0, 26.6, 25.6, 24.5. MS (ES+) m/z=348 [M+H]$^+$.

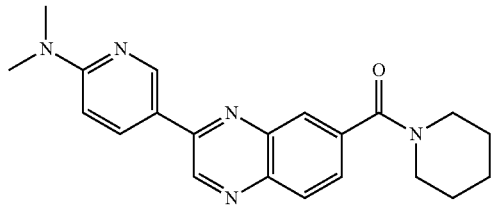 [SMILES: CN(C)c1ccc(-c2cnc3ccc(C(=O)N4CCCCC4)cc3n2)cn1]

The target compound 57b (74% yield) was obtained by the general procedure described above.

$^1$H NMR (400 MHz, Chloroform-d) δ 9.25 (s, 1H), 8.99 (d, J=2.2 Hz, 1H), 8.33 (dd, J=9.0, 2.5 Hz, 1H), 8.06 (d, J=8.5 Hz, 1H), 8.03 (d, J=1.6 Hz, 1H), 7.65 (dd, J=8.5, 1.8 Hz, 1H), 6.64 (d, J=9.0 Hz, 1H), 3.76 (s, 2H), 3.39 (s, 2H), 3.17 (s, 6H), 1.70 (s, 4H), 1.54 (s, 2H); $^{13}$C NMR (101 MHz, Chloroform-d) δ 169.1, 159.8, 151.0, 147.7, 143.1, 141.9, 141.0, 138.0, 136.0, 129.6, 127.1, 127.1, 119.8, 106.0, 48.8, 43.2, 38.1, 26.6, 25.6, 24.5. MS (ES+) m/z=362 [M+H]$^+$.

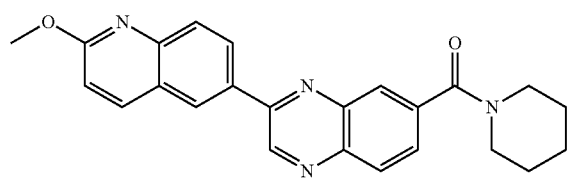

The target compound 58b (78% yield) was obtained by the general procedure described above.

$^1$H NMR (400 MHz, Chloroform-d) δ 9.27 (s, 1H), 9.00 (d, J=2.4 Hz, 1H), 8.38 (dd, J=9.0, 2.4 Hz, 1H), 8.10-8.05 (m, 2H), 7.68 (d, J=8.5 Hz, 1H), 6.76 (d, J=8.9 Hz, 1H), 3.83 (t, J=4.8 Hz, 4H), 3.77 (s, 2H), 3.65 (t, J=4.9 Hz, 4H), 3.40 (s, 2H), 1.70 (s, 4H), 1.55 (s, 2H); $^{13}$C NMR (101 MHz, Chloroform-d) δ 169.0, 159.8, 150.6, 147.6, 143.1, 141.9, 141.2, 138.2, 136.5, 129.6, 127.4, 127.2, 121.8, 106.7, 66.6, 48.8, 45.1, 43.2, 26.6, 25.6, 24.5. MS (ES+) m/z=404 [M+H]$^+$.

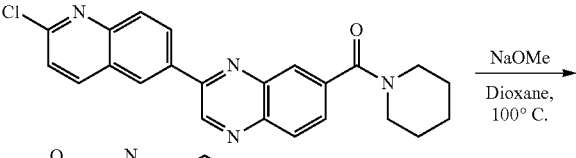

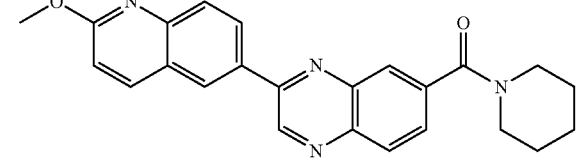

NaOMe (27 mg, 0.5 mmol) was added to a solution of (3-(2-chloroquinolin-6-yl)quinoxalin-6-yl)(piperidin-1-yl)

methanone (40 mg, 0.1 mmol) in 1,4-dioxane (2 mL). The mixture was heated at 100° C. for 24 h and the solvent was removed by reduced pressure. The resulting residue was purified by flash chromatography on silica gel to give the product 65b as a pale yellow solid (32% yield).

¹H NMR (400 MHz, Chloroform-d) δ 9.48 (s, 1H), 8.57 (s, 1H), 8.50 (d, J=8.8 Hz, 1H), 8.18-8.13 (m, 3H), 8.03 (d, J=8.7 Hz, 1H), 7.78 (d, J=8.6 Hz, 1H), 6.99 (d, J=8.9 Hz, 1H), 4.12 (s, 3H), 3.80 (s, 2H), 3.44 (s, 2H), 1.73 (s, 4H), 1.59 (s, 2H); ¹³C NMR (101 MHz, Chloroform-d) δ 168.9, 163.4, 152.0, 147.9, 144.0, 141.8, 141.5, 139.3, 138.3, 131.9, 129.8, 128.3, 128.2, 128.2, 127.5, 127.1, 125.1, 114.1, 53.7, 48.9, 43.3, 26.6, 25.6, 24.5. MS (ES+) m/z=399 [M+H]⁺.

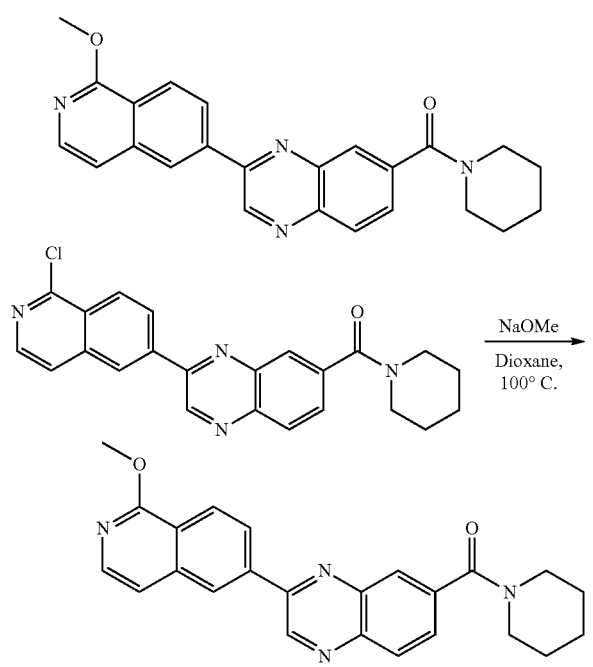

NaOMe (27 mg, 0.5 mmol) was added to a solution of (3-(1-chloroisoquinolin-6-yl)quinoxalin-6-yl)(piperidin-1-yl)methanone (40 mg, 0.1 mmol) in 1,4-dioxane (2 mL). The mixture was heated at 100° C. for 24 h and the solvent was removed by reduced pressure. The resulting residue was purified by flash chromatography on silica gel to give the product 66b as a pale yellow solid (35% yield).

¹H NMR (400 MHz, Chloroform-d) δ 9.50 (s, 1H), 8.56 (s, 1H), 8.44 (d, J=8.7 Hz, 1H), 8.39 (d, J=8.7 Hz, 1H), 8.21-8.19 (m, 2H), 8.10 (d, J=5.8 Hz, 1H), 7.82 (d, J=8.7 Hz, 1H), 7.38 (d, J=5.9 Hz, 1H), 4.18 (s, 3H), 3.81 (s, 2H), 3.44 (s, 2H), 1.74 (s, 4H), 1.58 (s, 2H); ¹³C NMR (101 MHz, Chloroform-d) δ 168.8, 161.0, 151.7, 144.1, 141.9, 141.7, 140.7, 138.5, 138.1, 138.0, 129.8, 128.7, 127.7, 125.6, 125.4, 125.3, 120.4, 115.4, 53.9, 48.9, 43.3, 26.6, 25.6, 24.5. MS (ES+) m/z=399 [M+H]⁺.

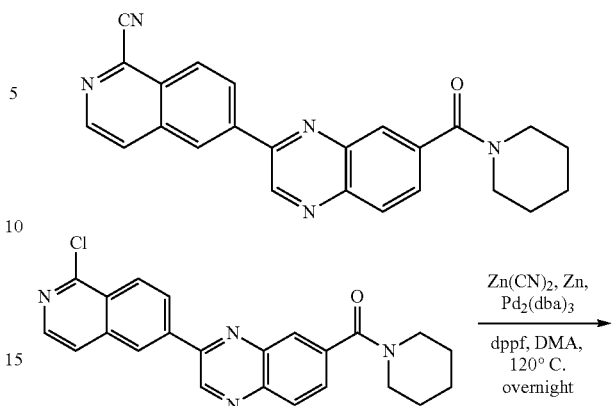

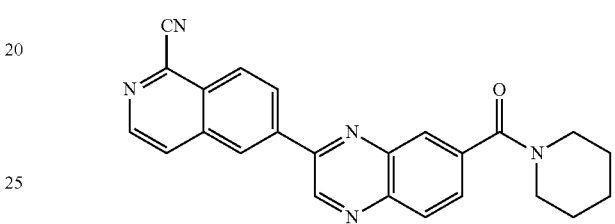

Under nitrogen atmosphere, Zn(CN)₂ (47 mg, 0.4 mmol) was added to a dry tube containing (3-(1-chloroisoquinolin-6-yl)quinoxalin-6-yl)(piperidin-1-yl)methanone (80 mg, 0.2 mmol), Pd₂(dba)₃ (8 mg, 1% mmol), dppf (11 mg, 2% mmol), Zn (13 mg, 0.2 mmol) and DMA (2 mL). The mixture was stirring at 120° C. overnight. The reaction mixture was cooled to room temperature, washed with water, extracted with ethyl acetate, dried over anhydrous Na₂SO₄ and concentrated by rotary evaporation. The crude was purified by flash chromatography on silica gel to give the product 67b as a white solid (50 mg, 63% yield).

¹H NMR (400 MHz, Chloroform-d) δ 9.53 (s, 1H), 8.76-8.74 (m, 2H), 8.70 (d, J=8.8 Hz, 1H), 8.53 (d, J=8.8 Hz, 1H), 8.22-8.21 (m, 2H), 8.08 (d, J=5.7 Hz, 1H), 7.85 (d, J=8.7 Hz, 1H), 3.81 (s, 2H), 3.44 (s, 2H), 1.74 (s, 4H), 1.60 (s, 2H); ¹³C NMR (101 MHz, Chloroform-d) δ 168.6, 150.3, 144.2, 143.7, 142.1, 141.7, 139.4, 138.9, 136.1, 134.9, 129.9, 129.6, 129.3, 128.6, 127.8, 126.5, 126.4, 125.0, 115.6, 48.9, 43.3, 26.6, 25.6, 24.5. MS (ES+) m/z=394 [M+H]⁺.

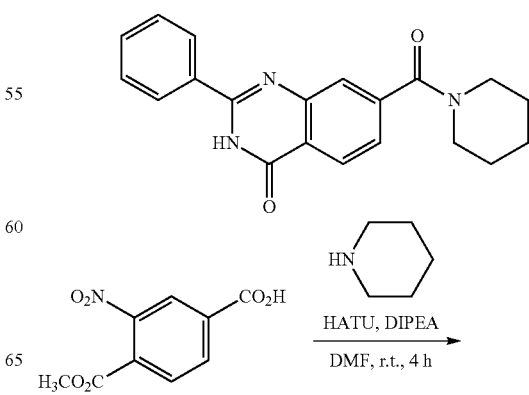

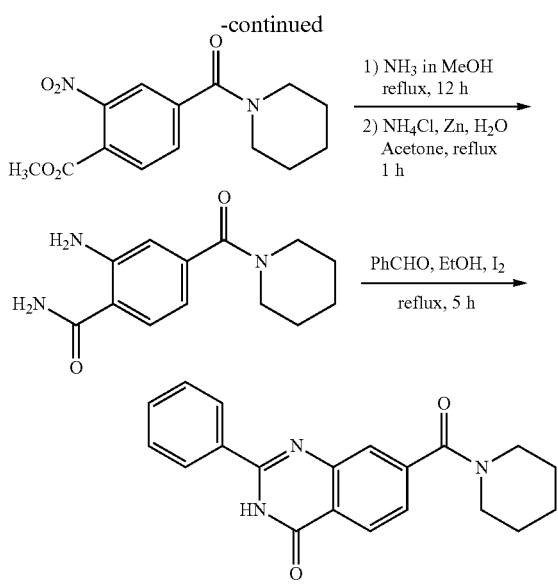

Step 1

To a solution of 4-(methoxycarbonyl)-3-nitrobenzoic acid (2.25 g, 10 mmol), HATU (4.2 g, 11 mmol), DIPEA (3.5 mL, 20 mmol) in DMF (20 mL) was added piperidine (1.09 mL, 11 mmol). The mixture was stirred at room temperature for 4 h. Water was added to the solution, and the mixture was extracted with ethyl acetate, washed with brine, dried over anhydrous $Na_2SO_4$ and concentrated by rotary evaporation. The crude was purified by flash chromatography on silica gel to give the product as yellow oil (2.63 g, 90% yield). MS (ES+) m/z=293 [M+H]$^+$.

$^1$H NMR (400 MHz, Chloroform-d) δ 7.94 (s, 1H), 7.78 (d, J=7.8 Hz, 1H), 7.68 (d, J=7.8 Hz, 1H), 3.94 (s, 3H), 3.72 (s, 2H), 3.32 (s, 2H), 1.71 (s, 4H), 1.54 (s, 2H).

Step 2

To a solution of methyl 2-nitro-4-(piperidine-1-carbonyl) benzoate (2.34 g, 8 mmol) in MeOH (18 mL) was added NH3 in MeOH (7N, 3.4 mL, 24 mmol), and the mixture was then heated at 100° C. for 12 h. The solvent was removed and the residue was dissolved in acetone (20 mL), and Zn powder (2.6 g, 40 mmol), ammonium chloride (2.14 g, 40 mmol) and water (2 mL) were added. The mixture was refluxed for 1 h, then filtered and concentrated. The residue was diluted with water and extracted with ethyl acetate. The combined organic extracts were washed with brine, dried over anhydrous $Na_2SO_4$ and concentrated by reduced pressure. The crude was purified by flash chromatography on silica gel to give the product as brown oil (889 mg, 45% yield). MS (ES+) m/z=248 [M+H]$^+$.

Step 3

To a solution of 2-amino-4-(piperidine-1-carbonyl)benzamide (247 mg, 1 mmol) in EtOH (5 mL) was added benzaldehyde (0.11 mL, 1.1 mmol) and $I_2$ (279 mg, 1.1 mmol). The mixture was refluxed for 5 h, and the solution was allowed to cool to room temperature. Sodium thiosulfate aqueous solution was added to quench excess $I_2$ and the resulting mixture was extracted with ethyl acetate. The combined organic extracts were washed with brine, dried over anhydrous $Na_2SO_4$ and concentrated by reduced pressure. The crude was purified by flash chromatography on silica gel to give the product 68b as a white solid (100 mg, 30% yield). MS (ES+) m/z=334 [M+H]$^+$.

$^1$H NMR (400 MHz, Chloroform-d) δ 12.10 (s, 1H), 8.35 (d, J=8.1 Hz, 1H), 8.30-8.27 (m, 2H), 7.80 (d, J=1.5 Hz, 1H), 7.62-7.57 (m, 3H), 7.49 (dd, J=8.1, 1.5 Hz, 1H), 3.76 (s, 2H), 3.36 (s, 2H), 1.70 (s, 4H), 1.55 (s, 2H); $^{13}$C NMR (101 MHz, Chloroform-d) δ 168.7, 163.6, 152.6, 149.5, 142.9, 132.5, 131.9, 129.0, 127.6, 127.0, 125.8, 125.0, 121.1, 48.7, 43.2, 26.6, 25.6, 24.5.

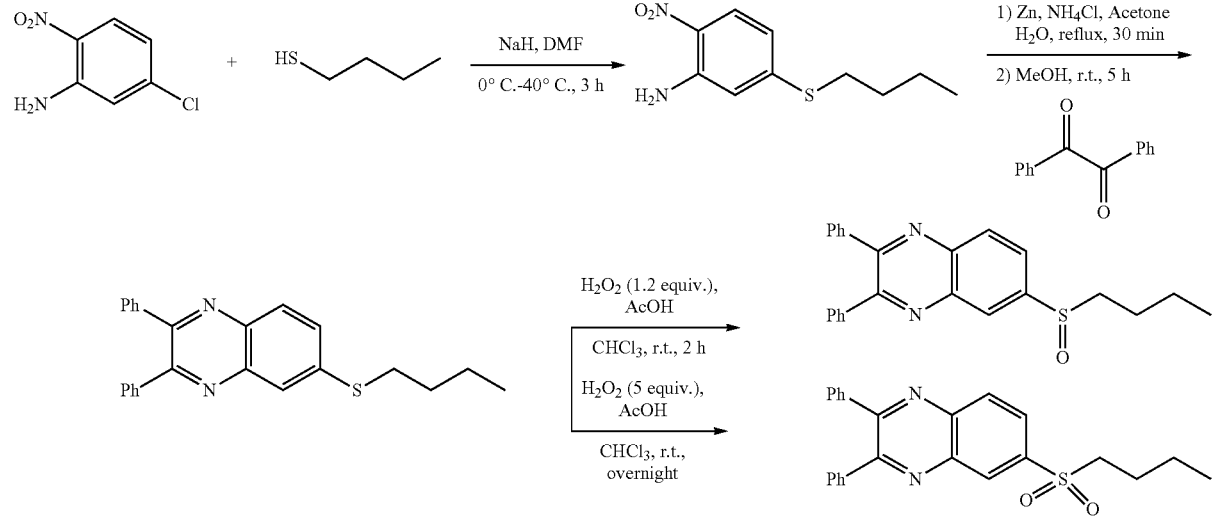

Step 1

To a solution of butane-1-thiol (990 mg, 11 mmol) in DMF (20 mL) was added NaH (480 mg, 12 mmol, 60% in mineral oil) slowly at 0° C. The mixture was stirred at 0° C. for 30 min and 5-chloro-2-nitroaniline (1.73 g, 10 mmol) was added to the solution. The reaction was heated up to 40° C. and continue to stir for an additional 2.5 h. The mixture was cooled to room temperature and quenched with water, extracted with ethyl acetate. The combined organic extracts were washed with brine, dried over anhydrous $Na_2SO_4$ and concentrated by reduced pressure. The crude was purified by flash chromatography on silica gel to give the product as a brown solid (1.97 g, 87% yield). MS (ES+) m/z=227 [M+H]⁺.

Step 2

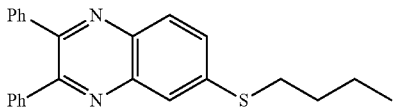 [SMILES: CCCCSc1ccc2nc(-c3ccccc3)c(-c3ccccc3)nc2c1]

To a solution of 5-(butylthio)-2-nitroaniline (1.81 g, 8 mmol) in acetone (16 mL) was added Zn powder (2.6 g, 40 mmol), ammonium chloride (2.14 g, 40 mmol) and water (2 mL). The mixture was refluxed for 30 min, then filtered and concentrated. The crude was dissolved in MeOH (16 mL), and benzil (1.68 g, 8 mmol) was added. The mixture was stirred at room temperature for 5 h. The solvent was removed, and the residue was diluted with ethyl acetate, washed with water, brine and dried over $Na_2SO_4$ and concentrated by reduced pressure. The crude was purified by flash chromatography on silica gel to give the product 2b as a yellow solid (1.88 g, 64% yield). ¹H NMR (400 MHz, Chloroform-d) δ 8.03 (d, J=8.8 Hz, 1H), 7.91 (s, 1H), 7.62 (dd, J=8.8, 2.0 Hz, 1H), 7.51-7.48 (m, 4H), 7.37-7.30 (m, 6H), 3.12 (t, J=7.4 Hz, 2H), 1.81-1.73 (m, 2H), 1.56-1.48 (m, 2H), 0.97 (t, J=7.3 Hz, 3H); ¹³C NMR (101 MHz, Chloroform-d) δ 152.3, 141.7, 141.4, 139.5, 139.1, 139.0, 130.2, 129.78, 129.76, 129.0, 128.8, 128.7, 128.3, 128.2, 123.7, 32.1, 30.6, 22.1, 13.7, (1 signal not observed). MS (ES+) m/z=371 [M+H]⁺.

Step 3

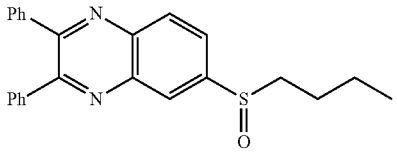 [SMILES: CCCCS(=O)c1ccc2nc(-c3ccccc3)c(-c3ccccc3)nc2c1]

Butyl(6,7-diphenylnaphthalen-2-yl)sulfane (37 mg, 0.1 mmol) was dissolved in chloroform (2 mL). $H_2O_2$ (3.7 μL, 0.12 mmol) and AcOH (0.5 mL) were added. The reaction was monitored by LC/MS. After the completion of the reaction, $NaHCO_3$ aq was added to quench the reaction. The mixture was extracted with dichloromethane, washed with brine, dried over anhydrous $Na_2SO_4$ and concentrated by rotary evaporation. The crude was purified by flash chromatography on silica gel to give the product 3b as a yellow solid (35 mg, 90% yield). ¹H NMR (400 MHz, Chloroform-d) δ 8.42 (s, 1H), 8.32 (d, J=8.7 Hz, 1H), 7.98 (d, J=8.7 Hz, 1H), 7.54-7.52 (m, 4H), 7.41-7.32 (m, 6H), 2.97-2.90 (m, 2H), 1.86-1.75 (m, 1H), 1.67-1.55 (m, 1H), 1.53-1.39 (m, 2H), 0.92 (t, J=7.1 Hz, 3H); ¹³C NMR (101 MHz, Chloroform-d) δ 154.9, 154.7, 145.8, 142.1, 140.6, 138.5, 138.4, 130.7, 129.8, 129.3, 128.38, 128.36, 125.8, 124.0, 56.7, 23.9, 21.9, 13.7, (missing 2 signals due to overlap). MS (ES+) m/z=387 [M+H]⁺.

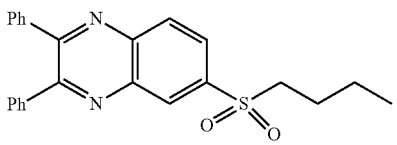 [SMILES: CCCCS(=O)(=O)c1ccc2nc(-c3ccccc3)c(-c3ccccc3)nc2c1]

The target compound 4b (25 mg, 62% yield) was obtained through the general procedure described above by using 5 equiv. of $H_2O_2$ instead.

¹H NMR (400 MHz, Chloroform-d) δ 8.78 (d, J=1.8 Hz, 1H), 8.33 (d, J=8.7 Hz, 1H), 8.17 (dd, J=8.7, 1.8 Hz, 1H), 7.56-7.53 (m, 4H), 7.43-7.33 (m, 6H), 3.24-3.20 (m, 2H), 1.78-1.70 (m, 2H), 1.45-1.36 (m, 2H), 0.88 (t, J=7.3 Hz, 3H); ¹³C NMR (101 MHz, Chloroform-d) δ 156.1, 155.3, 142.9, 140.1, 139.9, 138.2, 138.1, 131.0, 130.9, 129.9, 129.8, 129.6, 129.5, 128.4, 127.0, 56.1, 24.8, 21.6, 13.5, (missing 1 signal due to overlap). MS (ES+) m/z=403 [M+H]⁺.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

The following is claimed:

1. A method of inhibiting the activity of 15-PGDH enzyme, the method comprising:
   administering to the enzyme a compound having the structure of formula (II), or a pharmaceutically acceptable salt thereof;

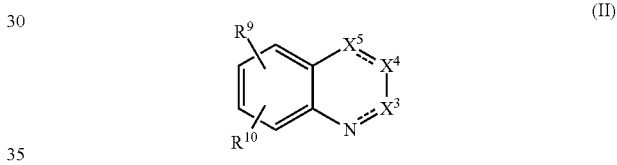

wherein $X^3$ is $CR^8$, the compound forming a polycyclic heteroaryl with 10 ring atoms;

$X^4$ is N, NH, or $CR^7$;

$X^5$ is N, C=O, or $CR^{16}$, wherein:
  $X^5$ is N if $X^4$ is $CR^7$;
  $X^4$ is NH if $X^5$ is C=O;
  $X^5$ is $CR^{16}$ if $X^4$ is N and $X^3$ is $CR^8$;

$R^9$, $R^{10}$, and $R^{16}$ are the same or different and are independently selected from the group consisting of hydrogen, oxygen, substituted or unsubstituted $C_1$-$C_{24}$ alkyl, $C_2$-$C_{24}$ alkenyl, $C_2$-$C_{24}$ alkynyl, $C_5$-$C_{20}$ aryl, heterocycloalkenyl containing from 5-7 ring atoms, heteroaryl or heterocyclyl containing from 5-14 ring atoms, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, sulfanamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkyl ethers, phosphates, phosphate esters, and combinations thereof;

R⁷ and R⁸ are same or different and are each independently selected from the group consisting of H, a substituted or unsubstituted aryl, a substituted or unsubstituted heteroaryl, a substituted or unsubstituted cycloalkyl, and a substituted or unsubstituted heterocyclyl, and at least one of R⁷ or R⁸ is not H; and wherein the compound of formula (II) is not

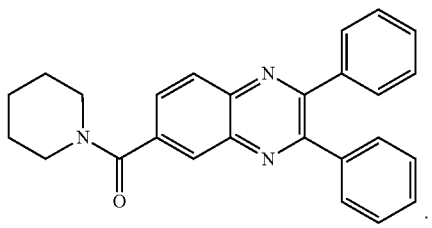 [SMILES: O=C(c1ccc2nc(-c3ccccc3)c(-c3ccccc3)nc2c1)N1CCCCC1]

2. A method of inhibiting the activity of 15-PGDH enzyme, the method comprising:

administering to the enzyme a compound having the structure of formula (IIa), (IIb), (IIc), (IId), (IIe), or (IIf), or a pharmaceutically acceptable salt thereof:

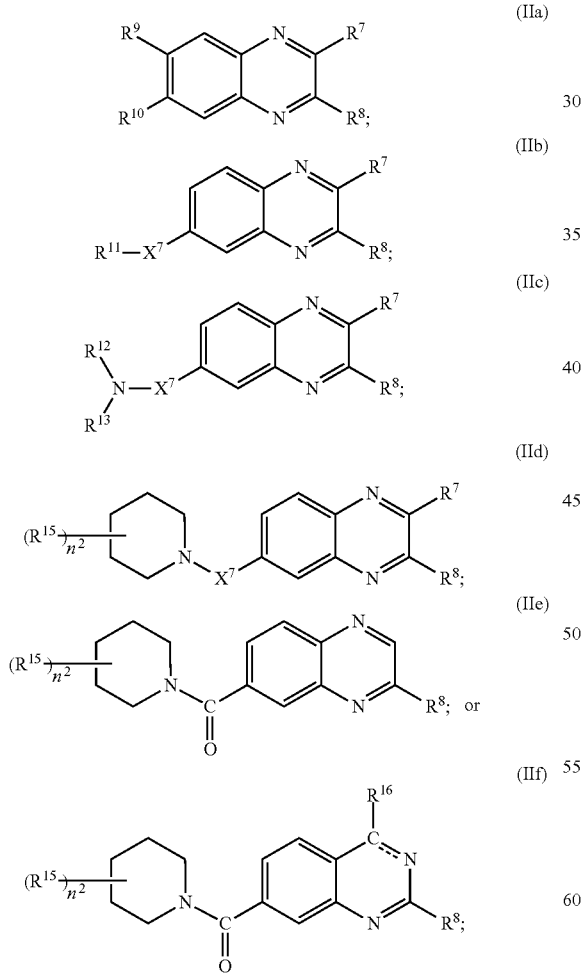

wherein $X^7$ is S, S=O, S(=O)$_2$, or C=O;
R⁷ and R⁸ are same or different and are each independently selected from the group consisting of H, a substituted or unsubstituted aryl, a substituted or unsubstituted heteroaryl, a substituted or unsubstituted cycloalkyl, and a substituted or unsubstituted heterocyclyl, and at least one of R⁷ or R⁸ is not H;

$R^9, R^{10}, R^{11}, R^{12}, R^{13}$ and $R^{15}$ are the same or different and are independently selected from the group consisting of hydrogen, oxygen, substituted or unsubstituted $C_1$-$C_{24}$ alkyl, $C_2$-$C_{24}$ alkenyl, $C_2$-$C_{24}$ alkynyl, $C_5$-$C_{20}$ aryl, heterocycloalkenyl containing from 5-7 ring atoms, heteroaryl or heterocyclyl containing from 5-14 ring atoms, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ acyloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, sulfanamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkyl ethers, phosphates, phosphate esters, and combinations thereof; wherein $R^{12}$ and $R^{13}$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl, $n^2$ is 0-4, and each $R^{15}$ is the same or different.

3. The method of claim 1, wherein the compound is selected from the group consisting of:

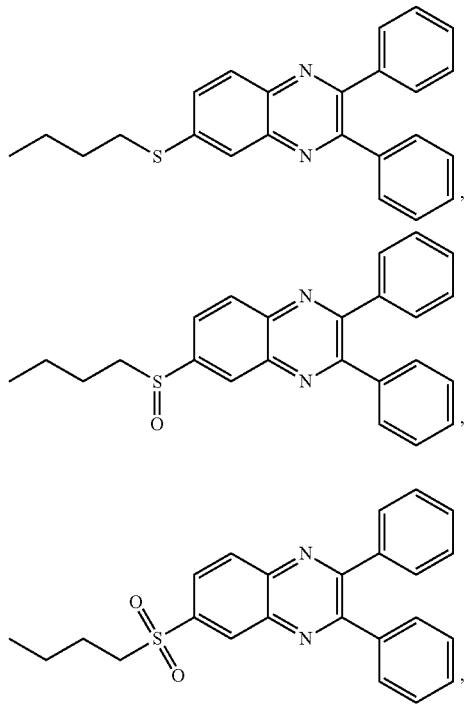

211
-continued
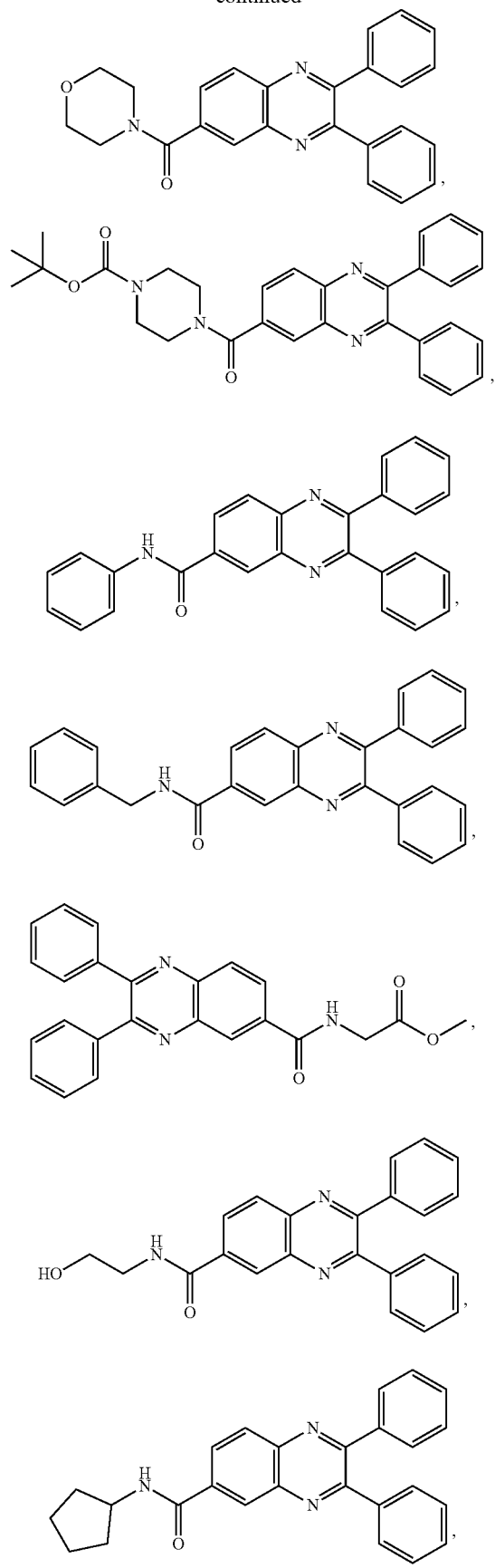
212
-continued
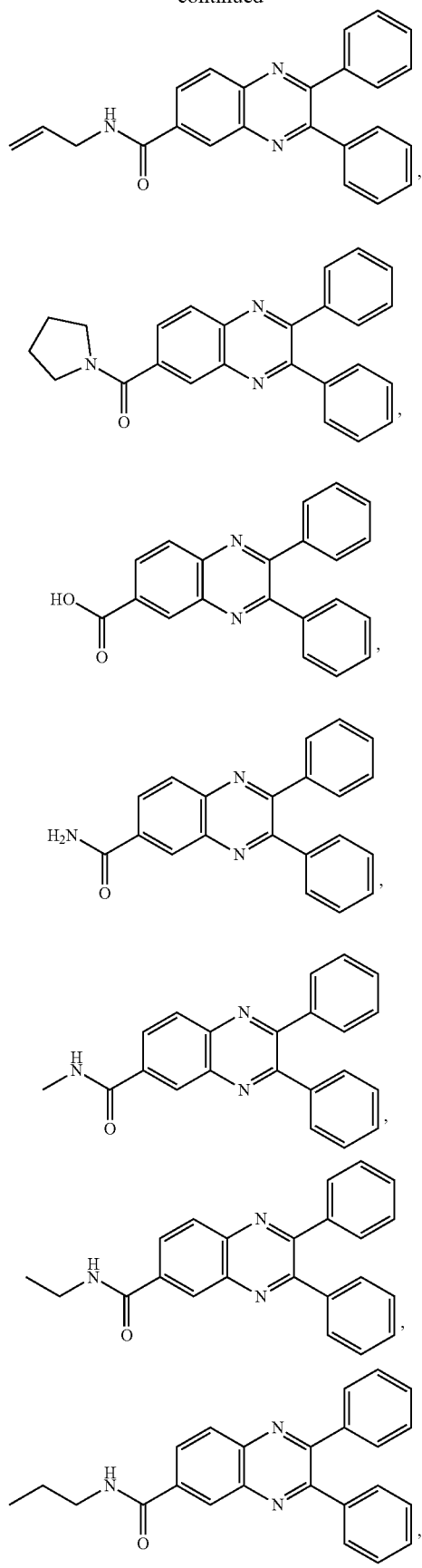

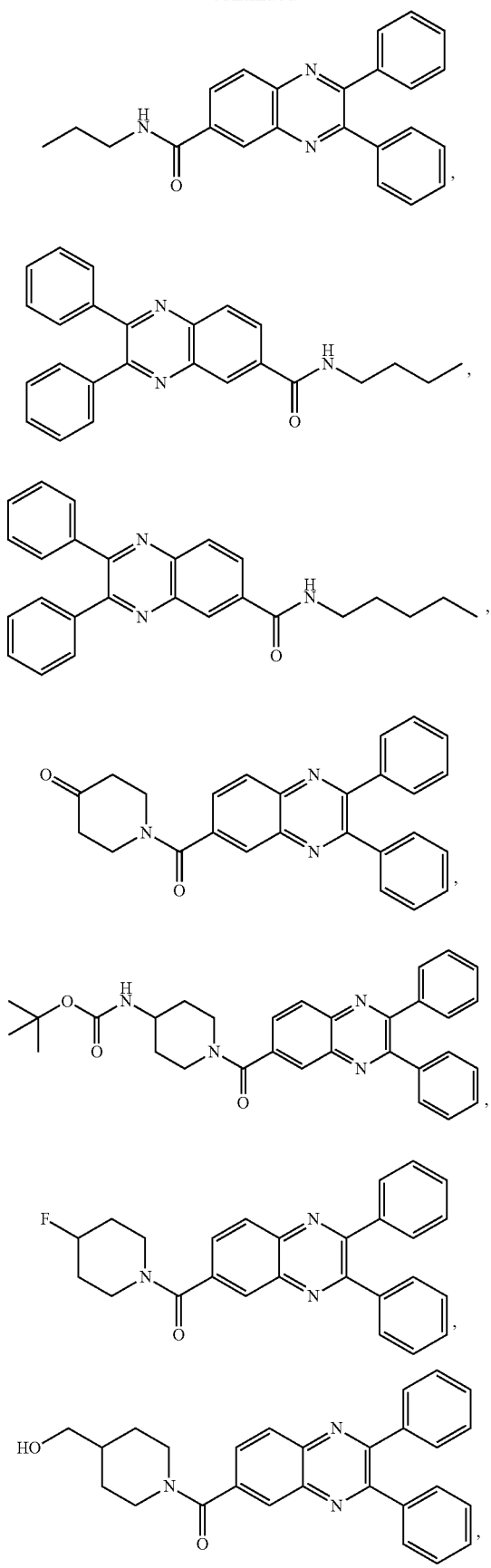
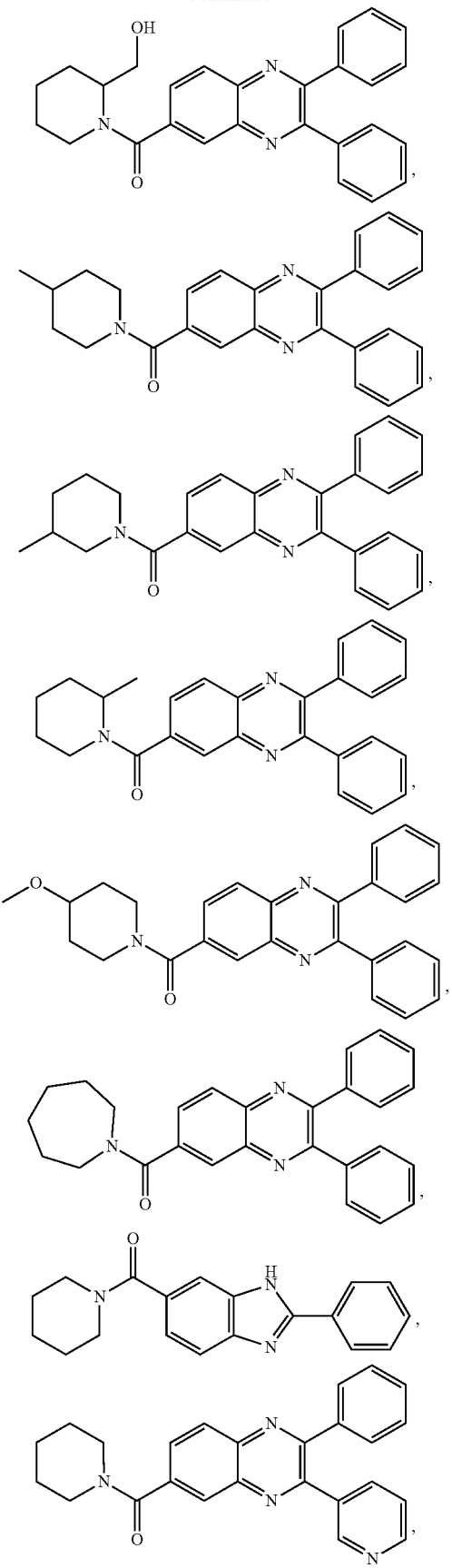

215
-continued
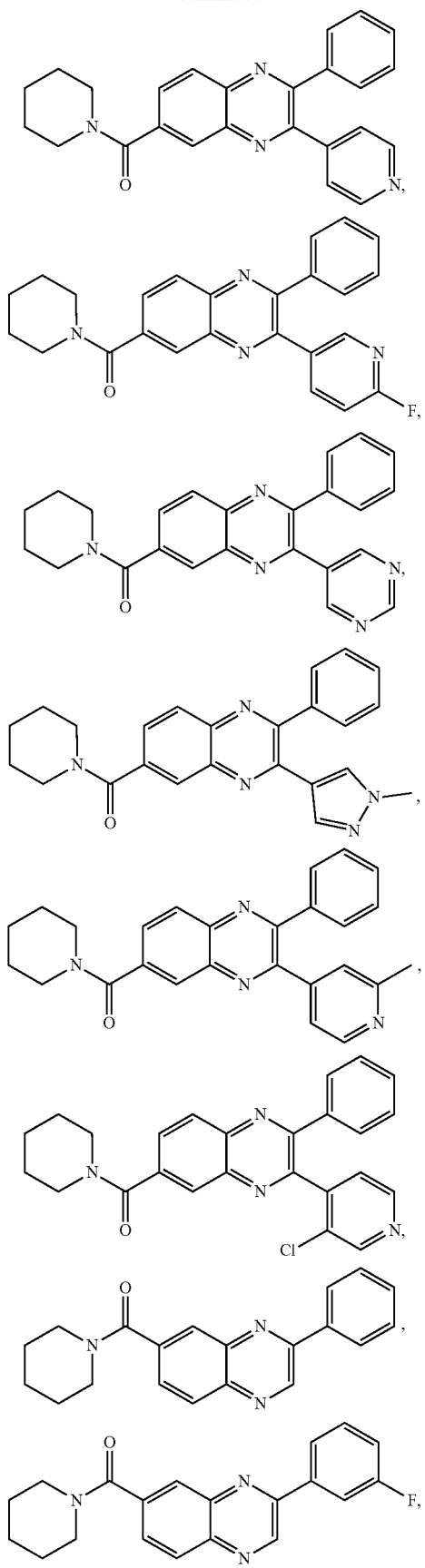
216
-continued
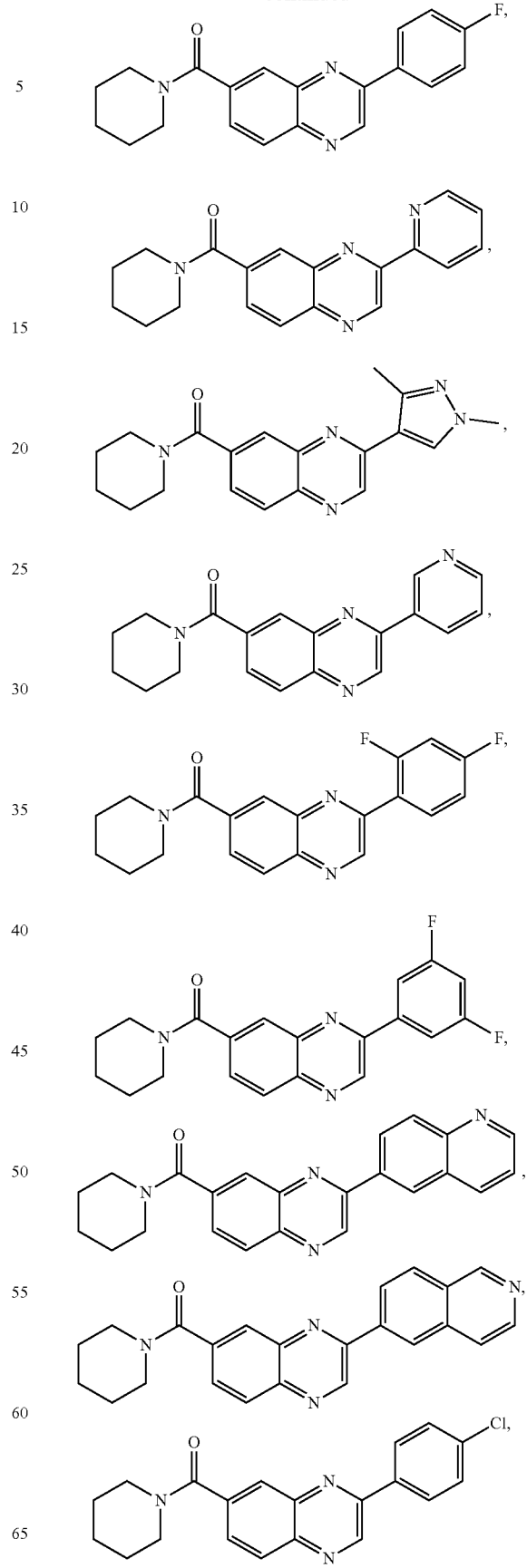

217
-continued
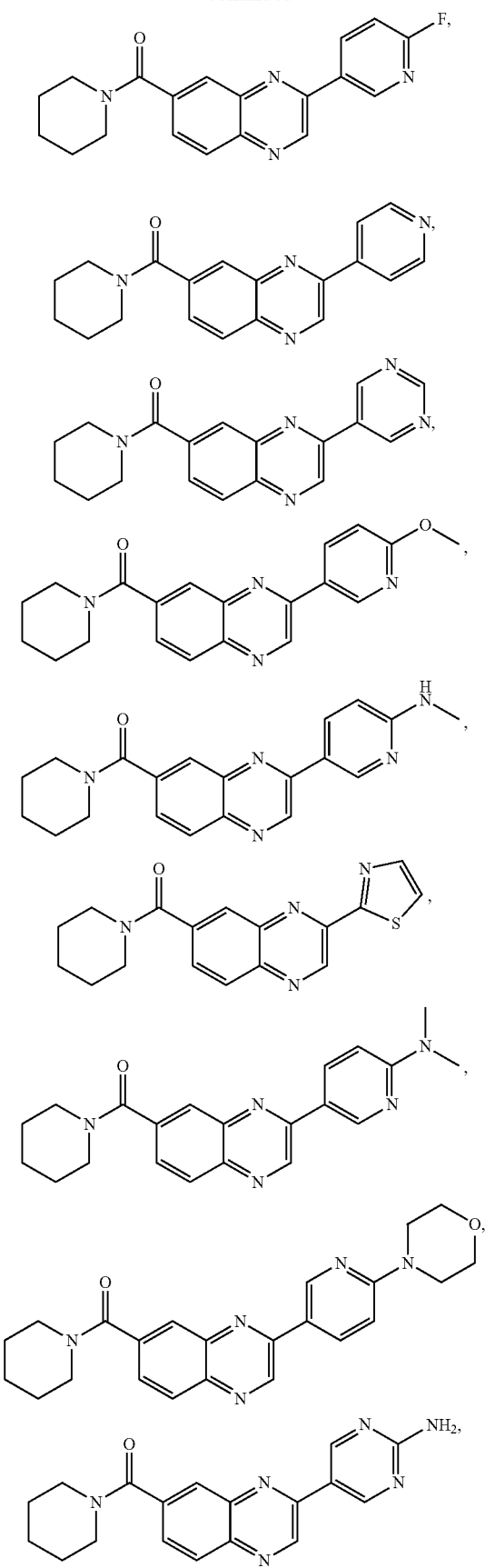
218
-continued
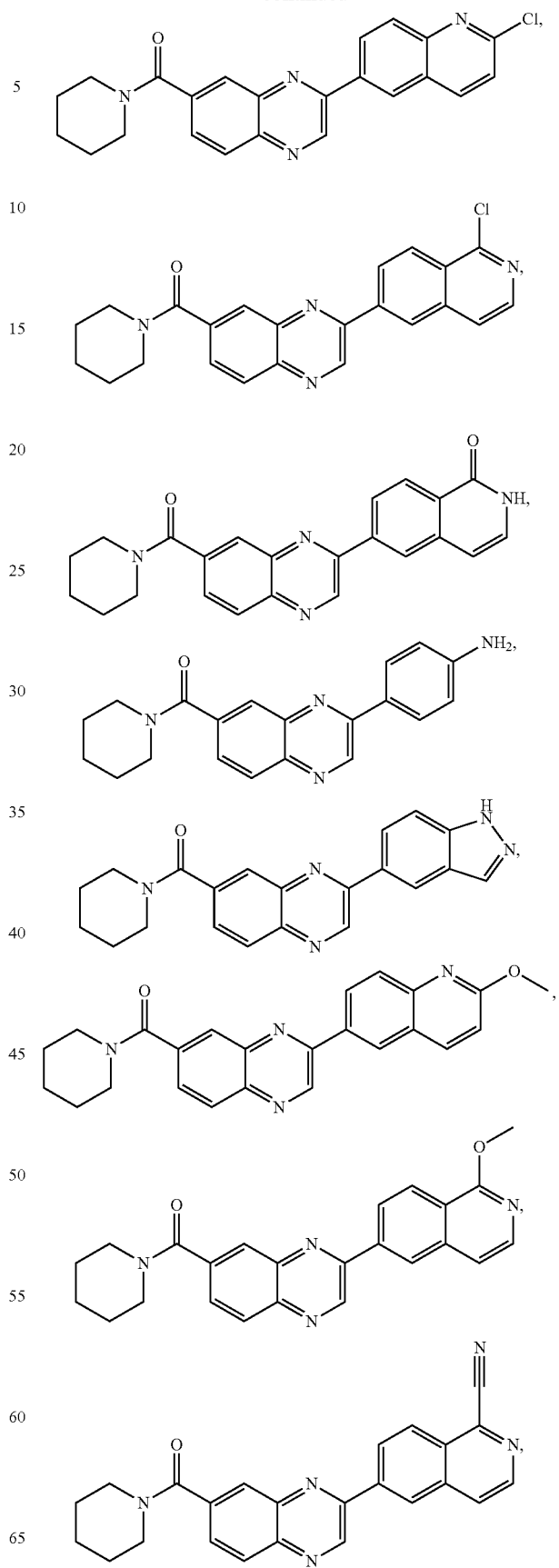

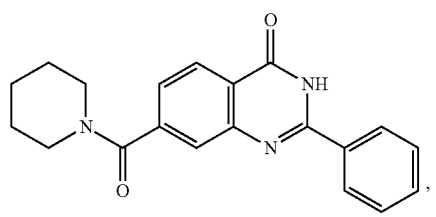
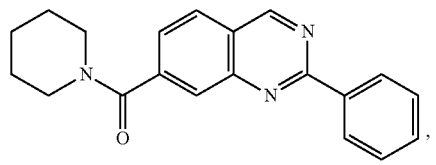
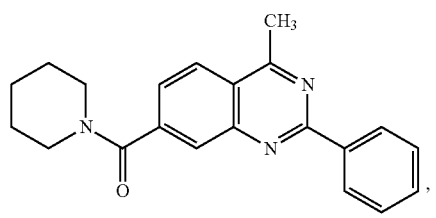
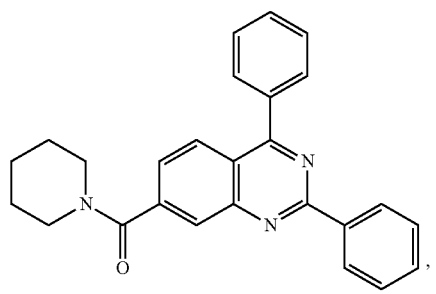
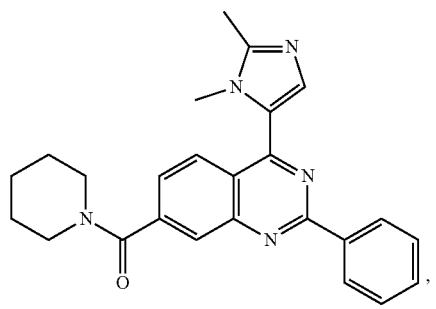
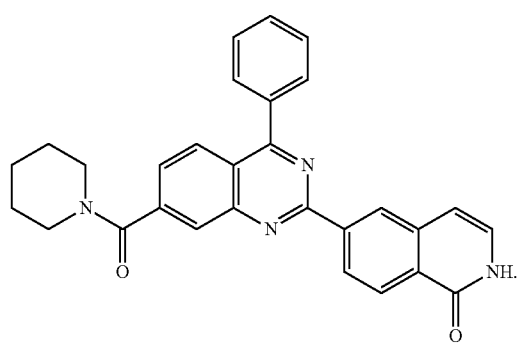
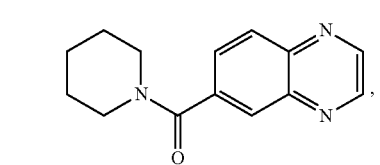
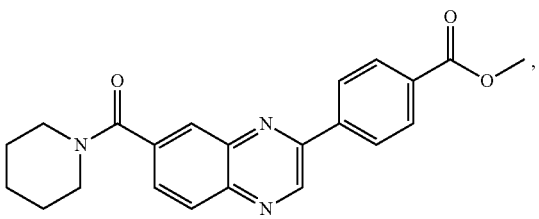
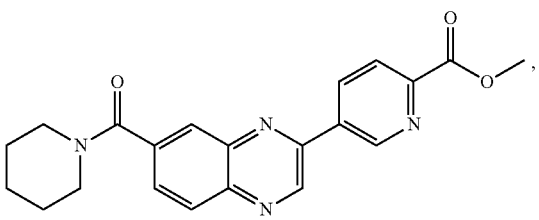
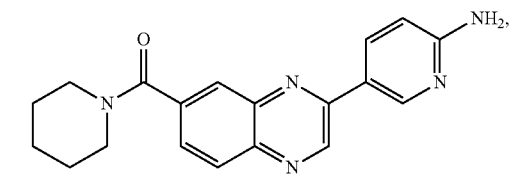
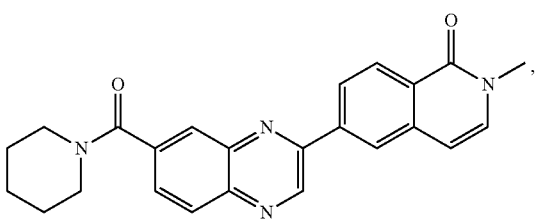
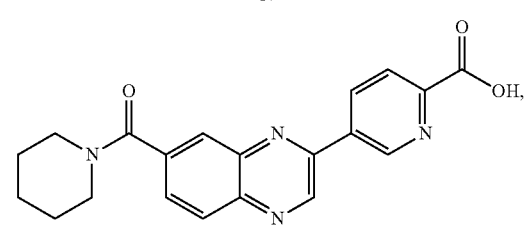
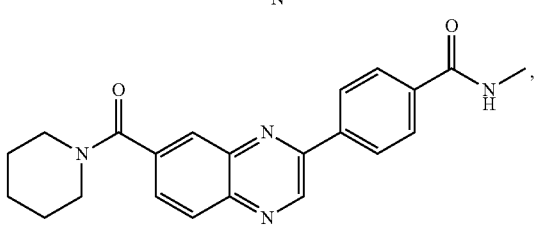
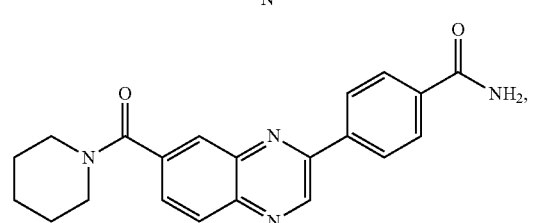
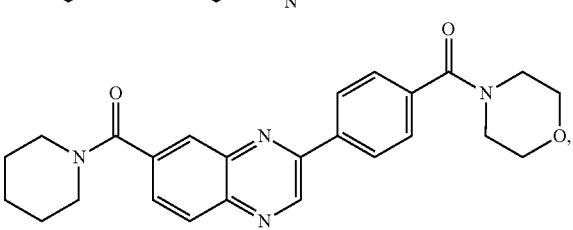

221
-continued

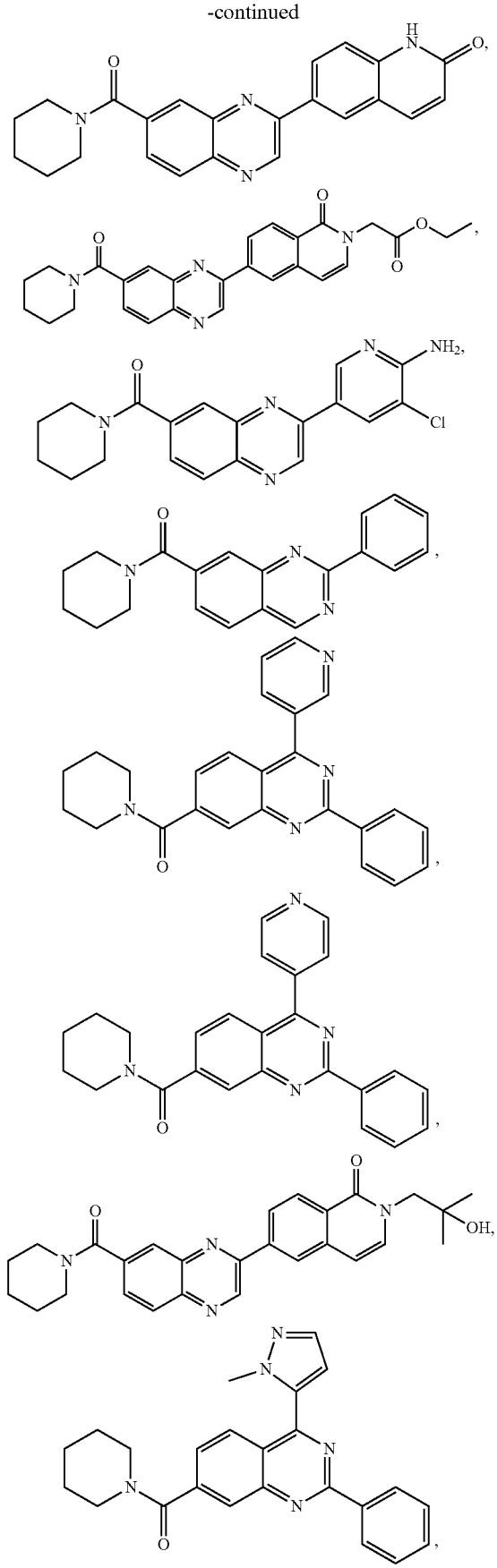

222
-continued

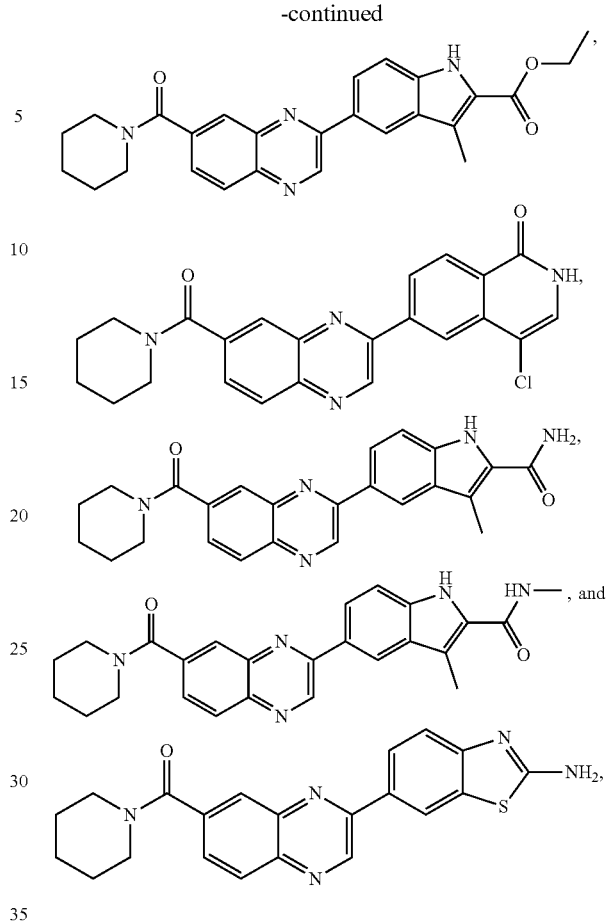

or a pharmaceutically acceptable salt thereof.

4. The method of claim 1, the compound being administered to a subject to treat at least one of oral ulcers, gum disease, colitis, ulcerative colitis, gastrointestinal ulcers, inflammatory bowel disease, vascular insufficiency, Raynaud's disease, Buerger's disease, diabetic neuropathy, pulmonary artery hypertension, and ischemia.

5. The method of claim 1, the compound being administered to a subject or to intestine of a subject as a treatment for colitis, ulcerative colitis, or inflammatory bowel disease.

6. The method of claim 1, wherein the compound is administered to a subject having at least one symptom associated with an ischemic tissue or a tissue damaged by ischemia.

7. The method of claim 6, wherein the ischemia is associated with at least one of acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, hereditary hemorrhagic telengiectasia, ischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, or wounds to tissues or organs.

\* \* \* \* \*